(12) United States Patent
Pandey et al.

(10) Patent No.: US 11,713,309 B2
(45) Date of Patent: *Aug. 1, 2023

(54) SOLID FORMS OF CERDULATINIB

(71) Applicant: Alexion Pharmaceuticals, Inc., Boston, MA (US)

(72) Inventors: Anjali Pandey, Fremont, CA (US); Julian Scott Northen, Sunderland (GB); Philippe Fernandes, Turnhout (BE); Ying Chen, Thousand Oaks, CA (US); Yuelie Lu, San Diego, CA (US); Sami Karaborni, Cupertino, CA (US); Gus Kodersha, Warren, NJ (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/098,852

(22) Filed: Nov. 16, 2020

(65) Prior Publication Data
US 2021/0130330 A1 May 6, 2021

Related U.S. Application Data

(63) Continuation of application No. 16/402,684, filed on May 3, 2019, now Pat. No. 10,865,198.

(60) Provisional application No. 62/667,226, filed on May 4, 2018.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .......................... C07D 239/08; C07D 403/12
See application file for complete search history.

(56) References Cited

U.S. PATENT DOCUMENTS

| | | | |
|---|---|---|---|
| 4,673,747 A | 6/1987 | Nohara et al. | |
| 5,760,032 A | 6/1998 | Kitajima et al. | |
| 6,627,626 B2 | 9/2003 | Minich et al. | |
| 7,449,456 B2 | 11/2008 | Nagashima et al. | |
| 7,557,210 B2 | 7/2009 | Singh et al. | |
| 8,012,959 B2 | 9/2011 | Nagashima et al. | |
| 8,138,339 B2 | 3/2012 | Bauer et al. | |
| 8,501,944 B2 | 8/2013 | Bauer et al. | |
| 8,937,070 B2 | 1/2015 | Bauer et al. | |
| 9,357,229 B2 | 6/2016 | Vannucchi et al. | |
| 9,676,756 B2 | 6/2017 | Bauer et al. | |
| 9,868,729 B2 | 1/2018 | Bauer et al. | |
| 10,533,001 B2 | 1/2020 | Bauer et al. | |
| 10,865,198 B2* | 12/2020 | Pandey ................ | C07D 239/48 |
| 2004/0029902 A1 | 2/2004 | Singh et al. | |
| 2005/0272753 A1 | 12/2005 | Nagashima et al. | |
| 2009/0281072 A1 | 11/2009 | Nagashima et al. | |
| 2009/0318407 A1 | 12/2009 | Bauer et al. | |
| 2011/0294749 A1 | 12/2011 | Nagashima et al. | |
| 2012/0129867 A1 | 5/2012 | Bauer et al. | |
| 2012/0157500 A1 | 6/2012 | Tao | |
| 2013/0040973 A1 | 2/2013 | Vannucchi et al. | |
| 2013/0237493 A1 | 9/2013 | Sinha et al. | |
| 2014/0031361 A1 | 1/2014 | Bauer et al. | |
| 2014/0371241 A1 | 12/2014 | Buggy et al. | |
| 2015/0094298 A1 | 4/2015 | Bauer et al. | |
| 2015/0259328 A1 | 9/2015 | Bauer et al. | |
| 2017/0042896 A1 | 2/2017 | Coffey et al. | |
| 2018/0147203 A1 | 5/2018 | Pandey et al. | |
| 2018/0353506 A1 | 12/2018 | Coffey et al. | |
| 2019/0337930 A1 | 11/2019 | Pandey et al. | |
| 2020/0061060 A1 | 2/2020 | Coffey et al. | |
| 2020/0222403 A1 | 7/2020 | Coffey et al. | |

FOREIGN PATENT DOCUMENTS

| | | |
|---|---|---|
| CN | 103476770 A | 12/2013 |
| EP | 1518855 | 3/2005 |
| WO | WO 2008/009458 | 1/2008 |
| WO | WO 2009/145856 | 12/2009 |
| WO | WO 2010/129802 | 11/2010 |
| WO | WO 2011/068898 | 6/2011 |
| WO | WO 2012/045020 | 4/2012 |
| WO | WO 2014/018567 | 1/2014 |
| WO | WO 2014/058921 | 4/2014 |
| WO | WO 2016/040858 | 3/2016 |
| WO | WO 2016/196385 | 12/2016 |
| WO | WO 2017/027829 | 2/2017 |
| WO | WO 2017/096303 | 6/2017 |

OTHER PUBLICATIONS

Coffey et al. (J'nal of Pharm & Exp. Ther.'2014.*
InvivoChem catalog et al. (2018).*
Akinleye et al. Ibrutinib and indolent B-cell lymphomas. Clinical Lymphoma, Myeloma and Leukemia (2014), vol. 14, pp. 253-260.
American Cancer Society. How Is Multiple Myeloma Staged? printed Aug. 17, 2017. https://www.cancer.org/cancer/multiple-myeloma/detection-diagnosis-istaging/staging.html.
Bartlett et al. Ibrutinib Monotherapy in Relapsed/Refractory Follicular Lymphoma (FL): Preliminary Results of a Phase 2 Consortium (P2C) Trial. Blood (2014) vol. 124, 800, p. 1-2.
Blunt et al., "The dual Syk/JAK inhibitor cerdulatinib antagonises B-cell receptor and microenvironmental signaling in chronic lymphocytic leukemia.", Clin Cancer Res. May 1, 2017;23(9):2313-2324.
Blunt et al., "The Syk\Jak Inhibitor Cerdulatinib (PRT062070) Shows Promising Preclinical Activity in Chronic Lymphocytic Leukemia by Antagonising B Cell Receptor and Microenvironmental Signalling", Blood, American Society of Hematology, US, vol. 126, No. 23, Dec. 3, 2015 (Dec. 3, 2015), XP009193491, ISSN: 0006-4971.
Burger, et al. Janus kinase inhibitor INCB20 has antiproliferative and apoptotic effects on human myeloma cells in vitro and in vivo. Molecular Cancer Therapeutics. 2009; 8:26-35.

(Continued)

*Primary Examiner* — Paul V Ward
(74) *Attorney, Agent, or Firm* — Sheppard Mullin Richter & Hampton LLP

(57) ABSTRACT

Forms of cerdulatinib and salts or co-crystals thereof were prepared and characterized in the solid state. Also provided are processes of manufacture and methods of using the forms cerdulatinib and salts or co-crystals thereof.

32 Claims, 95 Drawing Sheets

(56) References Cited

OTHER PUBLICATIONS

Cang, et al. ABT-199 (venetoclax) and BCL-2 inhibitors in clinical development. Journal of Hematology and Oncology. 2015; 8:129.
Cerdulatinib HCL—InvivoChem. Jan. 1, 2018. Retrieved from: https:www.invivochem.com/cerdulatinib-hcl/.
Cheng et al., "Functional characterization of BTKC481S mutation that confers irbrutinib resistance: exploration of alternative kinase inhibitors", Leukemia (201) 29, 895-900, (2015).
Coffey, et al. The Novel Kinase Inhibitor PRT062070 (Cerdulatinib) Demonstrates Efficacy in Models of Autoimmunity and B-Cell Cancer. The Journal of Pharmacology and Experimental Therapeutics. 2014; 351(3):538-548.
Extended European Search Report for EP Application No. 16804177.0 dated Jan. 30, 2019, 8 pages.
Extended European Search Report for EP Application No. 16835995.8 dated Feb. 11, 2019, 7 pages.
Hamlin et al., "Clinical and Correlative Results of a Phase 1 Study of Cerdulatinib (PRT062070) a Dual SYK/JAK Inhibitor in Patients with Relapsed/Refractory B Cell Malignancies", Blood, vol. 126, No. 23, Dec. 3, 2015 (Dec. 3, 2015), XP009193500, & 57th Annual Meeting of the American-Society-Of- Hematology; Orlando, FL, USA; Dec. 5 -8, 2015.
International Search Report and Written Opinion for PCT/US2016/034861 dated Sep. 7, 2016, 8 pages.
International Search Report and Written Opinion for PCT/US2016/046862 dated Oct. 31, 2016, 8 pages.
International Search Report and Written Opinion for PCT/US2016/064824 dated Jul. 5, 2017, 15 pages.
International Search Report and Written Opinion for PCT/US2019/030635 dated Aug. 20, 2019, 18 pages.
International Search Report and Written Opinion for PCT/US2019/030690 dated Jul. 15, 2019, 13 pages.
International Search Report and Written Opinion for PCT/US2019/030717 dated Oct. 30, 2019, 17 pages.
Ishikawa, et al. Anti-adult T-cell leukemia/lymphoma activity of cerdulatinib, a dual SYK/JAK kinase inhibitor. Int J Oncol. Oct. 2018;53(4):1681-1690.
Li, et al. INCB16562, a JAK1/2 Selective Inhibitor, Is Efficacious against Multiple Myeloma Cells and Reverses the Protective Effects of Cytokine and Stromal Cell Support. Neplasia. 2010; 12:28-38.
Ma et al., "Cerdulatinib, a novel dual SYK/JAK kinase inhibitor, has broad anti-tumor activity in both ABC and GCB types of diffuse large B cell lymphoma.", Oncotarget, vol. 6, No. 41, Nov. 5, 2015 (Nov. 5, 2015), pp. 43881-43896, XP002767267, ISSN: 1949-2553.
Patel et al., "A Phase I Open-Label, Multi-Dose Escalation Study of the Dual Syk/Jak Inhibitor PRT062070 (Cerdulatinib) in Patients with Relapsed/Refractory B Cell Malignancies", Blood, vol. 124, No. 21, Dec. 2014 (Dec. 2014), XP009193499, & 56th Annual Meeting of the American-Society-Of-Hematology; San Francisco, CA, USA; Dec. 6-9, 2014.
Reagan-Shaw et al., "Dose translation from animal to human studies revisited", FASEB Journal, 2007, vol. 22, pp. 659-661.
Ross et al. Comprehensive analysis of copy number and allele status identifies multiple chromosome defects underlying follicular lymphoma pathogenesis. Clin Cancer Res (2007) vol. 13, pp. 4777-4785.
Scuto et al., "The novel JAK inhibitor AZD1480 blocks STAT3 and FGFR3 signaling, resulting in suppression of human myeloma cell growth and survival", Leukemia, 2011, 25(3), pp. 538-550.
Shimura et al., "RSK2ser227 at N-Terminal Kinase Domain Is a Potential Therapeutic Target for Multiple Myeloma", Molecular Cancer Therapeutics, 2012, 11(12), pp. 2600-2609.
Stedman's Medical Dictionary 27th Edition, 2000, pp. 865-866.
Steele, et al. Abstract 305: Cerdulatinib induces Bim expression and synergistic cell kill in combination with venetoclax in follicular lymphoma cell lines. Molecular and Cellular Biology/Genetics. 2018; 78(13):305.
Wang et al., "SYK and STAT3 are active in diffuse large B-cell Lymphoma: Activity of cerdulatinib, a dual SYK/JAK inhibitor", Blood, 2014, 124:926, 6 pages.
Zahreddine et al. Mechanisms and insights into drug resistance in cancer. Frontiers in Pharmacology (2013), vol. 4 pp. 1-8.
Zhang et al., "Mechanisms of ibrutinib resistance in chronic lymphocytic leukaemia and non-Hodgkin lymphoma", British Journal of Haematology, 2015, 170, 445-456, 12 pages.
Berge, et al. Pharmaceutical Salts. Journal of Pharmaceutical Sciences. Jan. 1977; 66(1)1-19.
Kawaguchi, et al. Drug and crystal polymorphism. Journal of Human Environmental Engineering. 2002; 9(2):310-317.
Sharman, et al. Targeting B-cell receptor signaling kinases in chronic lymphocytic leukemia: the promise of entospletinib. Ther Adv Hematol. 2016, vol. 7(3) 157-170.
Takata, et al. API form screening and selection in drug discovery stage. Pharm Stage. Jan. 15, 2007, vol. 6, No. 10, pp. 20-25.

* cited by examiner

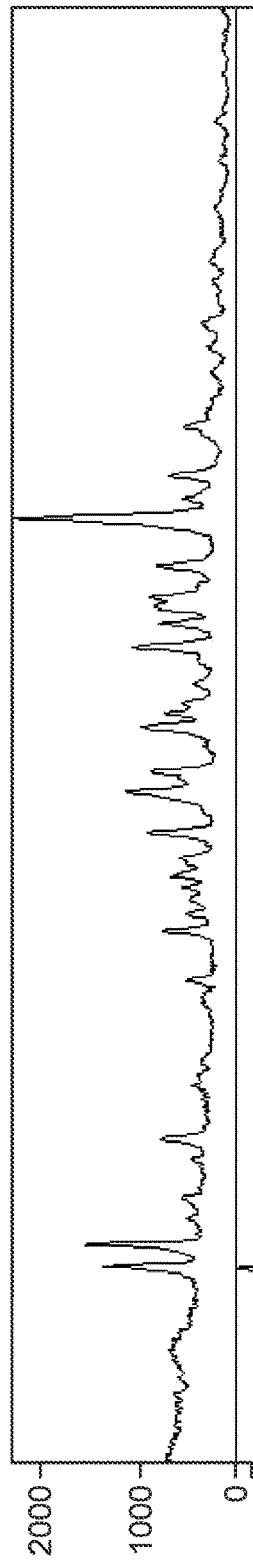
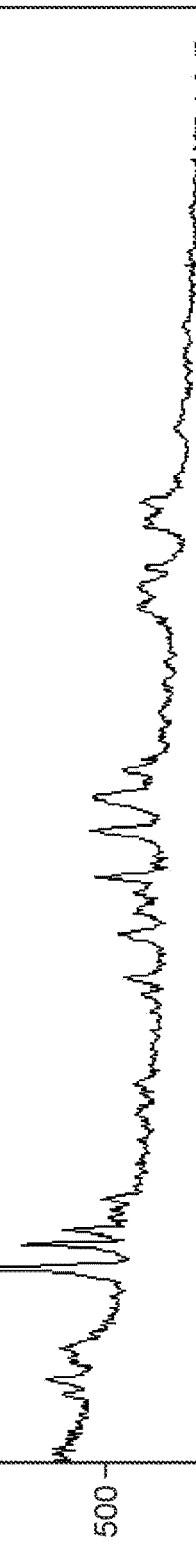
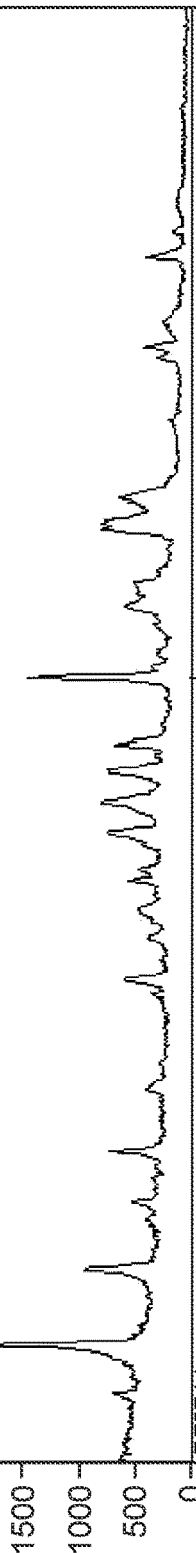
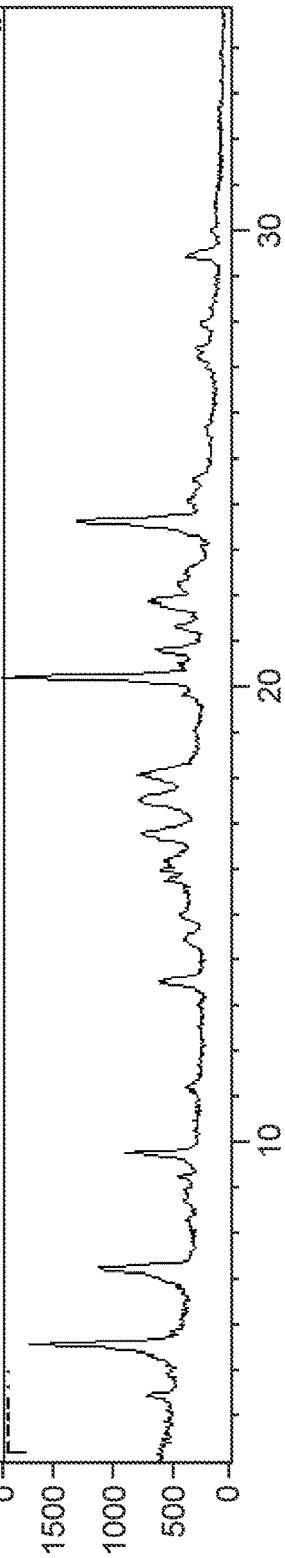
FIG. 30A
FIG. 30B
FIG. 30C
FIG. 30D

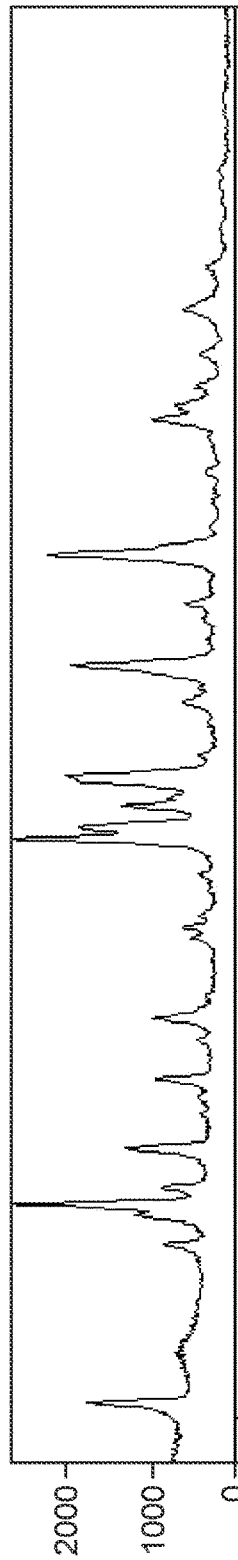
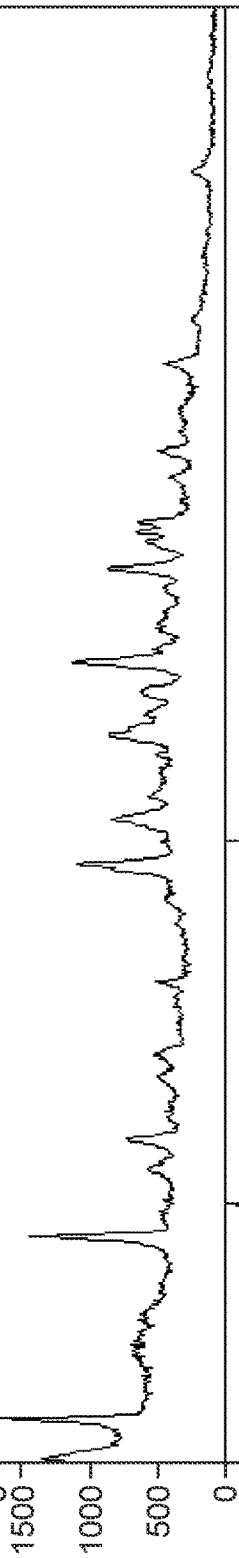
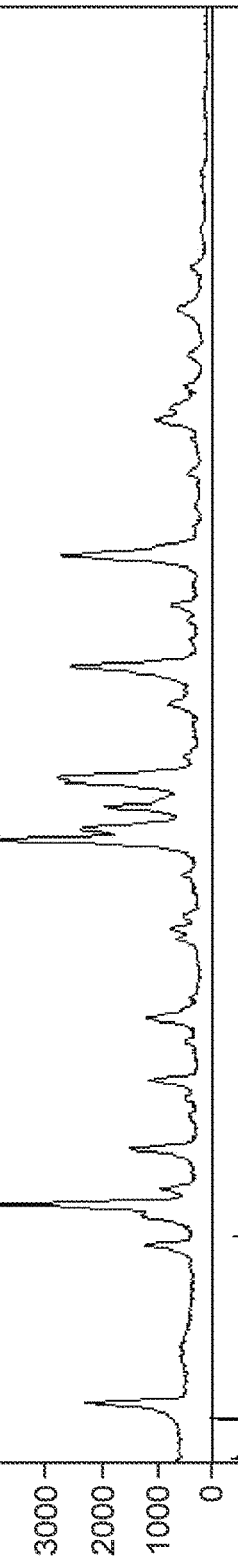
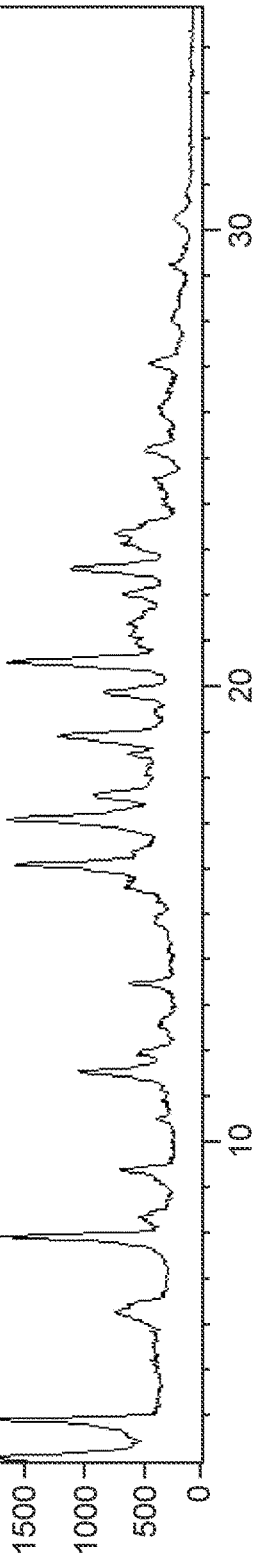
FIG. 32A
FIG. 32B
FIG. 32C
FIG. 32D

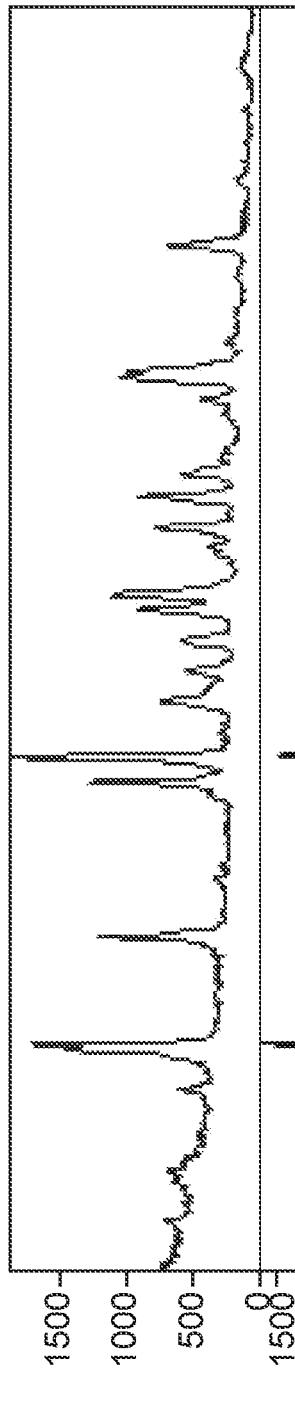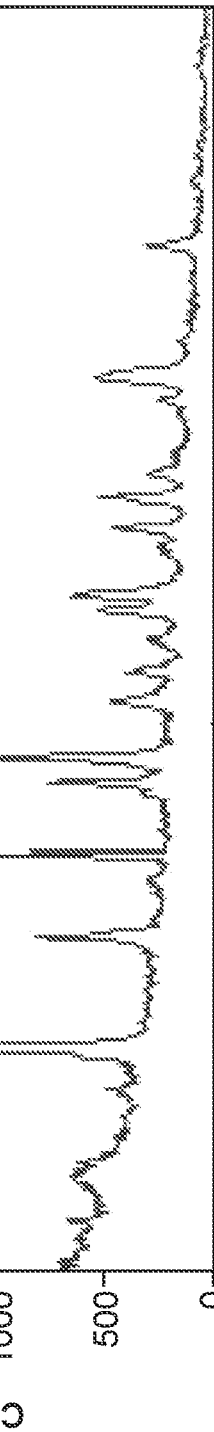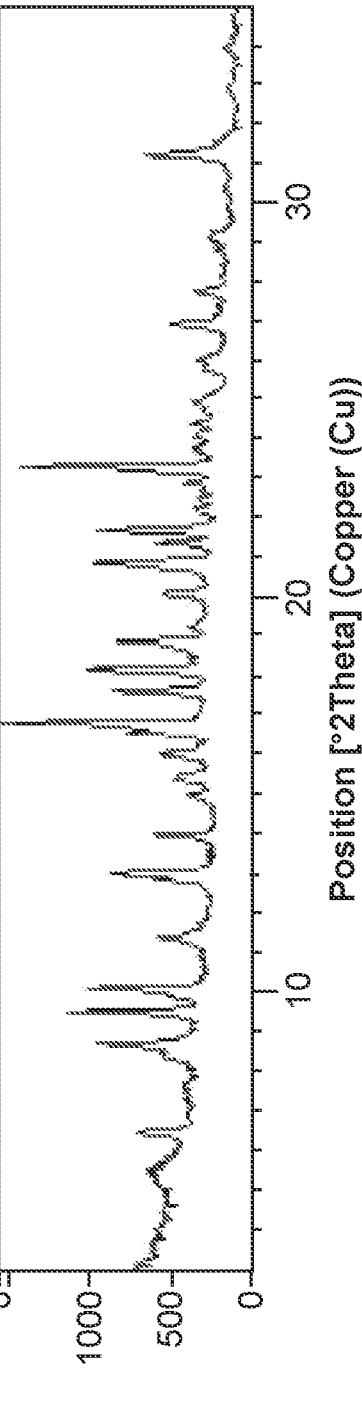
FIG. 41A
FIG. 41B
FIG. 41C
FIG. 41D

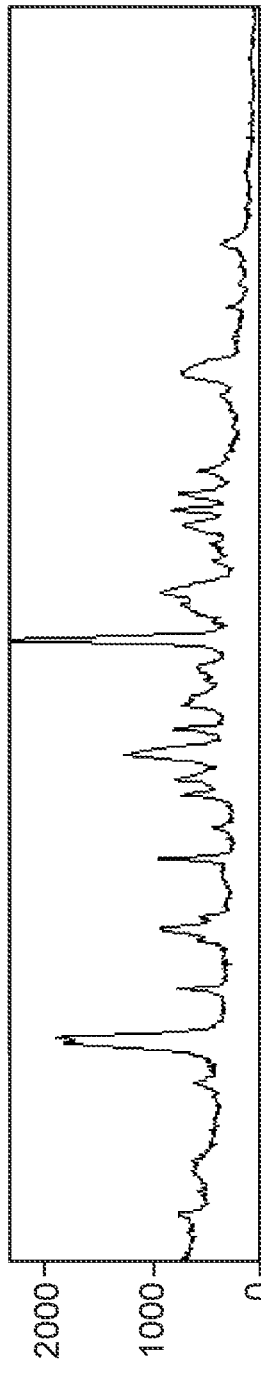
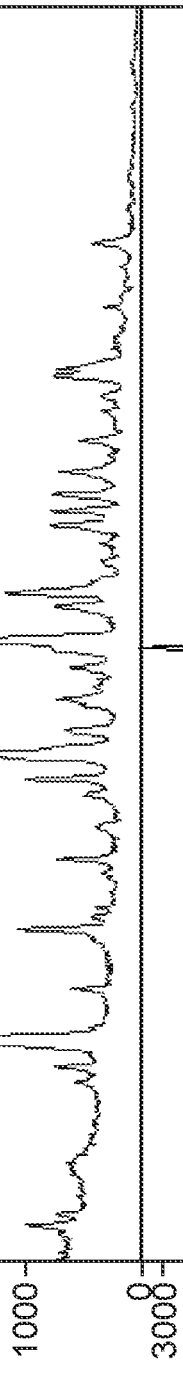
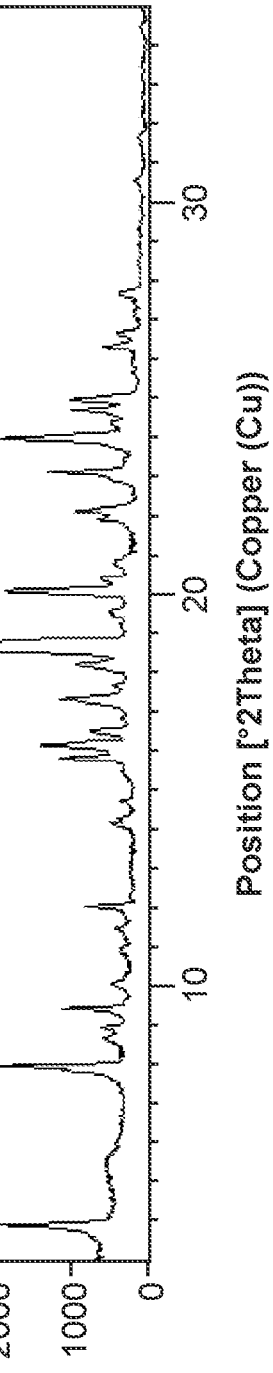
FIG. 42A
FIG. 42B
FIG. 42C
FIG. 42D

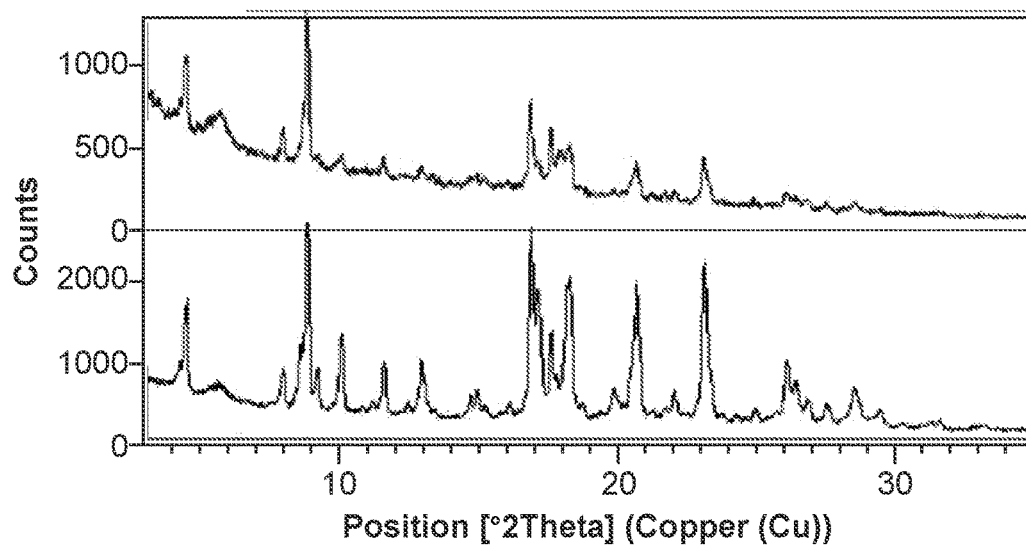
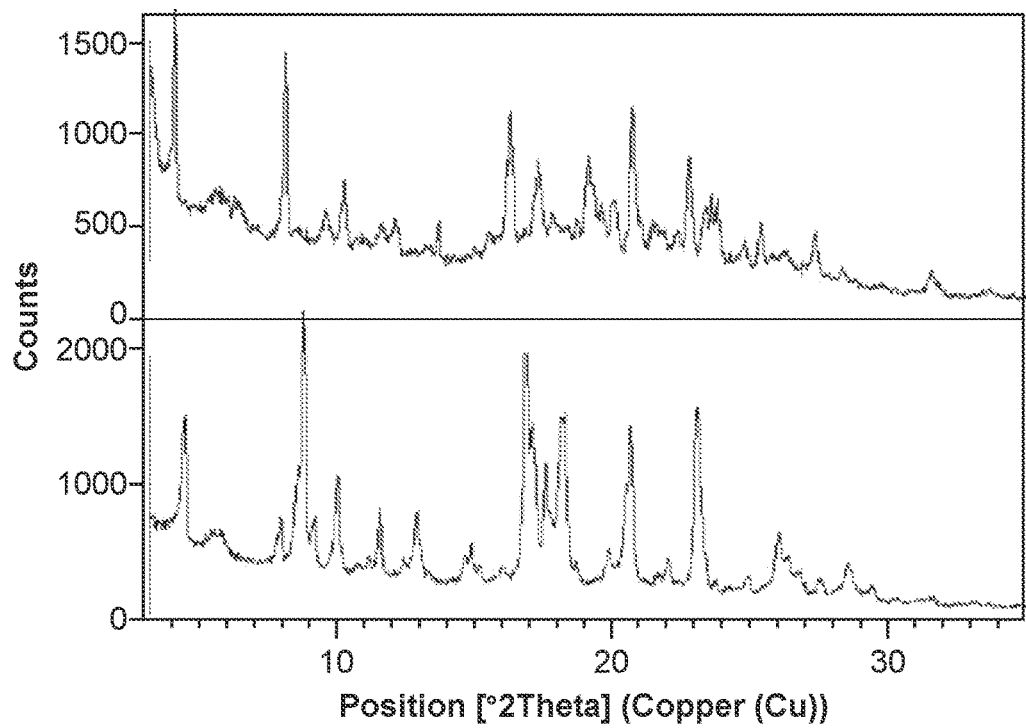

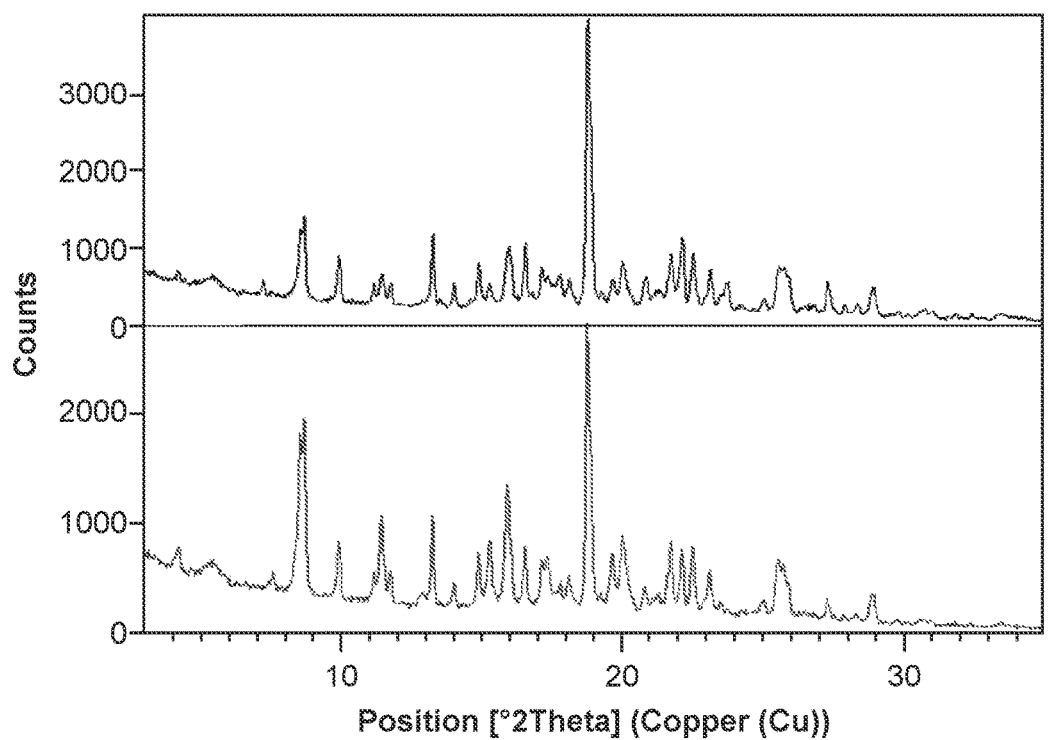

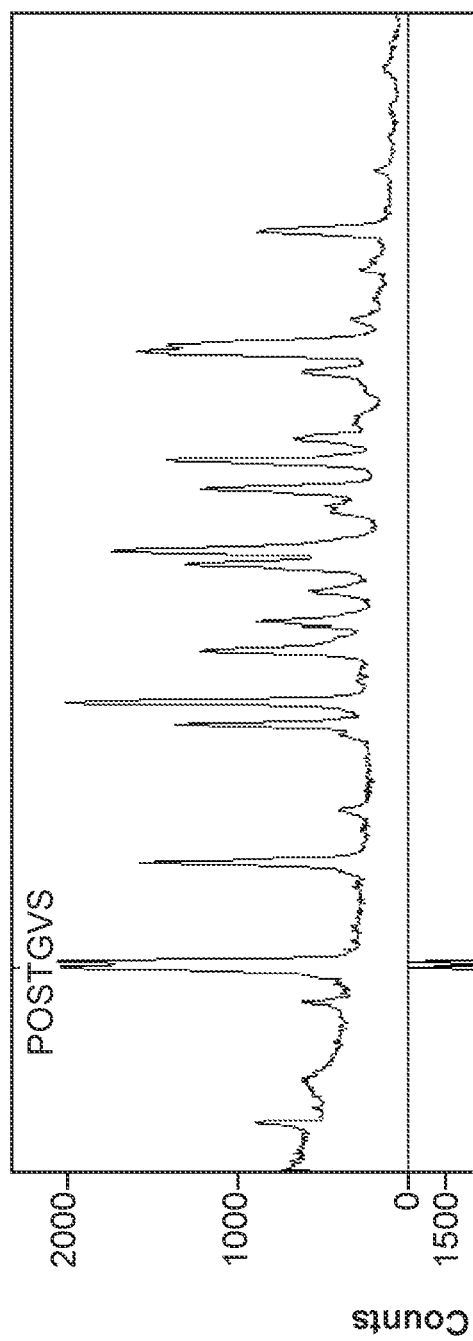
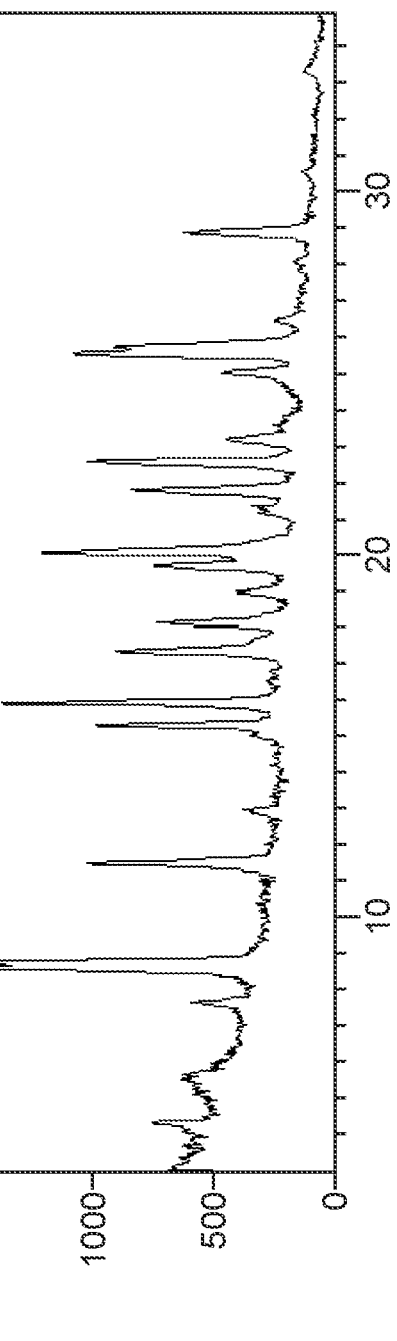
FIG. 50A
FIG. 50B

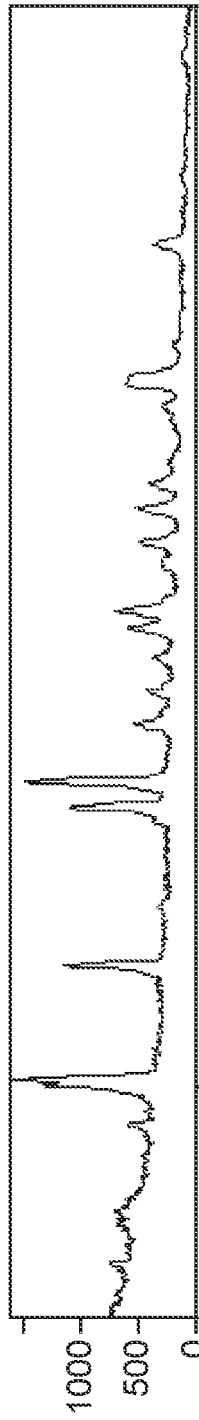
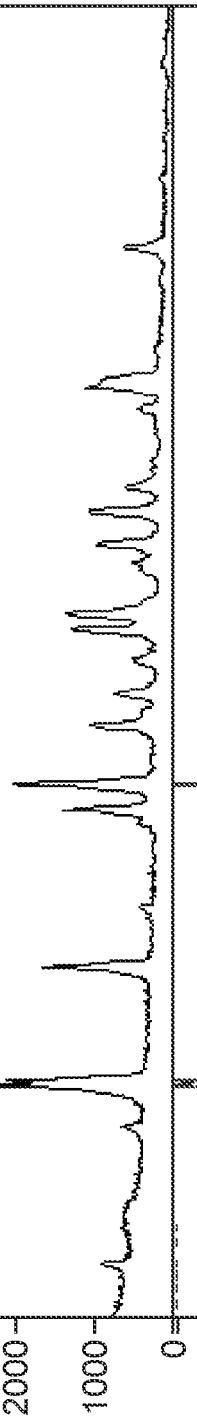
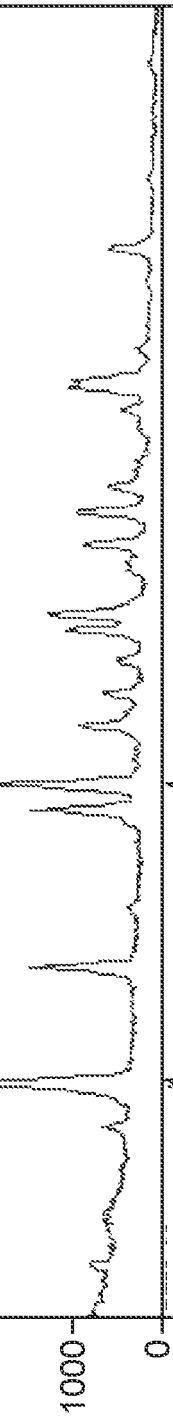
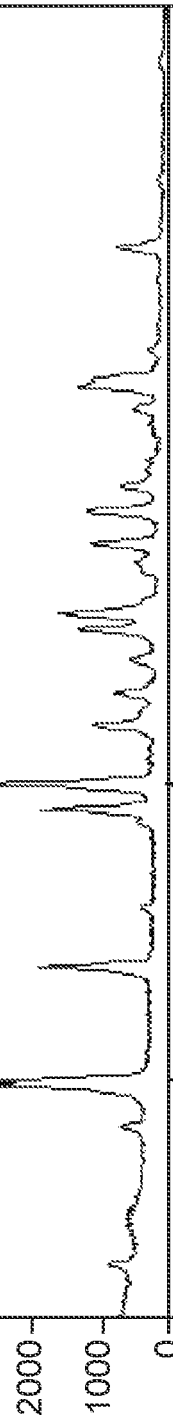
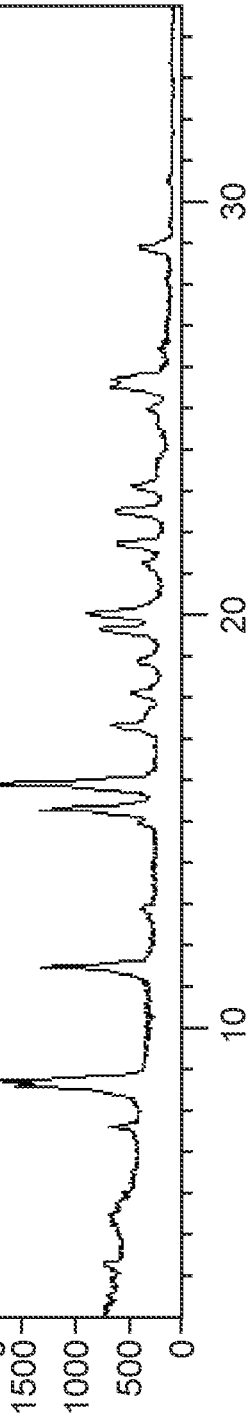
FIG. 53A
FIG. 53B
FIG. 53C
FIG. 53D
FIG. 53E

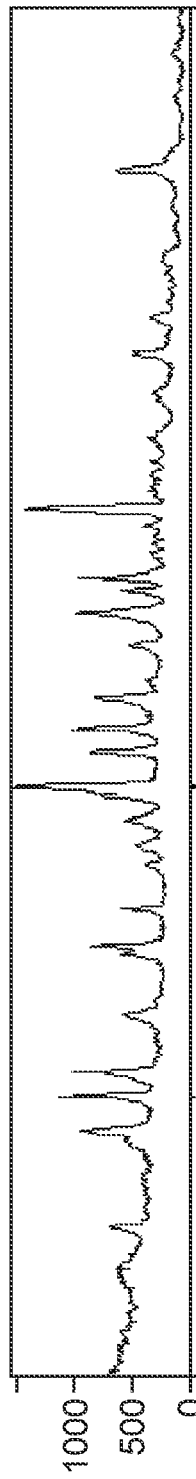
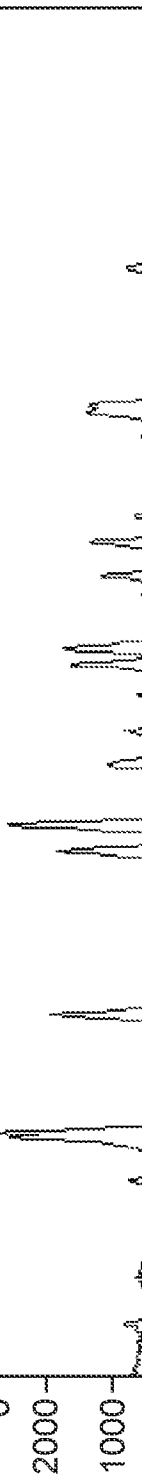
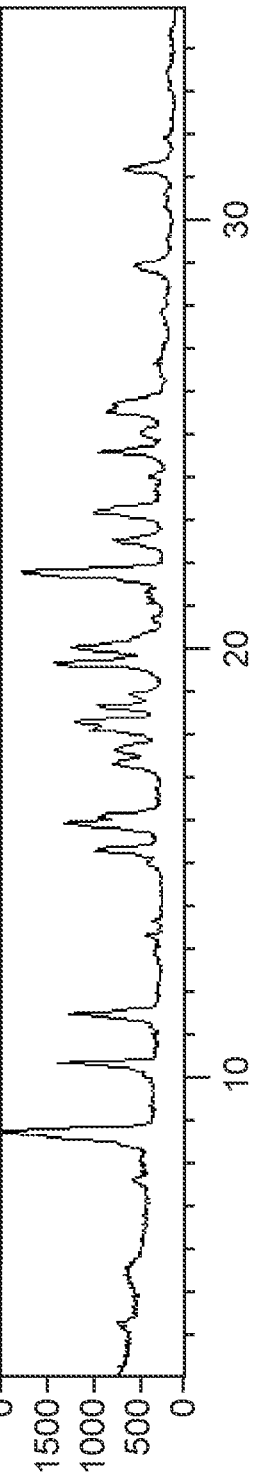
FIG. 54A
FIG. 54B
FIG. 54C
FIG. 54D
FIG. 54E

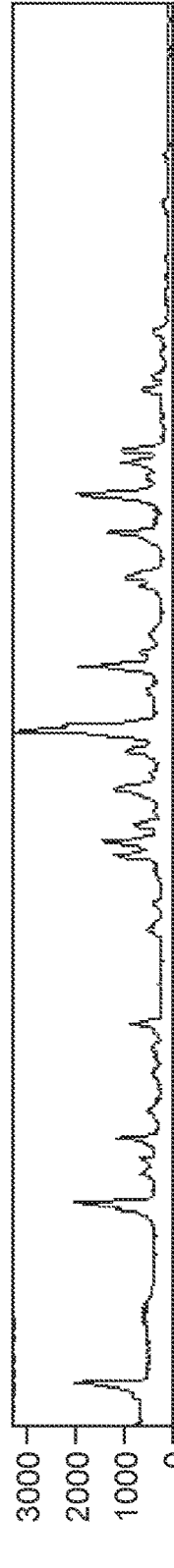
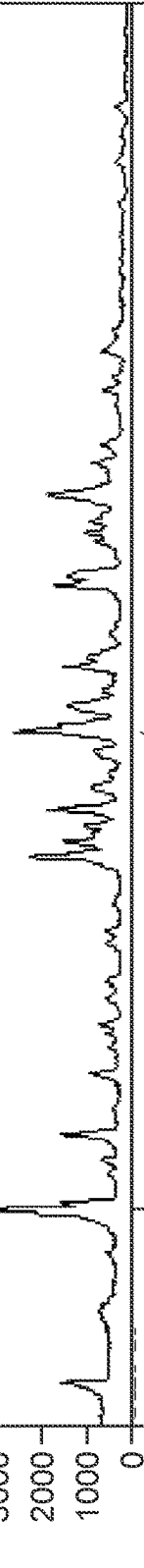
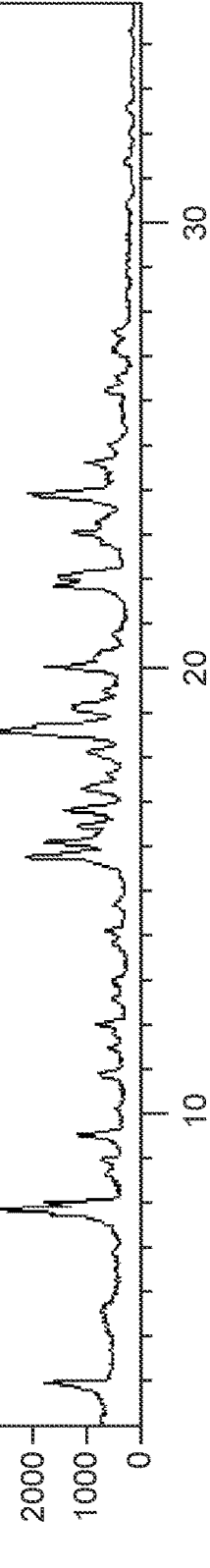
FIG. 56A
FIG. 56B
FIG. 56C
FIG. 56D
FIG. 56E

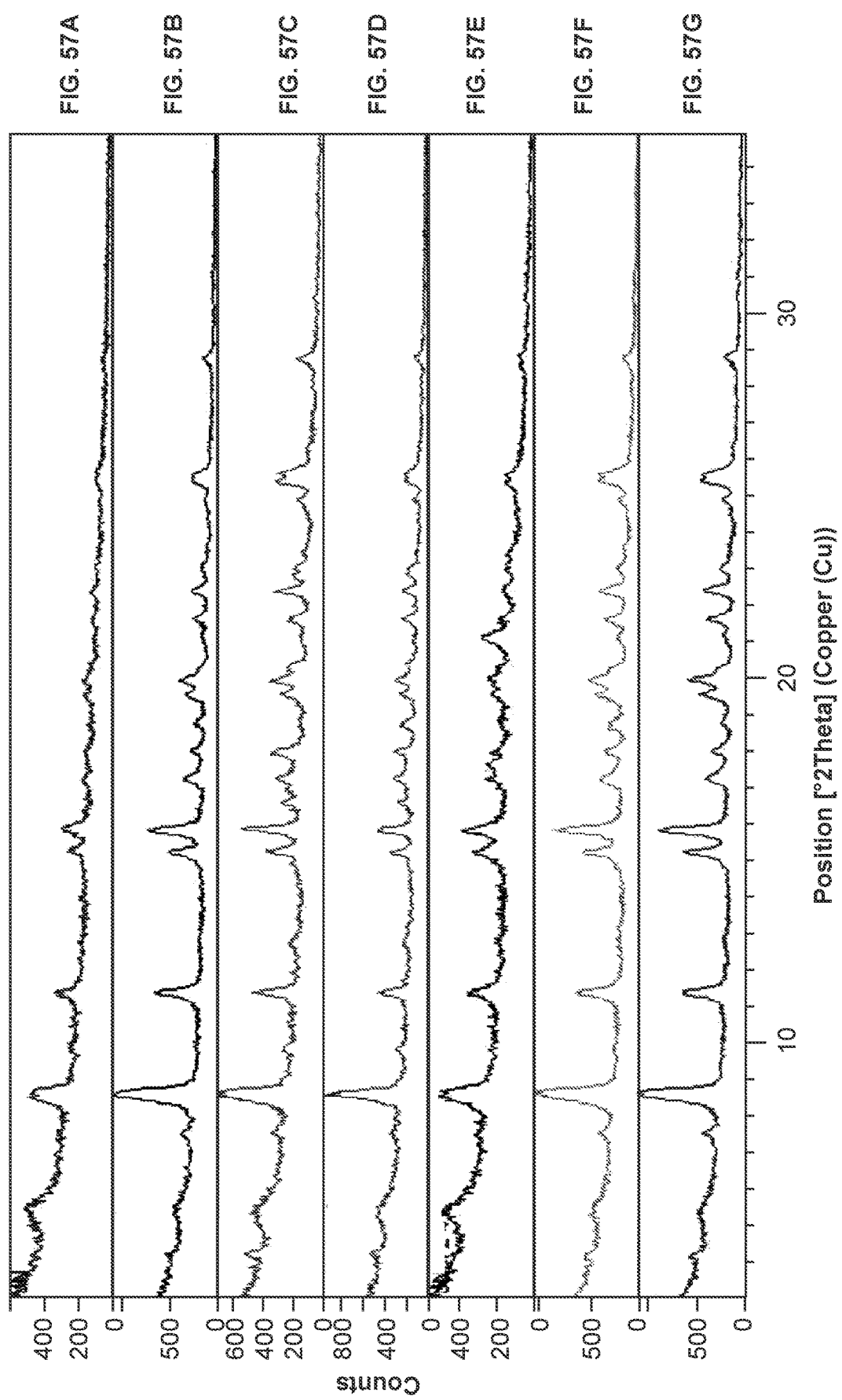

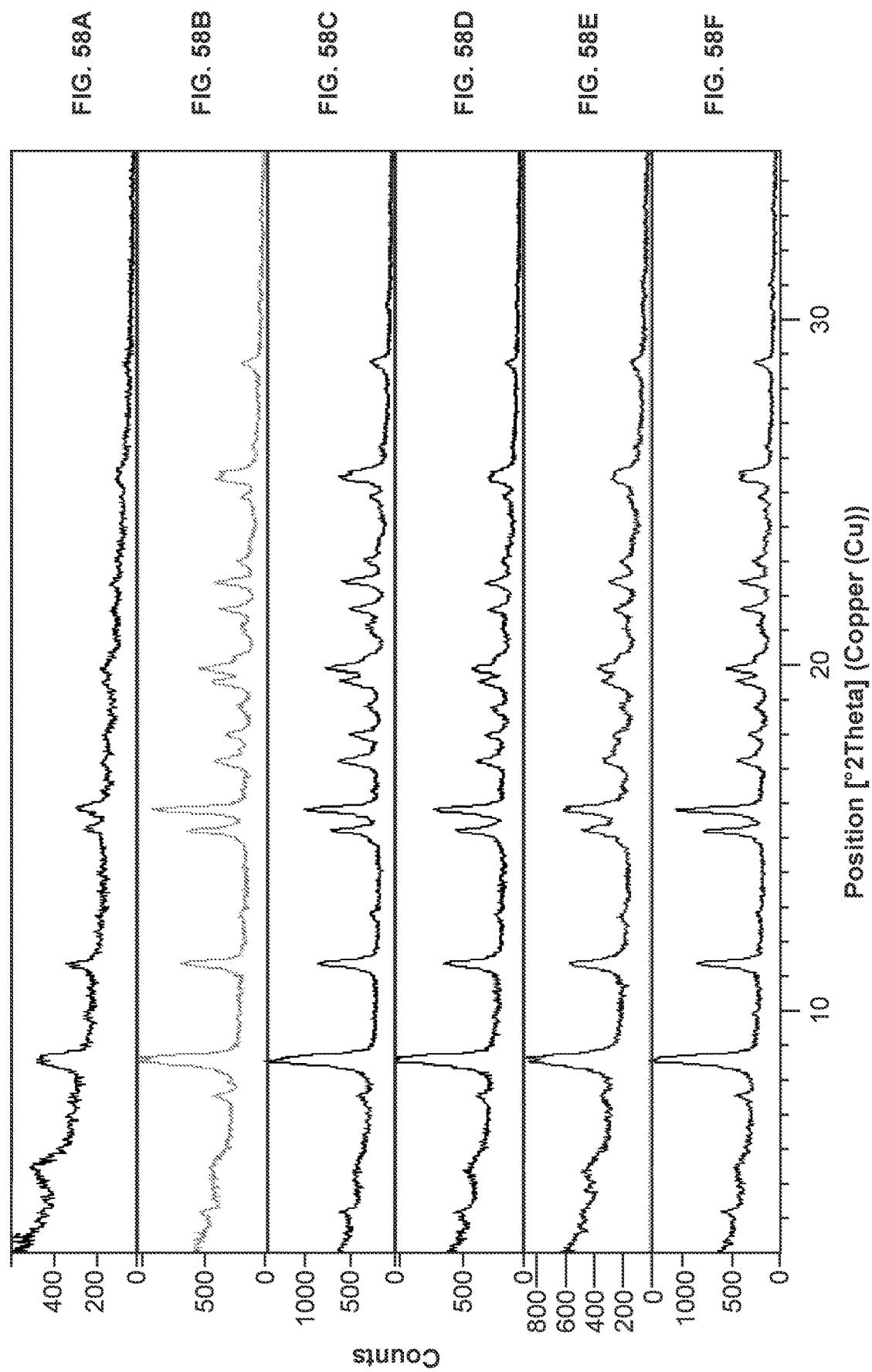

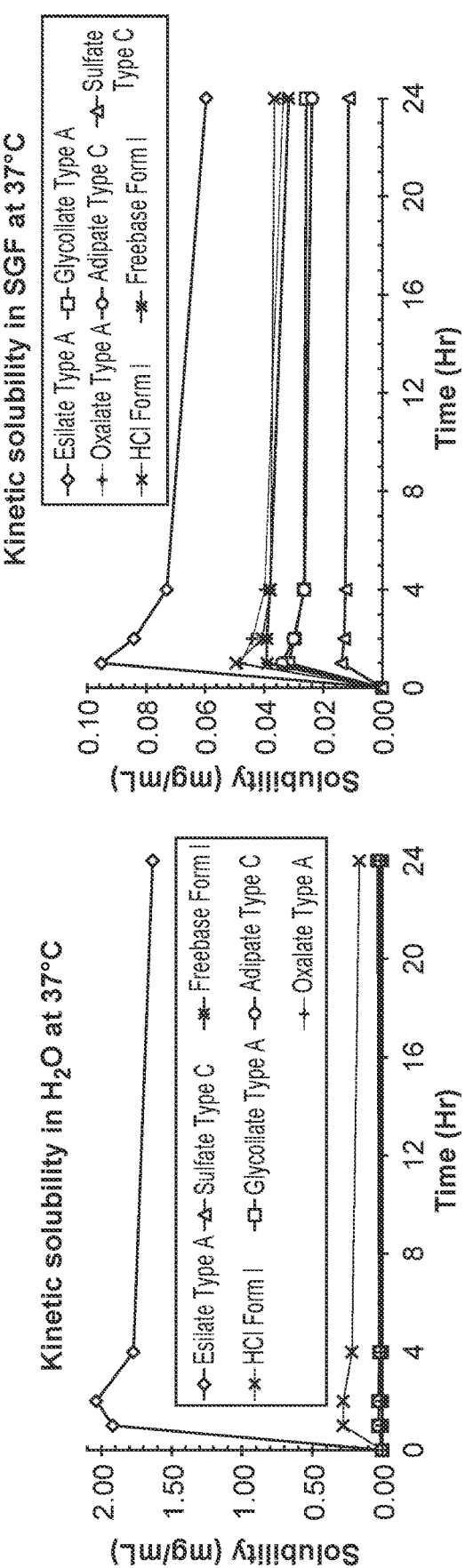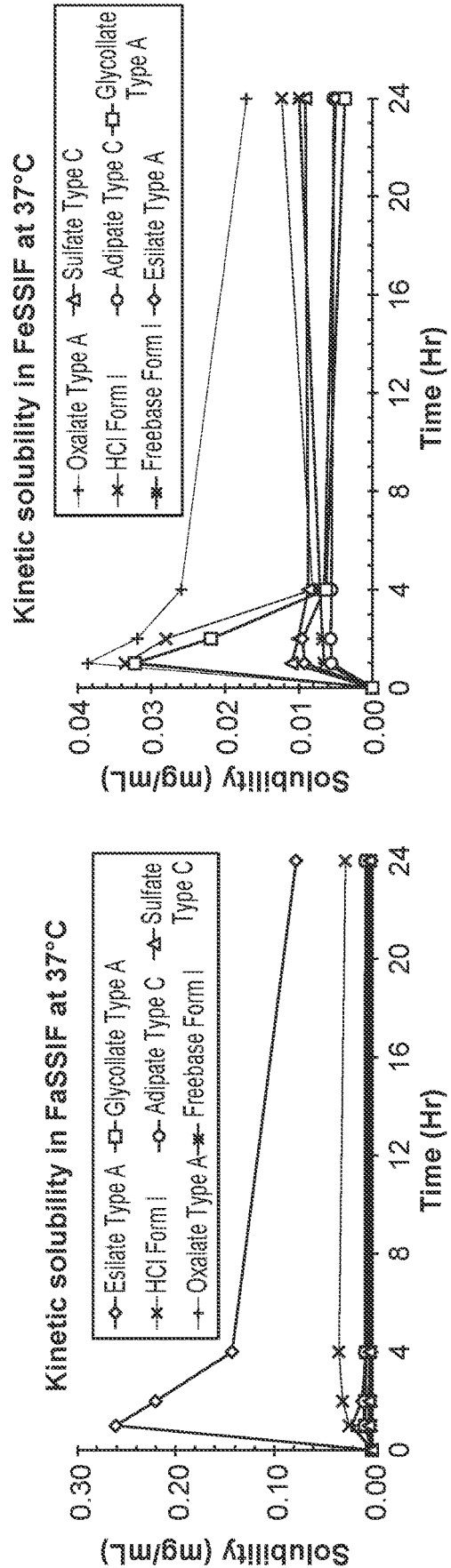
FIG. 76A
FIG. 76B
FIG. 76C
FIG. 76D

SOLID FORMS OF CERDULATINIB

CROSS-REFERENCE TO RELATED APPLICATIONS

This application is a continuation of U.S. application Ser. No. 16/402,684, filed May 3, 2019, now U.S. Pat. No. 10,865,198, which claims priority under 35 U.S.C. § 119 to U.S. Application No. 62/667,226, filed May 4, 2018, each of which is hereby incorporated by reference in its entirety.

FIELD

The present disclosure relates generally to solid forms of cerdulatinib and salts or co-crystals thereof, pharmaceutical compositions comprising the forms, therapeutic uses of the forms, and processes for making the forms.

BACKGROUND

There remains a need to develop effective treatments for subjects suffering from or at risk of protein kinase mediated diseases or conditions, such as those mediated, at least in part, by JAK and/or SYK activity. Suitable compounds, including cerdulatinib, for the treatment of such diseases and conditions are disclosed in U.S. Pat. Nos. 8,138,339 and 8,501,944, the disclosures of which are hereby incorporated by reference in their entirety.

There remains a need for solid forms of cerdulatinib or salts or co-crystals thereof that are efficacious and exhibit improved stability and solubility for the treatment of diseases mediated, at least in part, by protein kinases.

SUMMARY

Cerdulatinib is known to inhibit or modulate SYK and JAK activity and is described, for example, in U.S. Pat. Nos. 8,138,339 and 8,501,944, which are hereby incorporated by reference in their entirety. Cerdulatinib, designated herein as Compound I or Compound I (free base), has the formula:

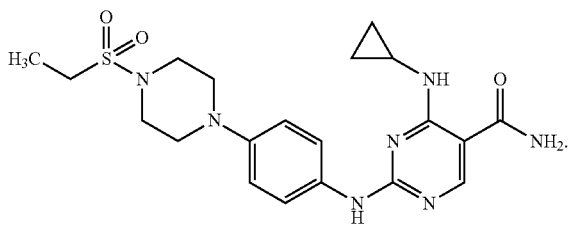

I

The present disclosure provides solid forms of Compound I and salts or co-crystals thereof. Also described herein are processes for making the forms of Compound I, pharmaceutical compositions comprising the solid forms of Compound I and salts or co-crystals thereof, and methods for using such forms and pharmaceutical compositions in the treatment of diseases mediated, at least in part, by SYK and/or JAK kinase activity.

Accordingly, in some embodiments, provided is a crystalline salt comprising Compound I:

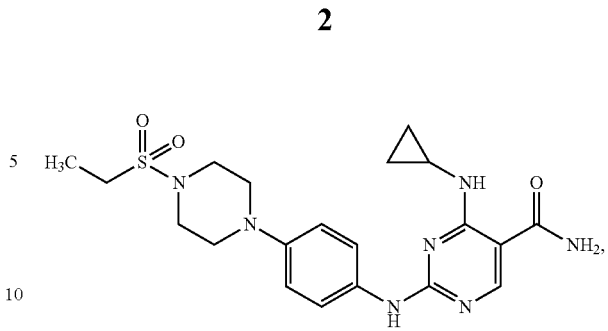

I and an acid selected from the group consisting of: hydrochloric acid, naphthalene-1,5-disulfonic acid, sulfuric acid, ethane-1,2-disulfonic acid, ethane sulfonic acid, p-tolyl sulfonic acid, and methane sulfonic acid. In some embodiments the acid is selected from hydrochloric acid, naphthalene-1,5-disulfonic acid, sulfuric acid, ethane-1,2-disulfonic acid, ethane sulfonic acid, p-tolyl sulfonic acid, methane sulfonic acid, glycolic acid, adipic acid, oxalic acid, phosphoric acid, maleic acid, tartaric acid, fumaric acid, citric acid, malic acid, gluconic acid, succinic acid, malonic acid, gentisic acid, benzenesulfonic acid, 2-hydroxyethanesulfonic acid, naphthalene-2-sulfonic acid, 4-chlorobenzenesulfonic acid, and camphorsulfonic acid. In some embodiments, the molar ratio of Compound I to the acid present may vary. For example, the molar ratio of Compound I to the acid may be 1, 2, or 3. The molar ratio may be a non-integer value, for example, 1:2, 2:1, 2:3, or 3:2.

In some embodiments, provided is a crystalline mono-hydrochloride salt of Compound I. In some embodiments, the crystalline mono-hydrochloride salt of Compound I is characterized by an X-ray powder diffractogram comprising peaks at 8.7, 15.9, and 20.0 °2θ, each ±0.2 °2θ, as determined on a diffractometer using Cu-Kα radiation (Compound I HCl Form I). In some embodiments, the X-ray powder diffractogram further comprises one or more peaks at 11.5, 22.5, and 25.5 °2θ, each ±0.2 °2θ. In some embodiments, the crystalline mono-hydrochloride salt of Compound I is further characterized by a differential scanning calorimetry curve comprising an endotherm with onset at about 288° C.

In some embodiments, provided is a pharmaceutical composition comprising a solid form, such as a crystalline salt, described herein and one or more pharmaceutically acceptable carriers. In some embodiments, the crystalline salt comprises at least about 50% w/w of Compound I HCl Form I.

In some embodiments, provided is a pharmaceutical composition comprising a solid form, such as a crystalline salt, described herein and another therapeutic agent.

In some embodiments, provided is a method for treating a disease or condition mediated, at least in part, by a protein kinase in a patient in need thereof, comprising administering to the patient a therapeutically effective amount of a solid form, such as a crystalline salt, or a composition described herein. In certain embodiments, the protein kinase is JAK or any mutation thereof. In certain embodiments, the protein kinase is SYK or any mutation thereof. In certain embodiments, the disease or condition is chronic lymphocytic leukemia (CLL), small lymphocytic lymphoma (SLL), follicular lymphoma (FL), transformed follicular lymphoma (tFL), diffuse large B-cell lymphoma (DLBCL), mantle cell lymphoma (MCL), B-cell non-Hodgkin's lymphoma (NHL), peripheral T-cell lymphoma (PTCL), cutaneous T-cell lymphoma (CTCL), marginal zone lymphoma, mucosa-associated lymphoid tissue (MALT), or Waldenstrom macroglobulinemia (WM).

BRIEF DESCRIPTION OF THE DRAWINGS

FIG. 30A, FIG. 30B, FIG. 30C, and FIG. 30D are X-ray powder diffractograms of esylate salts/co-crystals of Compound I prepared from different solvents and/or during different scale up processes. FIG. 30A and FIG. 30B respectively provide X-ray powder diffractograms of Compound I Material A prepared from toluene (FIG. 30A), and Compound I Material B prepared from IPA (FIG. 30B) during a scale up process (referred to herein, and particularly in the Examples, as the "second scale up process"). For comparison, FIG. 30C and FIG. 30D respectively provide X-ray powder diffractograms of Compound I esylate Form I prepared from IPA (FIG. 30C) and toluene (FIG. 30D) during a different scale up process (referred to herein, and particularly in the Examples, as the "first scale up process").

FIG. 32A, FIG. 32B, FIG. 32C, and FIG. 32D are X-ray powder diffractograms of sulfate salts/co-crystals of Compound I prepared from different solvents and/or during different scale up processes. FIG. 32A and FIG. 32B respectively provide X-ray powder diffractograms of Compound I sulfate having a form similar to Form II thereof and which was prepared from water during the second scale up process (FIG. 32A), and Compound I sulfate having a form similar to Form I and which was prepared from IPA during the second scale up process (FIG. 32B). For comparison, FIG. 32C and FIG. 32D respectively provide X-ray powder diffractograms of Compound I sulfate Form II prepared from water (FIG. 32C), and Compound I sulfate Form I prepared form IPA during the first scale up process (FIG. 32D).

FIG. 35A and FIG. 35B respectively provide X-ray powder diffractograms of Compound I HCl Form I prepared from aqueous HCl (about 2 equivalents) and ethanol during the second scale up process (FIG. 35A), and Compound I Form II prepared from dry HCl (about 1 equivalent) and acetonitrile during the second scale up process (FIG. 35B). For comparison, FIG. 35C and FIG. 35D respectively provide X-ray powder diffractograms of Compound I HCl Form I prepared from dry HCl (about 1 equivalent) and water (FIG. 35C), and from dry HCl (about 1 equivalent) and acetonitrile during the first scale up process (FIG. 35D).

FIG. 38A and FIG. 38B respectively provide X-ray powder diffractograms of Compound I mesylate Material A prepared from ethanol during the second scale up process (FIG. 38A), and Compound I mesylate having a form similar to Form III thereof and which was prepared from EtOAc during the second scale up process (FIG. 38B). For comparison, FIG. 38C and FIG. 38D respectively provide X-ray powder diffractograms of Compound I mesylate Form II prepared from water (FIG. 38C), and Compound I mesylate Form III prepared from ethanol during the first scale up process (FIG. 38D).

FIG. 41A and FIG. 41B are X-ray powder diffractograms of a Compound I HCl Form I as measured after (FIG. 41A) and prior to (FIG. 41B) a solubility analysis thereof, respectively. FIG. 41C and FIG. 41D are X-ray powder diffractograms of Compound I HCl Form II as measured after (FIG. 41C) and prior to (FIG. 41D) a solubility analysis thereof, respectively.

FIG. 42A and FIG. 42C are X-ray powder diffractograms of Compound I mesylate Material A as measured after (FIG. 42A) and prior to (FIG. 42C) a solubility analysis thereof, respectively. FIG. 42B and FIG. 42D are X-ray powder diffractograms of the Compound I mesylate having a form similar to Form III thereof as measured after (FIG. 42B) and prior to (FIG. 42D) a solubility analysis thereof, respectively.

FIG. 43A and FIG. 43B are X-ray powder diffractograms of Compound I sulfate Form II as measured after (FIG. 43A) and prior to (FIG. 43B) a solubility analysis thereof, respectively. FIG. 43C and FIG. 43D are X-ray powder diffractograms of Compound I sulfate Form I as measured prior to (FIG. 43C) and after (FIG. 43D) a solubility analysis thereof, respectively.

FIG. 44A and FIG. 44B are X-ray powder diffractograms of Compound I esylate Material A (FIG. 44A) and Compound I esylate Material B (FIG. 44B), respectively, as measured after a solubility analysis, respectively.

FIG. 50A and FIG. 50B are X-ray powder diffractograms of Compound I HCl Form I as measured after (FIG. 50A) and prior to (FIG. 50B) gravimetric vapor sorption (GVS) analysis thereof, respectively.

FIG. 53A is an X-ray powder diffractogram of Compound I HCl Form I starting material used in various slurry maturations. FIG. 53B, FIG. 53C, FIG. 53D, and FIG. 53E are the X-ray powder diffractograms of the resulting crystalline materials isolated from the slurries comprising acetonitrile (FIG. 53B), EtOAc (FIG. 53C), ethanol (FIG. 53D), and IPA (FIG. 53E).

FIG. 54A is an X-ray powder diffractogram of Compound I HCl Form II starting material used in various slurry maturations. FIG. 54B, FIG. 54C, FIG. 54D, and FIG. 54E are X-ray powder diffractograms of the resulting crystalline materials isolated from the slurries comprising acetonitrile (FIG. 54B), EtOAc (FIG. 54C), ethanol (FIG. 54D), and IPA (FIG. 54E).

FIG. 56A is an X-ray powder diffractogram of Compound I mesylate Form III starting material used in various slurry maturations. FIG. 56B, FIG. 56C, FIG. 56D, and FIG. 56E are X-ray powder diffractograms of the resulting crystalline materials isolated from the slurries comprising acetonitrile (FIG. 56B), EtOAc (FIG. 56C), ethanol (FIG. 56D), and IPA (FIG. 56E).

FIG. 57A, FIG. 57B, FIG. 57C, FIG. 57D, FIG. 57E, FIG. 57F, and FIG. 57G are X-ray powder diffractograms of the Compound I HCl amorphous starting material (FIG. 57A), and the resulting Compound I HCl amorphous samples formed from slurries with cumene (FIG. 57B), n-BuOAc (FIG. 57C), dioxane (FIG. 57D), water (FIG. 57E), IPA (FIG. 57F), and acetonitrile (FIG. 57G).

FIG. 58A, FIG. 58B, FIG. 58C, FIG. 58D, FIG. 58E, and FIG. 58F are X-ray powder diffractograms of the Compound I HCl amorphous starting material (FIG. 58A), and the resulting Compound I HCl amorphous samples formed from slurries with MEK (FIG. 58B), EtOH (FIG. 58C), EtOAc (FIG. 58D), TBME (FIG. 58E), and DCM (FIG. 58F).

FIG. 63A is an X-ray powder diffractogram of Compound I HCl Type B; FIG. 63B is a differential scanning calorimetry (DSC) curve (bottom) and thermogravimetric analysis (TGA) thermogram (top) for Compound I HCl Type B.

FIG. 64A is X-ray powder diffractograms of solid forms observed during temperature cycling of Compound I free base Form I; FIG. 64B is a differential scanning calorimetry (DSC) curve for three temperature cycles for Compound I free base Form I.

FIG. 65A is X-ray powder diffractograms of solid forms observed during temperature cycling of Compound I free base Form II; FIG. 65B is a differential scanning calorimetry (DSC) curve (bottom) and thermogravimetric analysis (TGA) thermogram (top) for Compound I free base Form II.

FIG. 76A, FIG. 76B, FIG. 76C and FIG. 76D are charts of kinetic solubility for Compound I esylate Type A (diamond symbols), Compound I oxalate Type A (plus symbols), Compound I HCl Form I ("X" symbols), Compound I glycollate Type A (square symbols), Compound I adipate Type C (circle symbols), Compound I sulfate Type C (triangle symbols), and Compound I Form I (asterisk symbols) in water (FIG. 76A), simulated gastric fluid ("SGF") (FIG. 76B), fasted state simulated gastric fluid ("FaSSIF") (FIG. 76C), and fed state simulated gastric fluid ("FeSSIF") (FIG. 76D).

DETAILED DESCRIPTION

Figure 1:
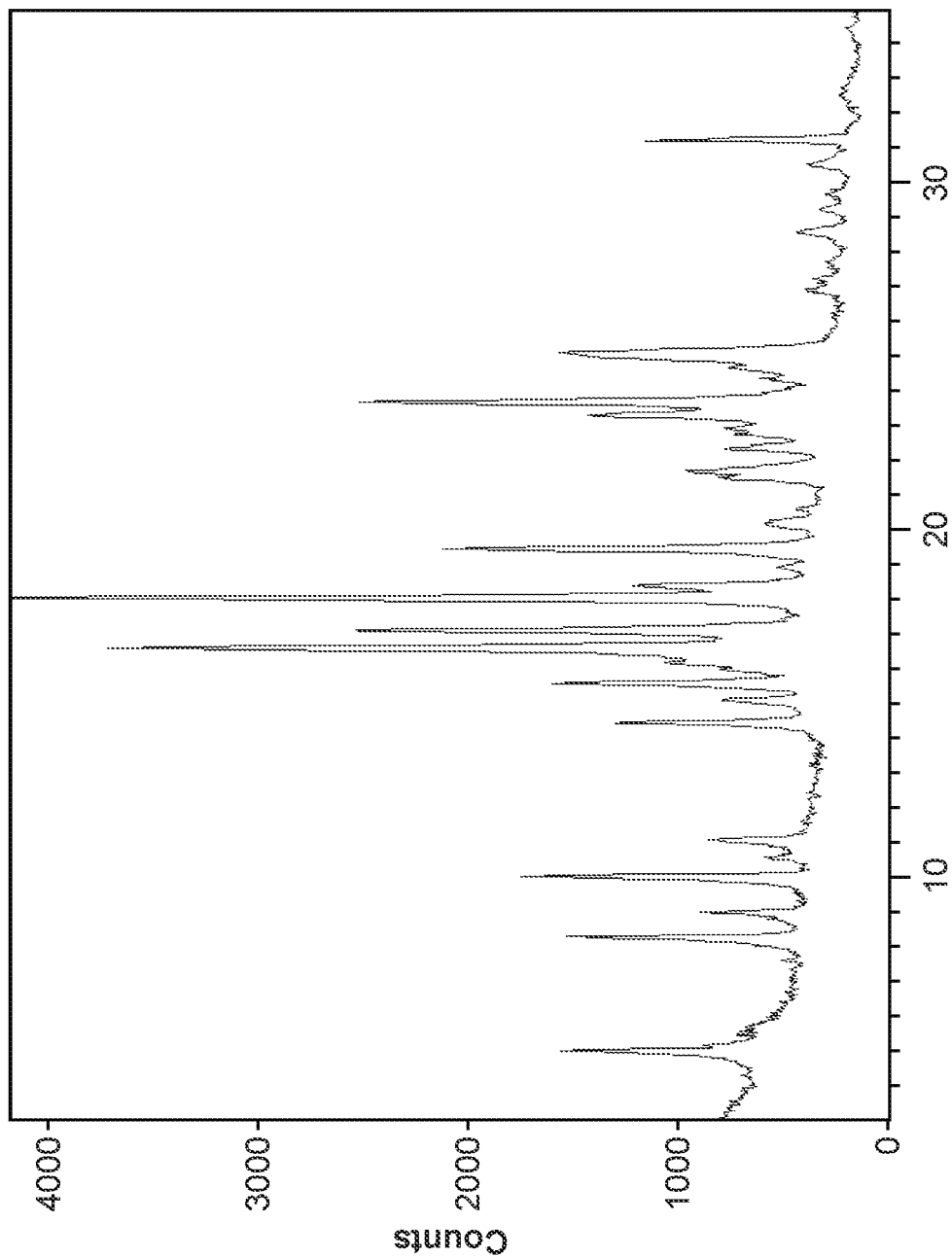
FIG. 1 is an X-ray powder diffractogram (XRPD) of Compound I Form I.

Cerdulatinib (4-(cyclopropylamino)-2-((4-(4-(ethylsulfonyl)piperazin-1-yl)phenyl)amino)pyrimidine-5-carboxamide or 4-(cyclopropylamino)-2-({4-[4-(ethanesulfonyl)piperazin-1-yl]phenyl}amino)pyrimidine-5-carboxamide), designated herein as Compound I or Compound I (free base), has the following formula:

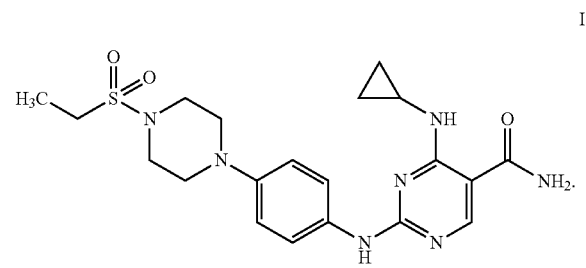 [SMILES: CCS(=O)(=O)N1CCN(c2ccc(Nc3ncc(C(N)=O)c(NC4CC4)n3)cc2)CC1]

Compound I is a small molecule, ATP-competitive, reversible inhibitor of both SYK and JAK family members. The synthesis and method of use thereof is described in U.S. Pat. No. 8,138,339, which is herein incorporated by reference in its entirety.

The present disclosure relates to various crystalline forms of Compound I, and processes for making such crystalline forms. For instance, forms of Compound I described herein include "Compound I Form I," "Compound I Form II," "Compound I free base Type C," "Compound I free base Type D," and "Compound I free base Type E."

Crystalline forms of salts or co-crystals of Compound I are also described herein. In some embodiments, salts or co-crystals of Compound I may have the following formula:

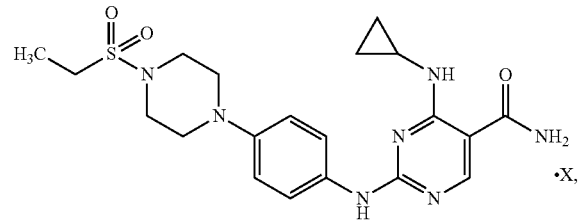 [SMILES: CCS(=O)(=O)N1CCN(c2ccc(Nc3ncc(C(N)=O)c(NC4CC4)n3)cc2)CC1]

where X may be hydrochloride (mono or bis), esylate, edisylate, mesylate (mono or bis), naphthalene disulfonate, sulfate, or tosylate. In some embodiments, X may be hydrochloride (mono or bis), esylate, edisylate, mesylate (mono or bis), naphthalene disulfonate, sulfate, tosylate, glycollate, adipate, oxalate, phosphate, maleate, tartrate, fumarate, citrate, malate, gluconate, succinate, malonate, gentisate, benzenesulfonate, 2-hydroxyethanesulfonate, naphthalene-2-sulfonate, 4-chlorobenzenesulfonate, and camphorsulfonate. The following exemplary forms of salts or co-crystals of Compound I described herein include: "Compound I HCl Form I," "Compound I HCl Form II," "Compound I bis-HCl Form I," "Compound I HCl amorphous," "Compound I esylate Form I," "Compound I edisylate Form I," Compound I edisylate Form II," "Compound I edisylate Form III," "Compound I edisylate Form IV," "Compound I mesylate Form I," "Compound I mesylate Form II," "Compound I mesylate Form III," "Compound I bis-mesylate Form I," "Compound I naphthalene disulfonate Form I," "Compound I naphthalene disulfonate Form II," "Compound I naphthalene disulfonate Form III," "Compound I naphthalene disulfonate Form IV," "Compound I sulfate Form I," "Compound I sulfate Form II," "Compound I sulfate Form III," Compound I tosylate Form I," "Compound I tosylate Form II," "Compound I tosylate Form III," Compound I tosylate Form IV," "Compound I tosylate Form V," "Compound I tosylate Form VI," "Compound I tosylate Form VII," "Compound I HCl Type B," "Compound I sulfate Type A," "Compound I sulfate Type B," "Compound I sulfate Type C," "Compound I glycollate Type A," "Compound I adipate Type A," "Compound I adipate Type B," "Compound I oxalate Type A," "Compound I esylate Type A," "Compound I phosphate Type A," "Compound I maleate Type A," "Compound I maleate Type B," "Compound I L-tartrate Type A," "Compound I fumarate Type A," "Compound I citrate Type A," "Compound I citrate Type B," "Compound I citrate Type C," "Compound I L-malate Type A," "Compound I L-malate Type B," "Compound I gluconate Type A," "Compound I succinate Type A," "Compound I tosylate Type A," "Compound I tosylate Type B," "Compound I mesylate Type A," "Compound I mesylate Type B," "Compound I malonate Type A," "Compound I gentisate Type A," "Compound I edisylate Type A," "Compound I edisylate Type B," "Compound I edisylate Type C," "Compound I edisylate Type D," "Compound I besylate Type A," "Compound I besylate Type B," "Compound I tosylate Type C," "Compound I tosylate Type D," "Compound I isethionate Type A," "Compound I naphthalene disulfonate Type A," "Compound I naphthalenesulfonate Type A," "Compound I naphthalenesulfonate Type B," "Compound I naphthalenesulfonate Type C," "Compound I chlorobenzenesulfate Type A," "Compound I chlorobenzenesulfate Type B," "Compound I camphorsulfonate Type A," "Compound I camphorsulfonate Type B," and "Compound I camphorsulfonate Type C."

Other forms of Compound I are further described herein, such as amorphous forms of hydrochloride salts of Compound I.

1. Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I and salts/co-crystals are provided herein. In one embodiment, reference to a form of Compound I means that at least 50% to 99% (e.g., at least 50%, at least 55%, at least 60%, at least 65%, at least 70%, at least 75%, at least 80%, at least 85%, at least 90%, at least 95%, or at least 99%) of Compound I or a salt or co-crystal thereof present in a composition is in the designated form. For instance, in one embodiment, reference to Compound I HCl Form I means that at least 50%, at least 55%, at least 60%, at least 65%, at least 70%, at least 75%, at least 80%, at least 85%, at least 90%, at least 95%, or at least 99% of the hydrochloride salt of Compound I present in a composition is in Form I.

The term "solid form" refers to a type of solid-state material that includes amorphous as well as crystalline forms.

The term "crystalline form" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point). The term "crystalline form" encompasses co-crystals as defined herein. A distinctive crystalline form may be designated by the term "Form," Material," or "Type," which terms are used interchangeably.

The term "substantially crystalline" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in crystalline form. "Substantially crystalline" can also refer to material which has no more than about 20%, or no more than about 10%, or no more than about 5%, or no more than about 2% in the amorphous form. Likewise, the term "substantially" when qualifying any form of a compound described herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound is present in the designated form.

The term "amorphous form" refers to a state in which the material lacks long range order at the molecular level and, depending upon temperature, may exhibit the physical properties of a solid or a liquid. Typically such materials do not give distinctive X-ray diffraction patterns.

The term "co-crystal" refers to a molecular complex of a compound and one or more co-crystal formers connected through non-covalent interactions. In some embodiments, the co-crystals disclosed herein may include a non-ionized form of Compound I (e.g., Compound I free base) and one or more non-ionized co-crystal formers, where non-ionized Compound I and the co-crystal former(s) are connected through non-covalent interactions. In some embodiments, co-crystals disclosed herein may include an ionized form of Compound I (e.g., a salt of Compound I) and one or more non-ionized co-crystal formers, where ionized Compound I and the co-crystal former(s) are connected through non-covalent interactions. Co-crystals may additionally be present in anhydrous, solvated or hydrated forms. In some embodiments, there is no hydrogen transfer between the compound and the co-crystal former.

The term "co-crystal former" or "co-former" refers to one or more pharmaceutically acceptable compounds that can be in association with a compound, such as Compound I, to form a co-crystal.

The term "solvate" refers to a complex formed by combining Compound I, or a salt or co-crystal thereof, and a solvent. As used herein, the term "solvate" includes a hydrate (i.e., a solvate when the solvent is water).

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially desolvated wherein solvent molecules are present in stoichiometric or non-stoichiometric amounts.

The term "pharmaceutical composition" refers to a pharmaceutical preparation suitable for administration to an intended subject for therapeutic purposes that comprises one or more of the solid forms of Compound I or a salt/co-crystal thereof as described herein. The composition may include at least one pharmaceutically acceptable component to provide an improved formulation of the compound, such as a suitable carrier or excipient.

Any formula or structure given herein, including Compound I, is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}$H (deuterium, D), $^{3}$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which isotopes such as $^{3}$H, $^{13}$C and $^{14}$C are incorporated, may be prepared. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen" the position is understood to have hydrogen at its natural abundance isotopic composition. Accordingly, in the compounds of this disclosure any atom specifically designated as a deuterium (D) is meant to represent deuterium.

The term "treatment" or "treating" refers to an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

The term "prevention" or "preventing" refers to any treatment of a disease or condition that causes the clinical symptoms of the disease or condition not to develop. Compounds as described herein may, in some embodiments, be administered to a subject (including a human) who is at risk or has a family history of the disease or condition.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g., agonist, activator), or decreasing (e.g., antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

The term "protein kinase mediated disease or condition," refers to a disease or condition in which the biological function of a protein kinase, including any mutations thereof, affects the development, course, and/or symptoms of the disease or condition, and/or in which modulation of the protein kinase alters the development, course, and/or symptoms of the disease or condition. The protein kinase mediated disease or condition includes a disease or condition for which inhibition provides a therapeutic benefit, e.g. wherein treatment with protein kinase inhibitor(s), including one or more solid, crystalline or polymorphs of Compound I or as described herein, provides a therapeutic benefit to the subject suffering from or at risk of the disease or condition.

The term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

The term "therapeutically effective amount" or "effective amount" of a compound described herein means an amount sufficient to effect treatment when administered to a subject, to provide a therapeutic benefit such as amelioration of symptoms or slowing of disease progression. The therapeutically effective amount may vary depending on the subject, and disease or condition being treated, the weight and age of the subject, the severity of the disease or condition, and the manner of administering, which can readily be determined by one or ordinary skill in the art.

The phrase "substantially as shown in" a figure as applied to X-ray powder diffractogram is meant to include a variation of ±0.2 °2θ for each peak, as applied to DSC thermograms is meant to include a variation of ±3° Celsius, as applied to DSC thermograms is meant to include a variation of ±3° Celsius, and as applied to thermogravimetric analysis (TGA) is meant to include a variation of ±2% in weight loss or gain.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In addition, abbreviations as used herein have respective meanings as follows:

| | |
|---|---|
| ACN (MeCN) | acetonitrile |
| DCM | dichloromethane |
| besylate | benzenesulfonate |
| BuOH | butanol |
| BuOAc | butyl acetate |
| CPME | cyclopentyl methyl ether |
| DMAc | dimethylacetamide |
| DMF | dimethylformamide |
| DMSO | dimethylsulfoxide |
| DSC | differential scanning calorimetry |
| edisylate | ethanedisulfonate |
| esylate or esilate | ethanesulfonate |
| EtOAc | ethyl acetate |
| EtOH | ethanol |
| FB | free base |
| FaSSIF | fasted state simulated intestinal fluid |
| FeSSIF | fed state simulated intestinal fluid |
| FIG. | figure |
| HP-β-CD | hydroxypropyl beta cyclodextrin |
| HPLC | high pressure liquid chromatography |
| isethionate | 2-hydroxyethanesulfonate |
| IPA | isopropanol |
| IPAc | isopropyl acetate |
| MEK | methyl ethyl ketone |
| MeOH | methanol |
| 2-MeTHF | 2-methyl tetrahydrofuran |
| mesylate | methanesulfonate |
| MIBK | methyl isobutyl ketone |
| napadisylate | naphthalene disulfonate |
| NMP | N-methyl-2-pyrrolidione |
| PEG | polyethylene glycol |
| PG | propylene glycol |
| RH | relative humidity |
| RT | room temperature |
| SGF | simulated gastric fluid |
| TBME | tert-butyl methyl ether |
| TGA | thermogravimetric analysis |
| THF | tetrahydrofuran |
| tosylate | p-toluenesulfonate |
| XRPD | X-ray powder diffraction |

2. Forms of Cerdulatinib

As described generally above, the present disclosure provides crystalline forms of Compound I and salts/co-crystals thereof. Additional forms (including amorphous forms) are also discussed further herein. Crystalline forms of Compound I (free base), the crystalline forms of salts/co-crystals of Compound I, and other forms (e.g., amorphous or disordered forms) of Compound I (free base) and salts/co-crystals thereof, are collectively referred to herein as "forms of Compound I."

The hydrochloride salts/co-crystals of Compound I were unexpectedly and surprisingly found to exhibit superior stability, hygroscopicity, solubility, and thermal properties compared to Compound I, and other solid forms of Compound I, and particularly the esylate, edisylate, mesylate, naphthalene disulfonate, sulfate, and tosylate salts/co-crystals of Compound I. For example, the mesylate and esylate salts/co-crystals of Compound I, while highly soluble, exhibited multiple form variations/solvations during handling without the isolation of a single, stable crystalline entity. The sulfate salts/co-crystals of Compound I were found to be highly insoluble and exhibited the form variation noted for the mesylate and esylate salts/co-crystals of Compound I. Other salts/co-crystals (e.g., the edisylate, naphthalene disulfonate, and tosylate salts/co-crystals) of Compound I also exhibited form variation.

Further, the mono-hydrochloride (e.g., Compound I HCl Form I) and mono-mesylate salts/co-crystals of Compound I were found to be more stable than the corresponding bis-salts/co-crystals thereof, as the bis-salts/co-crystals dissociated back to the mono version when handled in solution. Moreover, the solid forms of the mono-hydrochloride salt/co-crystal of Compound I (e.g., Compound I HCl Form I) was found to exhibit superior stability compared to solid forms of the mono-mesylate salts/co-crystals of Compound I.

Compound I HCl Form I was surprisingly and unexpectedly found to be the most physico-chemically stable solid form of Compound I. As discussed in greater detail below, Compound I HCl Form I is stable at room temperature under ambient conditions and remains crystalline while hydrated. The hydration behavior of Compound I HCl Form I is reversible, such that rehydration of Compound I HCl Form I returns the single, crystalline form, allowing Compound I HCl Form I be stored at ambient conditions without desiccant.

It is also contemplated that the mono-hydrochloride (Compound I HCl Form I) salt exhibits improved, compared to other salts, gross from variation, DVS stability, solubility and crystallization process control. It is further contemplated that the sulfonate salts (e.g., crystalline forms of the esylate, mesylate, isethionate, naphthalenesulfonate, chlorobenzenesulfate, tosylate, besylate, edisylate, and/or camphorsulfonate), compared to other salts, exhibits improved solubility.

a. Compound I Form I (Also Referred to as "Compound I Type A" or "Compound I Free Base Type A")

The present disclosure provides, in one embodiment, a crystalline form of 4-(cyclopropylamino)-2-(4-(4-(ethylsulfonyl)piperazin-1-yl)phenylamino)pyrimidine-5-carboxamide (Compound I Form I) characterized by an X-ray powder diffractogram comprising the following peaks: 16.6, 18.0, and 23.7 °2θ, each ±0.2 °2θ, as determined on a diffractometer using Cu-Kα radiation (1.54 Å). In one embodiment, the diffractogram of Compound I Form I further comprises one or more peaks at: 10.0, 17.1, and 19.4 °2θ, each ±0.2 °2θ.

In one embodiment, Compound I Form I is characterized by an X-ray powder diffractogram comprising at least two of the following peaks: 5.0, 8.3, 10.0, 14.4, 15.6, 16.6, 17.1, 18.0, 18.4, 19.4, 21.7, 23.3, 23.7, 25.1, and 31.2 °2θ, each ±0.2 °2θ. In one embodiment, Compound I Form I is characterized by an X-ray powder diffractogram comprising at least four of the following peaks: 5.0, 8.3, 10.0, 14.4, 15.6, 16.6, 17.1, 18.0, 18.4, 19.4, 21.7, 23.3, 23.7, 25.1, and 31.2 °2θ, each ±0.2 °2θ. In one embodiment, Compound I Form I is characterized by an X-ray powder diffractogram comprising at least six of the following peaks: 5.0, 8.3, 10.0, 14.4, 15.6, 16.6, 17.1, 18.0, 18.4, 19.4, 21.7, 23.3, 23.7, 25.1, and 31.2 °2θ, each ±0.2 °2θ. In one embodiment, Compound I Form I is characterized by an X-ray powder diffractogram comprising at least eight of the following peaks: 5.0, 8.3, 10.0, 14.4, 15.6, 16.6, 17.1, 18.0, 18.4, 19.4, 21.7, 23.3, 23.7, 25.1, and 31.2 °2θ, each ±0.2 °2θ. In one embodiment, Compound I Form I is characterized by an X-ray powder diffractogram comprising each of the following peaks: 5.0, 8.3, 10.0, 14.4, 15.6, 16.6, 17.1, 18.0, 18.4, 19.4, 21.7, 23.3, 23.7, 25.1, and 31.2 °2θ, each ±0.2 °2θ. In one embodiment, Compound I Form I is characterized by the full X-ray powder diffractogram as substantially shown in FIG. 1.

In another embodiment, provided is a process for making Compound I Form I. In one embodiment, the process for making Compound I Form I is as described in the Examples provided herein.

b. Compound I Form II (Also Referred to as "Compound I Type B" or "Compound I Free Base Type B")

The present disclosure provides, in one embodiment, a crystalline form of 4-(cyclopropylamino)-2-(4-(4-(ethylsulfonyl)piperazin-1-yl)phenylamino)pyrimidine-5-carboxamide (Compound I Form II) characterized by an X-ray powder diffractogram comprising the following peaks: 13.2, 18.7, and 22.0 °2θ, each ±0.2 °2θ, as determined on a diffractometer using Cu-Kα radiation. In one embodiment, the diffractogram of Compound I Form II further comprises one or more peaks at: 8.6, 10.0, and 16.5 °2θ±0.2 °2θ, each ±0.2 °2θ.

In one embodiment, Compound I Form II is characterized by an X-ray powder diffractogram comprising at least two of the following peaks: 8.6, 10.0, 11.7, 13.2, 14.0, 14.8, 15.9, 16.0, 16.5, 17.1, 18.7, 18.8, 22.0, 23.0, and 27.2 °2θ, each ±0.2 °2θ. In one embodiment, Compound I Form II is characterized by an X-ray powder diffractogram comprising at least four of the following peaks: 8.6, 10.0, 11.7, 13.2, 14.0, 14.8, 15.9, 16.0, 16.5, 17.1, 18.7, 18.8, 22.0, 23.0, and 27.2 °2θ, each ±0.2 °2θ. In one embodiment, Compound I Form II is characterized by an X-ray powder diffractogram comprising at least six of the following peaks: 8.6, 10.0, 11.7, 13.2, 14.0, 14.8, 15.9, 16.0, 16.5, 17.1, 18.7, 18.8, 22.0, 23.0, and 27.2 °2θ, each ±0.2 °2θ. In one embodiment, Compound I Form II is characterized by an X-ray powder diffractogram comprising at least eight of the following peaks: 8.6, 10.0, 11.7, 13.2, 14.0, 14.8, 15.9, 16.0, 16.5, 17.1, 18.7, 18.8, 22.0, 23.0, and 27.2 °2θ, each ±0.2 °2θ. In one embodiment, Compound I Form II is characterized by an X-ray powder diffractogram comprising each of the following peaks: 8.6, 10.0, 11.7, 13.2, 14.0, 14.8, 15.9, 16.0, 16.5, 17.1, 18.7, 18.8, 22.0, 23.0, and 27.2 °2θ, each ±0.2 °2θ. In one embodiment, Compound I Form I is characterized by the full X-ray powder diffractogram as substantially shown in FIG. 2.

In another embodiment, provided is a process for making Compound I Form II. In one embodiment, the process for making Compound I Form II is as described in the Examples provided herein.

c. Compound I Type C

Figure 64A:
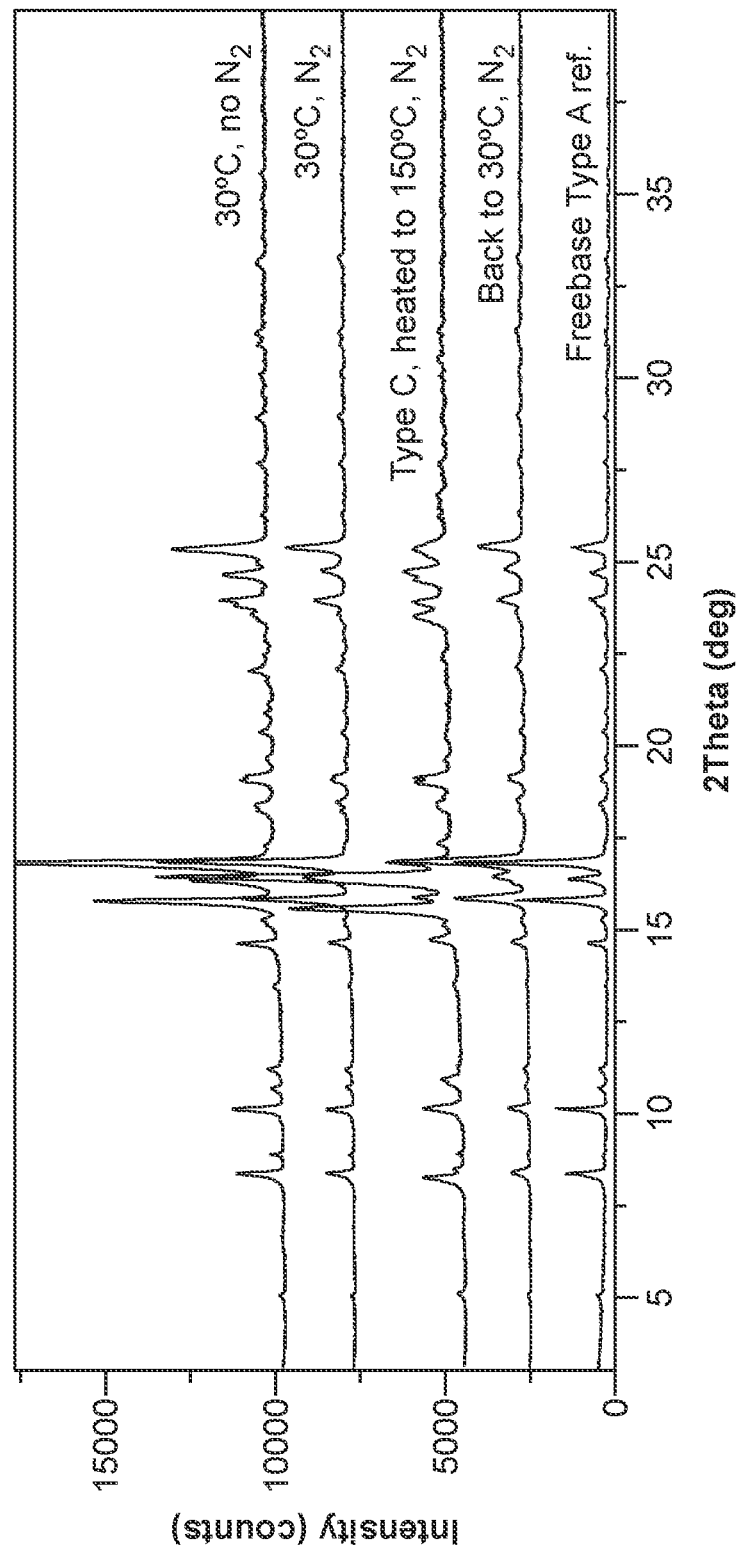
FIG. 64A and FIG. 64B provide analysis of Compound I free base Form I according to Example 13.
Figure 64B:
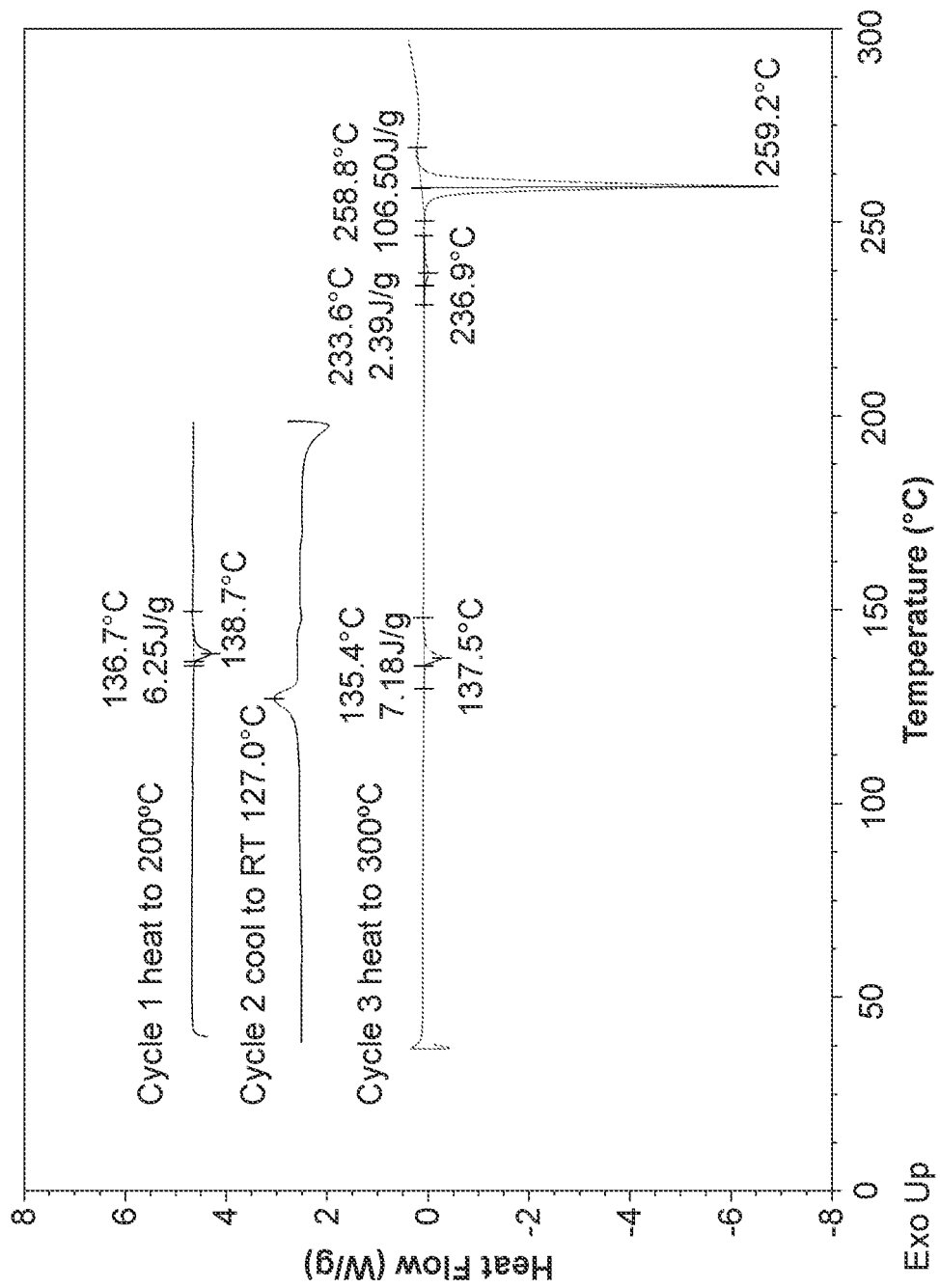

The present disclosure provides, in one embodiment, a crystalline form of 4-(cyclopropylamino)-2-(4-(4-(ethylsulfonyl)piperazin-1-yl)phenylamino)pyrimidine-5-carboxamide (Compound I Type C) characterized by an X-ray powder diffractogram as substantially shown in FIG. 64A.

In another embodiment, provided is a process for making Compound I Type C. In one embodiment, the process for making Compound I Type C is as described in the Examples provided herein.

d. Compound I Type D

Figure 65A:
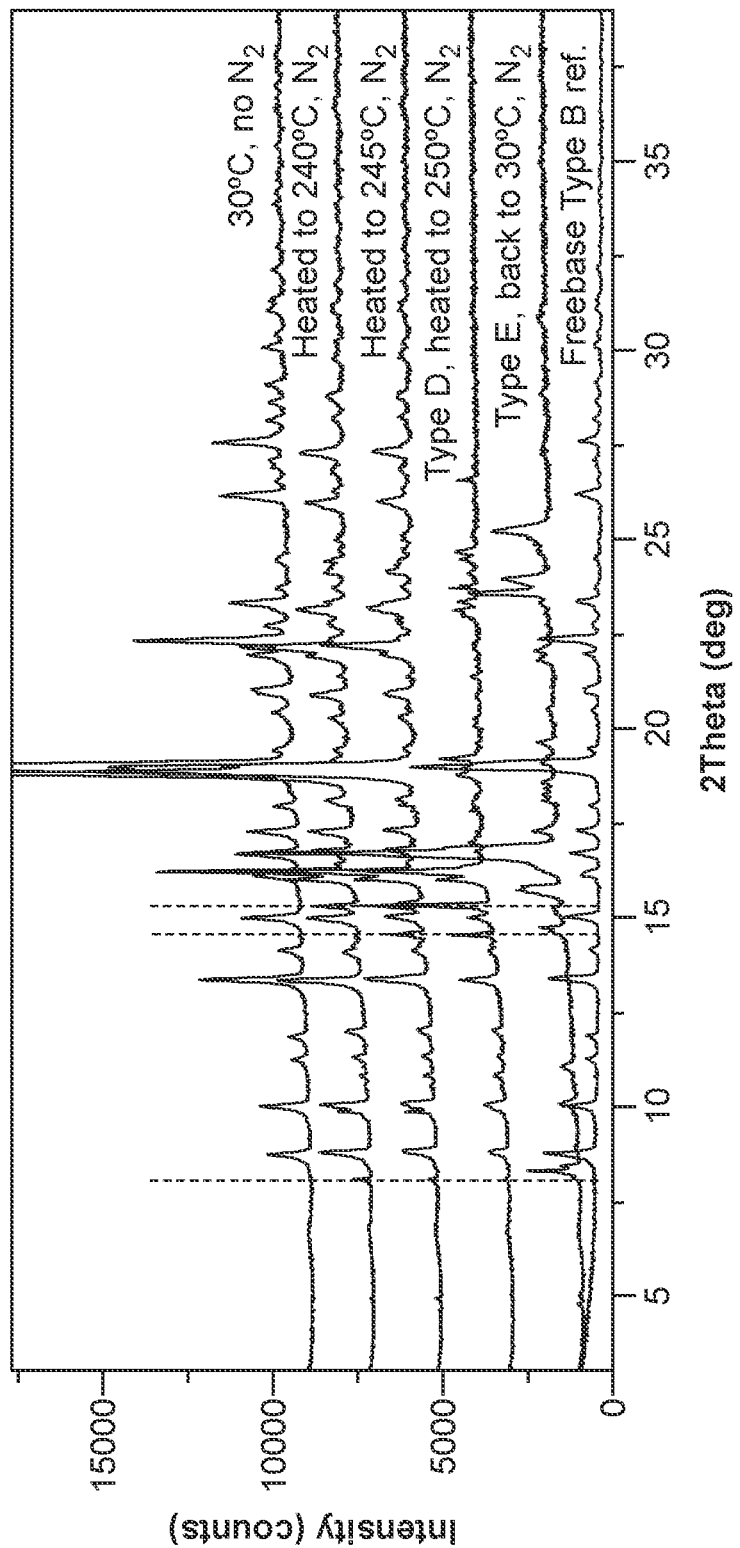
FIG. 65A and FIG. 65B provide analysis of Compound I free base Form II according to Example 13.
Figure 65B:
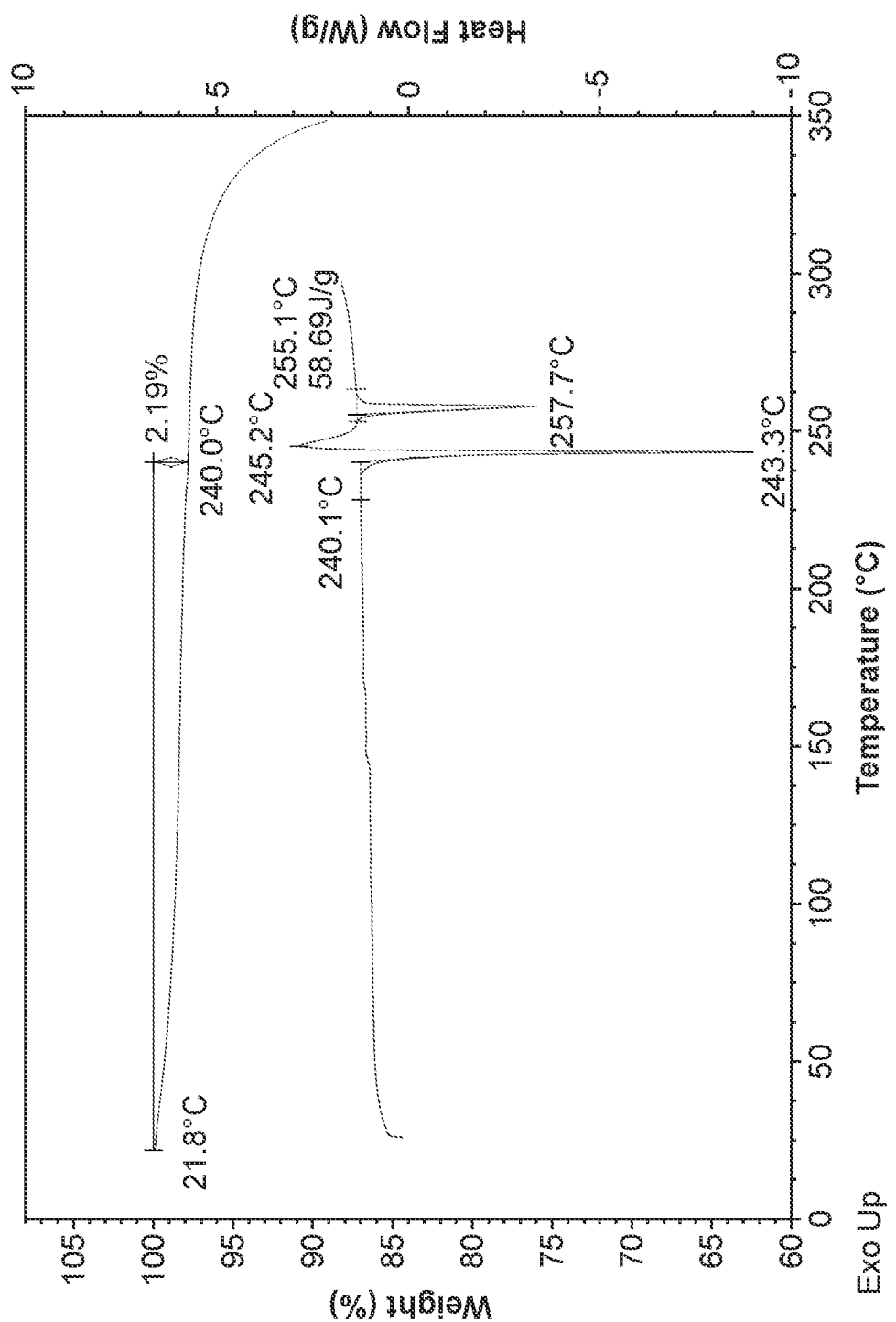
Figure 66:
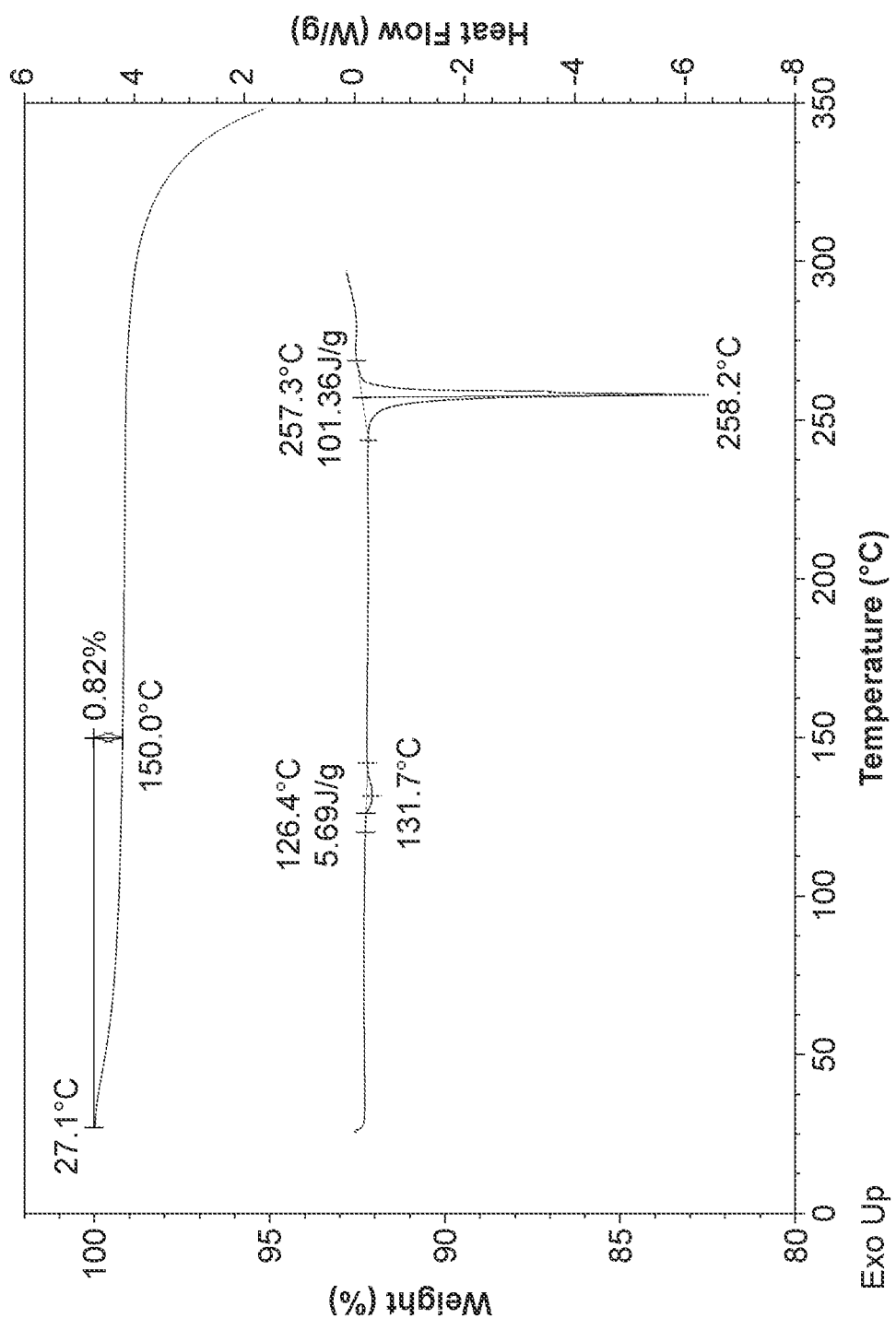
FIG. 66 is a differential scanning calorimetry (DSC) curve (bottom) and thermogravimetric analysis (TGA) thermogram (top) for Compound I free base Type E.
Figure 67:
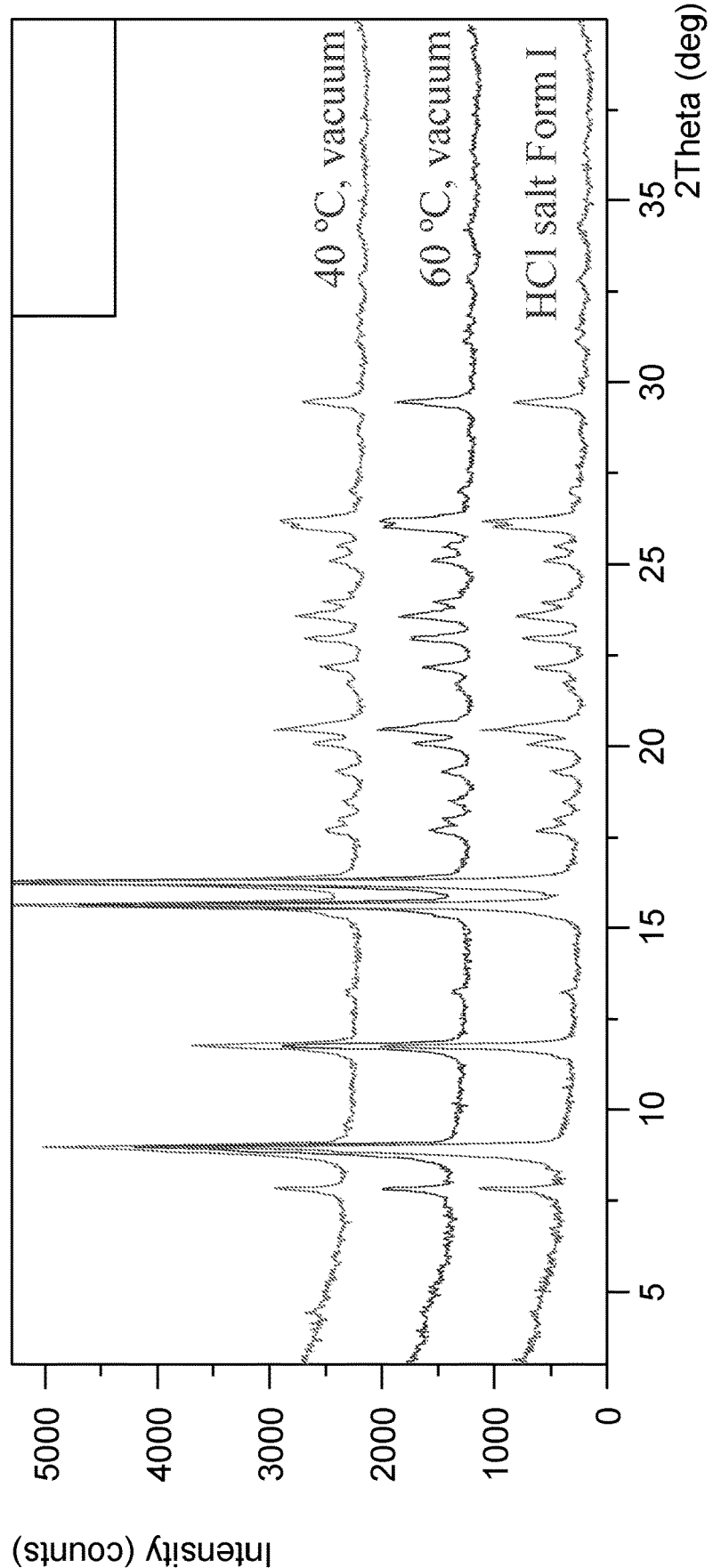
FIG. 67 is an overlay of XRPD diffractograms of solid forms observed during stability testing, under vacuum at 40° C. and at 60° C., of Compound I HCl salt Form I according to Example 14.
Figure 68:
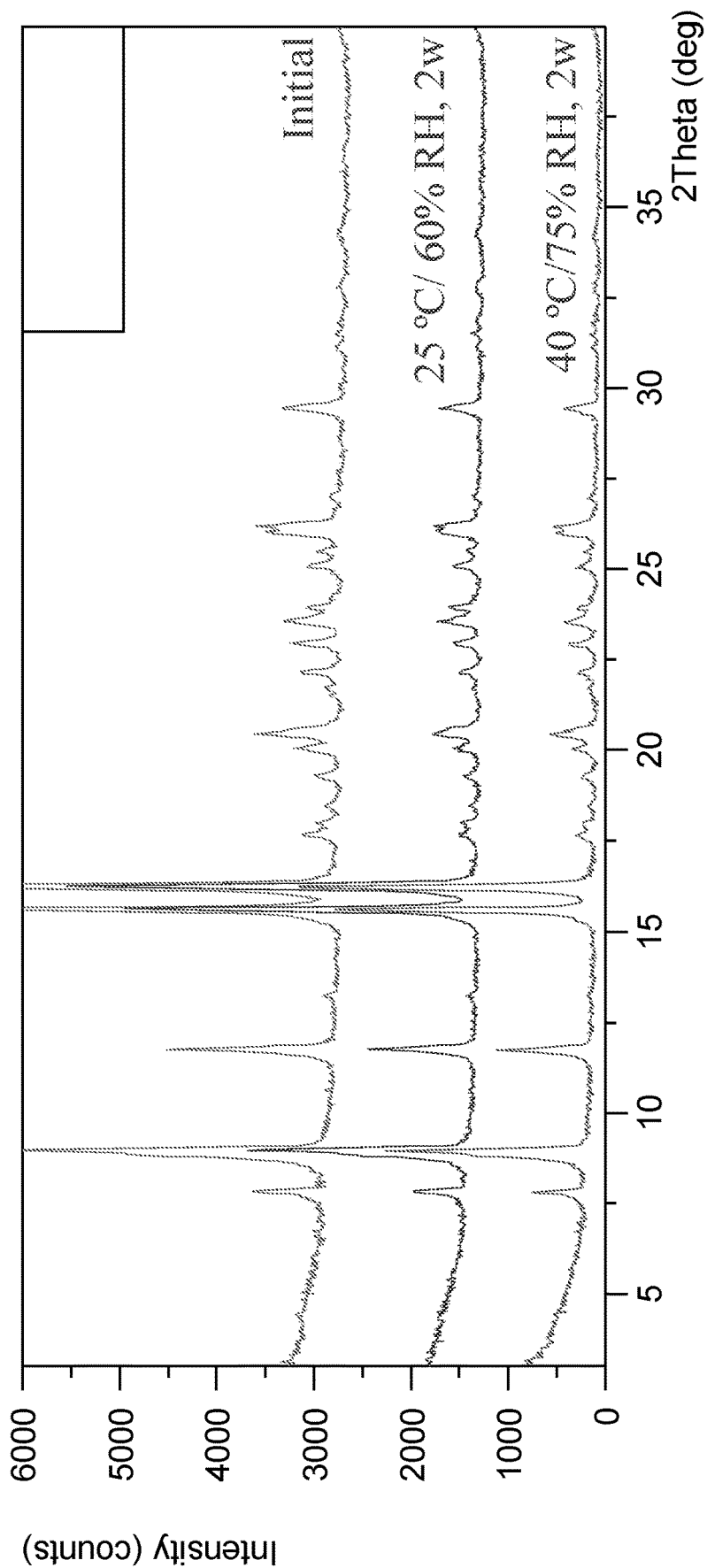
FIG. 68 is an overlay of XRPD diffractograms of solid forms observed during stability testing, at 25° C./60% RH and at 40° C./75% RH, of Compound I HCl salt Form I according to Example 14.
Figure 69A:
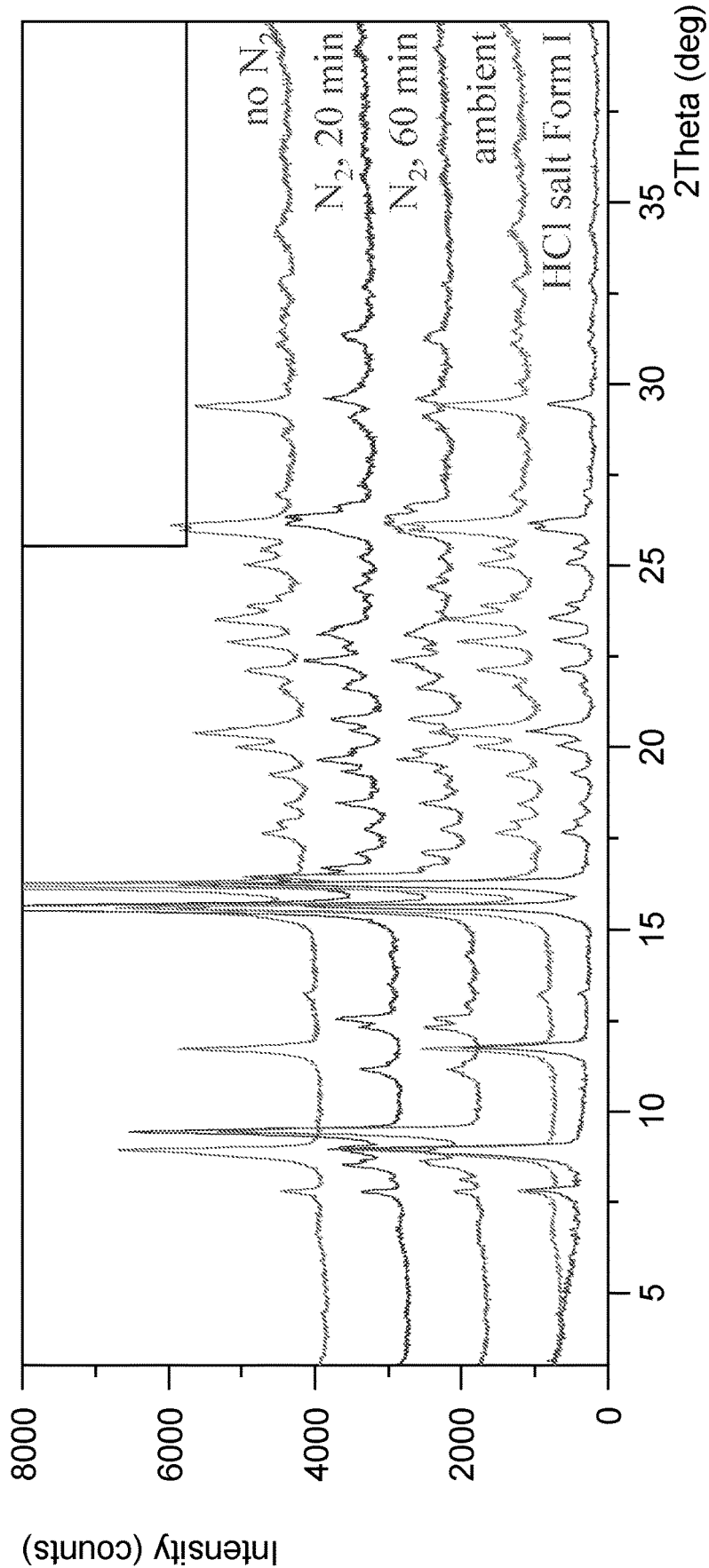
FIG. 69A is an overlay of XRPD diffractograms of solid forms observed during low humidity testing of Compound I HCl salt Form I according to Example 14.
Figure 69B:
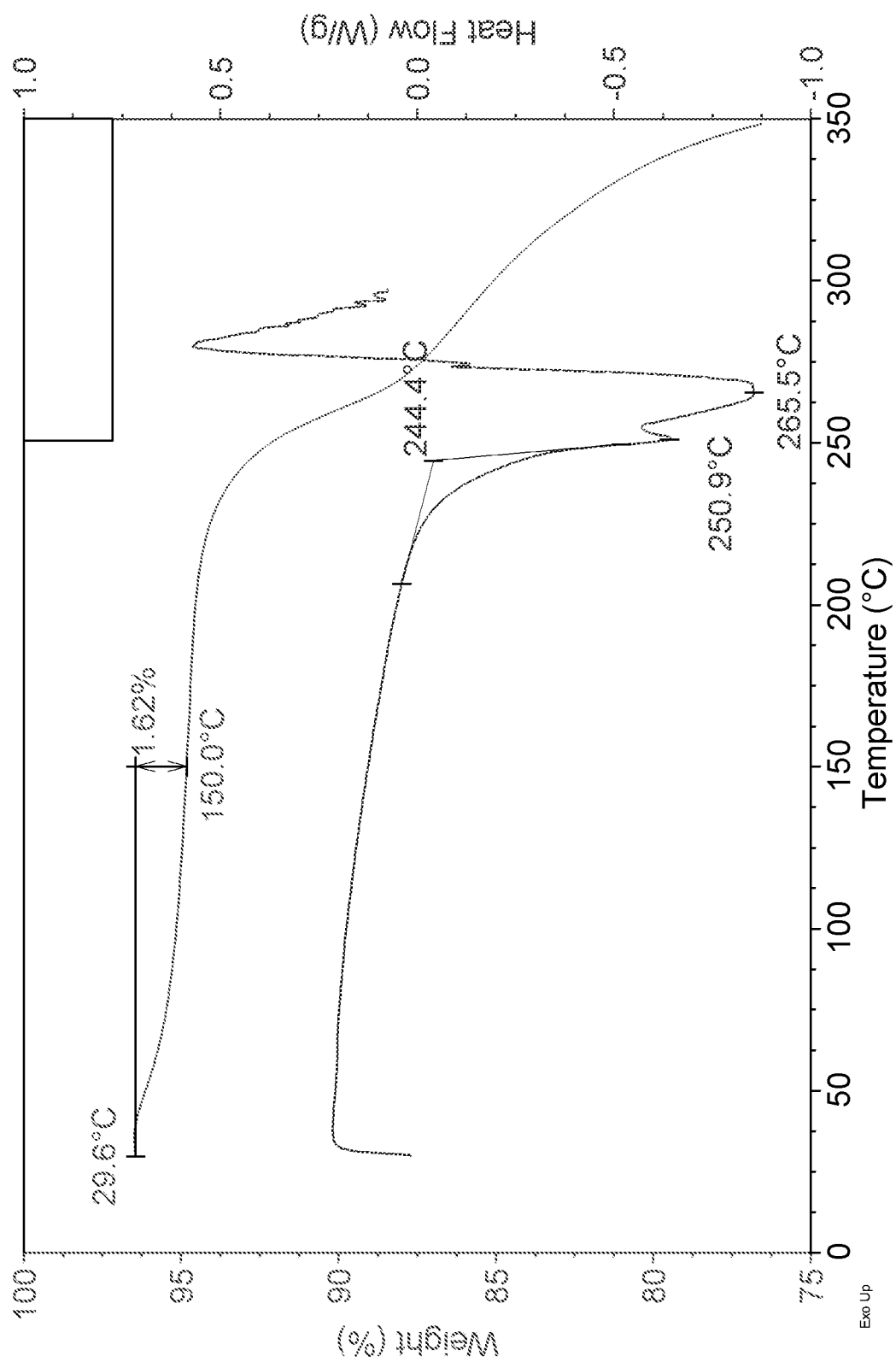
FIG. 69B is a differential scanning calorimetry (DSC) curve (bottom) and thermogravimetric analysis (TGA) thermogram (top) for Compound I HCl salt Form I measured following the low humidity testing.
Figure 70A:
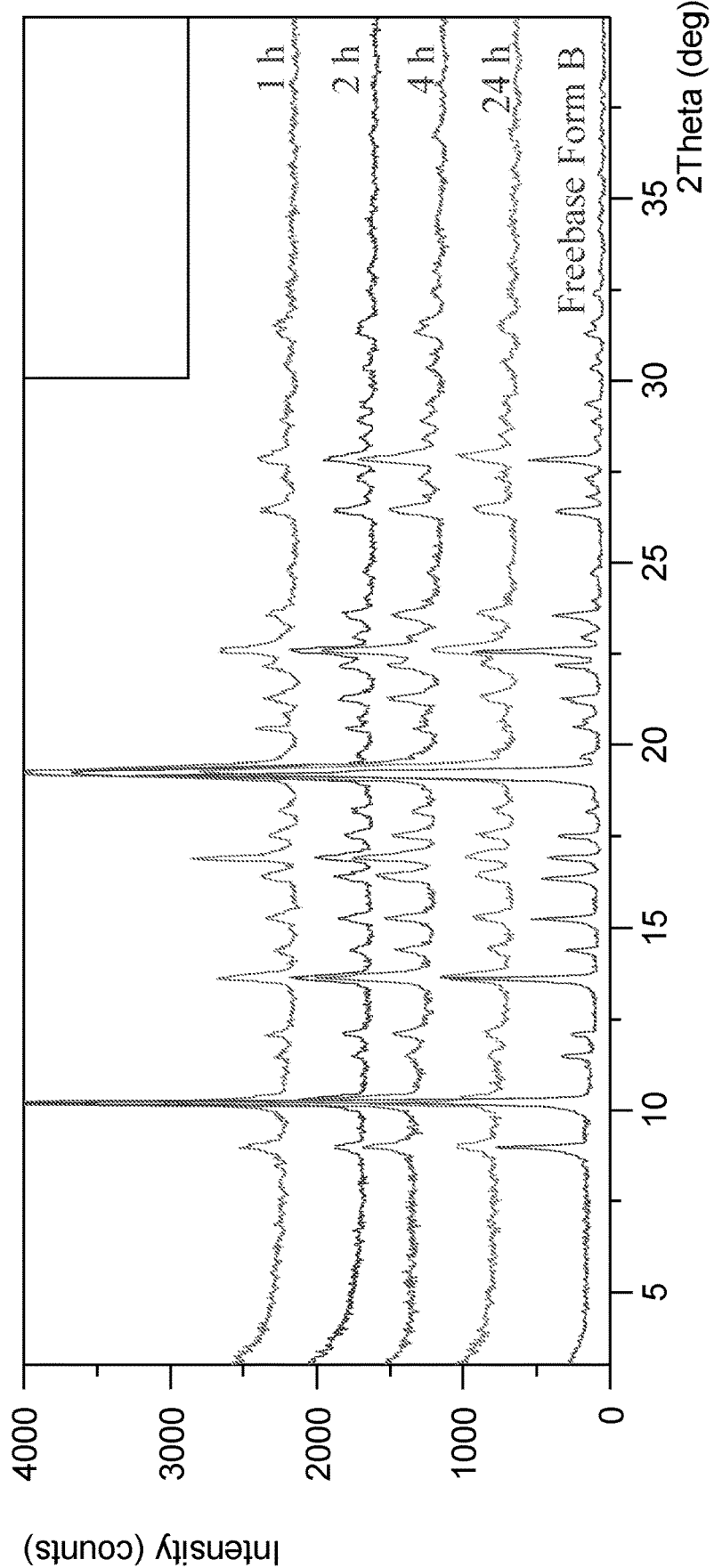
FIG. 70A, FIG. 70B, FIG. 70C and FIG. 70D are X-ray powder diffractograms of solid materials isolated during Compound I esylate Type A kinetic solubility experiments in water (FIG. 70A), simulated gastric fluid ("SGF") (FIG. 70B), fasted state simulated gastric fluid ("FaSSIF") (FIG. 70C), and fed state simulated gastric fluid ("FeSSIF") (FIG. 70D).
Figure 70B:
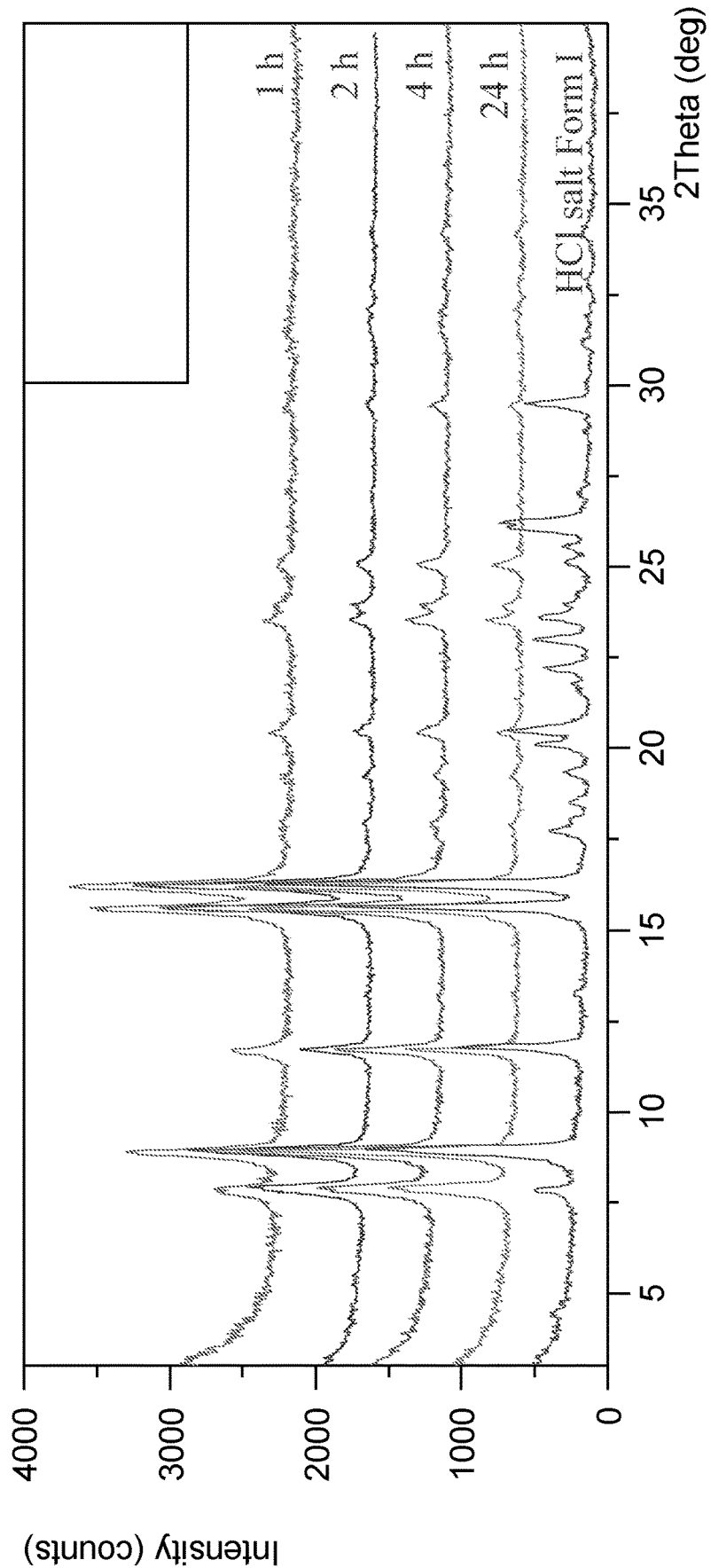
Figure 70C:
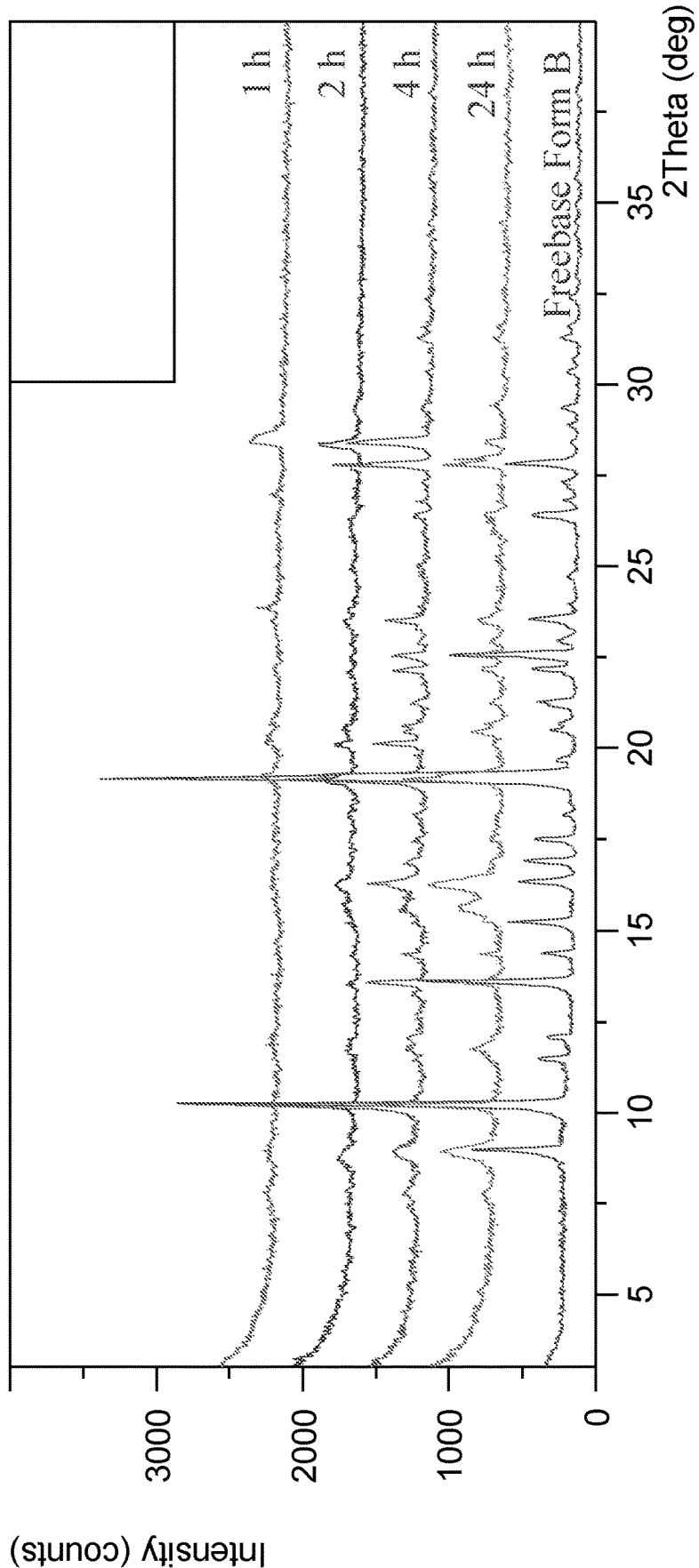
Figure 70D:
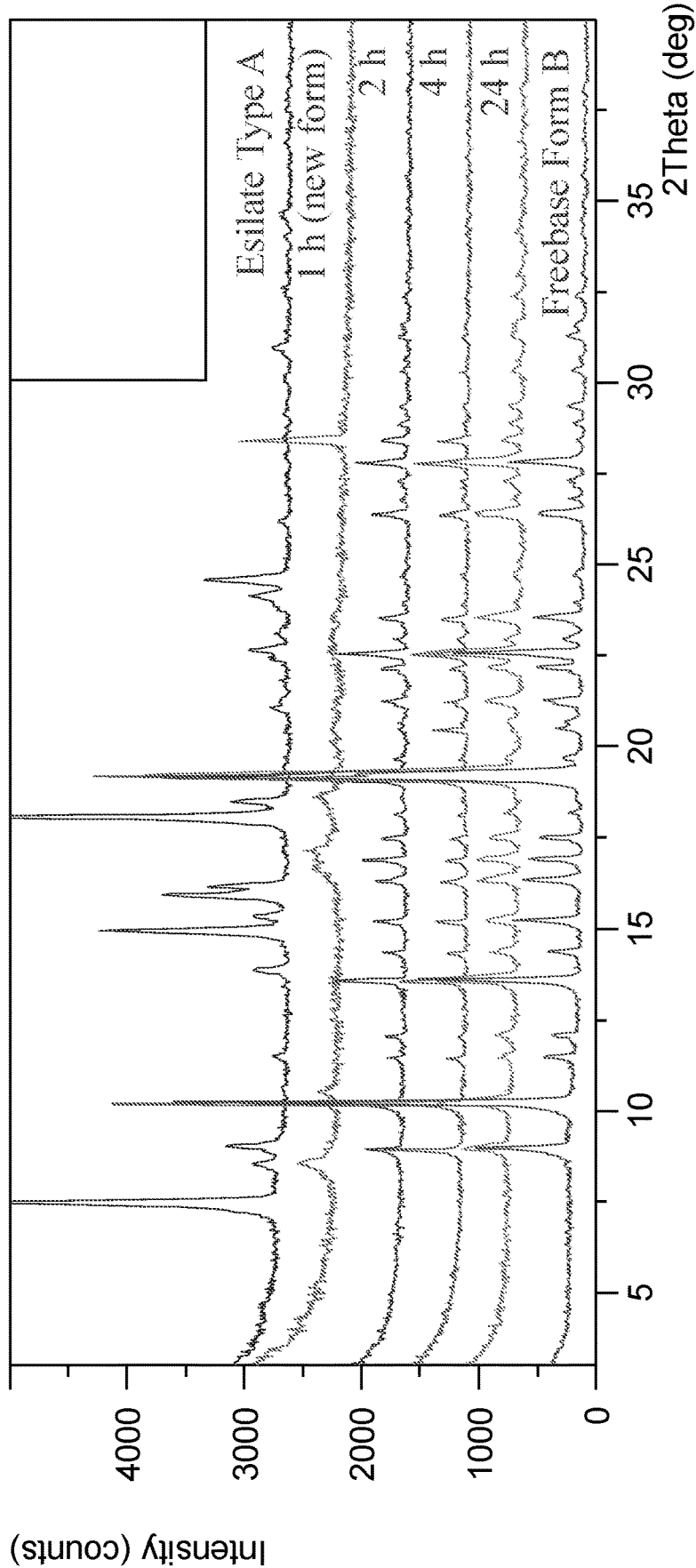
Figure 71A:
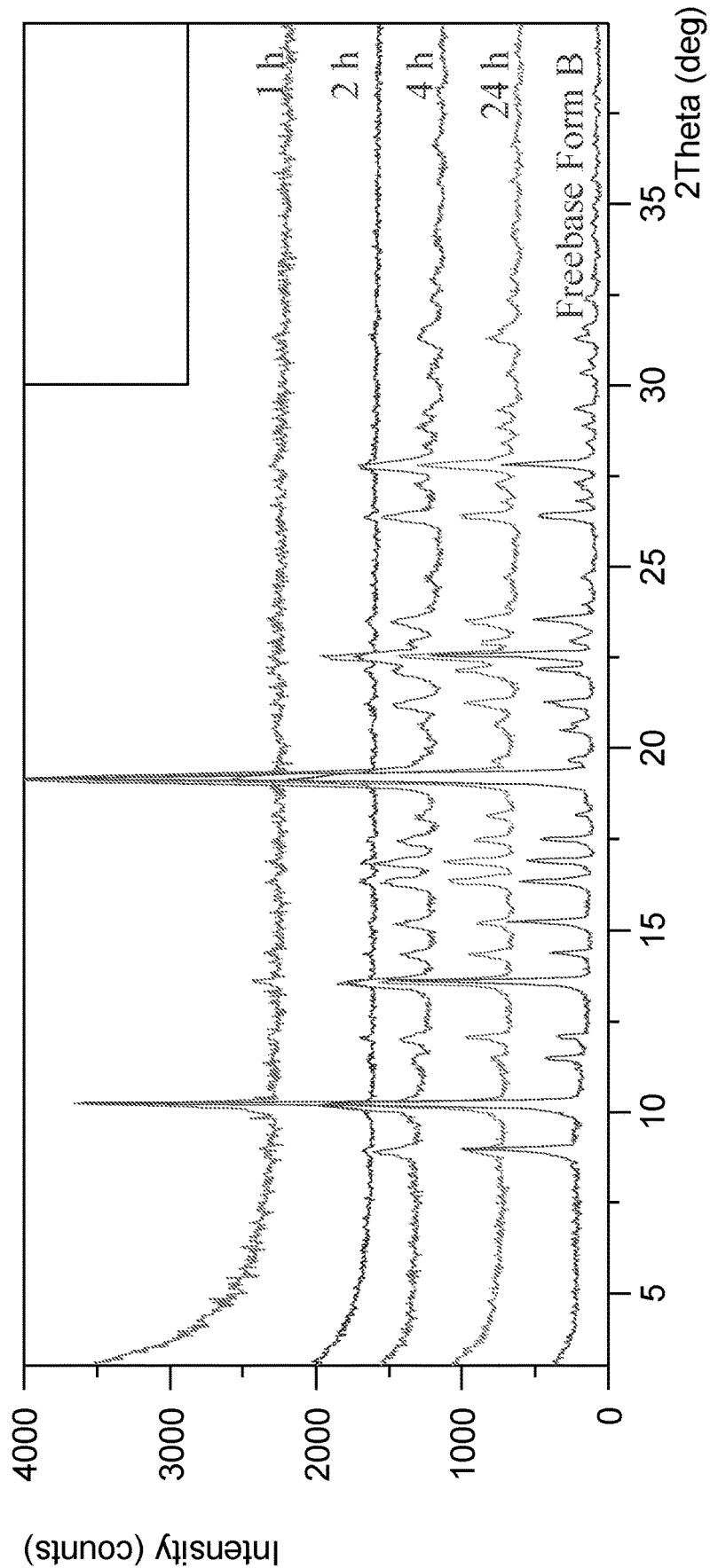
FIG. 71A, FIG. 71B, FIG. 71C and FIG. 71D are X-ray powder diffractograms of solid materials isolated during Compound I isethionate Type A kinetic solubility experiments in water (FIG. 71A), simulated gastric fluid ("SGF") (FIG. 71B), fasted state simulated gastric fluid ("FaSSIF") (FIG. 71C), and fed state simulated gastric fluid ("FeSSIF") (FIG. 71D).
Figure 71B:
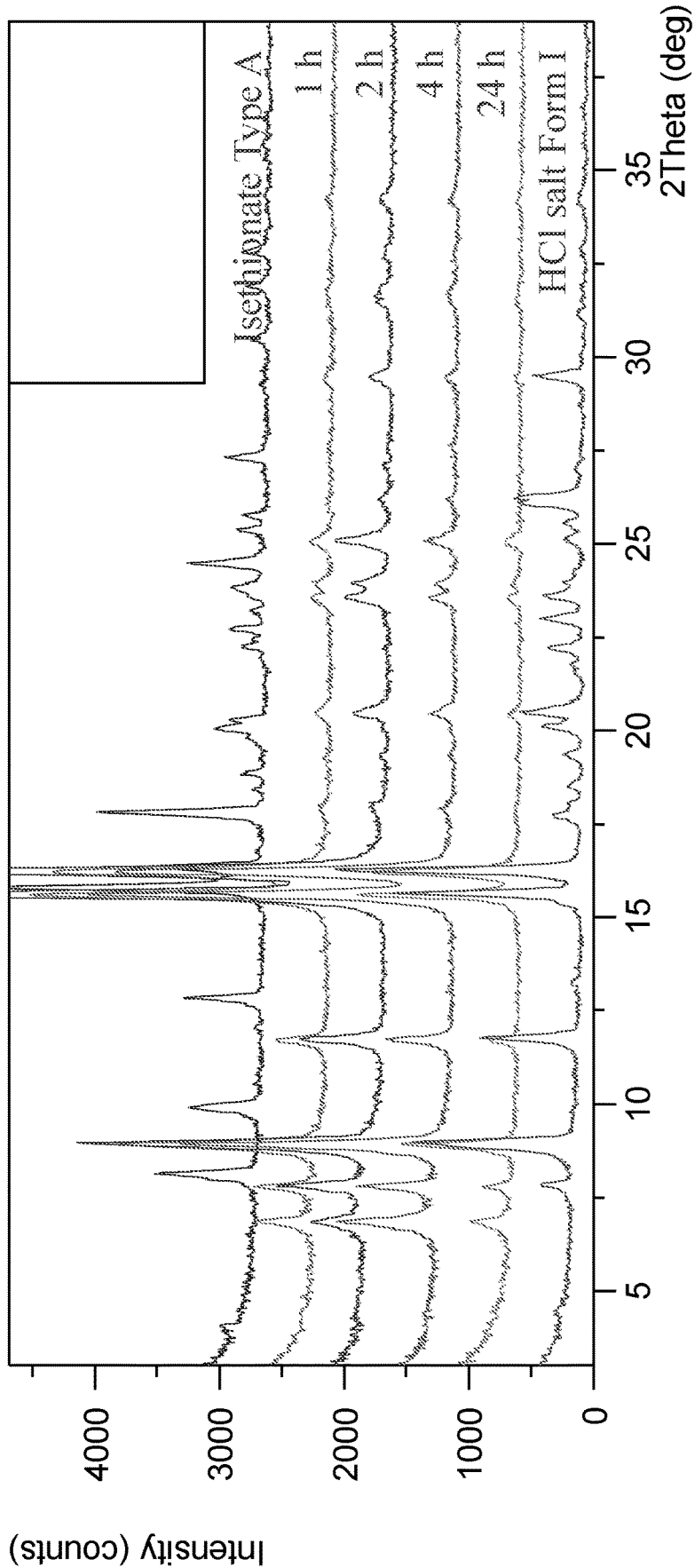
Figure 71C:
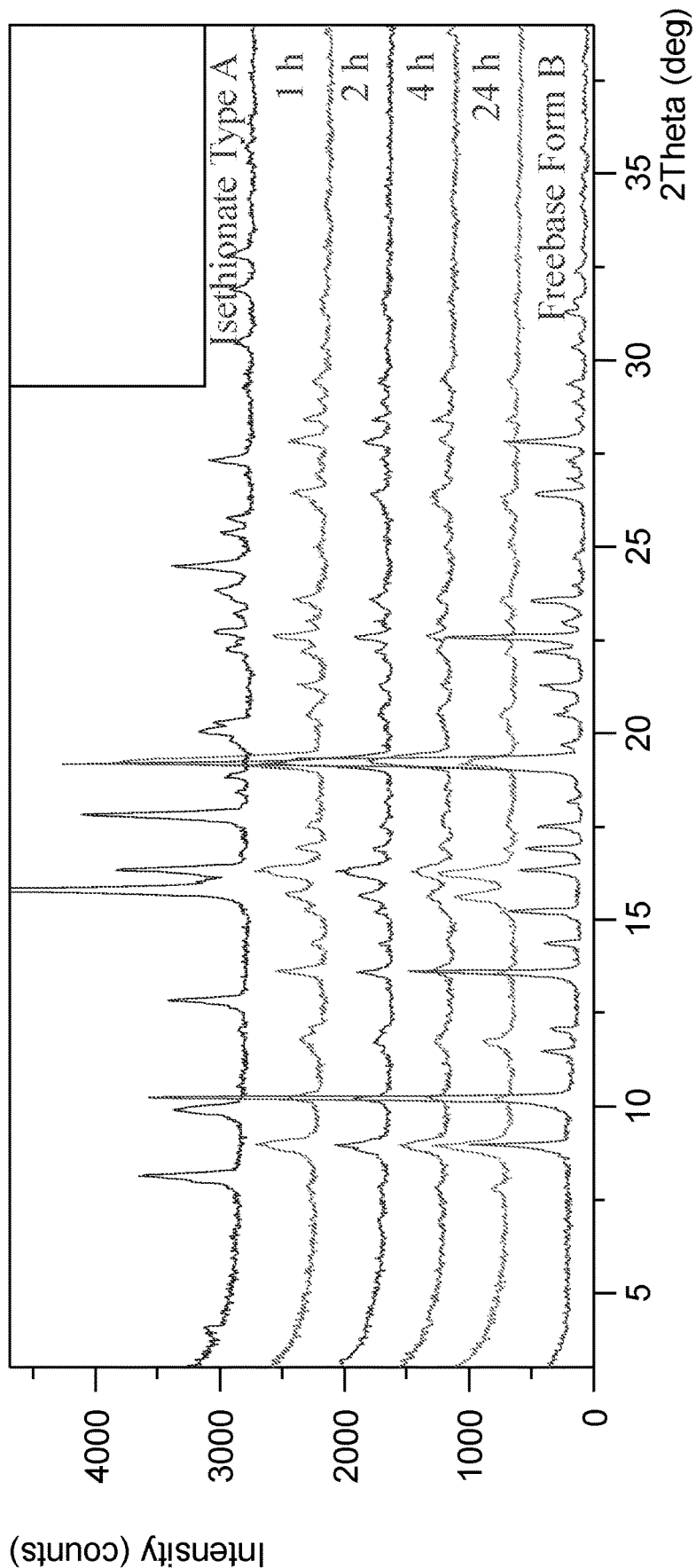
Figure 71D:
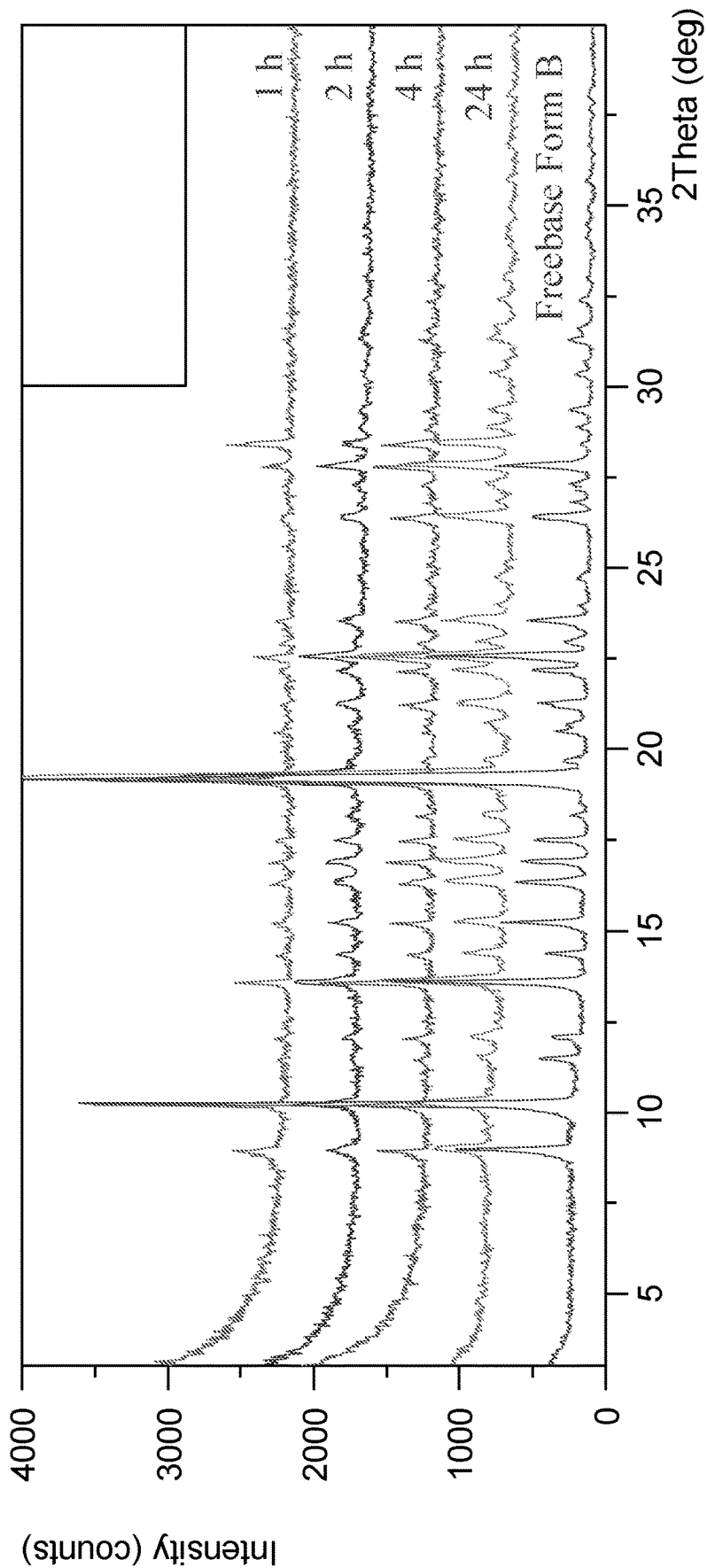
Figure 72A:
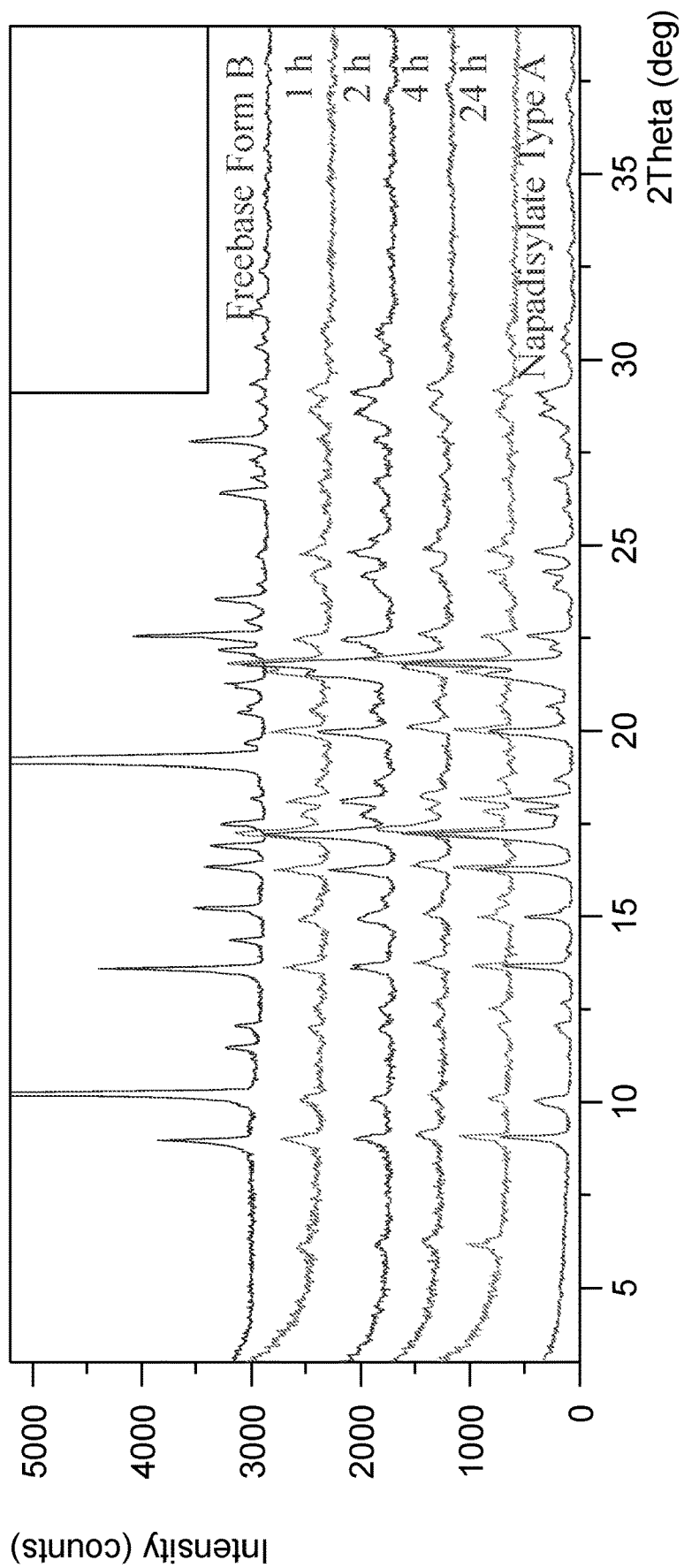
FIG. 72A, FIG. 72B, FIG. 72C and FIG. 72D are X-ray powder diffractograms of solid materials isolated during Compound I naphthalene disulfonate Type A kinetic solubility experiments in water (FIG. 72A), simulated gastric fluid ("SGF") (FIG. 72B), fasted state simulated gastric fluid ("FaSSIF") (FIG. 72C), and fed state simulated gastric fluid ("FeSSIF") (FIG. 72D).
Figure 72B:
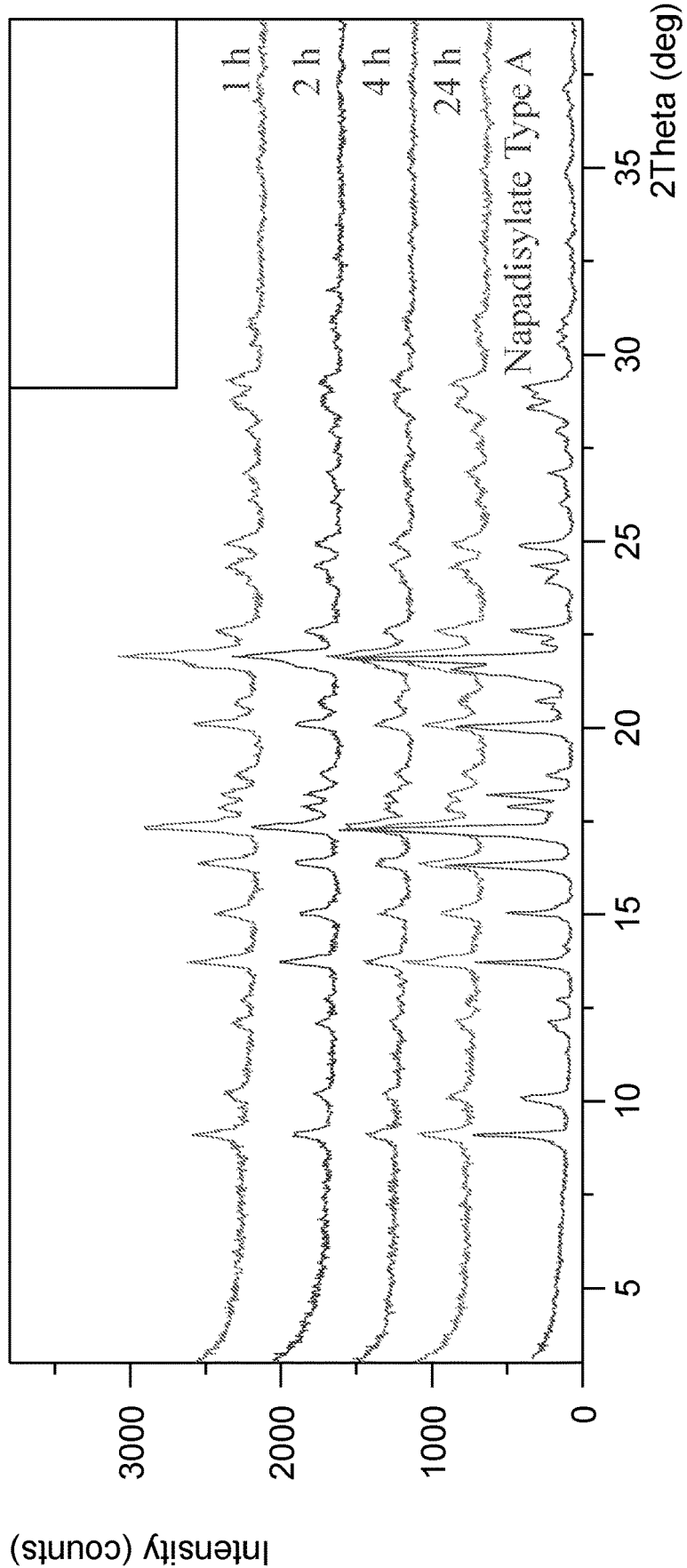
Figure 72C:
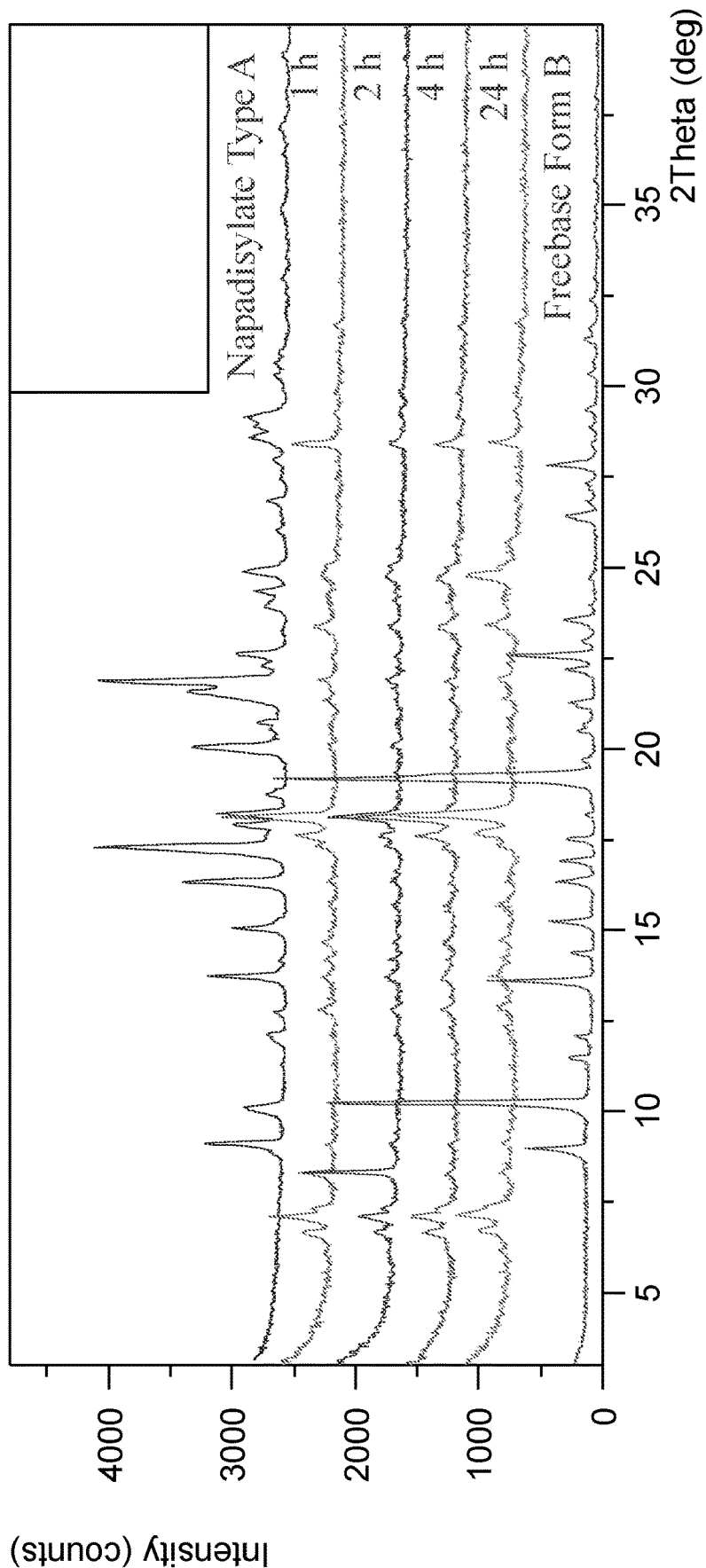
Figure 72D:
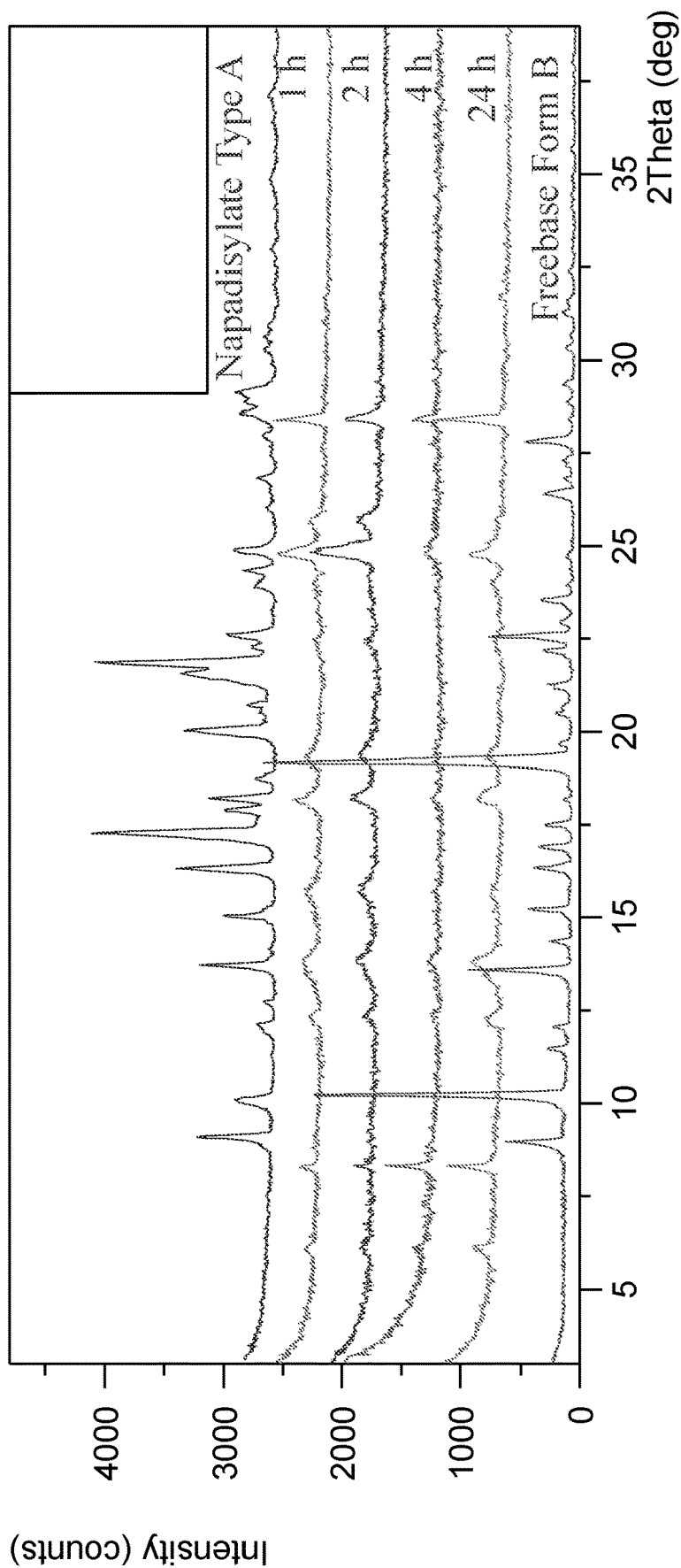
Figure 73A:
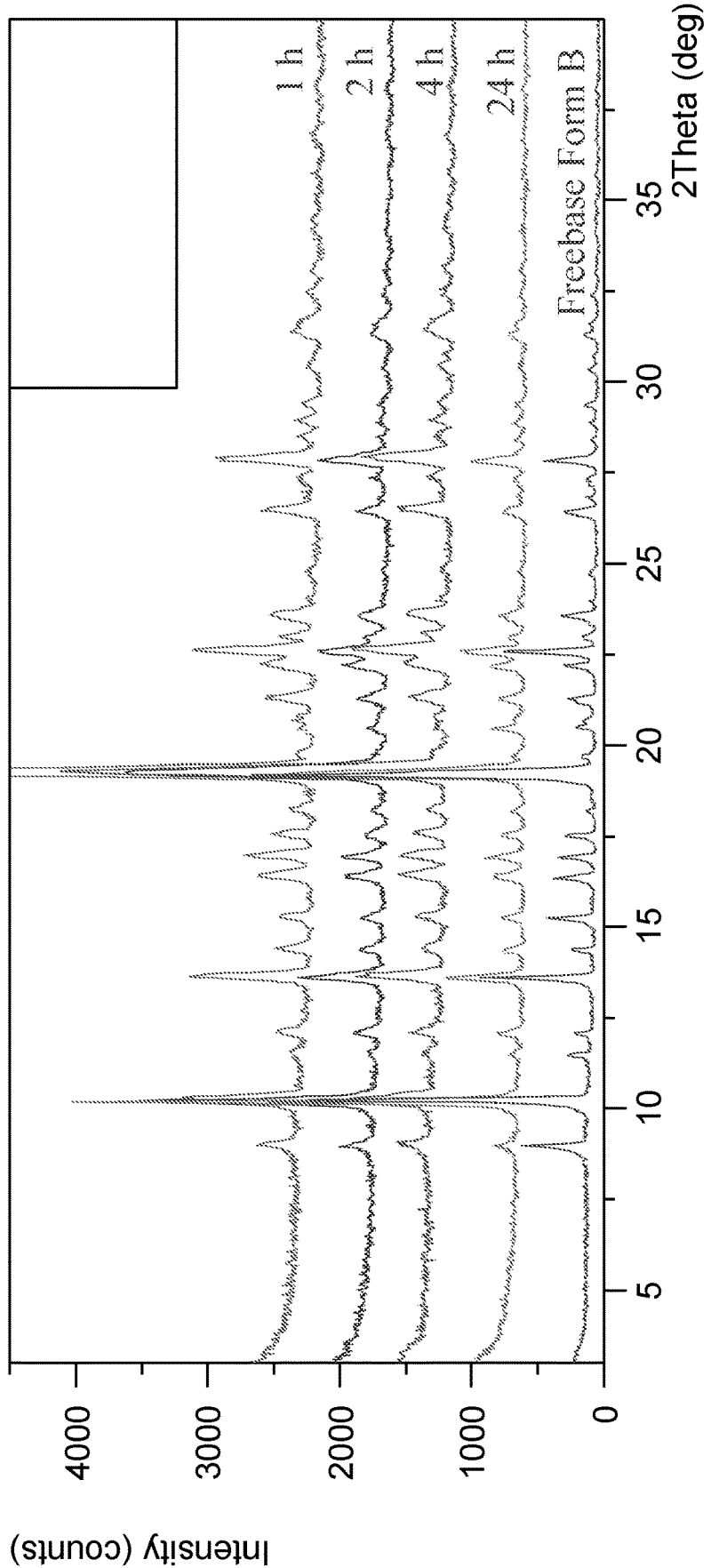
FIG. 73A, FIG. 73B, FIG. 73C and FIG. 73D are X-ray powder diffractograms of solid materials isolated during Compound I mesylate Type A kinetic solubility experiments in water (FIG. 73A), simulated gastric fluid ("SGF") (FIG. 73B), fasted state simulated gastric fluid ("FaSSIF") (FIG. 73C), and fed state simulated gastric fluid ("FeSSIF") (FIG. 73D).
Figure 73B:
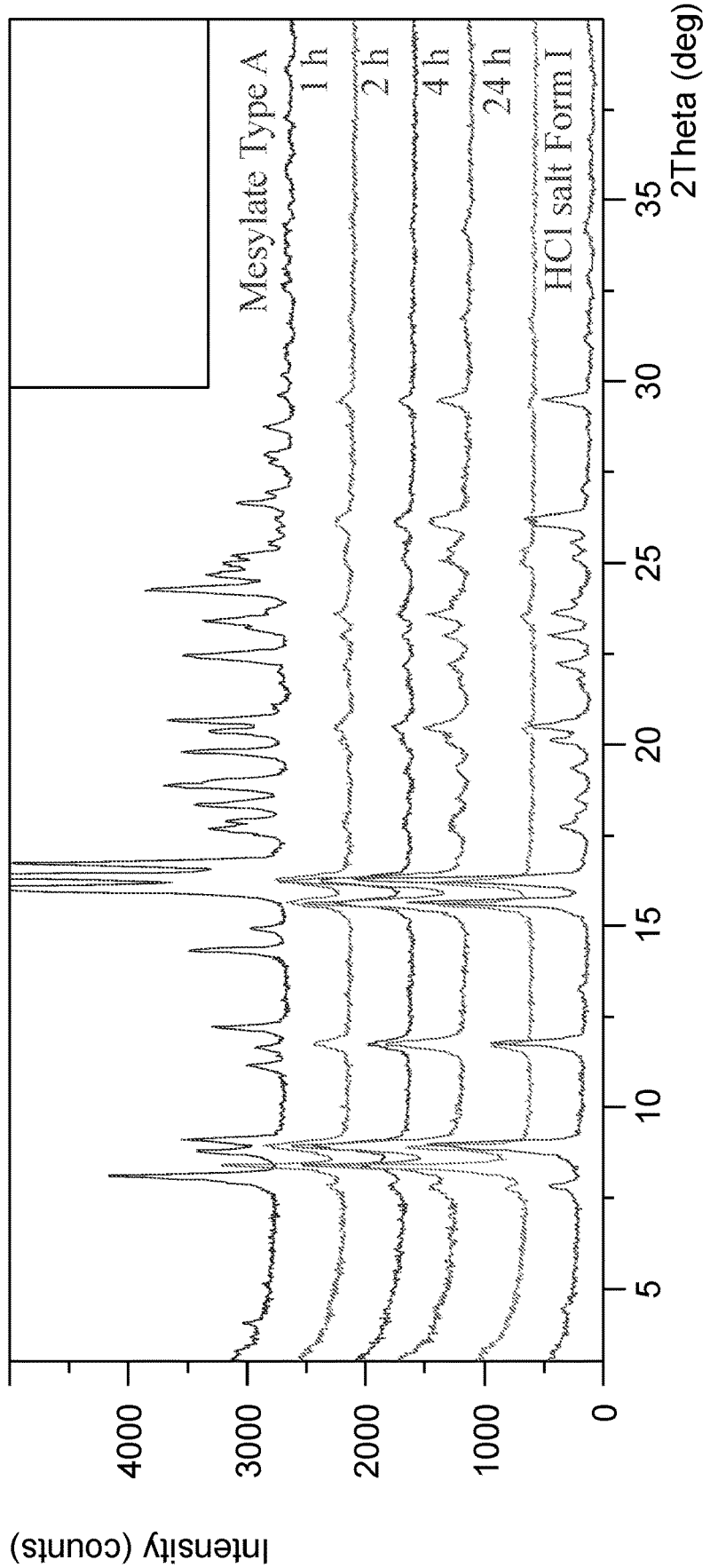
Figure 73C:
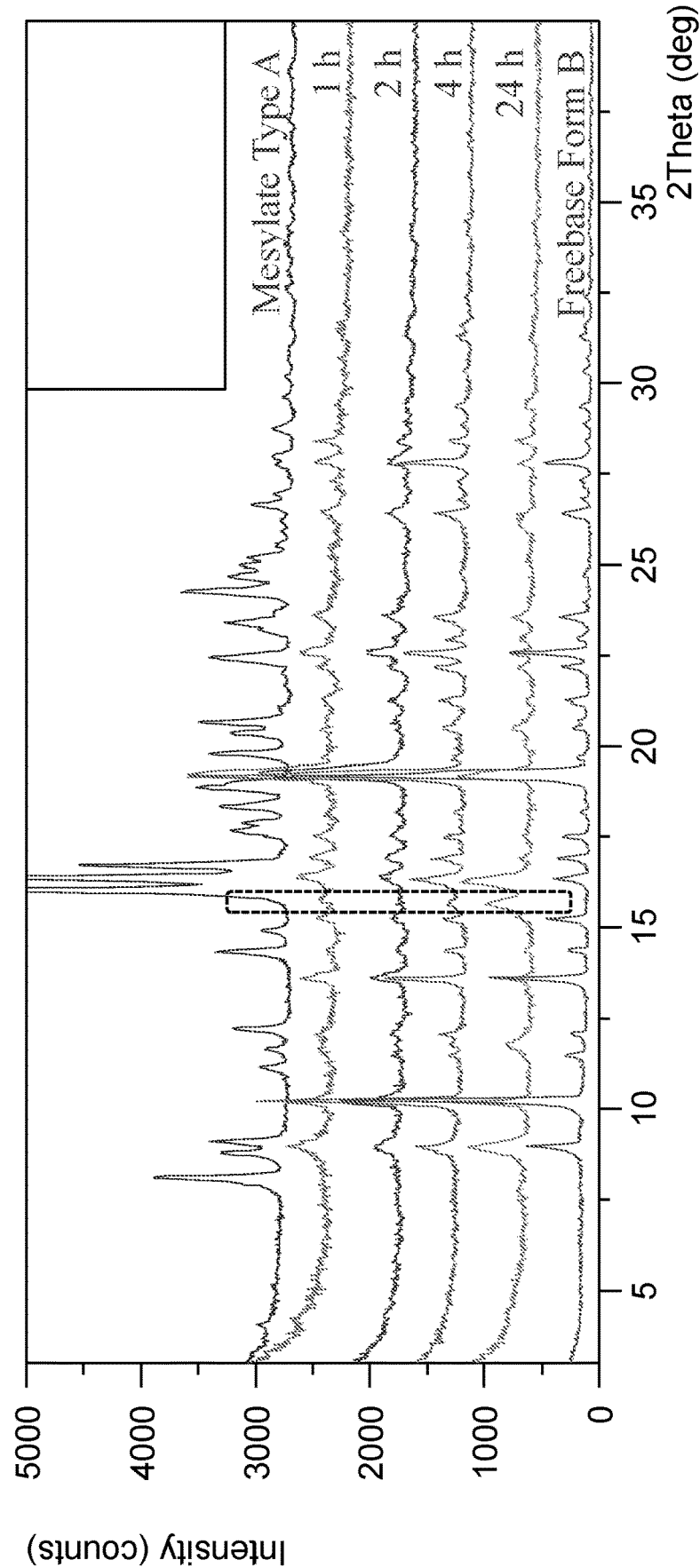
Figure 73D:
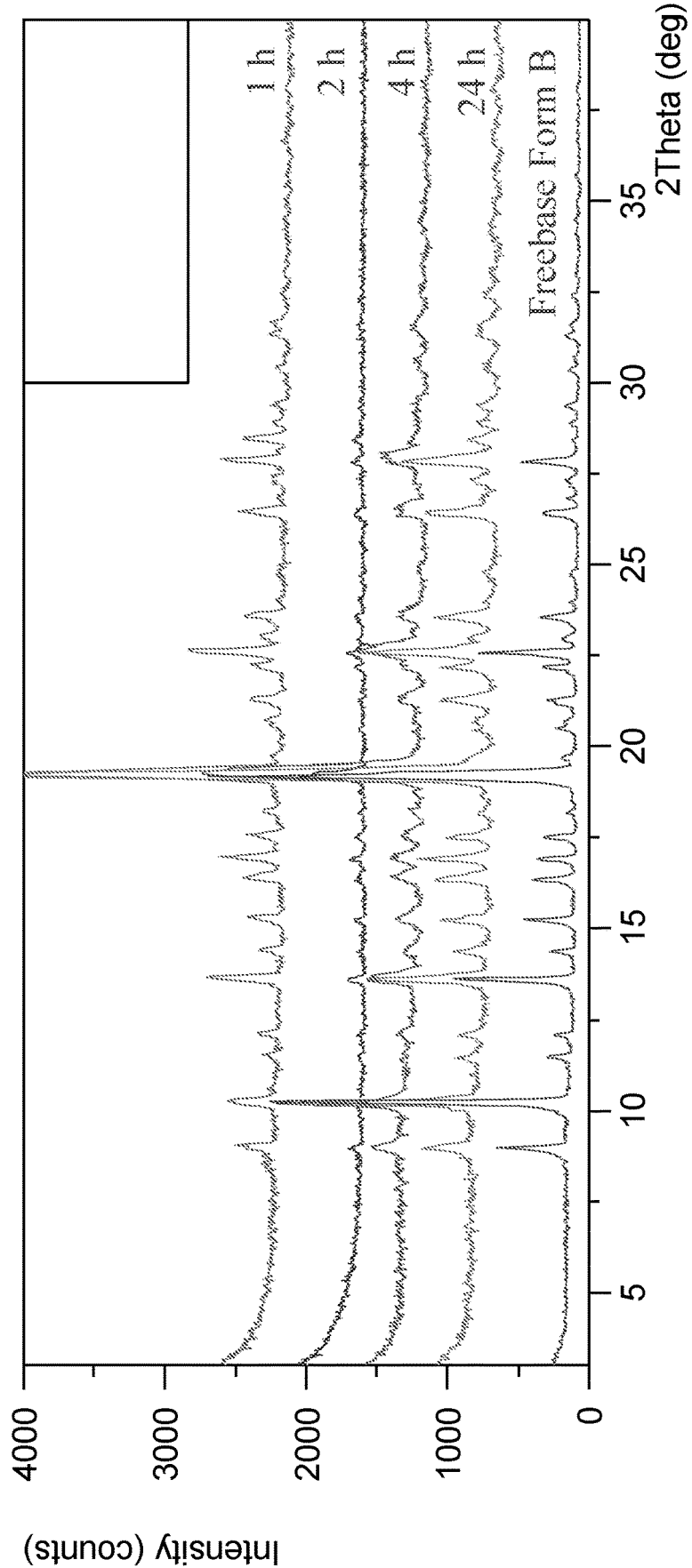
Figure 74A:
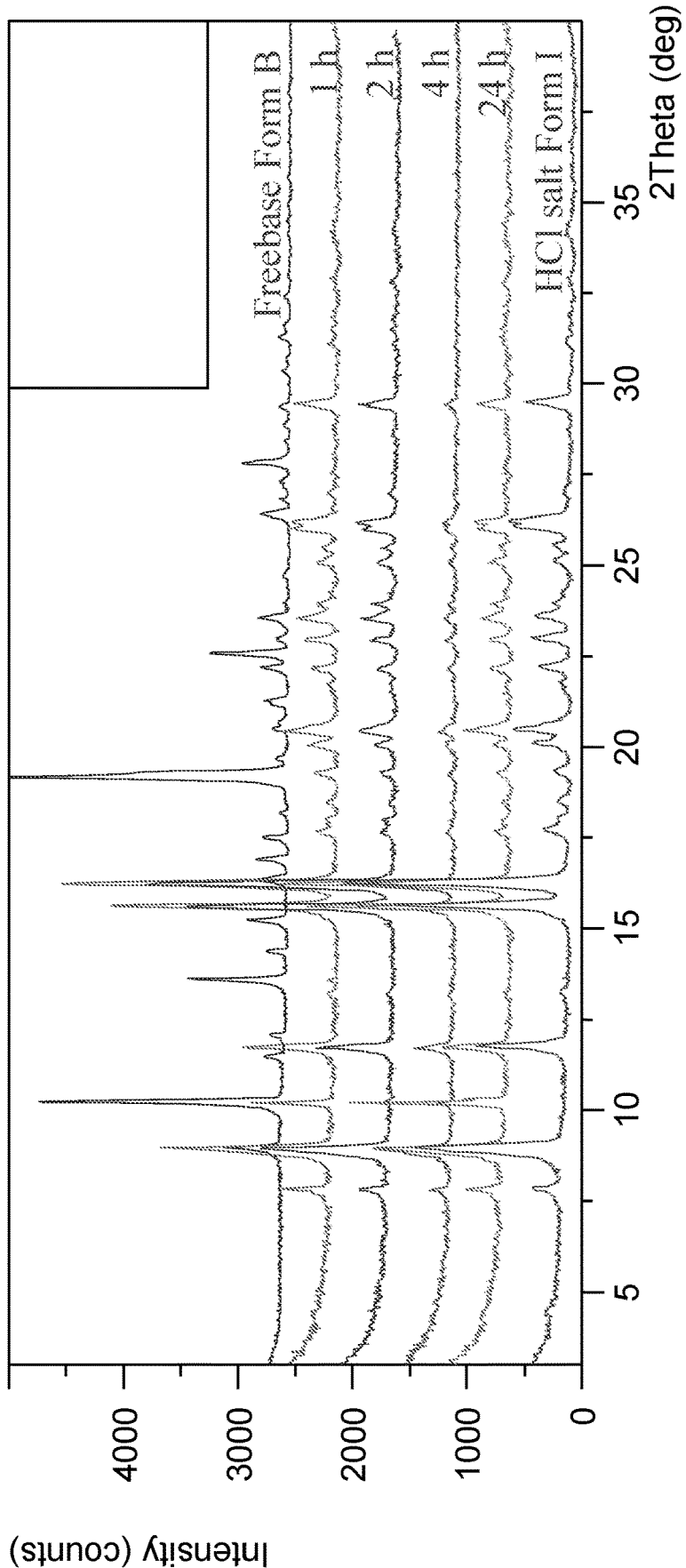
FIG. 74A, FIG. 74B, FIG. 74C and FIG. 74D are X-ray powder diffractograms of solid materials isolated during Compound I HCl Form I kinetic solubility experiments in water (FIG. 74A), simulated gastric fluid ("SGF") (FIG. 74B), fasted state simulated gastric fluid ("FaSSIF") (FIG. 74C), and fed state simulated gastric fluid ("FeSSIF") (FIG. 74D).
Figure 74B:
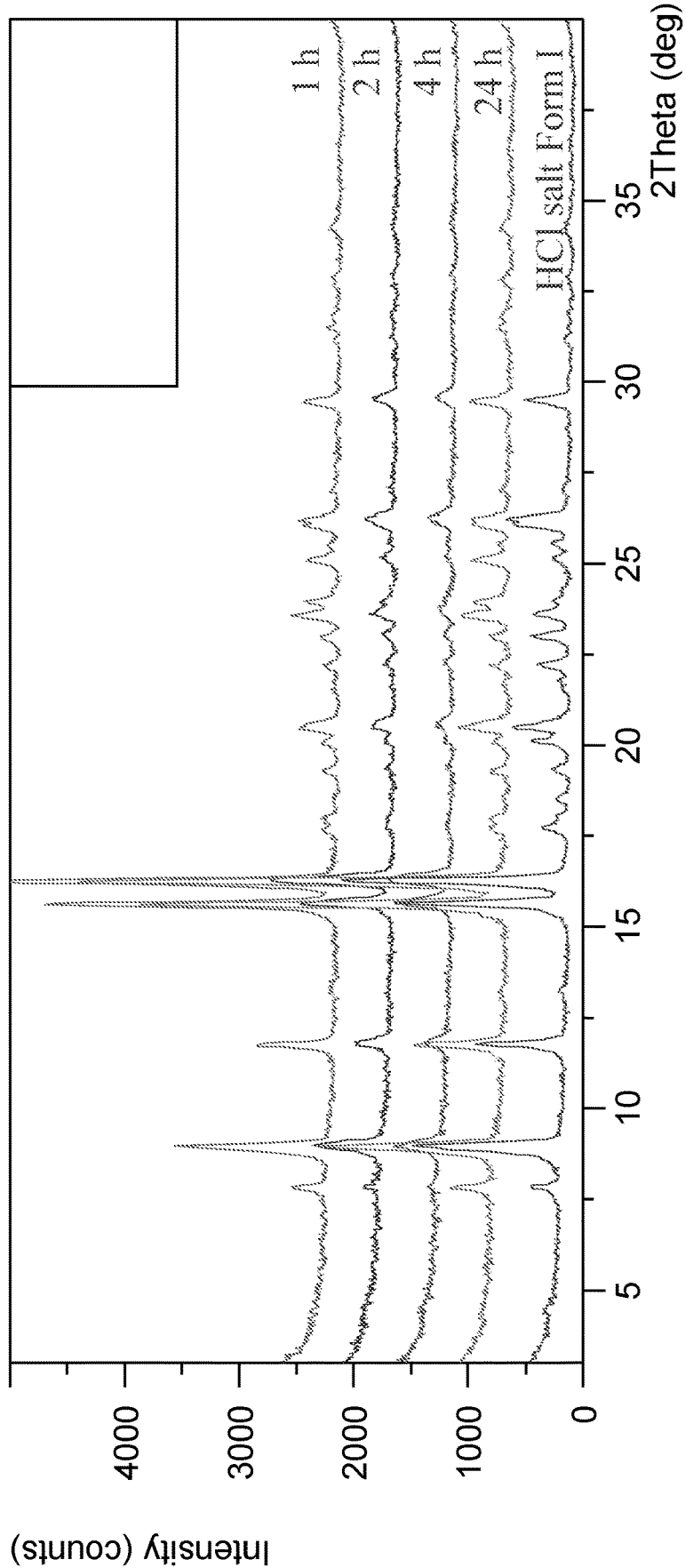
Figure 74C:
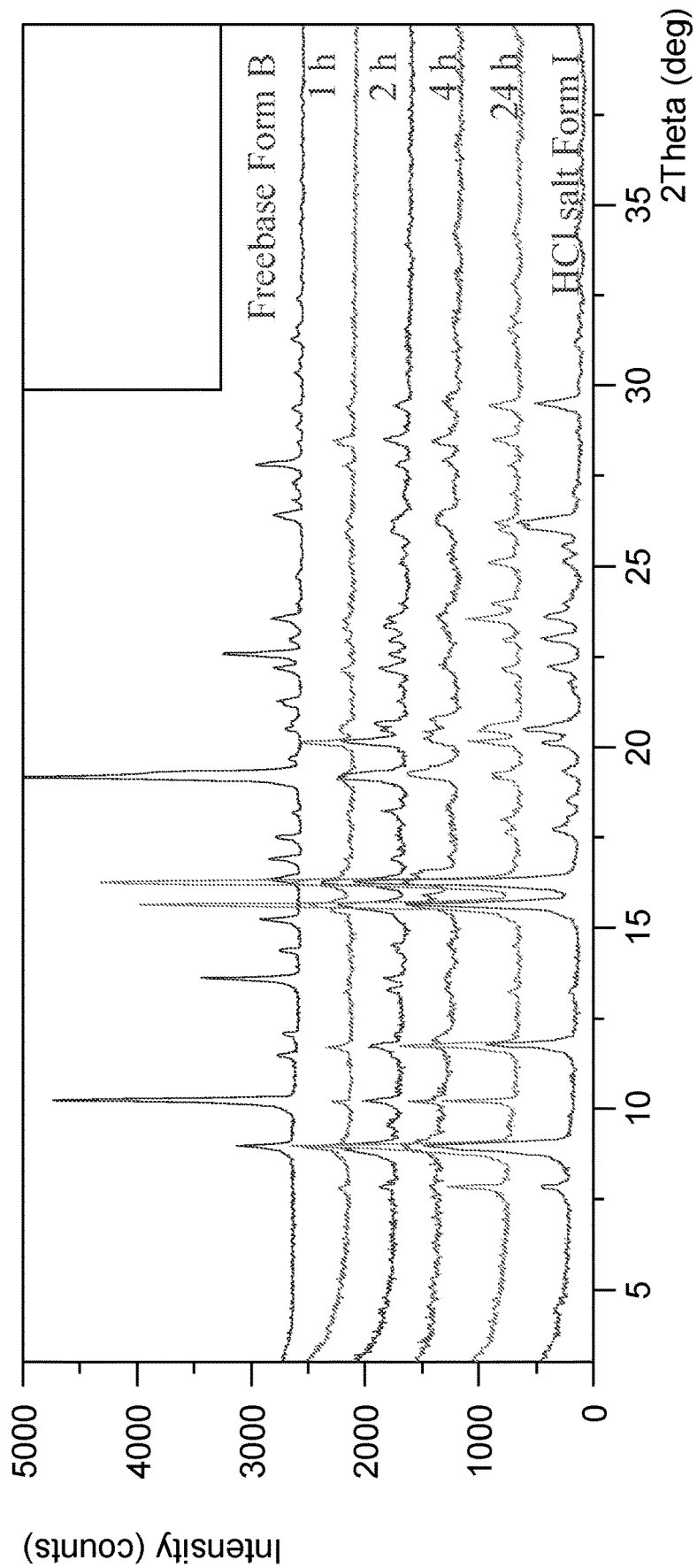
Figure 74D:
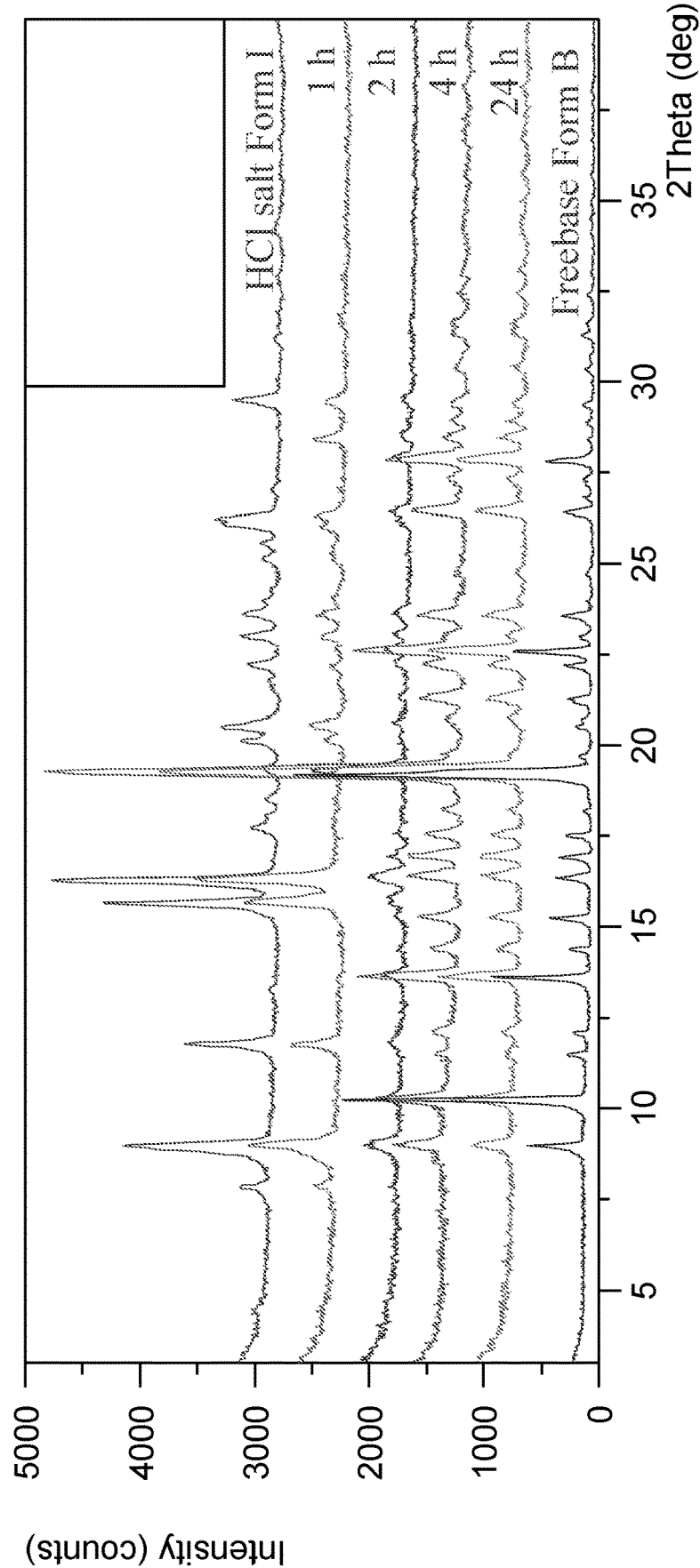
Figure 75A:
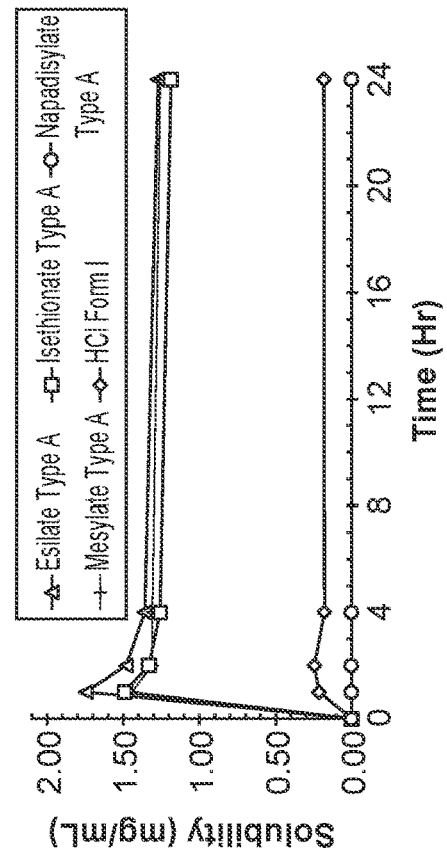
FIG. 75A, FIG. 75B, FIG. 75C and FIG. 75D are charts of kinetic solubility for Compound I esylate Type A (triangle symbols), Compound I 2-hydroxyethanesulfonate ("isethionate") hydroxyethanesulfonate (square symbols), Compound I naphthalene disulfonate Type A (circle symbols), Compound I mesylate Type A (plus symbols), and Compound I HCl Form I (diamond symbols) in water (FIG. 75A), simulated gastric fluid ("SGF") (FIG. 75B), fasted state simulated gastric fluid ("FaSSIF") (FIG. 75C), and fed state simulated gastric fluid ("FeSSIF") (FIG. 75D).
Figure 75B:
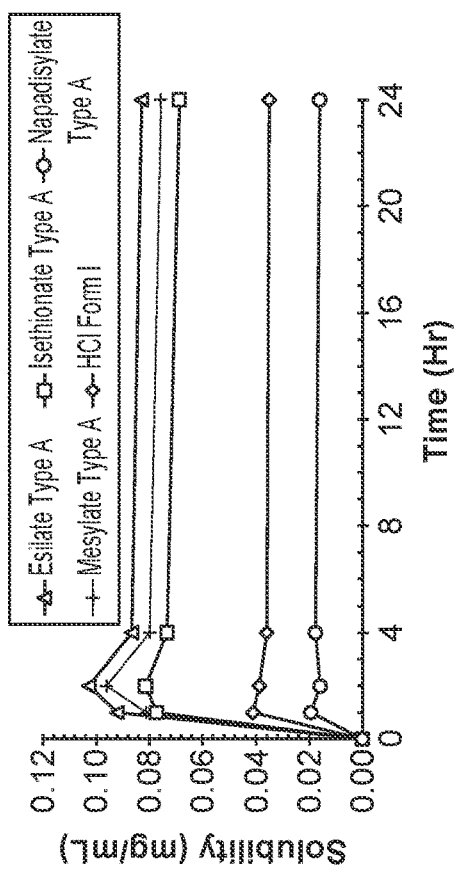
Figure 75C:
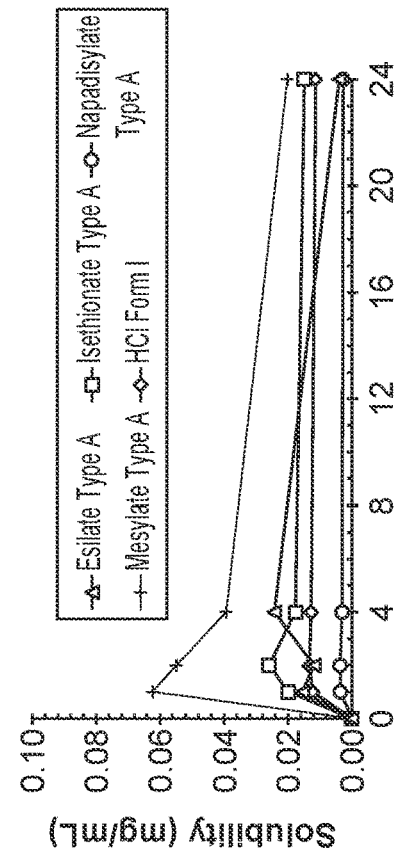
Figure 75D:
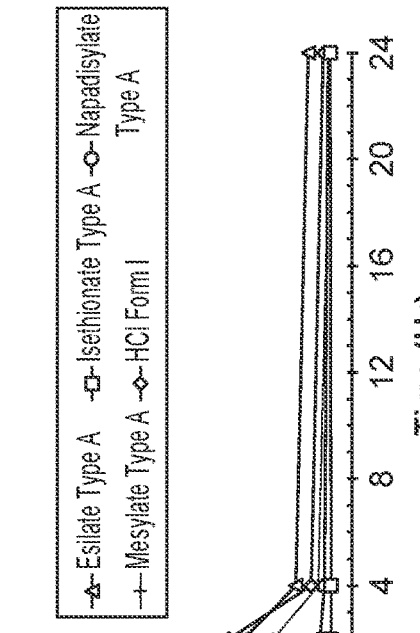

The present disclosure provides, in one embodiment, a crystalline form of 4-(cyclopropylamino)-2-(4-(4-(ethylsulfonyl)piperazin-1-yl)phenylamino)pyrimidine-5-carboxamide (Compound I Type D) characterized by an X-ray powder diffractogram as substantially shown in FIG. 65A.

In another embodiment, provided is a process for making Compound I Type D. In one embodiment, the process for making Compound I Type D is as described in the Examples provided herein.

e. Compound I Type E

The present disclosure provides, in one embodiment, a crystalline form of 4-(cyclopropylamino)-2-(4-(4-(ethylsulfonyl)piperazin-1-yl)phenylamino)pyrimidine-5-carboxamide (Compound I Type E) characterized by an X-ray powder diffractogram as substantially shown in FIG. 65A.

In another embodiment, provided is a process for making Compound I Type E. In one embodiment, the process for making Compound I Type E is as described in the Examples provided herein.

Cerdulatinib Salts

HCl Salts a. Compound I HCl Form I

The present disclosure provides, in one embodiment, a crystalline form of a hydrochloride salt of 4-(cyclopropylamino)-2-(4-(4-(ethylsulfonyl)piperazin-1-yl)phenylamino)pyrimidine-5-carboxamide (Compound I HCl Form I, also referred to herein as Compound I mono-HCl Form I) characterized by an X-ray powder diffractogram comprising the following peaks: 8.7, 15.9, and 20.0 °2θ, each ±0.2 °2θ, as determined on a diffractometer using Cu-Kα radiation. In one embodiment, the diffractogram of Compound I HCl Form I further comprises one or more peaks at: 11.5, 22.5, and 25.5 °2θ, each ±0.2 °2θ.

In one embodiment, Compound I HCl Form I is characterized by an X-ray powder diffractogram comprising at least two of the following peaks: 4.3, 8.0, 8.6, 8.7, 11.5, 15.3, 15.9, 17.3, 18.1, 20.0, 21.7, 22.5, 25.0, 25.5, and 28.9 °2θ, each ±0.2 °2θ. In one embodiment, Compound I HCl Form I is characterized by an X-ray powder diffractogram comprising at least four of the following peaks: 4.3, 8.0, 8.6, 8.7, 11.5, 15.3, 15.9, 17.3, 18.1, 20.0, 21.7, 22.5, 25.0, 25.5, and 28.9 °2θ, each ±0.2 °2θ. In one embodiment, Compound I HCl Form I is characterized by an X-ray powder diffractogram comprising at least six of the following peaks: 4.3, 8.0, 8.6, 8.7, 11.5, 15.3, 15.9, 17.3, 18.1, 20.0, 21.7, 22.5, 25.0, 25.5, and 28.9 °2θ, each ±0.2 °2θ. In one embodiment, Compound I HCl Form I is characterized by an X-ray powder diffractogram comprising at least eight of the following peaks: 4.3, 8.0, 8.6, 8.7, 11.5, 15.3, 15.9, 17.3, 18.1, 20.0, 21.7, 22.5, 25.0, 25.5, and 28.9 °2θ, each ±0.2 °2θ.

In one embodiment, Compound I HCl Form I is characterized by an X-ray powder diffractogram comprising each of the following peaks: 4.3, 8.0, 8.6, 8.7, 11.5, 15.3, 15.9, 17.3, 18.1, 20.0, 21.7, 22.5, 25.0, 25.5, and 28.9 °2θ, each ±0.2 °2θ. In one embodiment, Compound I Form I is characterized by the full X-ray powder diffractogram as substantially shown in FIG. 3.

In one embodiment, Compound I HCl Form I is characterized as a hydrated form. In one embodiment, Compound I HCl Form I is characterized as a mono hydrate.

In another embodiment, provided is a process for making Compound I HCl Form I. In one embodiment, the process comprises contacting Compound I free base and hydrochloric acid in a solvent. In one embodiment, the solvent comprises one or more of DMSO, DMF, 3-Me-1-BuOH, n-BuOAc, toluene, water, IPA, EtOH and THF. In one embodiment, the process comprises contacting a solution of Compound I Form I in a solvent, such as DMSO, with hydrochloric acid and a solvent, such as DMF, 3-Me-1-BuOH, n-BuOAc, toluene, water, IPA, EtOH or THF, whereby Compound I HCl Form I is formed. In one embodiment, the process for making Compound I HCl Form I is as described in the Examples provided herein.

In certain embodiments, Compound I HCl Form I has one or more improved properties as compared to Compound I free base or other salts or solid forms thereof described herein. These improved properties may include: increased solubility, increased dissolution, increased bioavailability, increased dose response, decreased hygroscopicity, more desired morphology, and the like.

b. Compound I HCl Form II

The present disclosure provides, in one embodiment, a crystalline form of a hydrochloride salt of 4-(cyclopropylamino)-2-(4-(4-(ethylsulfonyl)piperazin-1-yl)phenylamino)pyrimidine-5-carboxamide (Compound I HCl Form II, also referred to herein as Compound I mono-HCl Form II) characterized by an X-ray powder diffractogram comprising the following peaks: 9.6, 16.8, and 23.3 °2θ, each ±0.2 °2θ, as determined on a diffractometer using Cu-Kα radiation. In one embodiment, the diffractogram of Compound I HCl Form II further comprises one or more peaks at: 18.1, 20.9, and 21.7 °2θ, each ±0.2 °2θ.

Figure 4:
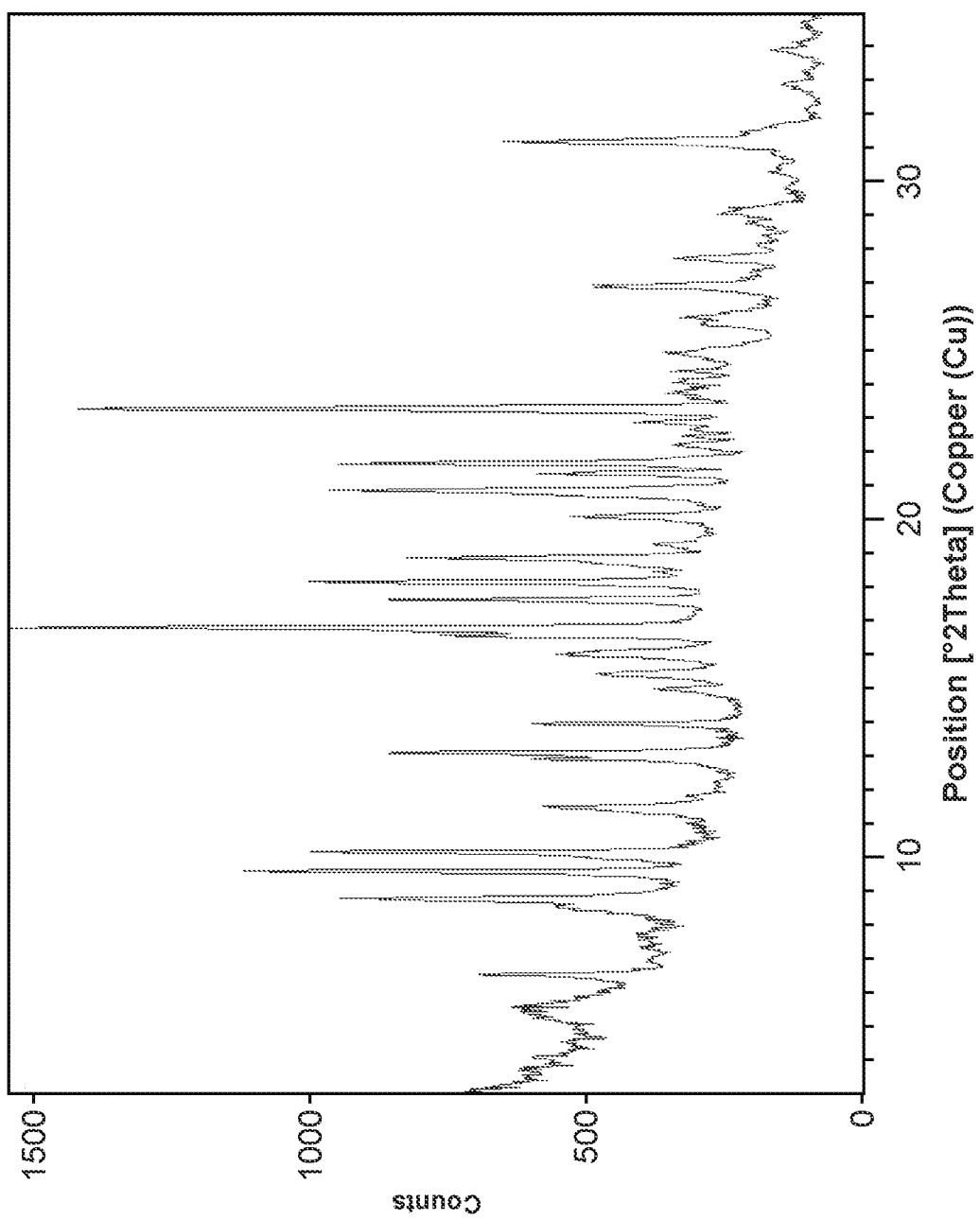
FIG. 4 is an X-ray powder diffractogram of Compound I HCl Form II.

In one embodiment, Compound I HCl Form II is characterized by an X-ray powder diffractogram comprising at least two of the following peaks: 8.8, 9.6, 10.2, 11.5, 13.1, 14.0, 16.8, 17.6, 18.1, 18.9, 20.1, 20.9, 21.7, 23.3, and 31.2 °2θ, each ±0.2 °2θ. In one embodiment, Compound I HCl Form II is characterized by an X-ray powder diffractogram comprising at least four of the following peaks: 8.8, 9.6, 10.2, 11.5, 13.1, 14.0, 16.8, 17.6, 18.1, 18.9, 20.1, 20.9, 21.7, 23.3, and 31.2 °2θ, each ±0.2 °2θ. In one embodiment, Compound I HCl Form II is characterized by an X-ray powder diffractogram comprising at least six of the following peaks: 8.8, 9.6, 10.2, 11.5, 13.1, 14.0, 16.8, 17.6, 18.1, 18.9, 20.1, 20.9, 21.7, 23.3, and 31.2 °2θ, each ±0.2 °2θ. In one embodiment, Compound I HCl Form II is characterized by an X-ray powder diffractogram comprising at least eight of the following peaks: 8.8, 9.6, 10.2, 11.5, 13.1, 14.0, 16.8, 17.6, 18.1, 18.9, 20.1, 20.9, 21.7, 23.3, and 31.2 °2θ, each ±0.2 °2θ. In one embodiment, Compound I HCl Form II is characterized by an X-ray powder diffractogram comprising each of the following peaks: 8.8, 9.6, 10.2, 11.5, 13.1, 14.0, 16.8, 17.6, 18.1, 18.9, 20.1, 20.9, 21.7, 23.3, and 31.2 °2θ, each ±0.2 °2θ. In one embodiment, Compound I HCl Form II is characterized by the full X-ray powder diffractogram as substantially shown in FIG. 4.

In one embodiment, Compound I HCl Form II is characterized as anhydrous.

In one embodiment, provided is a process for making Compound I HCl Form II. In one embodiment, the process comprises contacting a solution of Compound I Form I in DMSO with hydrochloric acid and acetonitrile, whereby Compound I HCl Form II is formed. In one embodiment, the process for making Compound I HCl Form II is as described in the Examples provided herein.

c. Compound I HCl Type B

The present disclosure provides, in one embodiment, a crystalline form of a hydrochloride salt of 4-(cyclopropylamino)-2-(4-(4-(ethylsulfonyl)piperazin-1-yl)phenylamino)pyrimidine-5-carboxamide (Compound I HCl Type B) characterized by an X-ray powder diffractogram comprising the following peaks: 7.9, 19.6, and 13.3 °2θ, each ±0.2 °2θ, as determined on a diffractometer using Cu-Kα radiation. In one embodiment, the diffractogram of Compound I HCl Type B further comprises one or more peaks at: 22.5, 17.2, and 9.7 °2θ, each ±0.2 °2θ.

Figure 63A:
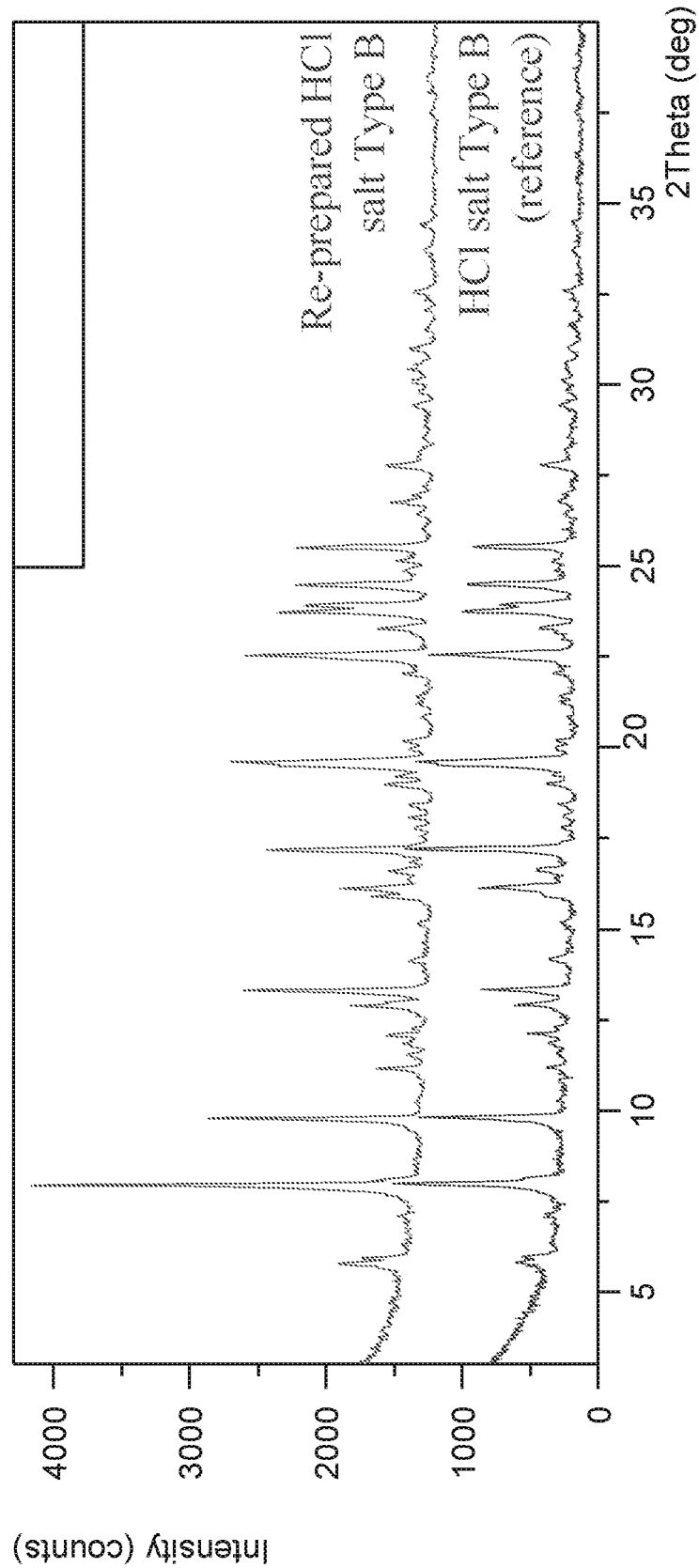
FIG. 63A and FIG. 63B provide analysis of Compound I HCl Type B prepared according to Example 12.
Figure 63B:
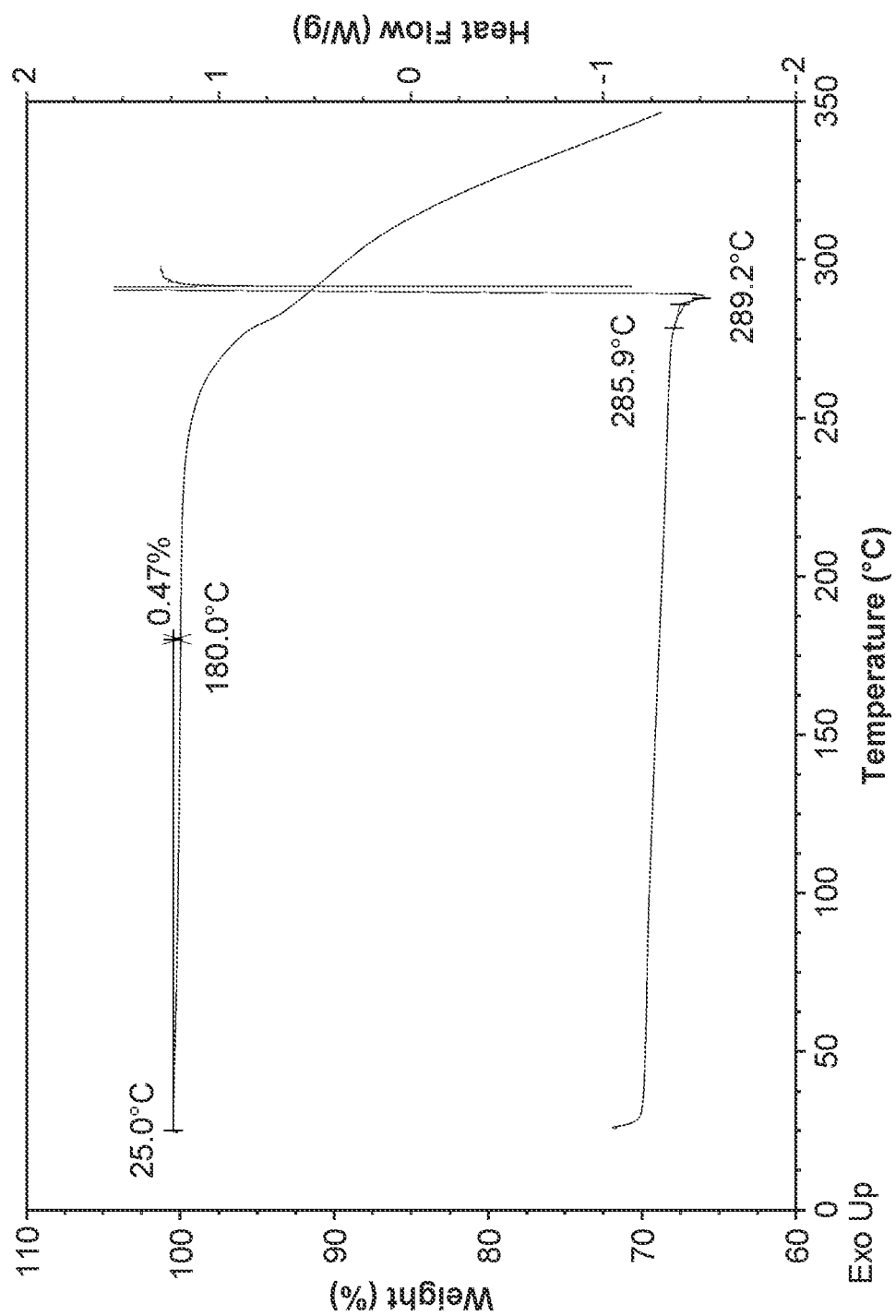

In one embodiment, Compound I HCl Type B is characterized by the full X-ray powder diffractogram as substantially shown in FIG. 63A.

In one embodiment, the process for making Compound I HCl Type B is as described in the Examples provided herein.

d. Compound I Bis-HCl Form I

The present disclosure provides, in one embodiment, a crystalline form of a bis-hydrochloride salt of 4-(cyclopropylamino)-2-(4-(4-(ethylsulfonyl)piperazin-1-yl)phenylamino)pyrimidine-5-carboxamide (Compound I bis-HCl Form I) characterized by an X-ray powder diffractogram comprising the following peaks: 10.1, 19.4, and 20.9 °2θ, each ±0.2 °2θ, as determined on a diffractometer using Cu-Kα radiation. In one embodiment, the diffractogram of Compound I bis-HCl Form I further comprises one or more peaks at: 13.1, 19.6, and 23.6 °2θ, each ±0.2 °2θ.

Figure 5:
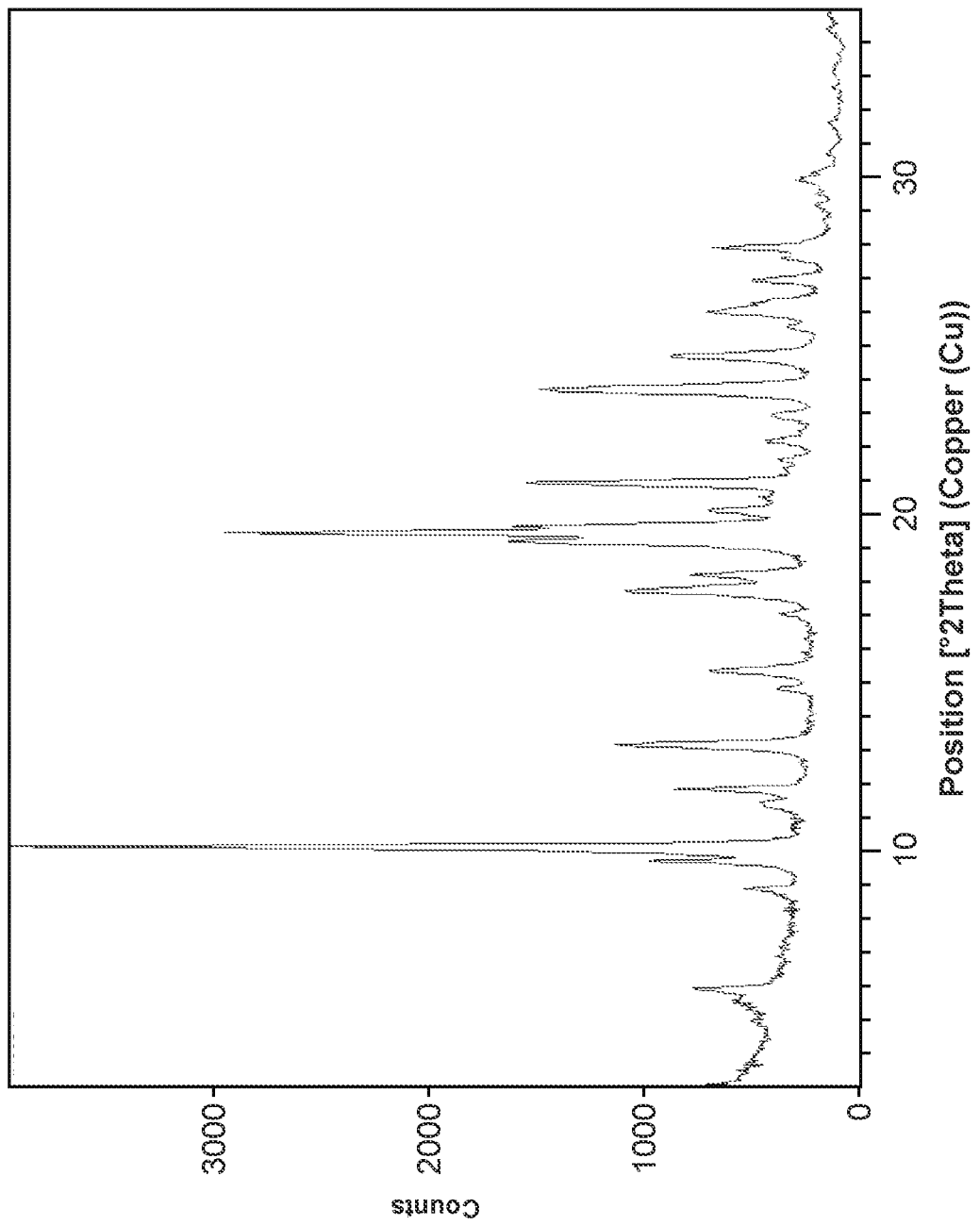
FIG. 5 is an X-ray powder diffractogram of Compound I bis-HCl Form I.

In one embodiment, Compound I bis-HCl Form I is characterized by an X-ray powder diffractogram comprising at least two of the following peaks: 9.7, 10.1, 11.8, 13.1, 15.3, 17.7, 18.2, 19.1, 19.4, 19.6, 20.9, 23.6, 24.7, 26.0, and 27.9 °2θ, each ±0.2 °2θ. In one embodiment, Compound I bis-HCl Form I is characterized by an X-ray powder diffractogram comprising at least four of the following peaks: 9.7, 10.1, 11.8, 13.1, 15.3, 17.7, 18.2, 19.1, 19.4, 19.6, 20.9, 23.6, 24.7, 26.0, and 27.9 °2θ, each ±0.2 °2θ. In one embodiment, Compound I bis-HCl Form I is characterized by an X-ray powder diffractogram comprising at least six of the following peaks: 9.7, 10.1, 11.8, 13.1, 15.3, 17.7, 18.2, 19.1, 19.4, 19.6, 20.9, 23.6, 24.7, 26.0, and 27.9 °2θ, each ±0.2 °2θ. In one embodiment, Compound I bis-HCl Form I is characterized by an X-ray powder diffractogram comprising at least eight of the following peaks: 9.7, 10.1, 11.8, 13.1, 15.3, 17.7, 18.2, 19.1, 19.4, 19.6, 20.9, 23.6, 24.7, 26.0, and 27.9 °2θ, each ±0.2 °2θ. In one embodiment, Compound I bis-HCl Form I is characterized by an X-ray powder diffractogram comprising each of the following peaks: 9.7, 10.1, 11.8, 13.1, 15.3, 17.7, 18.2, 19.1, 19.4, 19.6, 20.9, 23.6, 24.7, 26.0, and 27.9 °2θ, each ±0.2 °2θ. In one embodiment, Compound I bis-HCl Form I is characterized by the full X-ray powder diffractogram as substantially shown in FIG. 5.

In one embodiment, provided is a process for making Compound I bis-HCl Form I. In one embodiment, the process comprises contacting a solution of Compound I Form I in DMSO with acetonitrile at room temperature, followed by addition of dry hydrochloric acid in THF, whereby Compound I bis-HCl form I is formed. Alternatively, in another embodiment, this process comprises contacting a solution of Compound I Form I in DMSO with acetonitrile at room temperature, followed by addition of aqueous hydrochloric acid in THF, whereby Compound I bis-HCl form I is formed.

e. Compound I HCl Amorphous

Figure 6:
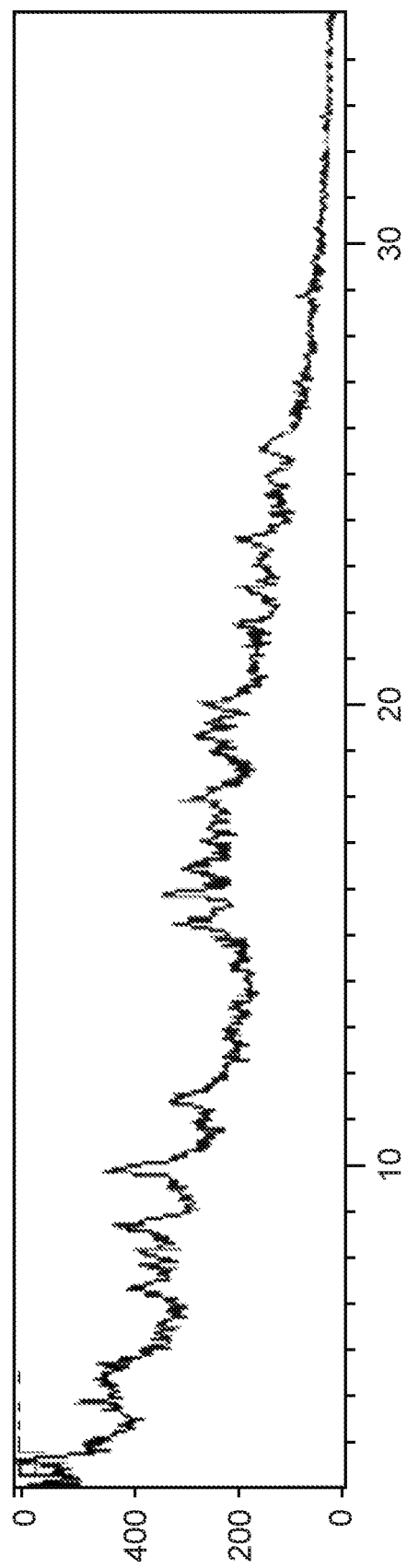
FIG. 6 is an X-ray powder diffractogram of Compound I HCl Form I amorphous.

The present disclosure provides, in one embodiment, an amorphous form of a hydrochloride salt of 4-(cyclopropylamino)-2-(4-(4-(ethylsulfonyl)piperazin-1-yl)phenylamino)pyrimidine-5-carboxamide (Compound I HCl Amorphous) characterized by an X-ray powder as substantially shown in FIG. 6. The X-ray powder diffractogram of Compound I HCl amorphous also indicates the presence of a minimal amount of Compound I HCl Form I.

In one embodiment, provided is a process for making Compound I HCl amorphous. For instance, in one embodiment Compound I HCl amorphous is formed via lyophilization of a solution comprising Compound I HCl Form I, water and THF.

Esylate Salts a. Compound I Esylate Form I

The present disclosure provides, in one embodiment, a crystalline form of an esylate salt of 4-(cyclopropylamino)-2-(4-(4-(ethylsulfonyl)piperazin-1-yl)phenylamino)pyrimidine-5-carboxamide (Compound I esylate Form I) characterized by an X-ray powder diffractogram comprising the following peaks: 5.6, 20.2, and 23.5 °2θ, each ±0.2 °2θ, as determined on a diffractometer using Cu-Kα radiation. In one embodiment, the diffractogram of Compound I esylate Form I further comprises one or more peaks at: 7.2, 16.8, and 17.5 °2θ, each ±0.2 °2θ.

Figure 7:
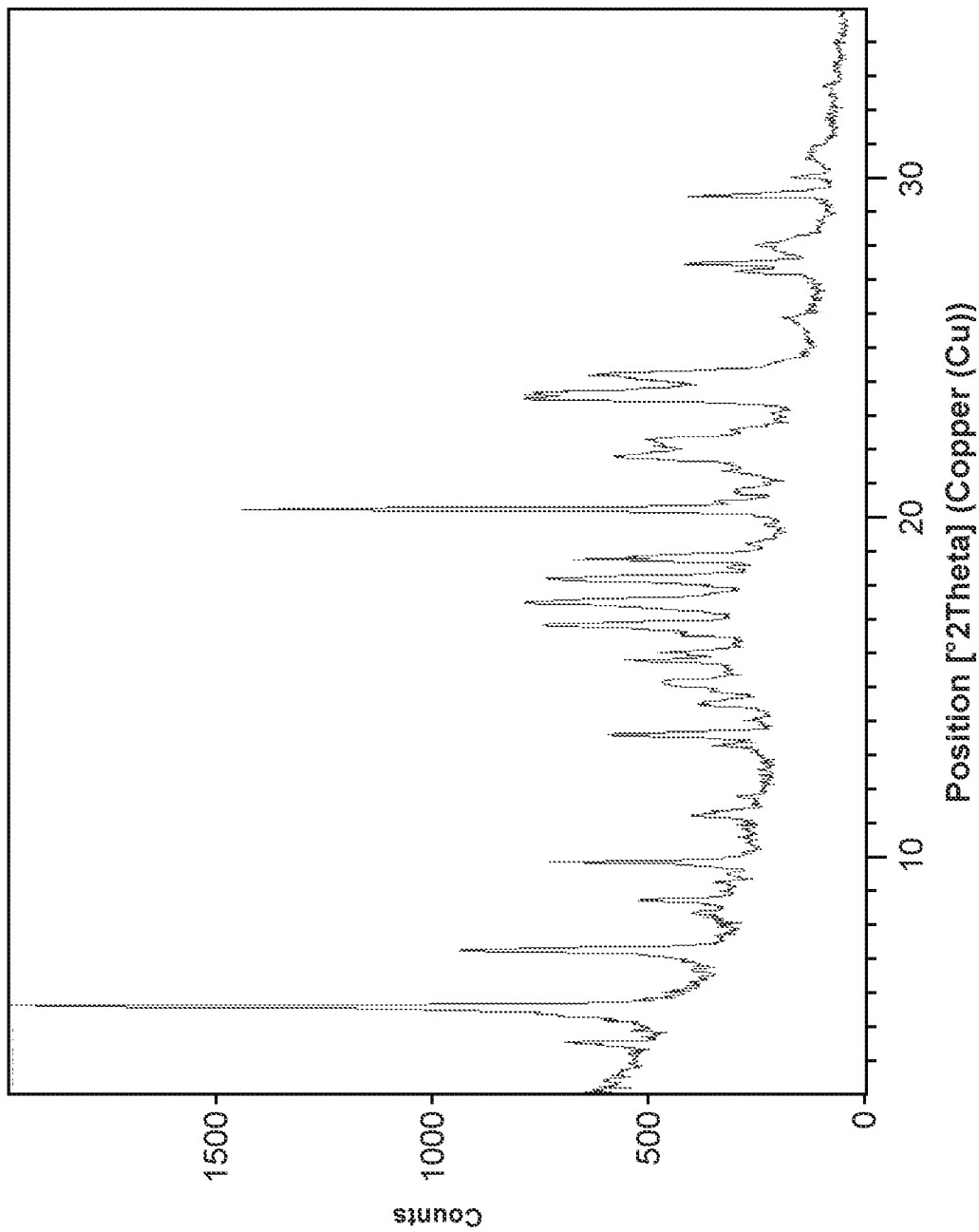
FIG. 7 is an X-ray powder diffractogram of Compound I esylate Form I.

In one embodiment, Compound I esylate Form I is characterized by an X-ray powder diffractogram comprising at least two of the following peaks: 5.6, 7.2, 9.9, 13.6, 15.8, 16.8, 17.5, 18.2, 18.7, 20.2, 21.8, 22.3, 23.5, 24.2, and 29.4 °2θ, each ±0.2 °2θ. In one embodiment, Compound I esylate Form I is characterized by an X-ray powder diffractogram comprising at least four of the following peaks: 5.6, 7.2, 9.9, 13.6, 15.8, 16.8, 17.5, 18.2, 18.7, 20.2, 21.8, 22.3, 23.5, 24.2, and 29.4 °2θ, each ±0.2 °2θ. In one embodiment, Compound I esylate Form I is characterized by an X-ray powder diffractogram comprising at least six of the following peaks: 5.6, 7.2, 9.9, 13.6, 15.8, 16.8, 17.5, 18.2, 18.7, 20.2, 21.8, 22.3, 23.5, 24.2, and 29.4 °2θ, each ±0.2 °2θ. In one embodiment, Compound I esylate Form I is characterized by an X-ray powder diffractogram comprising at least eight of the following peaks: 5.6, 7.2, 9.9, 13.6, 15.8, 16.8, 17.5, 18.2, 18.7, 20.2, 21.8, 22.3, 23.5, 24.2, and 29.4 °2θ, each ±0.2 °2θ. In one embodiment, Compound I esylate Form I is characterized by an X-ray powder diffractogram comprising each of the following peaks: 5.6, 7.2, 9.9, 13.6, 15.8, 16.8, 17.5, 18.2, 18.7, 20.2, 21.8, 22.3, 23.5, 24.2, and 29.4 °2θ, each ±0.2 °2θ. In one embodiment, Compound I esylate Form I is characterized by the full X-ray powder diffractogram as substantially shown in FIG. 7.

In one embodiment, provided is a process for making Compound I esylate Form I. In one embodiment, the process comprises contacting a solution of Compound I Form I in DMSO with ethane sulfonic acid and a solvent such as 3-Me-1-BuOH, n-BuOAc, toluene, water, IPA, acetonitrile, MEK, EtOH, or THF, whereby Compound I esylate Form I is formed. In one embodiment, the process for making Compound I esylate Form I is as described in the Examples provided herein.

b. Compound I esylate Type A

The present disclosure provides, in one embodiment, a crystalline form of an esylate salt of 4-(cyclopropylamino)-2-(4-(4-(ethylsulfonyl)piperazin-1-yl)phenylamino)pyrimidine-5-carboxamide (Compound I esylate Type A) characterized by an X-ray powder diffractogram comprising the following peaks: 7.5, 18.1, and 14.9 °2θ, each ±0.2 °2θ, as determined on a diffractometer using Cu-Kα radiation. In one embodiment, the diffractogram of Compound I esylate Type A further comprises one or more peaks at: 15.9, 16.2, and 24.6 °2θ±0.2 °2θ, each ±0.2 °2θ.

In another embodiment, provided is a process for making Compound I esylate Type A. In one embodiment, the process for making Compound I esylate Type A is as described in the Examples provided herein.

Edisylate Salts a. Compound I Edisylate Form I

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Form I) characterized by the full X-ray powder diffractogram comprising the following peaks: 17.0, 17.7, and 19.3 °2θ, each ±0.2 °2θ, as determined on a diffractometer using Cu-Kα radiation. In one embodiment, the diffractogram of Compound I edisylate Form I further comprises one or more peaks at: 10.4, 18.3, and 22.1 °2θ, each ±0.2 °2θ.

Figure 8:
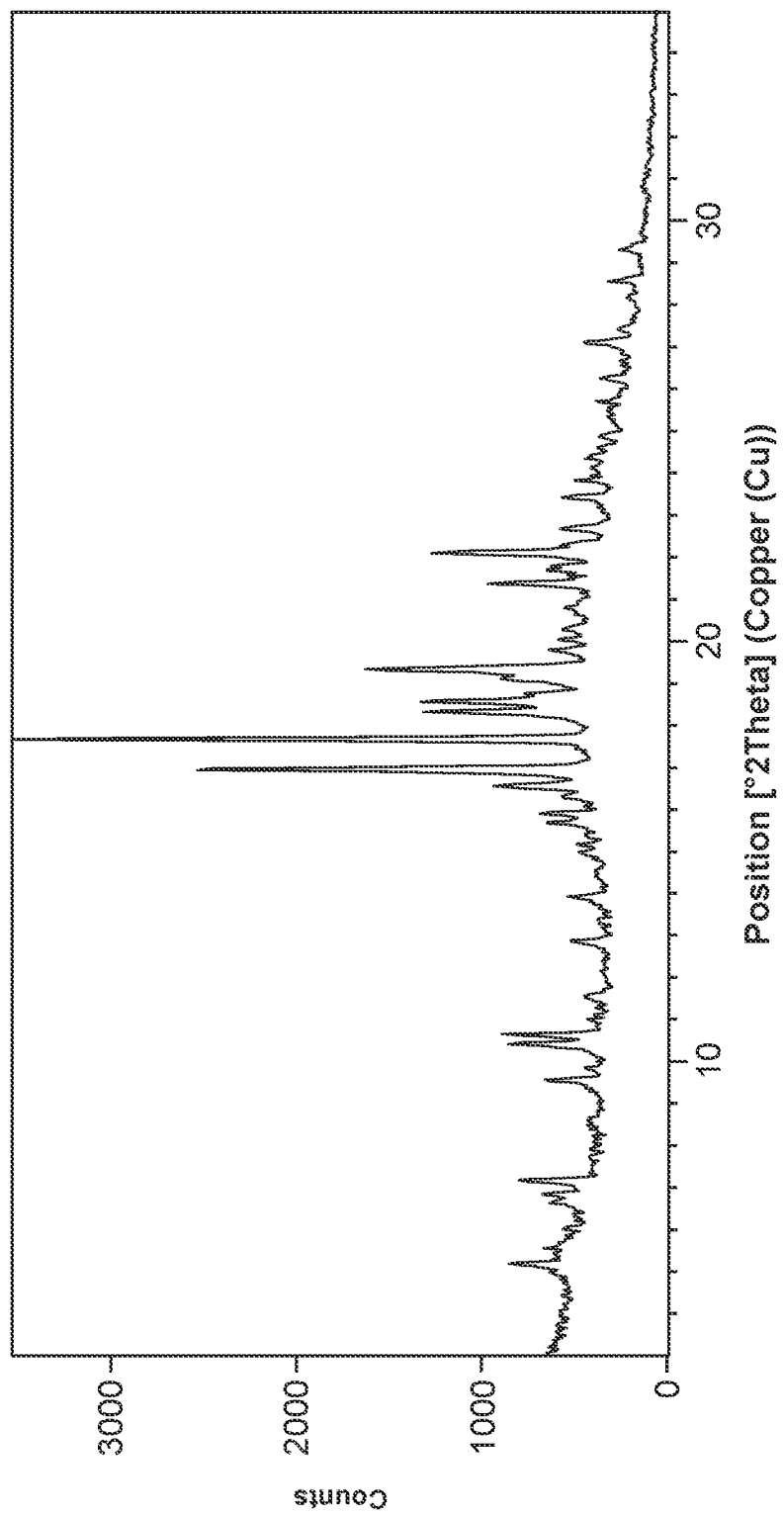
FIG. 8 is an X-ray powder diffractogram of Compound I edisylate Form I.

In one embodiment, Compound I edisylate Form I is characterized by an X-ray powder diffractogram comprising at least two of the following peaks: 5.2, 6.8, 7.2, 9.6. 10.4, 10.6, 15.7, 15.9, 16.5, 17.0 17.7, 18.3, 18.6, 19.3, 21.4, and 22.1 °2θ, each ±0.2 °2θ. In one embodiment, Compound I edisylate Form I is characterized by an X-ray powder diffractogram comprising at least four of the following peaks: 5.2, 6.8, 7.2, 9.6. 10.4, 10.6, 15.7, 15.9, 16.5, 17.0 17.7, 18.3, 18.6, 19.3, 21.4, and 22.1 °2θ, each ±0.2 °2θ. In one embodiment, Compound I edisylate Form I is characterized by an X-ray powder diffractogram comprising at least six of the following peaks: 5.2, 6.8, 7.2, 9.6. 10.4, 10.6, 15.7, 15.9, 16.5, 17.0 17.7, 18.3, 18.6, 19.3, 21.4, and 22.1 °2θ, each ±0.2 °2θ. In one embodiment, Compound I edisylate Form I is characterized by an X-ray powder diffractogram comprising at least eight of the following peaks: 5.2, 6.8, 7.2, 9.6. 10.4, 10.6, 15.7, 15.9, 16.5, 17.0 17.7, 18.3, 18.6, 19.3, 21.4, and 22.1 °2θ, each ±0.2 °2θ. In one embodiment, Compound I edisylate Form I is characterized by an X-ray powder diffractogram comprising each of the following peaks: 5.2, 6.8, 7.2, 9.6. 10.4, 10.6, 15.7, 15.9, 16.5, 17.0 17.7, 18.3, 18.6, 19.3, 21.4, and 22.1 °2θ, each ±0.2 °2θ. In one embodiment, Compound I edisylate Form I is characterized by the full X-ray powder diffractogram as substantially shown in FIG. 8.

In one embodiment, provided is a process for making Compound I edisylate Form I. In one embodiment, the process comprises contacting a solution of Compound I Form I in DMSO with ethane 1,2-disulfonic acid and a solvent such as 3-Me-1-BuOH or IPA, whereby Compound I edisylate Form I is formed. In one embodiment, the process for making Compound I edisylate Form I is as described in the Examples provided herein.

b. Compound I Edisylate Form II

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Form II) characterized by the full X-ray powder diffractogram comprising the following peaks: 9.1, 17.8, and 18.6 °2θ, each ±0.2 °2θ, as determined on a diffractometer using Cu-Kα radiation. In one embodiment, the diffractogram of Compound I edisylate Form II further comprises one or more peaks at: 13.7, 19.5, and 20.1 °2θ, each ±0.2 °2θ.

Figure 9:
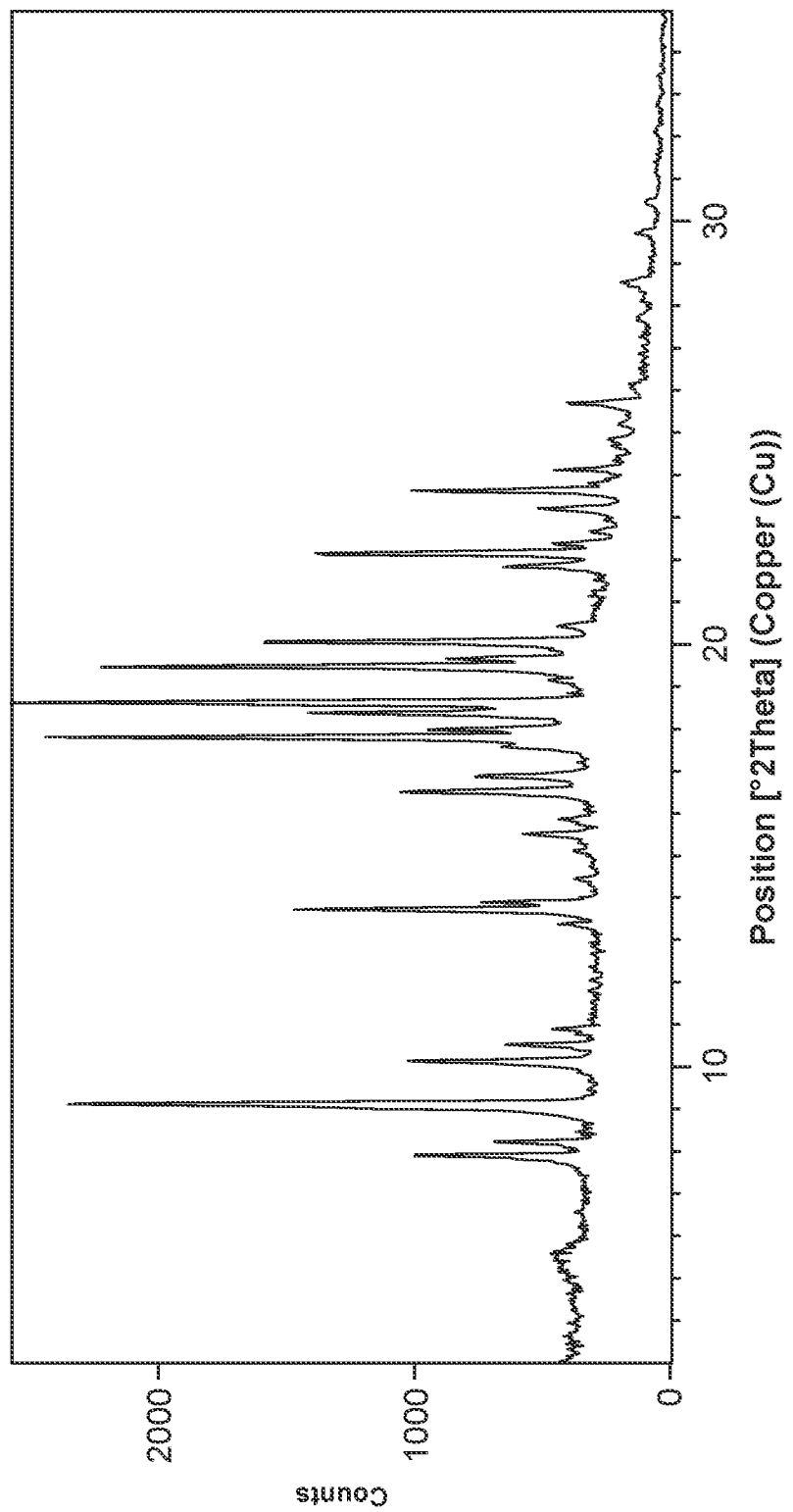
FIG. 9 is an X-ray powder diffractogram of Compound I edisylate Form II.

In one embodiment, Compound I edisylate Form II is characterized by an X-ray powder diffractogram comprising at least two of the following peaks: 7.9, 8.2, 9.1, 10.1, 13.7, 16.5, 16.9, 17.8, 18.4, 18.6, 19.5, 20.1, 22.1, and 23.6 °2θ, each ±0.2 °2θ. In one embodiment, Compound I edisylate Form II is characterized by an X-ray powder diffractogram comprising at least four of the following peaks: 7.9, 8.2, 9.1, 10.1, 13.7, 16.5, 16.9, 17.8, 18.4, 18.6, 19.5, 20.1, 22.1, and 23.6 °2θ, each ±0.2 °2θ. In one embodiment, Compound I edisylate Form II is characterized by an X-ray powder diffractogram comprising at least six of the following peaks: 7.9, 8.2, 9.1, 10.1, 13.7, 16.5, 16.9, 17.8, 18.4, 18.6, 19.5, 20.1, 22.1, and 23.6 °2θ, each ±0.2 °2θ. In one embodiment, Compound I edisylate Form II is characterized by an X-ray powder diffractogram comprising at least eight of the following peaks: 7.9, 8.2, 9.1, 10.1, 13.7, 16.5, 16.9, 17.8, 18.4, 18.6, 19.5, 20.1, 22.1, and 23.6 °2θ, each ±0.2 °2θ. In one embodiment, Compound I edisylate Form II is characterized by an X-ray powder diffractogram comprising each of the following peaks: 7.9, 8.2, 9.1, 10.1, 13.7, 16.5, 16.9, 17.8, 18.4, 18.6, 19.5, 20.1, 22.1, and 23.6 °2θ, each ±0.2 °2θ. In one embodiment, Compound I edisylate Form II is characterized by the full X-ray powder diffractogram as substantially shown in FIG. 9.

In one embodiment, provided is a process for making Compound I edisylate Form II. In one embodiment, the process comprises contacting a solution of Compound I Form I in DMSO with ethane 1,2-disulfonic acid and a solvent such as n-BuOAc, toluene, MEK, EtOH, or THF, whereby Compound I edisylate Form II is formed. In one embodiment, the process for making Compound I edisylate Form II is as described in the Examples provided herein.

c. Compound I Edisylate Form III

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Form III) characterized by the full X-ray powder diffractogram comprising the following peaks: 4.1, 16.3, and 21.8 °2θ, each ±0.2 °2θ, as determined on a diffractometer using Cu-Kα radiation. In one embodiment, the diffractogram of Compound I edisylate Form III further comprises one or more peaks at: 8.2, 13.1, and 17.0 °2θ, each ±0.2 °2θ.

Figure 10:
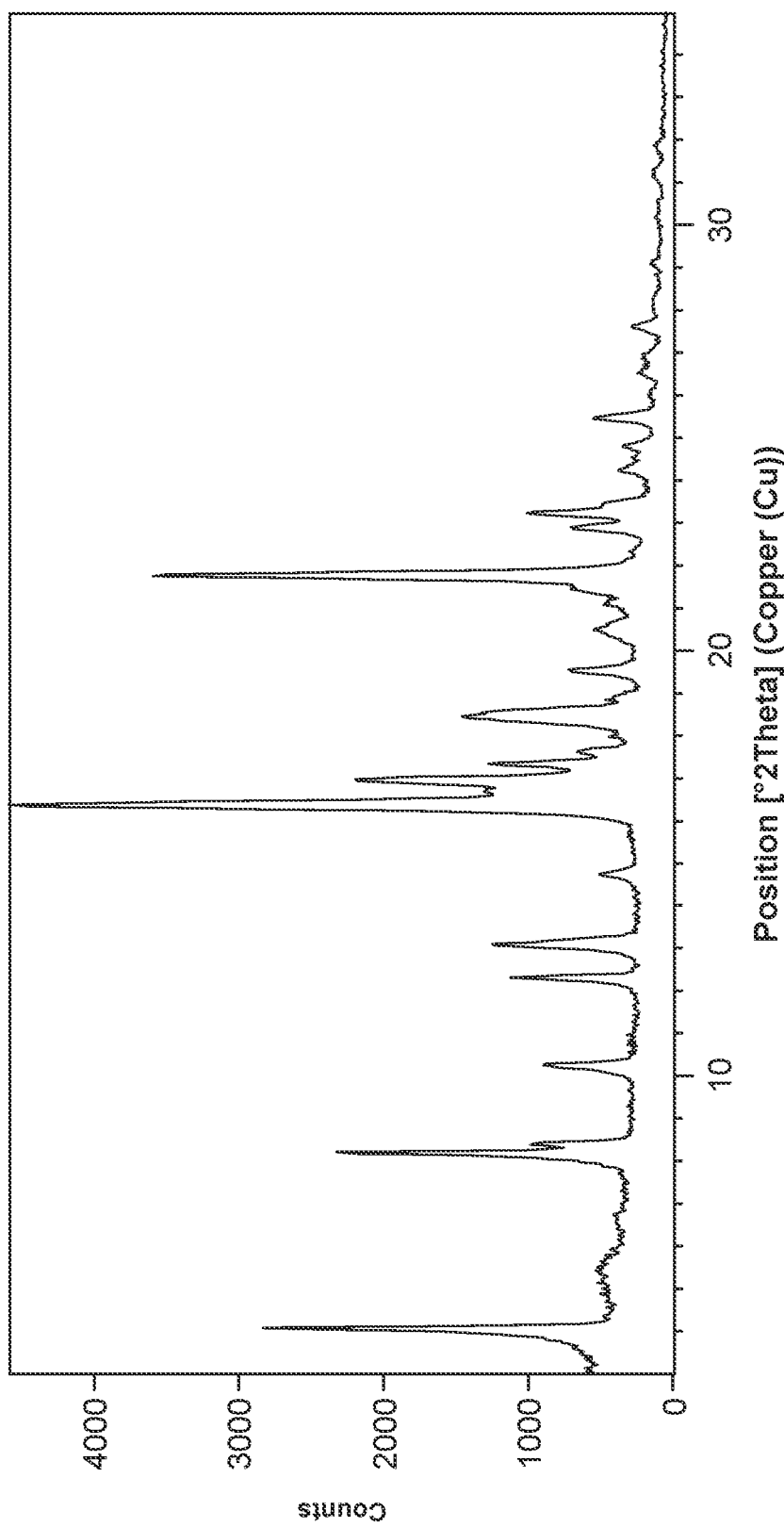
FIG. 10 is an X-ray powder diffractogram of Compound I edisylate Form III.

In one embodiment, Compound I edisylate Form III is characterized by an X-ray powder diffractogram comprising at least two of the following peaks: 4.1, 8.2, 8.4, 10.3, 12.3, 13.1, 16.3, 17.0, 17.3, 18.4, 18.6, 21.7, 22.9, and 23.2 °2θ, each ±0.2 °2θ. In one embodiment, Compound I edisylate Form III is characterized by an X-ray powder diffractogram comprising at least four of the following peaks: 4.1, 8.2, 8.4, 10.3, 12.3, 13.1, 16.3, 17.0, 17.3, 18.4, 18.6, 21.7, 22.9, and 23.2 °2θ, each ±0.2 °2θ. In one embodiment, Compound I edisylate Form III is characterized by an X-ray powder diffractogram comprising at least six of the following peaks: 4.1, 8.2, 8.4, 10.3, 12.3, 13.1, 16.3, 17.0, 17.3, 18.4, 18.6, 21.7, 22.9, and 23.2 °2θ, each ±0.2 °2θ. In one embodiment, Compound I edisylate Form III is characterized by an X-ray powder diffractogram comprising at least eight of the following peaks: 4.1, 8.2, 8.4, 10.3, 12.3, 13.1, 16.3, 17.0, 17.3, 18.4, 18.6, 21.7, 22.9, and 23.2 °2θ, each ±0.2 °2θ. In one embodiment, Compound I edisylate Form III is characterized by an X-ray powder diffractogram comprising each of the following peaks: 4.1, 8.2, 8.4, 10.3, 12.3, 13.1, 16.3, 17.0, 17.3, 18.4, 18.6, 21.7, 22.9, and 23.2 °2θ, each ±0.2 °2θ. In one embodiment, Compound I edisylate Form III is characterized by the full X-ray powder diffractogram as substantially shown in FIG. 10.

In one embodiment, provided is a process for making Compound I edisylate Form III. In one embodiment, the process comprises contacting a solution of Compound I Form I in DMSO with ethane 1,2-disulfonic acid and water, whereby Compound I edisylate Form III is formed. In one embodiment, the process for making Compound I edisylate Form III is as described in the Examples provided herein.

d. Compound I Edisylate Form IV

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Form IV) characterized by the full X-ray powder diffractogram comprising the following peaks: 3.4, 10.1, and 20.1 °2θ, each ±0.2 °2θ, as determined on a diffractometer using Cu-Kα radiation. In one embodiment, the diffractogram of Compound I edisylate Form IV further comprises one or more peaks at: 16.8, 19.5, and 22.8 °2θ, each ±0.2 °2θ.

Figure 11:
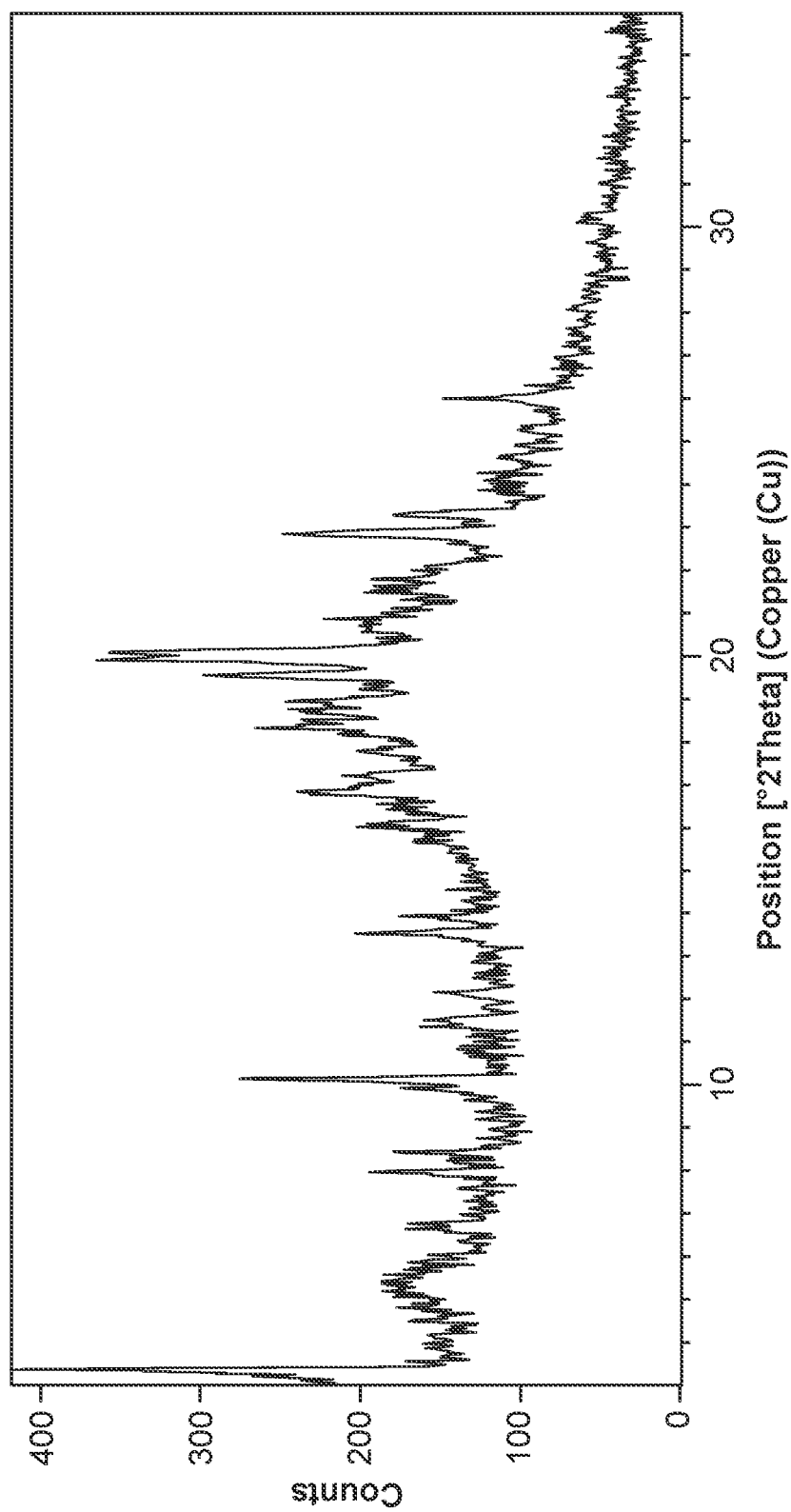
FIG. 11 is an X-ray powder diffractogram of Compound I edisylate Form IV.

In one embodiment, Compound I edisylate Form IV is characterized by an X-ray powder diffractogram comprising at least two of the following peaks: 3.4, 5.5, 8.2, 10.1, 11.4, 13.5, 16.8, 18.6, 19.5, 20.1, 22.8, 23.3, and 26.0 °2θ, each ±0.2 °2θ. In one embodiment, Compound I edisylate Form IV is characterized by an X-ray powder diffractogram comprising at least four of the following peaks: 3.4, 5.5, 8.2, 10.1, 11.4, 13.5, 16.8, 18.6, 19.5, 20.1, 22.8, 23.3, and 26.0 °2θ, each ±0.2 °2θ. In one embodiment, Compound I edisylate Form IV is characterized by an X-ray powder diffractogram comprising at least six of the following peaks: 3.4, 5.5, 8.2, 10.1, 11.4, 13.5, 16.8, 18.6, 19.5, 20.1, 22.8, 23.3, and 26.0 °2θ, each ±0.2 °2θ. In one embodiment, Compound I edisylate Form IV is characterized by an X-ray powder diffractogram comprising at least eight of the following peaks: 3.4, 5.5, 8.2, 10.1, 11.4, 13.5, 16.8, 18.6, 19.5, 20.1, 22.8, 23.3, and 26.0 °2θ, each ±0.2 °2θ. In one embodiment, Compound I edisylate Form IV is characterized by an X-ray powder diffractogram comprising each of the following peaks: 3.4, 5.5, 8.2, 10.1, 11.4, 13.5, 16.8, 18.6, 19.5, 20.1, 22.8, 23.3, and 26.0 °2θ, each ±0.2 °2θ. In one embodiment, Compound I edisylate Form IV is characterized by the full X-ray powder diffractogram as substantially shown in FIG. 11.

In one embodiment, provided is a process for making Compound I edisylate Form IV. In one embodiment, the process comprises contacting a solution of Compound I Form I in DMSO with ethane 1,2-disulfonic acid and acetonitrile, whereby Compound I edisylate Form IV is formed. In one embodiment, the process for making Compound I edisylate Form IV is as described in the Examples provided herein.

e. Compound I Edisylate Type A

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Type A).

In one embodiment, provided is a process for making Compound I edisylate Type A. In one embodiment, the process for making Compound I edisylate Type A is as described in the Examples provided herein.

f. Compound I Edisylate Type B

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Type B).

In one embodiment, provided is a process for making Compound I edisylate Type B. In one embodiment, the process for making Compound I edisylate Type B is as described in the Examples provided herein.

g. Compound I Edisylate Type C

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Type C).

In one embodiment, provided is a process for making Compound I edisylate Type C. In one embodiment, the process for making Compound I edisylate Type C is as described in the Examples provided herein.

h. Compound I Edisylate Type D

The present disclosure provides, in one embodiment, a crystalline form of an edisylate salt of 4-(cyclopropylamino)-2-(4-(4-(ethylsulfonyl)piperazin-1-yl)phenylamino)pyrimidine-5-carboxamide (Compound I edisylate Type D) characterized by the full X-ray powder diffractogram comprising the following peaks: 14.7, 24.5, and 19.1 °2θ, each ±0.2 °2θ, as determined on a diffractometer using Cu-Kα radiation. In one embodiment, the diffractogram of Compound I edisylate Type D further comprises one or more peaks at: 10.7, 22.8, and 20.7 °2θ, each ±0.2 °2θ.

In one embodiment, provided is a process for making Compound I edisylate Type D. In one embodiment, the process for making Compound I edisylate Type D is as described in the Examples provided herein.

Mesylate Salts a. Compound I Mesylate Form I

The present disclosure provides, in one embodiment, a crystalline form of a mesylate salt of 4-(cyclopropylamino)-2-(4-(4-(ethylsulfonyl)piperazin-1-yl)phenylamino)pyrimidine-5-carboxamide (Compound I mesylate Form I) characterized by the full X-ray powder diffractogram comprising the following peaks: 4.0, 8.0, and 18.7 °2θ, each ±0.2 °2θ, as determined on a diffractometer using Cu-Kα radiation. In one embodiment, the diffractogram of Compound I mesylate Form I further comprises one or more peaks at: 5.5, 17.3, and 20.0 °2θ, each ±0.2 °2θ.

Figure 12:
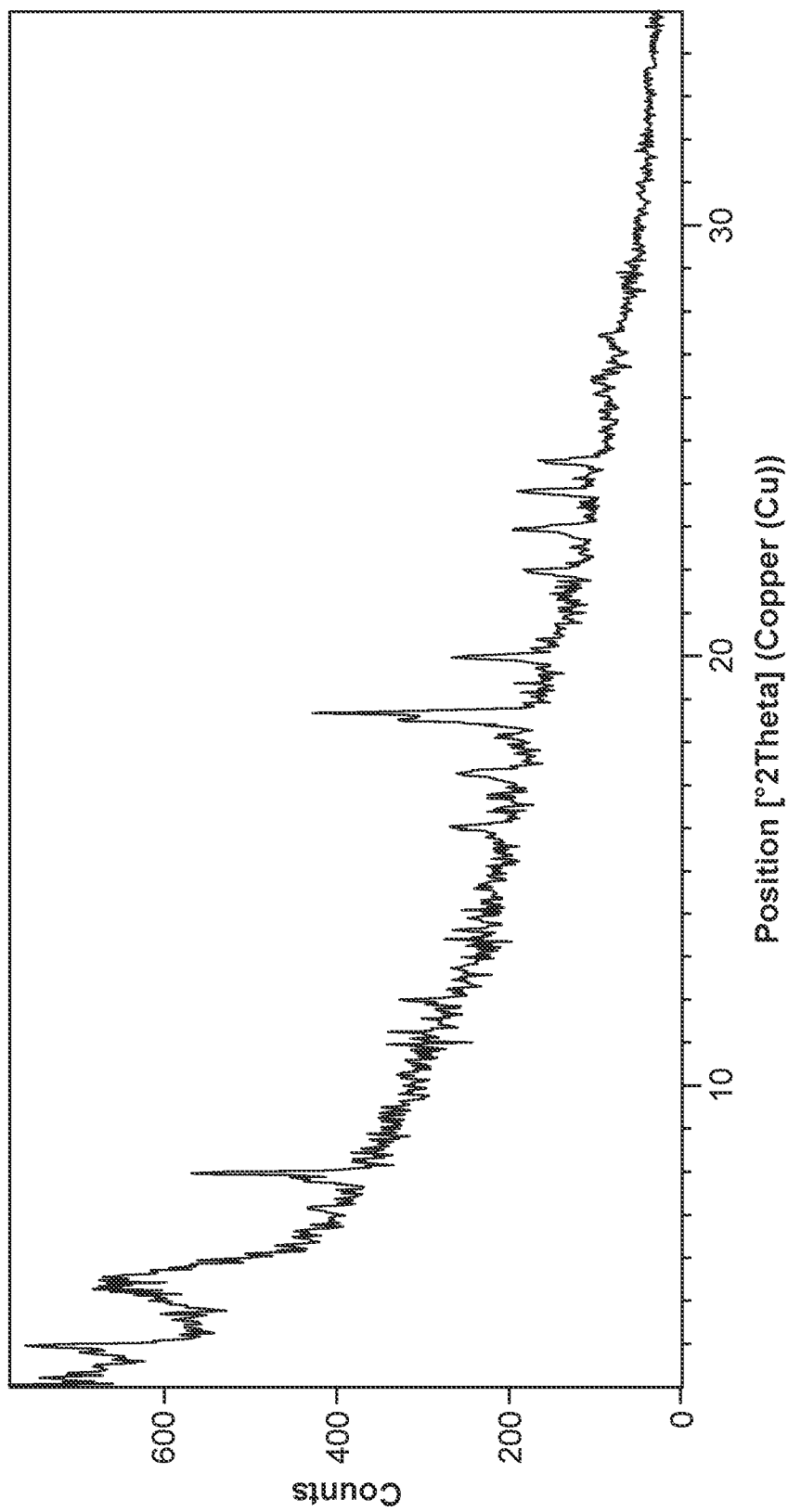
FIG. 12 is an X-ray powder diffractogram of Compound I mesylate Form I.

In one embodiment, Compound I mesylate Form I is characterized by an X-ray powder diffractogram comprising at least two of the following peaks: 4.0, 5.5, 8.0, 16.0, 17.3, 18.7, 20.0, 21.9, 23.0, 23.8, and 24.5 °2θ, each ±0.2 °2θ. In one embodiment, Compound I mesylate Form I is characterized by an X-ray powder diffractogram comprising at least four of the following peaks: 4.0, 5.5, 8.0, 16.0, 17.3, 18.7, 20.0, 21.9, 23.0, 23.8, and 24.5 °2θ, each ±0.2 °2θ. In one embodiment, Compound I mesylate Form I is characterized by an X-ray powder diffractogram comprising at least six of the following peaks: 4.0, 5.5, 8.0, 16.0, 17.3, 18.7, 20.0, 21.9, 23.0, 23.8, and 24.5 °2θ, each ±0.2 °2θ. In one embodiment, Compound I mesylate Form I is characterized by an X-ray powder diffractogram comprising at least eight of the following peaks: 4.0, 5.5, 8.0, 16.0, 17.3, 18.7, 20.0, 21.9, 23.0, 23.8, and 24.5 °2θ, each ±0.2 °2θ. In one embodiment, Compound I mesylate Form I is characterized by an X-ray powder diffractogram comprising each of the following peaks: 4.0, 5.5, 8.0, 16.0, 17.3, 18.7, 20.0, 21.9, 23.0, 23.8, and 24.5 °2θ, each ±0.2 °2θ. In one embodiment, Compound I mesylate Form I is characterized by the full X-ray powder diffractogram as substantially shown in FIG. 12.

In one embodiment, provided is a process for making Compound I mesylate Form I. In one embodiment, the process comprises contacting a solution of Compound I Form I in DMSO with methane sulfonic acid and IPA, whereby Compound I mesylate Form I is formed. In one embodiment, the process for making Compound I mesylate Form I is as described in the Examples provided herein.

b. Compound I Mesylate Form II

The present disclosure provides, in one embodiment, a crystalline form of a mesylate salt of 4-(cyclopropylamino)-2-(4-(4-(ethylsulfonyl)piperazin-1-yl)phenylamino)pyrimidine-5-carboxamide (Compound I mesylate Form II) characterized by the full X-ray powder diffractogram comprising the following peaks: 4.0, 8.0, and 18.7 °2θ, each ±0.2 °2θ, as determined on a diffractometer using Cu-Kα radiation. In one embodiment, the diffractogram of Compound I mesylate Form II further comprises one or more peaks at: 12.0, 20.0, and 23.8 °2θ, each ±0.2 °2θ.

Figure 13:
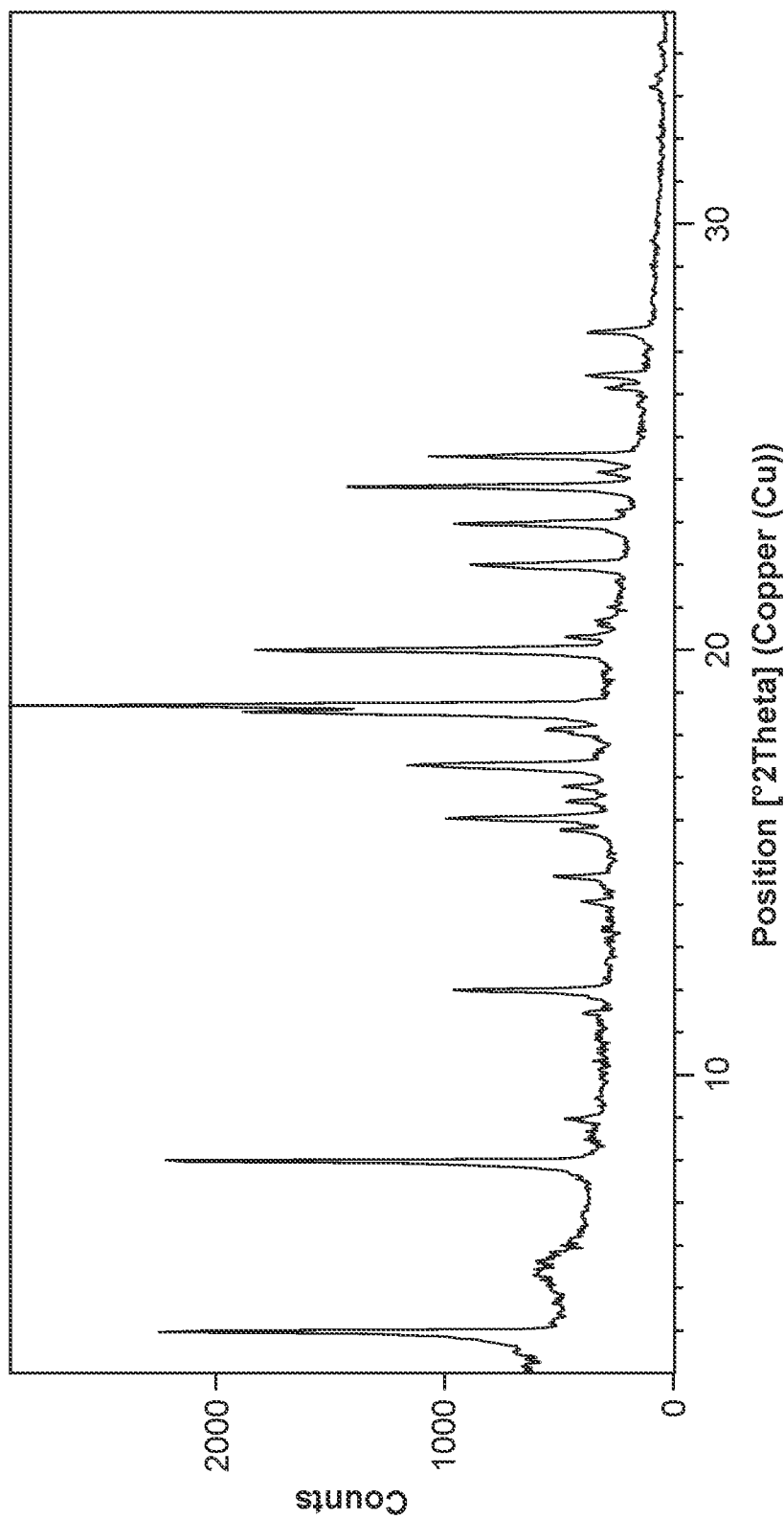
FIG. 13 is an X-ray powder diffractogram of Compound I mesylate Form II.

In one embodiment, Compound I mesylate Form II is characterized by an X-ray powder diffractogram comprising at least two of the following peaks: 4.0, 5.5, 8.0, 12.0, 16.0, 17.3, 18.5, 18.7, 20.0, 22.0, 23.0, 23.8, 24.5, 26.1, 26.4, and 27.5 °2θ, each ±0.2 °2θ. In one embodiment, Compound I mesylate Form II is characterized by an X-ray powder diffractogram comprising at least four of the following peaks: 4.0, 5.5, 8.0, 12.0, 16.0, 17.3, 18.5, 18.7, 20.0, 22.0, 23.0, 23.8, 24.5, 26.1, 26.4, and 27.5 °2θ, each ±0.2 °2θ. In one embodiment, Compound I mesylate Form II is characterized by an X-ray powder diffractogram comprising at least six of the following peaks: 4.0, 5.5, 8.0, 12.0, 16.0, 17.3, 18.5, 18.7, 20.0, 22.0, 23.0, 23.8, 24.5, 26.1, 26.4, and 27.5 °2θ, each ±0.2 °2θ. In one embodiment, Compound I mesylate Form II is characterized by an X-ray powder diffractogram comprising at least eight of the following peaks: 4.0, 5.5, 8.0, 12.0, 16.0, 17.3, 18.5, 18.7, 20.0, 22.0, 23.0, 23.8, 24.5, 26.1, 26.4, and 27.5 °2θ, each ±0.2 °2θ. In one embodiment, Compound I mesylate Form II is characterized by an X-ray powder diffractogram comprising each of the following peaks: 4.0, 5.5, 8.0, 12.0, 16.0, 17.3, 18.5, 18.7, 20.0, 22.0, 23.0, 23.8, 24.5, 26.1, 26.4, and 27.5 °2θ, each ±0.2 °2θ. In one embodiment, Compound I mesylate Form II is characterized by the full X-ray powder diffractogram as substantially shown in FIG. 13.

In one embodiment, provided is a process for making Compound I mesylate Form II. In one embodiment, the process comprises contacting a solution of Compound I Form I in DMSO with methane sulfonic acid and a solvent such as DMF, 3-Me-1-BuOH, n-BuOH, toluene, water, acetonitrile, MEK, EtOH, or THF, whereby Compound I mesylate Form I is formed. In one embodiment, the process for making Compound I mesylate Form II is as described in the Examples provided herein.

c. Compound I Mesylate Form III

The present disclosure provides, in one embodiment, a crystalline form of a mesylate salt of 4-(cyclopropylamino)-2-(4-(4-(ethylsulfonyl)piperazin-1-yl)phenylamino)pyrimidine-5-carboxamide (Compound I mesylate Form III) characterized by an X-ray powder diffractogram comprising the following peaks: 4.0, 8.0, and 18.5 °2θ, each ±0.2 °2θ, as determined on a diffractometer using Cu-Kα radiation. In one embodiment, the diffractogram of Compound I mesylate Form III further comprises one or more peaks at: 18.7, 20.1, and 23.9 °2θ, each ±0.2 °2θ.

Figure 14:
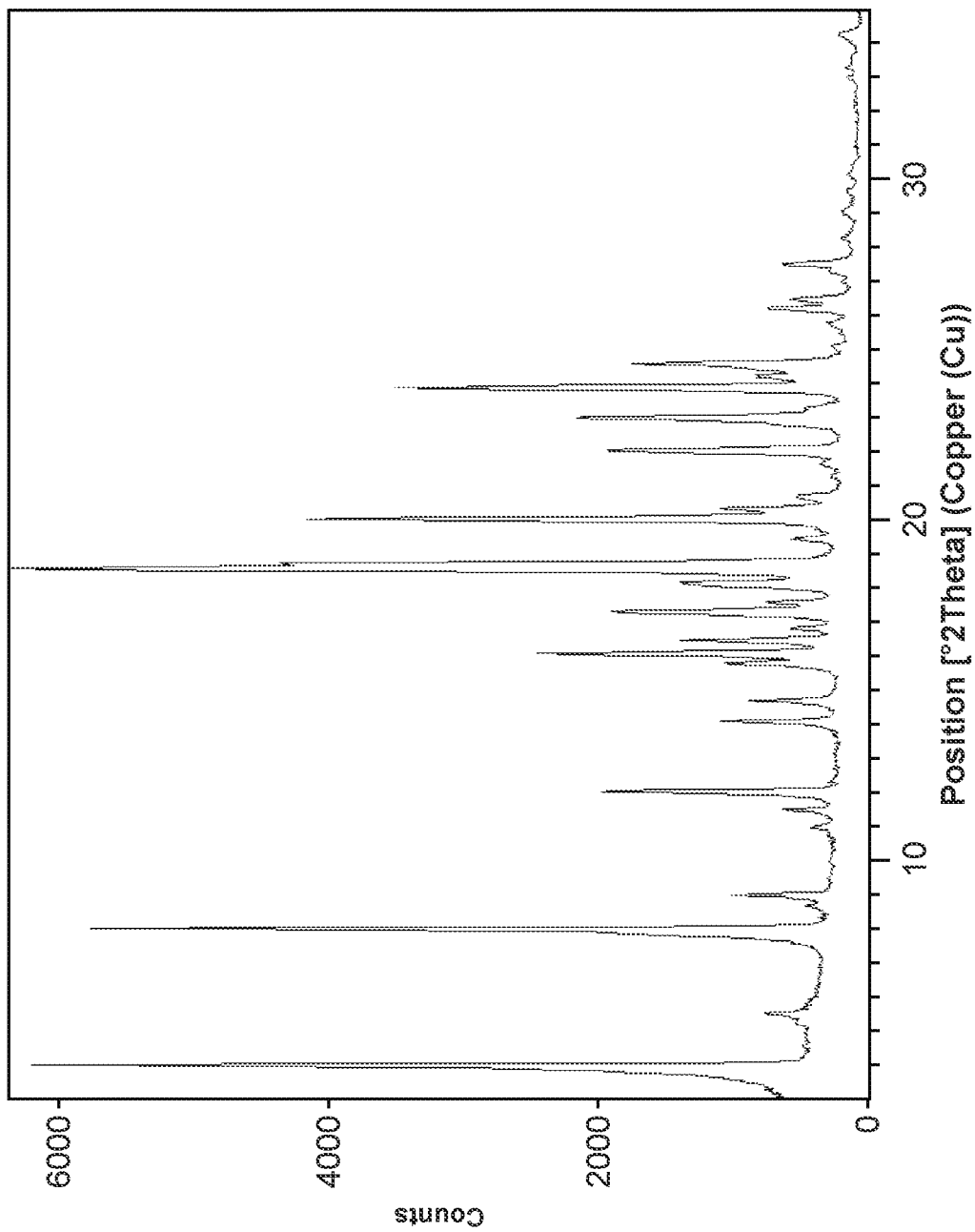
FIG. 14 is an X-ray powder diffractogram of Compound I mesylate Form III.

In one embodiment, Compound I mesylate Form III is characterized by an X-ray powder diffractogram comprising at least two of the following peaks: 4.0, 8.0, 9.0, 12.0, 14.1, 16.0, 16.5, 17.3, 18.5, 18.7, 20.1, 22.0, 23.0, 23.9, 24.6 °2θ, each ±0.2 °2θ. In one embodiment, Compound I mesylate Form III is characterized by an X-ray powder diffractogram comprising at least four of the following peaks: 4.0, 8.0, 9.0, 12.0, 14.1, 16.0, 16.5, 17.3, 18.5, 18.7, 20.1, 22.0, 23.0, 23.9, and 24.6 °2θ, each ±0.2 °2θ. In one embodiment, Compound I mesylate Form III is characterized by an X-ray powder diffractogram comprising at least six of the following peaks: 4.0, 8.0, 9.0, 12.0, 14.1, 16.0, 16.5, 17.3, 18.5, 18.7, 20.1, 22.0, 23.0, 23.9, and 24.6 °2θ, each ±0.2 °2θ. In one embodiment, Compound I mesylate Form III is characterized by an X-ray powder diffractogram comprising at least eight of the following peaks: 4.0, 8.0, 9.0, 12.0, 14.1, 16.0, 16.5, 17.3, 18.5, 18.7, 20.1, 22.0, 23.0, 23.9, and 24.6 °2θ, each ±0.2 °2θ. In one embodiment, Compound I mesylate Form III is characterized by an X-ray powder diffractogram comprising each of the following peaks: 4.0, 8.0, 9.0, 12.0, 14.1, 16.0, 16.5, 17.3, 18.5, 18.7, 20.1, 22.0, 23.0, 23.9, and 24.6 °2θ, each ±0.2 °2θ. In one embodiment, Compound I mesylate Form III is characterized by the full X-ray powder diffractogram as substantially shown in FIG. 14.

In one embodiment, provided is a process for making Compound I mesylate Form III. In one embodiment, the process comprises contacting a solution of Compound I Form III in DMSO with methane sulfonic acid and a solvent such as ethanol or EtOAc, whereby Compound I mesylate Form III is formed. In one embodiment, the process for making Compound I mesylate Form III is as described in the Examples provided herein.

d. Compound I Bis-Mesylate Form I

The present disclosure provides, in one embodiment, a crystalline form of a bis-mesylate salt of 4-(cyclopropylamino)-2-(4-(4-(ethylsulfonyl)piperazin-1-yl)phenylamino)pyrimidine-5-carboxamide (Compound I bis-mesylate Form I) characterized by an X-ray powder diffractogram comprising the following peaks: 10.1, 18.0, and 20.0 °2θ, each ±0.2 °2θ, as determined on a diffractometer using Cu-Kα radiation. In one embodiment, the diffractogram of Compound I bis-mesylate Form I further comprises one or more peaks at: 7.9, 9.7, and 17.1 °2θ, each ±0.2 °2θ.

Figure 15:
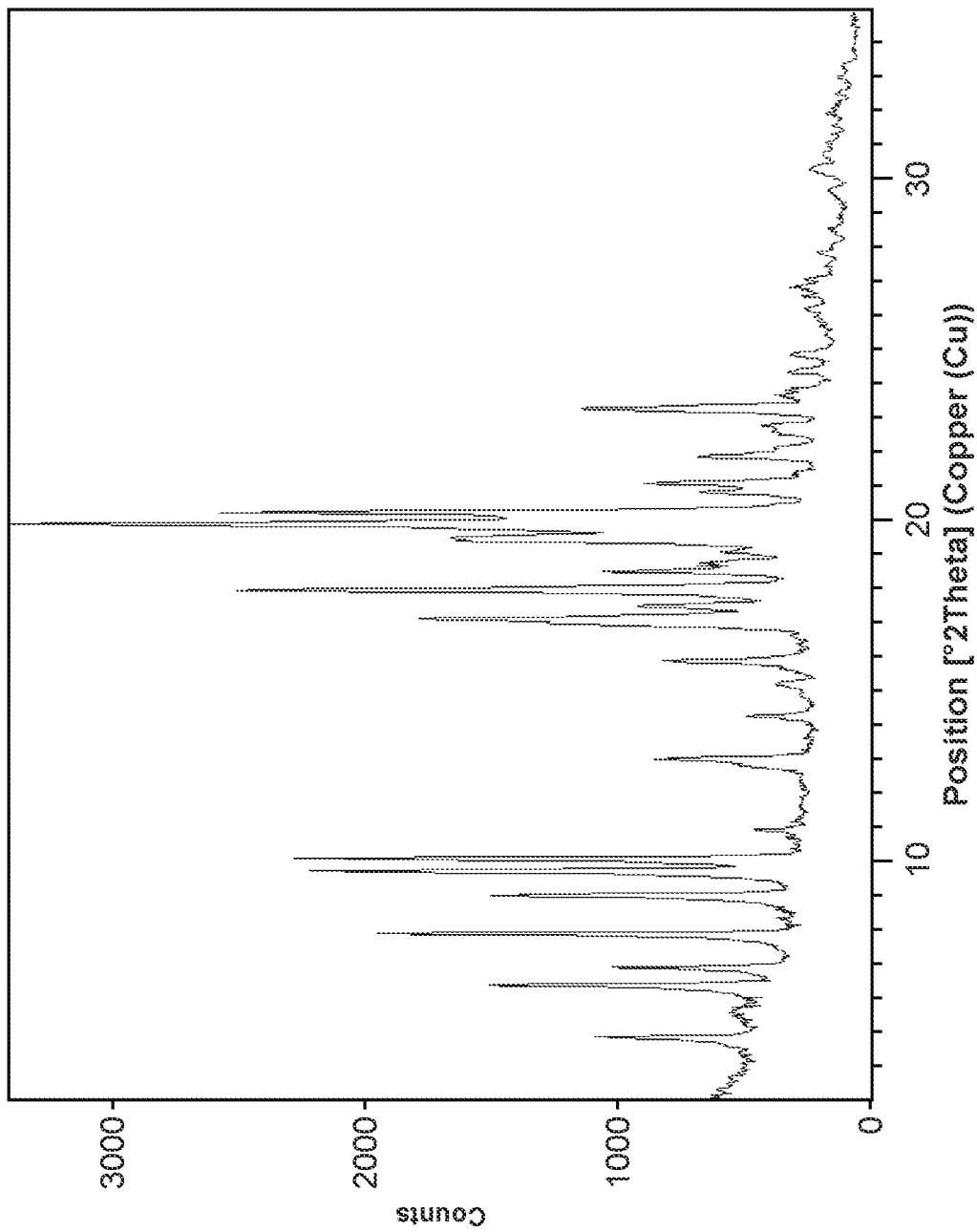
FIG. 15 is an X-ray powder diffractogram of Compound I bis-mesylate Form II.

In one embodiment, Compound I bis-mesylate Form I is characterized by an X-ray powder diffractogram comprising at least two of the following peaks: 5.0, 6.4, 6.9, 7.9, 9.0, 9.7, 10.1, 17.1, 18.0, 18.5, 19.5, 20.0, 20.2, 21.1, and 23.2 °2θ, each ±0.2 °2θ. In one embodiment, Compound I bis-mesylate Form I is characterized by an X-ray powder diffractogram comprising at least four of the following peaks: 5.0, 6.4, 6.9, 7.9, 9.0, 9.7, 10.1, 17.1, 18.0, 18.5, 19.5, 20.0, 20.2, 21.1, and 23.2 °2θ, each ±0.2 °2θ. In one embodiment, Compound I bis-mesylate Form I is characterized by an X-ray powder diffractogram comprising at least six of the following peaks: 5.0, 6.4, 6.9, 7.9, 9.0, 9.7, 10.1, 17.1, 18.0, 18.5, 19.5, 20.0, 20.2, 21.1, and 23.2 °2θ, each ±0.2 °2θ. In one embodiment, Compound I bis-mesylate Form I is characterized by an X-ray powder diffractogram comprising at least eight of the following peaks: 5.0, 6.4, 6.9, 7.9, 9.0, 9.7, 10.1, 17.1, 18.0, 18.5, 19.5, 20.0, 20.2, 21.1, and 23.2 °2θ, each ±0.2 °2θ. In one embodiment, Compound I bis-mesylate Form I is characterized by an X-ray powder diffractogram comprising each of the following peaks: 5.0, 6.4, 6.9, 7.9, 9.0, 9.7, 10.1, 17.1, 18.0, 18.5, 19.5, 20.0, 20.2, 21.1, and 23.2 °2θ, each ±0.2 °2θ. In one embodiment, Compound I bis-mesylate Form I is characterized by the full X-ray powder diffractogram as substantially shown in FIG. 15.

In one embodiment, provided is a process for making Compound I bis-mesylate Form I. In one embodiment, the process comprises contacting a solution of Compound I Form I in DMSO with methane sulfonic acid and a solvent such as EtOH, EtOAc, and ethanol, whereby Compound I bis-mesylate Form I is formed. In one embodiment, the process for making Compound I bis-mesylate Form I is as described in the Examples provided herein.

e. Compound I Mesylate Type A

The present disclosure provides, in one embodiment, a crystalline form of a mesylate salt of 4-(cyclopropylamino)-2-(4-(4-(ethylsulfonyl)piperazin-1-yl)phenylamino)pyrimidine-5-carboxamide (Compound I mesylate Type A) characterized by an X-ray powder diffractogram comprising the following peaks: 16.0, 16.4, and 16.7 °2θ, each ±0.2 °2θ, as determined on a diffractometer using Cu-Kα radiation. In one embodiment, the diffractogram of Compound I mesylate Type A further comprises one or more peaks at: 24.2, 8.1, and 18.3 °2θ, each ±0.2 °2θ.

In one embodiment, provided is a process for making Compound I mesylate Type A. In one embodiment, the process for making Compound I mesylate Type A is as described in the Examples provided herein.

f. Compound I Mesylate Type B

The present disclosure provides, in one embodiment, a crystalline form of a mesylate salt of 4-(cyclopropylamino)-2-(4-(4-(ethylsulfonyl)piperazin-1-yl)phenylamino)pyrimidine-5-carboxamide (Compound I mesylate Type B).

In one embodiment, provided is a process for making Compound I mesylate Type B. In one embodiment, the process for making Compound I mesylate Type B is as described in the Examples provided herein.

Naphthalene Disulfonate Salts a. Compound I Naphthalene Disulfonate Form I

The present disclosure provides, in one embodiment, a crystalline form of a naphthalene disulfonate salt of 4-(cyclopropylamino)-2-(4-(4-(ethylsulfonyl)piperazin-1-yl)phenylamino)pyrimidine-5-carboxamide (Compound I naphthalene disulfonate Form I) characterized by the full X-ray powder diffractogram comprising the following peaks: 11.7, 19.3, and 22.3 °2θ, each ±0.2 °2θ, as determined on a diffractometer using Cu-Kα radiation. In one embodiment, the diffractogram of Compound I naphthalene disulfonate Form I further comprises one or more peaks at: 5.4, 15.6, and 23.0 °2θ, each ±0.2 °2θ.

Figure 16:
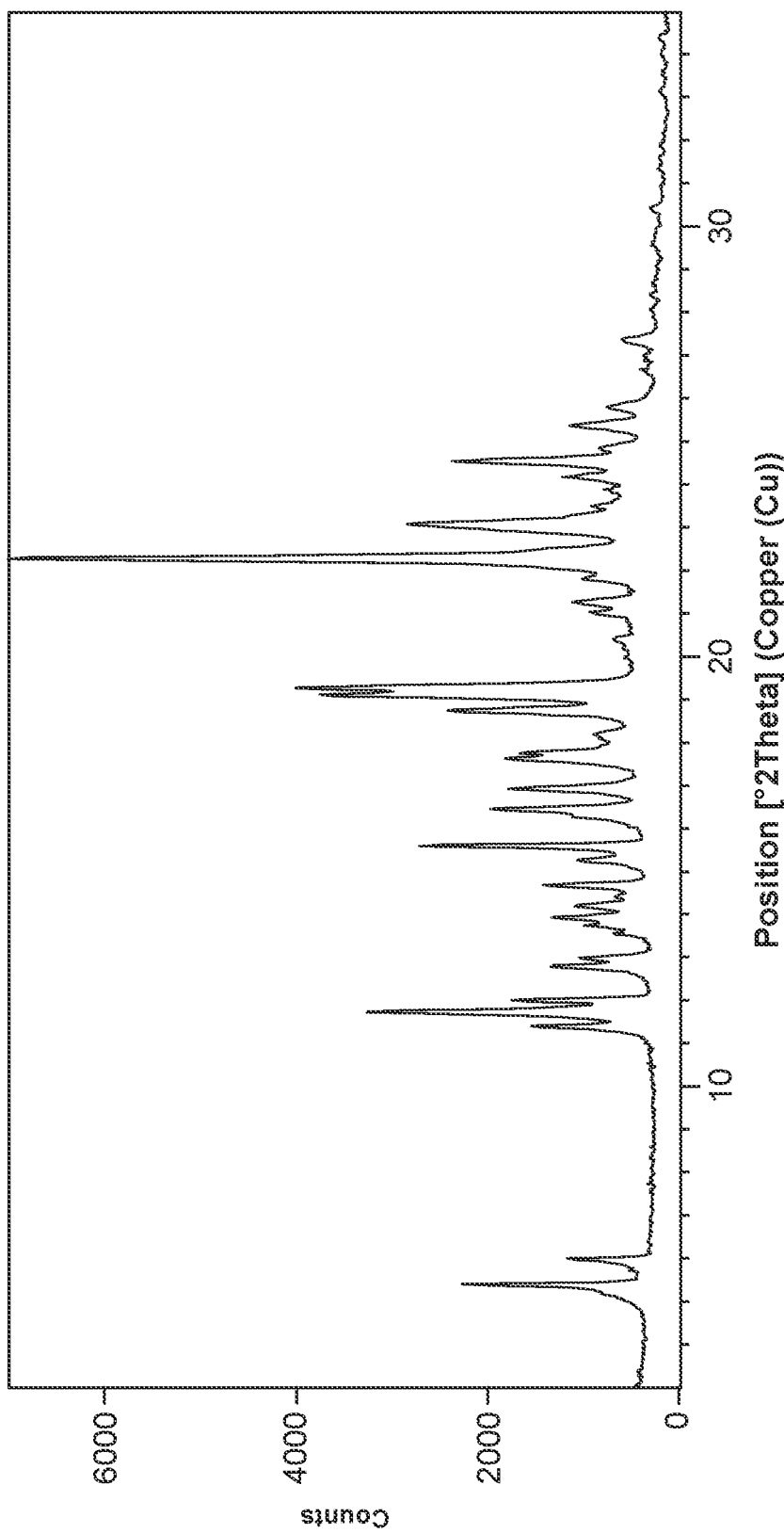
FIG. 16 is an X-ray powder diffractogram of Compound I naphthalene disulfonate Form I.

In one embodiment, Compound I naphthalene disulfonate Form I is characterized by an X-ray powder diffractogram comprising at least two of the following peaks: 5.4, 6.0, 11.4, 11.7, 12.0, 15.6, 16.5, 16.9, 17.6, 18.7, 19.1, 19.3, 22.3, 23.1, and 24.5 °2θ, each ±0.2 °2θ. In one embodiment, Compound I naphthalene disulfonate Form I is characterized by an X-ray powder diffractogram comprising at least four of the following peaks: 5.4, 6.0, 11.4, 11.7, 12.0, 15.6, 16.5, 16.9, 17.6, 18.7, 19.1, 19.3, 22.3, 23.1, and 24.5 °2θ, each ±0.2 °2θ. In one embodiment, Compound I naphthalene disulfonate Form I is characterized by an X-ray powder diffractogram comprising at least six of the following peaks: 5.4, 6.0, 11.4, 11.7, 12.0, 15.6, 16.5, 16.9, 17.6, 18.7, 19.1, 19.3, 22.3, 23.1, and 24.5 °2θ, each ±0.2 °2θ. In one embodiment, Compound I naphthalene disulfonate Form I is characterized by an X-ray powder diffractogram comprising at least eight of the following peaks: 5.4, 6.0, 11.4, 11.7, 12.0, 15.6, 16.5, 16.9, 17.6, 18.7, 19.1, 19.3, 22.3, 23.1, and 24.5 °2θ, each ±0.2 °2θ. In one embodiment, Compound I naphthalene disulfonate Form I is characterized by an X-ray powder diffractogram comprising each of the following peaks: 5.4, 6.0, 11.4, 11.7, 12.0, 15.6, 16.5, 16.9, 17.6, 18.7, 19.1, 19.3, 22.3, 23.1, and 24.5 °2θ, each ±0.2 °2θ. In one embodiment, Compound I naphthalene disulfonate Form I is characterized by the full X-ray powder diffractogram as substantially shown in FIG. 16.

In another embodiment, provided is a process for making Compound I naphthalene disulfonate Form I. In one embodiment, the process comprises contacting a solution of Compound I Form I in DMSO with naphthalene disulfonate and a solvent such as DMF, n-BuOH, or EtOH, whereby Compound I naphthalene disulfonate Form I is formed. In one embodiment, the process for making Compound I naphthalene disulfonate Form I is as described in the Examples provided herein.

b. Compound I Naphthalene Disulfonate Form II

The present disclosure provides, in one embodiment, a crystalline form of a naphthalene disulfonate salt of 4-(cyclopropylamino)-2-(4-(4-(ethylsulfonyl)piperazin-1-yl)phenylamino)pyrimidine-5-carboxamide (Compound I naphthalene disulfonate Form II) characterized by the full X-ray powder diffractogram comprising the following peaks: 7.2, 9.4, and 11.3 °2θ, each ±0.2 °2θ, as determined on a diffractometer using Cu-Kα radiation. In one embodiment, the diffractogram of Compound I naphthalene disulfonate Form II further comprises one or more peaks at: 15.9, 17.9, 20.6, and 20.8 °2θ, each ±0.2 °2θ.

Figure 17:
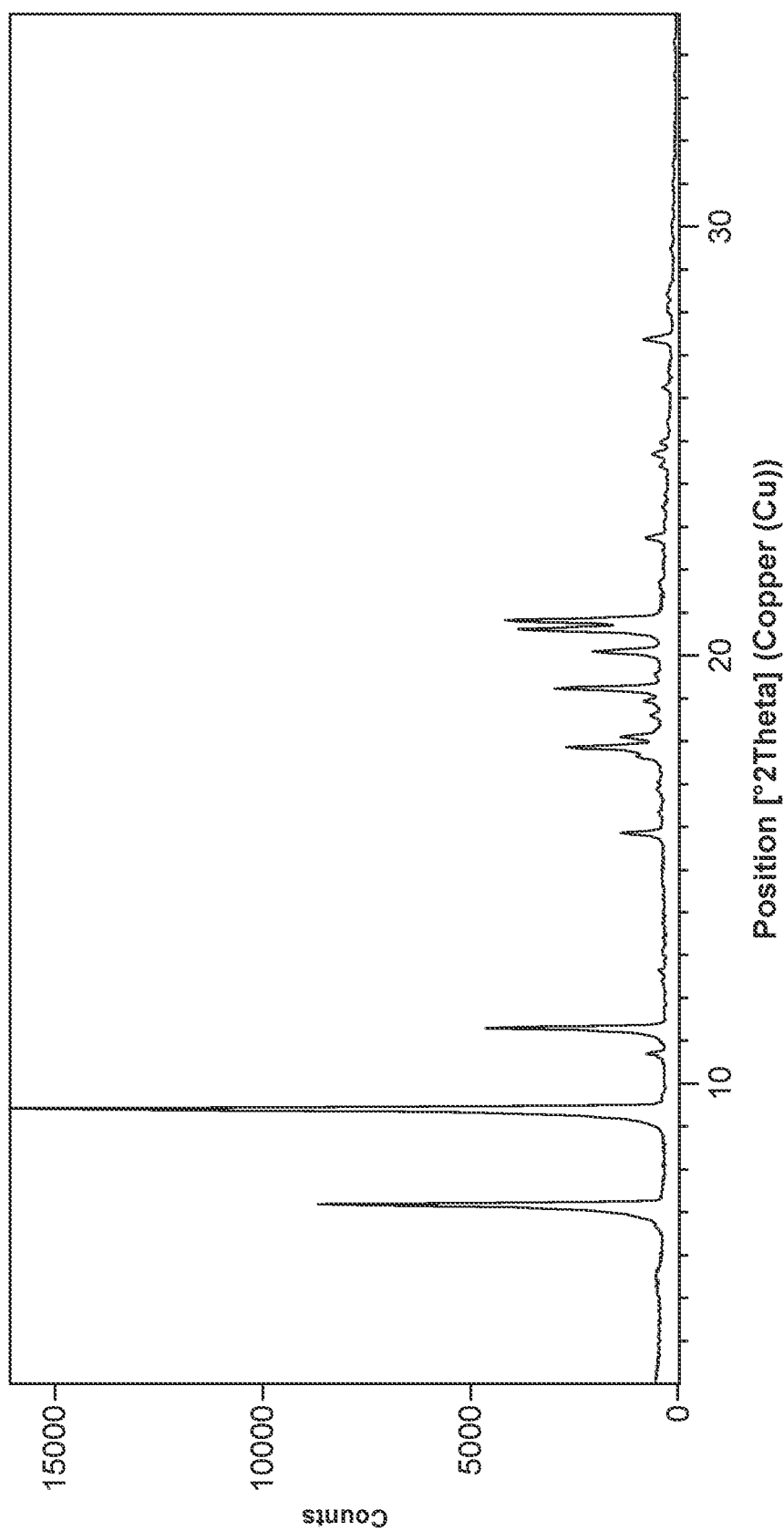
FIG. 17 is an X-ray powder diffractogram of Compound I naphthalene disulfonate Form II.

In one embodiment, Compound I naphthalene disulfonate Form II is characterized by an X-ray powder diffractogram comprising at least two of the following peaks: 7.2, 9.4, 11.3, 15.9, 17.9, 19.2, 20.1, 20.6, 20.8, 22.7, and 27.4 °2θ, each ±0.2 °2θ. In one embodiment, Compound I naphthalene disulfonate Form II is characterized by an X-ray powder diffractogram comprising at least four of the following peaks: 7.2, 9.4, 11.3, 15.9, 17.9, 19.2, 20.1, 20.6, 20.8, 22.7, and 27.4 °2θ, each ±0.2 °2θ. In one embodiment, Compound I naphthalene disulfonate Form II is characterized by an X-ray powder diffractogram comprising at least six of the following peaks: 7.2, 9.4, 11.3, 15.9, 17.9, 19.2, 20.1, 20.6, 20.8, 22.7, and 27.4 °2θ, each ±0.2 °2θ. In one embodiment, Compound I naphthalene disulfonate Form II is characterized by an X-ray powder diffractogram comprising at least eight of the following peaks: 7.2, 9.4, 11.3, 15.9, 17.9, 19.2, 20.1, 20.6, 20.8, 22.7, and 27.4 °2θ, each ±0.2 °2θ. In one embodiment, Compound I naphthalene disulfonate Form II is characterized by an X-ray powder diffractogram comprising each of the following peaks: 7.2, 9.4, 11.3, 15.9, 17.9, 19.2, 20.1, 20.6, 20.8, 22.7, and 27.4 °2θ, each ±0.2 °2θ. In one embodiment, Compound I naphthalene disulfonate Form II is characterized by the full X-ray powder diffractogram as substantially shown in FIG. 17.

In one embodiment, provided is a process for making Compound I naphthalene disulfonate Form II. In one embodiment, the process comprises contacting a solution of Compound I Form I in DMSO with naphthalene disulfonate acid and a solvent such as acetonitrile, MEK, or THF, whereby Compound I naphthalene disulfonate Form II is formed. In one embodiment, the process for making Compound I naphthalene disulfonate Form II is as described in the Examples provided herein.

c. Compound I Naphthalene Disulfonate Form III

The present disclosure provides, in one embodiment, a crystalline form of a naphthalene disulfonate salt of 4-(cyclopropylamino)-2-(4-(4-(ethylsulfonyl)piperazin-1-yl)phenylamino)pyrimidine-5-carboxamide (Compound I naphthalene disulfonate Form III) characterized by the full X-ray powder diffractogram comprising the following peaks: 13.4, 16.9, and 19.2 °2θ, each ±0.2 °2θ, as determined on a diffractometer using Cu-Kα radiation. In one embodiment, the diffractogram of Compound I naphthalene disulfonate Form III further comprises one or more peaks at: 8.9, 16.0, and 21.4 °2θ, each ±0.2 °2θ.

Figure 18:
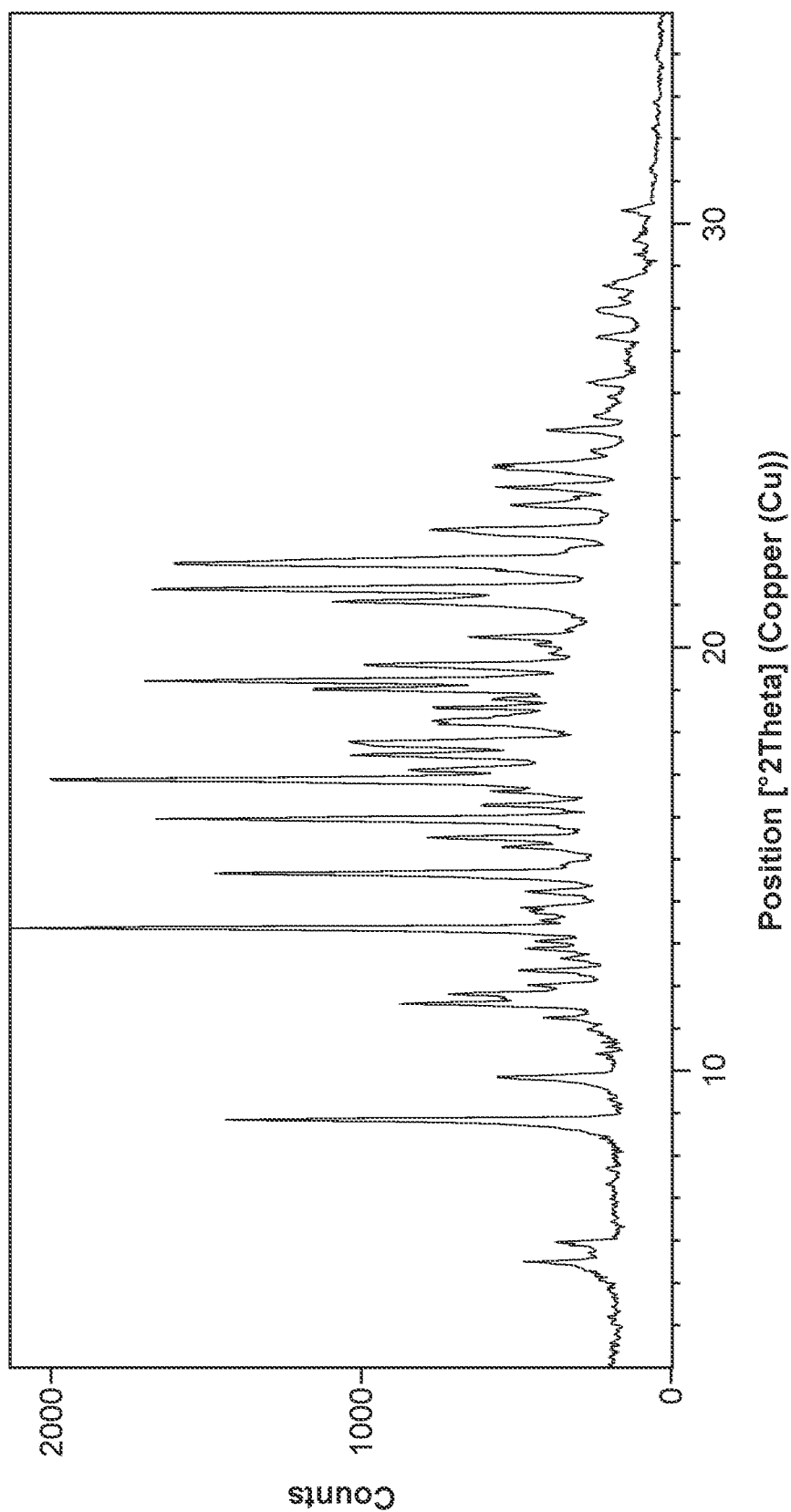
FIG. 18 is an X-ray powder diffractogram of Compound I naphthalene disulfonate Form III.

In one embodiment, Compound I naphthalene disulfonate Form III is characterized by an X-ray powder diffractogram comprising at least two of the following peaks: 8.9, 9.9, 11.6, 13.4, 14.7, 16.0, 16.9, 17.5, 17.8, 19.0, 19.2, 19.6, 20.2, 21.1, 21.4, 22.0, and 22.8 °2θ, each ±0.2 °2θ. In one embodiment, Compound I naphthalene disulfonate Form III is characterized by an X-ray powder diffractogram comprising at least four of the following peaks: 8.9, 9.9, 11.6, 13.4, 14.7, 16.0, 16.9, 17.5, 17.8, 19.0, 19.2, 19.6, 20.2, 21.1, 21.4, 22.0, and 22.8 °2θ, each ±0.2 °2θ. In one embodiment, Compound I naphthalene disulfonate Form III is characterized by an X-ray powder diffractogram comprising at least six of the following peaks: 8.9, 9.9, 11.6, 13.4, 14.7, 16.0, 16.9, 17.5, 17.8, 19.0, 19.2, 19.6, 20.2, 21.1, 21.4, 22.0, and 22.8 °2θ, each ±0.2 °2θ. In one embodiment, Compound I naphthalene disulfonate Form III is characterized by an X-ray powder diffractogram comprising at least eight of the following peaks: 8.9, 9.9, 11.6, 13.4, 14.7, 16.0, 16.9, 17.5, 17.8, 19.0, 19.2, 19.6, 20.2, 21.1, 21.4, 22.0, and 22.8 °2θ, each ±0.2 °2θ. In one embodiment, Compound I naphthalene disulfonate Form III is characterized by an X-ray powder diffractogram comprising each of the following peaks: 8.9, 9.9, 11.6, 13.4, 14.7, 16.0, 16.9, 17.5, 17.8, 19.0, 19.2, 19.6, 20.2, 21.1, 21.4, 22.0, and 22.8 °2θ, each ±0.2 °2θ. In one embodiment, Compound I naphthalene disulfonate Form III is characterized by the full X-ray powder diffractogram as substantially shown in FIG. 18.

In one embodiment, provided is a process for making Compound I naphthalene disulfonate Form III. In one embodiment, the process comprises contacting a solution of Compound I Form I in DMSO with naphthalene disulfonate acid and a solvent such as toluene 3, Me-1BuOH, or IPA, whereby Compound I naphthalene disulfonate Form III is formed. In one embodiment, the process for making Compound I naphthalene disulfonate Form III is as described in the Examples provided herein.

d. Compound I Naphthalene Disulfonate Form IV

The present disclosure provides, in one embodiment, a crystalline form of a naphthalene disulfonate salt of 4-(cyclopropylamino)-2-(4-(4-(ethylsulfonyl)piperazin-1-yl)phenylamino)pyrimidine-5-carboxamide (Compound I naphthalene disulfonate Form IV) characterized by the full X-ray powder diffractogram comprising the following peaks: 6.1, 12.1 and 15.0 °2θ, each ±0.2 °2θ, as determined on a diffractometer using Cu-Kα radiation. In one embodiment, the diffractogram of Compound I naphthalene disulfonate Form IV further comprises one or more peaks at: 13.8, 14.0, and 17.7 °2θ, each ±0.2 °2θ.

Figure 19:
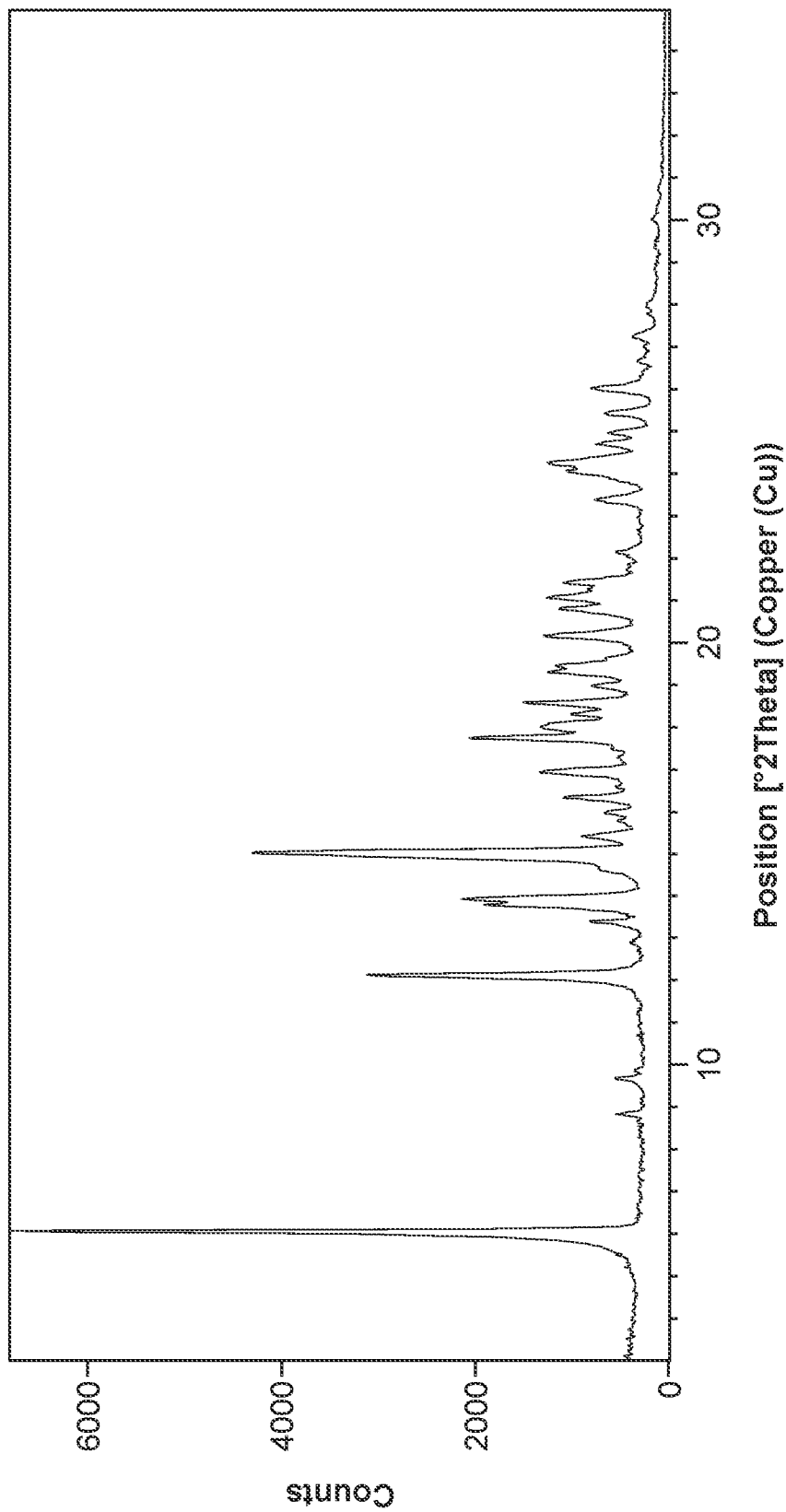
FIG. 19 is an X-ray powder diffractogram of Compound I naphthalene disulfonate Form IV.

In one embodiment, Compound I naphthalene disulfonate Form IV is characterized by an X-ray powder diffractogram comprising at least two of the following peaks: 6.1, 12.1, 13.8, 14.0, 15.0, 16.3, 17.0, 17.7, 18.6, 20.2, 20.8, 21.1, 23.4, and 24.2 °2θ, each ±0.2 °2θ. In one embodiment, Compound I naphthalene disulfonate Form IV is characterized by an X-ray powder diffractogram comprising at least four of the following peaks: 6.1, 12.1, 13.8, 14.0, 15.0, 16.3, 17.0, 17.7, 18.6, 20.2, 20.8, 21.1, 23.4, and 24.2 °2θ, each ±0.2 °2θ. In one embodiment, Compound I naphthalene disulfonate Form IV is characterized by an X-ray powder diffractogram comprising at least six of the following peaks: 6.1, 12.1, 13.8, 14.0, 15.0, 16.3, 17.0, 17.7, 18.6, 20.2, 20.8, 21.1, 23.4, and 24.2 °2θ, each ±0.2 °2θ. In one embodiment, Compound I naphthalene disulfonate Form IV is characterized by an X-ray powder diffractogram comprising at least eight of the following peaks: 6.1, 12.1, 13.8, 14.0, 15.0, 16.3, 17.0, 17.7, 18.6, 20.2, 20.8, 21.1, 23.4, and 24.2 °2θ, each ±0.2 °2θ. In one embodiment, Compound I naphthalene disulfonate Form IV is characterized by an X-ray powder diffractogram comprising each of the following peaks: 6.1, 12.1, 13.8, 14.0, 15.0, 16.3, 17.0, 17.7, 18.6, 20.2, 20.8, 21.1, 23.4, and 24.2 °2θ, each ±0.2 °2θ. In one embodiment, Compound I naphthalene disulfonate Form IV is characterized by the full X-ray powder diffractogram as substantially shown in FIG. 19.

In one embodiment, provided is a process for making Compound I naphthalene disulfonate Form IV. In one embodiment, the process comprises contacting a solution of Compound I Form I in DMSO with naphthalene disulfonate acid and water, whereby Compound I naphthalene disulfonate Form IV is formed. In one embodiment, the process for making Compound I naphthalene disulfonate Form IV is as described in the Examples provided herein.

e. Compound I Naphthalene Disulfonate Type A

The present disclosure provides, in one embodiment, a crystalline form of a naphthalene disulfonate salt of 4-(cyclopropylamino)-2-(4-(4-(ethylsulfonyl)piperazin-1-yl)phenylamino)pyrimidine-5-carboxamide (Compound I naphthalene disulfonate Type A) characterized by the full X-ray powder diffractogram comprising the following peaks: 21.9, 17.3, and 13.7 °2θ, each ±0.2 °2θ, as determined on a diffractometer using Cu-Kα radiation. In one embodiment, the diffractogram of Compound I naphthalene disulfonate Type A further comprises one or more peaks at: 20.1, 16.4, and 9.1 °2θ, each ±0.2 °2θ.

In another embodiment, provided is a process for making Compound I naphthalene disulfonate Type A. In one embodiment, the process for making Compound I naphthalene disulfonate Type A is as described in the Examples provided herein.

Sulfate Salts a. Compound I Sulfate Form I

The present disclosure provides, in one embodiment, a crystalline form of a sulfate salt of 4-(cyclopropylamino)-2-(4-(4-(ethylsulfonyl)piperazin-1-yl)phenylamino)pyrimidine-5-carboxamide (Compound I sulfate Form I) characterized by the full X-ray powder diffractogram comprising the following peaks: 4.0, 8.0, and 20.6 °2θ, each ±0.2 °2θ, as determined on a diffractometer using Cu-Kα radiation. In one embodiment, the diffractogram of Compound I sulfate Form I further comprises one or more peaks at: 10.1, 16.1, and 22.6 °2θ, each ±0.2 °2θ.

Figure 20:
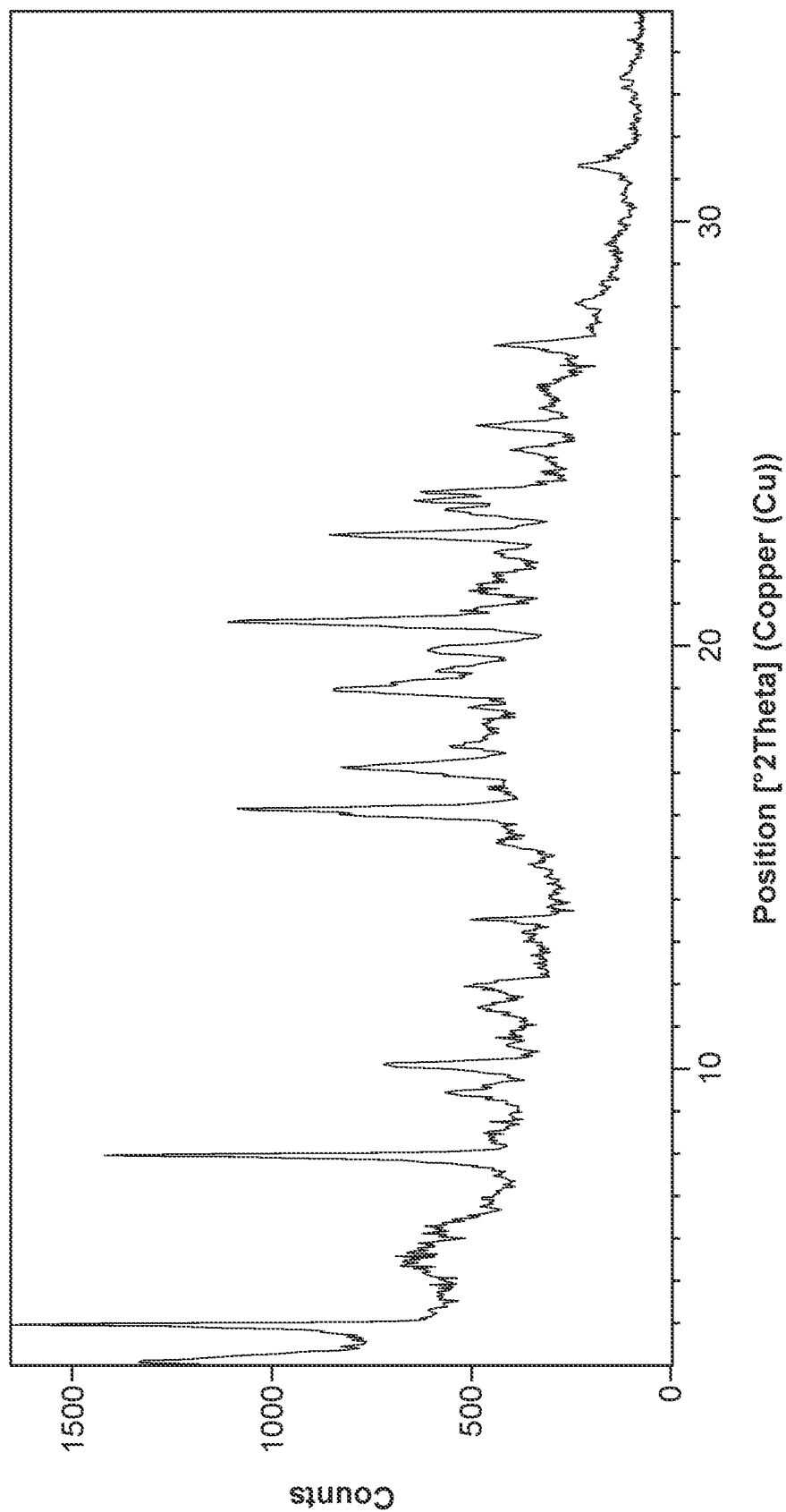
FIG. 20 is an X-ray powder diffractogram of Compound I sulfate Form I.

In one embodiment, Compound I sulfate Form I is characterized by an X-ray powder diffractogram comprising at least two of the following peaks: 3.1, 4.0, 8.0, 9.4, 10.1, 13.5, 16.1, 17.1, 19.0, 20.6, 22.6, and 27.1 °2θ, each ±0.2 °2θ. In one embodiment, Compound I sulfate Form I is characterized by an X-ray powder diffractogram comprising at least four of the following peaks: 3.1, 4.0, 8.0, 9.4, 10.1, 13.5, 16.1, 17.1, 19.0, 20.6, 22.6, and 27.1 °2θ, each ±0.2 °2θ. In one embodiment, Compound I sulfate Form I is characterized by an X-ray powder diffractogram comprising at least six of the following peaks: 3.1, 4.0, 8.0, 9.4, 10.1, 13.5, 16.1, 17.1, 19.0, 20.6, 22.6, and 27.1 °2θ, each ±0.2 °2θ. In one embodiment, Compound I sulfate Form I is characterized by an X-ray powder diffractogram comprising at least eight of the following peaks: 3.1, 4.0, 8.0, 9.4, 10.1, 13.5, 16.1, 17.1, 19.0, 20.6, 22.6, and 27.1 °2θ, each ±0.2 °2θ. In one embodiment, Compound I sulfate Form I is characterized by an X-ray powder diffractogram comprising each of the following peaks: 3.1, 4.0, 8.0, 9.4, 10.1, 13.5, 16.1, 17.1, 19.0, 20.6, 22.6, and 27.1 °2θ, each ±0.2 °2θ. In one embodiment, Compound I sulfate Form I is characterized by the full X-ray powder diffractogram as substantially shown in FIG. 20.

In one embodiment, Compound I Sulfate Form I is characterized as a hydrated form.

In one embodiment, provided is a process for making Compound I sulfate Form I. In one embodiment, the process comprises contacting a solution of Compound I Form I in DMSO with sulfuric acid and a solvent such as DMF, toluene, IPA, acetonitrile, MEK or THF, whereby Compound I sulfate Form I is formed. In one embodiment, the process for making Compound I sulfate Form I is as described in the Examples provided herein.

b. Compound I Sulfate Form II

The present disclosure provides, in one embodiment, a crystalline form of a sulfate salt of 4-(cyclopropylamino)-2-(4-(4-(ethylsulfonyl)piperazin-1-yl)phenylamino)pyrimidine-5-carboxamide (Compound I sulfate Form II) characterized by an X-ray powder diffractogram comprising the following peaks: 8.7, 16.7, and 22.9 °2θ, each ±0.2 °2θ, as determined on a diffractometer using Cu-Kα radiation. In one embodiment, the diffractogram of Compound I sulfate Form II further comprises one or more peaks at: 16.9, 18.0, and 20.5 °2θ, each ±0.2 °2θ.

Figure 21:
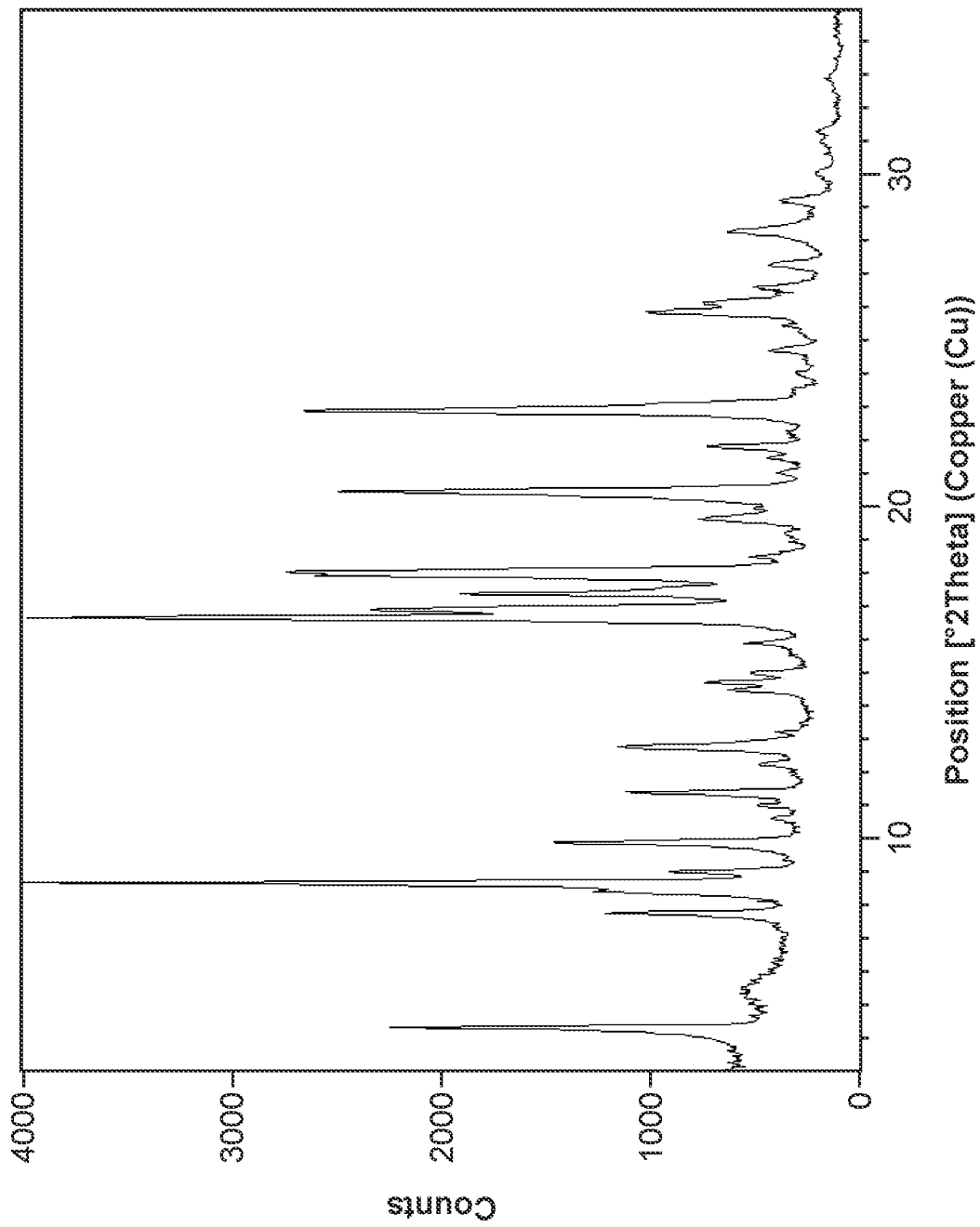
FIG. 21 is an X-ray powder diffractogram of Compound I sulfate Form II.

In one embodiment, Compound I sulfate Form II is characterized by an X-ray powder diffractogram comprising at least two of the following peaks: 4.3, 7.8, 8.7, 9.0, 9.9, 11.4, 12.8, 13.3, 16.7, 16.9, 17.4, 18.0, 18.2, 18.7, 18.9, 20.5, 22.9, and 25.8 °2θ, each ±0.2 °2θ. In one embodiment, Compound I sulfate Form II is characterized by an X-ray powder diffractogram comprising at least four of the following peaks: 4.3, 7.8, 8.7, 9.0, 9.9, 11.4, 12.8, 13.3, 16.7, 16.9, 17.4, 18.0, 18.2, 18.7, 18.9, 20.5, 22.9, and 25.8 °2θ, each ±0.2 °2θ. In one embodiment, Compound I sulfate Form II is characterized by an X-ray powder diffractogram comprising at least six of the following peaks: 4.3, 7.8, 8.7, 9.0, 9.9, 11.4, 12.8, 13.3, 16.7, 16.9, 17.4, 18.0, 18.2, 18.7, 18.9, 20.5, 22.9, and 25.8 °2θ, each ±0.2 °2θ. In one embodiment, Compound I sulfate Form II is characterized by an X-ray powder diffractogram comprising at least eight of the following peaks: 4.3, 7.8, 8.7, 9.0, 9.9, 11.4, 12.8, 13.3, 16.7, 16.9, 17.4, 18.0, 18.2, 18.7, 18.9, 20.5, 22.9, and 25.8 °2θ, each ±0.2 °2θ. In one embodiment, Compound I sulfate Form II is characterized by an X-ray powder diffractogram comprising each of the following peaks: 4.3, 7.8, 8.7, 9.0, 9.9, 11.4, 12.8, 13.3, 16.7, 16.9, 17.4, 18.0, 18.2, 18.7, 18.9, 20.5, 22.9, and 25.8 °2θ, each ±0.2 °2θ. In one embodiment, Compound I sulfate Form II is characterized by the full X-ray powder diffractogram as substantially shown in FIG. 21.

In one embodiment, Compound I Sulfate Form II is characterized as a hydrated form.

In one embodiment, provided is a process for making Compound I sulfate Form II. In one embodiment, the process comprises contacting a solution of Compound I Form I in DMSO with sulfuric acid and water, whereby Compound I sulfate Form II is formed. In one embodiment, the process for making Compound I sulfate Form II is as described in the Examples provided herein.

c. Compound I Sulfate Form III

The present disclosure provides, in one embodiment, a crystalline form of a sulfate salt of 4-(cyclopropylamino)-2-(4-(4-(ethylsulfonyl)piperazin-1-yl)phenylamino)pyrimidine-5-carboxamide (Compound I sulfate Form III) characterized by the full X-ray powder diffractogram comprising the following peaks: 13.4, 16.7, and 18.3 °2θ, each ±0.2 °2θ, as determined on a diffractometer using Cu-Kα radiation. In one embodiment, the diffractogram of Compound I sulfate Form III further comprises one or more peaks at: 11.6, 19.7, and 24.6 °2θ, each ±0.2 °2θ.

Figure 22:
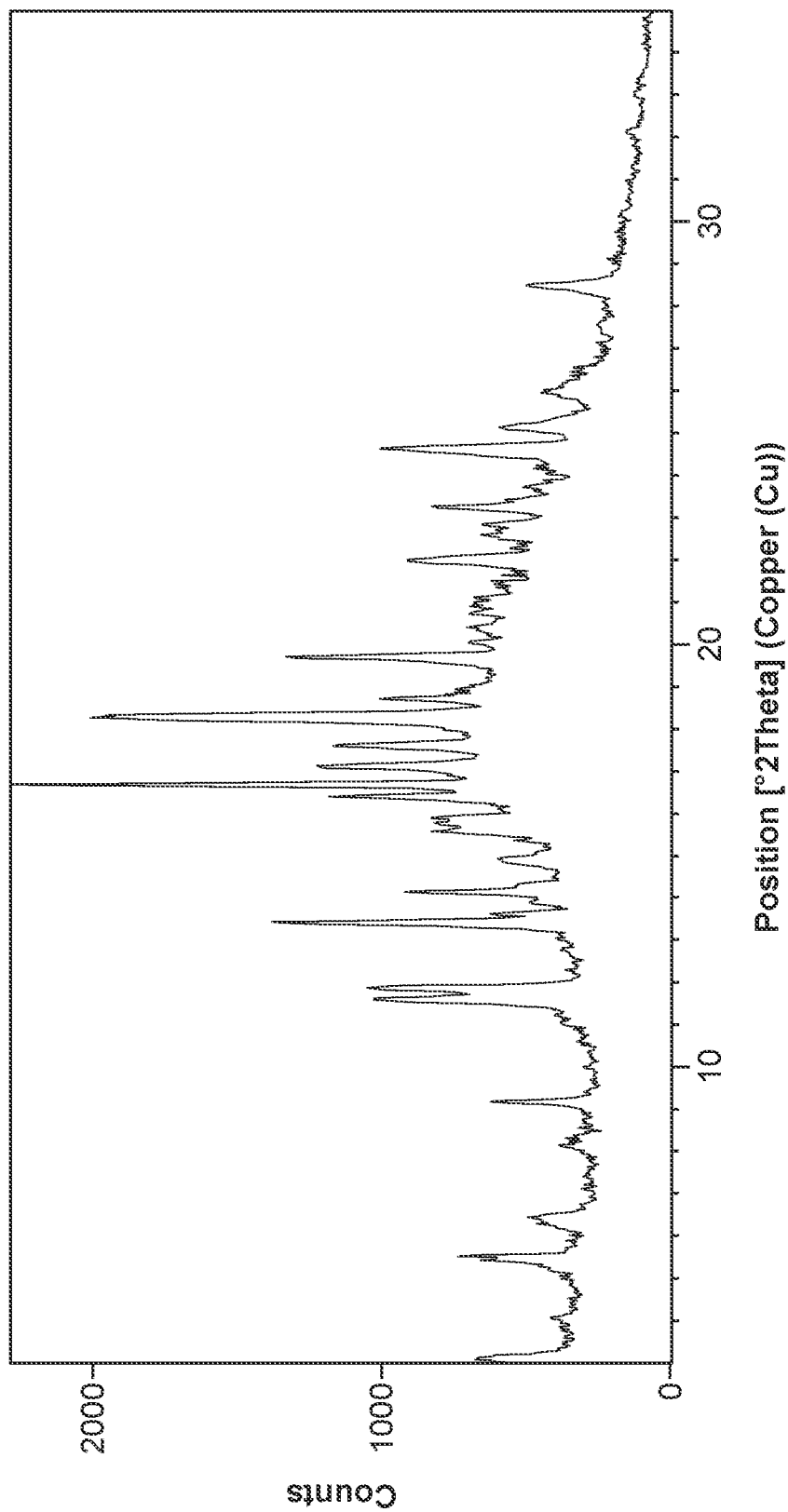
FIG. 22 is an X-ray powder diffractogram of Compound I sulfate Form III.

In one embodiment, Compound I sulfate Form III is characterized by an X-ray powder diffractogram comprising at least two of the following peaks: 5.5, 9.2, 11.6, 11.9, 13.4, 14.1, 16.4, 16.7, 17.1, 18.3, 18.7, 19.7, 22.0, and 24.6 °2θ, each ±0.2 °2θ. In one embodiment, Compound I sulfate Form III is characterized by an X-ray powder diffractogram comprising at least four of the following peaks: 5.5, 9.2, 11.6, 11.9, 13.4, 14.1, 16.4, 16.7, 17.1, 18.3, 18.7, 19.7, 22.0, and 24.6 °2θ, each ±0.2 °2θ. In one embodiment, Compound I sulfate Form III is characterized by an X-ray powder diffractogram comprising at least six of the following peaks: 5.5, 9.2, 11.6, 11.9, 13.4, 14.1, 16.4, 16.7, 17.1, 18.3, 18.7, 19.7, 22.0, and 24.6 °2θ, each ±0.2 °2θ. In one embodiment, Compound I sulfate Form III is characterized by an X-ray powder diffractogram comprising at least eight of the following peaks: 5.5, 9.2, 11.6, 11.9, 13.4, 14.1, 16.4, 16.7, 17.1, 18.3, 18.7, 19.7, 22.0, and 24.6 °2θ, each ±0.2 °2θ. In one embodiment, Compound I sulfate Form III is characterized by an X-ray powder diffractogram comprising each of the following peaks: 5.5, 9.2, 11.6, 11.9, 13.4, 14.1, 16.4, 16.7, 17.1, 18.3, 18.7, 19.7, 22.0, and 24.6 °2θ, each ±0.2 °2θ. In one embodiment, Compound I sulfate Form III is characterized by the full X-ray powder diffractogram as substantially shown in FIG. 22.

In one embodiment, provided is a process for making Compound I sulfate Form III. In one embodiment, the process comprises contacting a solution of Compound I Form I in DMSO with sulfuric acid and a solvent such as n-BuOAc or EtOH, whereby Compound I sulfate Form III is formed. In one embodiment, the process for making Compound I sulfate Form III is as described in the Examples provided herein.

d. Compound I Sulfate Type A

The present disclosure provides, in one embodiment, a crystalline form of a sulfate salt of 4-(cyclopropylamino)-2-(4-(4-(ethylsulfonyl)piperazin-1-yl)phenylamino)pyrimidine-5-carboxamide (Compound I sulfate Type A).

In one embodiment, the process for making Compound I sulfate Type A is as described in the Examples provided herein.

e. Compound I Sulfate Type B

The present disclosure provides, in one embodiment, a crystalline form of a sulfate salt of 4-(cyclopropylamino)-2-(4-(4-(ethylsulfonyl)piperazin-1-yl)phenylamino)pyrimidine-5-carboxamide (Compound I sulfate Type B).

In one embodiment, the process for making Compound I sulfate Type B is as described in the Examples provided herein.

f. Compound I Sulfate Type C

The present disclosure provides, in one embodiment, a crystalline form of a sulfate salt of 4-(cyclopropylamino)-2-(4-(4-(ethylsulfonyl)piperazin-1-yl)phenylamino)pyrimidine-5-carboxamide (Compound I sulfate Type C).

In one embodiment, the process for making Compound I sulfate Type C is as described in the Examples provided herein.

Tosylate Salts a. Compound I Tosylate Form I

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form I) characterized by the full X-ray powder diffractogram comprising the following peaks: 17.5, 19.1, and 20.7 °2θ, each ±0.2 °2θ, as determined on a diffractometer using Cu-Kα radiation. In one embodiment, the diffractogram of Compound I tosylate Form I further comprises one or more peaks at: 18.1, 24.0, and 24.7 °2θ, each ±0.2 °2θ.

Figure 23:
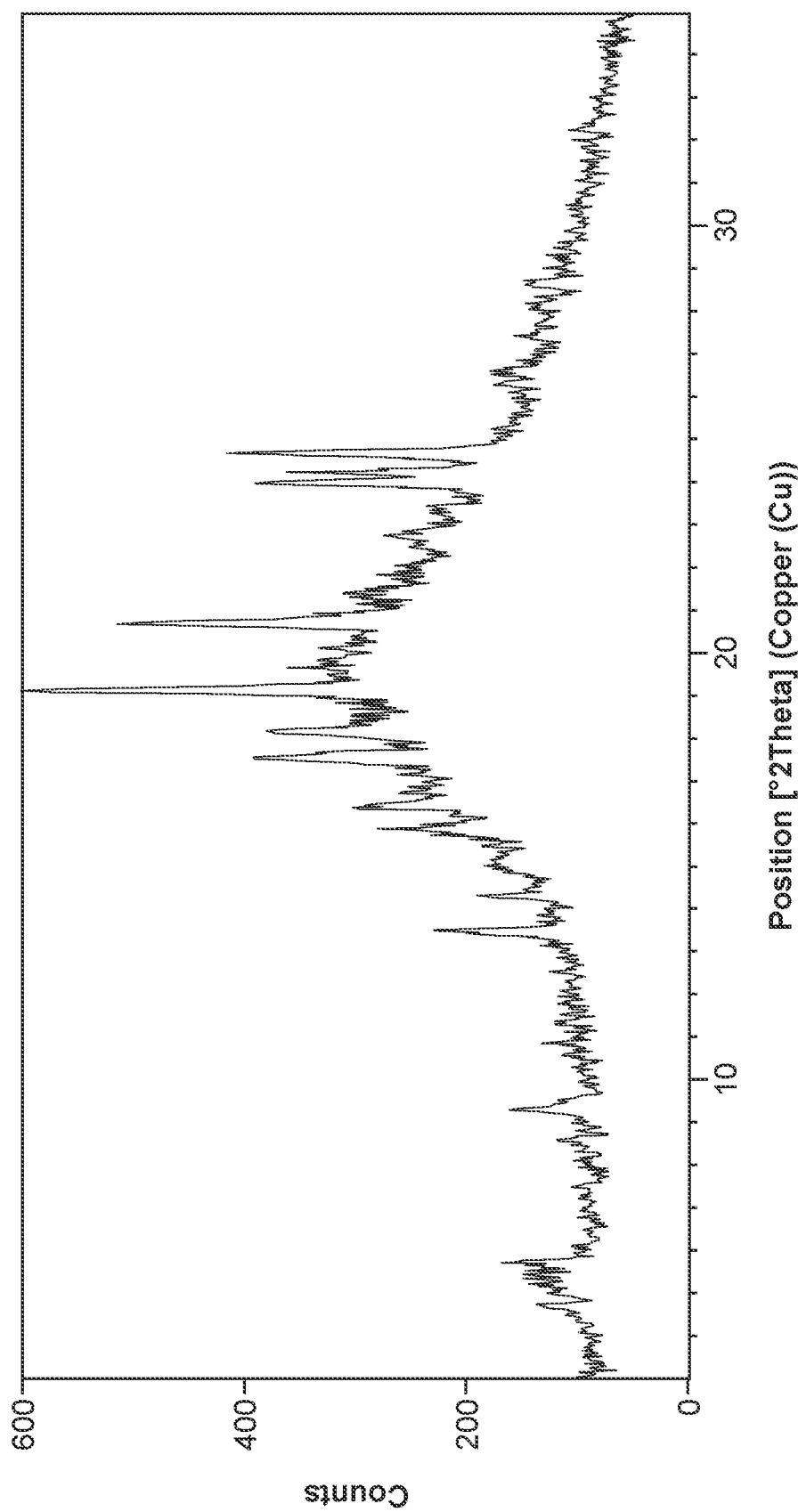
FIG. 23 is an X-ray powder diffractogram of Compound I tosylate Form I.

In one embodiment, Compound I tosylate Form I is characterized by an X-ray powder diffractogram comprising at least two of the following peaks: 9.3, 13.5, 15.9, 16.4, 17.5, 18.1, 19.1, 20.7, 24.0, 24.2, and 24.7 °2θ, each ±0.2 °2θ. In one embodiment, Compound I tosylate Form I is characterized by an X-ray powder diffractogram comprising at least four of the following peaks: 9.3, 13.5, 15.9, 16.4, 17.5, 18.1, 19.1, 20.7, 24.0, 24.2, and 24.7 °2θ, each ±0.2 °2θ. In one embodiment, Compound I tosylate Form I is characterized by an X-ray powder diffractogram comprising at least six of the following peaks: 9.3, 13.5, 15.9, 16.4, 17.5, 18.1, 19.1, 20.7, 24.0, 24.2, and 24.7 °2θ, each ±0.2 °2θ. In one embodiment, Compound I tosylate Form I is characterized by an X-ray powder diffractogram comprising at least eight of the following peaks: 9.3, 13.5, 15.9, 16.4, 17.5, 18.1, 19.1, 20.7, 24.0, 24.2, and 24.7 °2θ, each ±0.2 °2θ. In one embodiment, Compound I tosylate Form I is characterized by an X-ray powder diffractogram comprising each of the following peaks: 9.3, 13.5, 15.9, 16.4, 17.5, 18.1, 19.1, 20.7, 24.0, 24.2, and 24.7 °2θ, each ±0.2 °2θ. In one embodiment, Compound I tosylate Form I is characterized by the full X-ray powder diffractogram as substantially shown in FIG. 23.

In one embodiment, provided is a process for making Compound I tosylate Form I. In one embodiment, the process comprises contacting a solution of Compound I Form I in DMSO with p-tolyl sulfonic acid and a solvent such as n-BuOAc or MEK, whereby Compound I tosylate Form I is formed. In one embodiment, the process for making Compound I tosylate Form I is as described in the Examples provided herein.

b. Compound I Tosylate Form II

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form II) characterized by the full X-ray powder diffractogram comprising the following peaks: 5.7, 17.6, and 19.9 °2θ, each ±0.2 °2θ, as determined on a diffractometer using Cu-Kα radiation. In one embodiment, the diffractogram of Compound I tosylate Form II further comprises one or more peaks at: 14.4, 18.2, and 20.6 °2θ, each ±0.2 °2θ.

Figure 24:
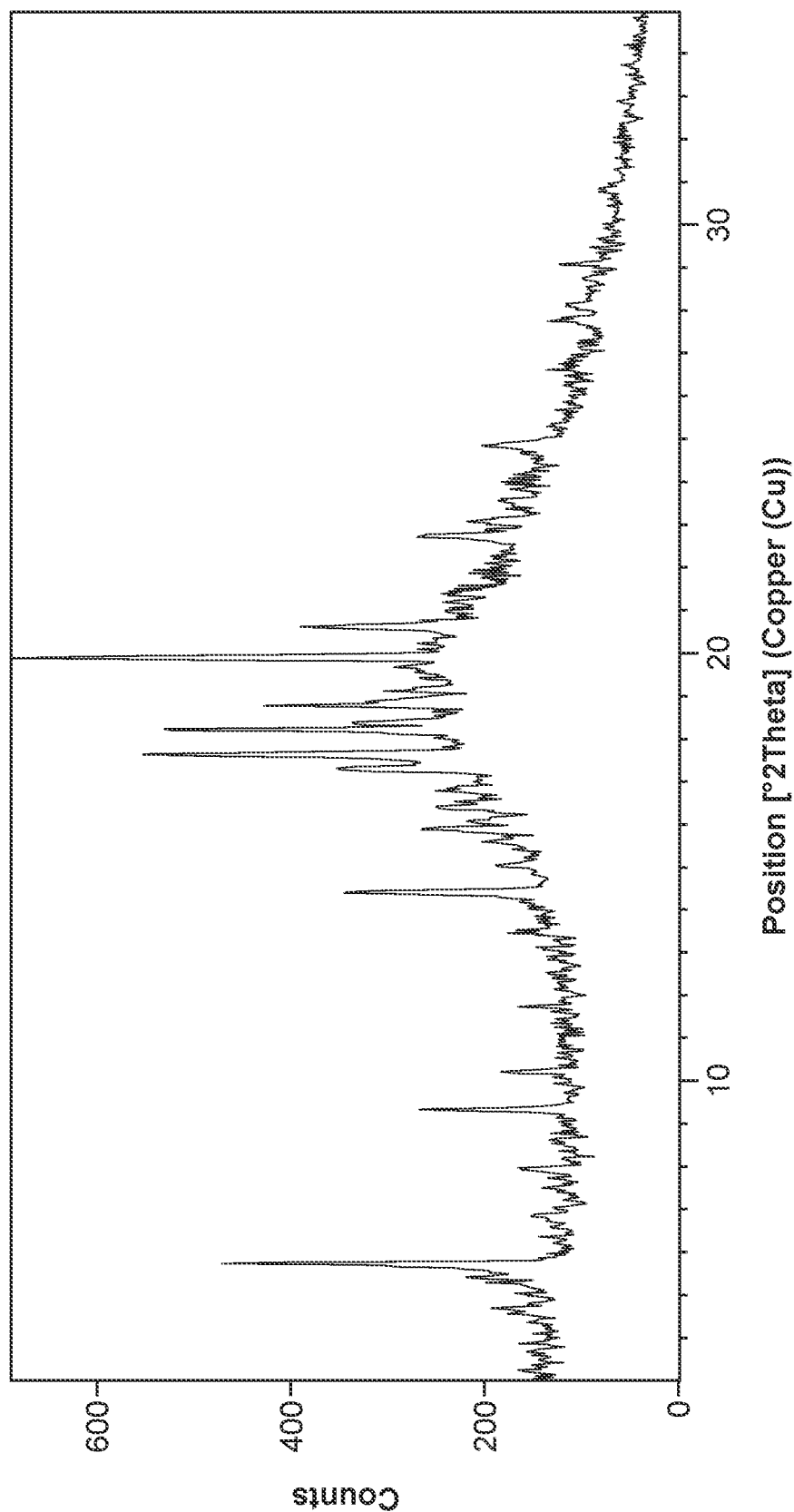
FIG. 24 is an X-ray powder diffractogram of Compound I tosylate Form II.

In one embodiment, Compound I tosylate Form II is characterized by an X-ray powder diffractogram comprising at least two of the following peaks: 5.7, 9.3, 14.4, 15.9, 17.3, 17.6, 18.2, 18.8, 19.9, 20.6, 22.7, and 24.9 °2θ, each ±0.2 °2θ. In one embodiment, Compound I tosylate Form II is characterized by an X-ray powder diffractogram comprising at least four of the following peaks: 5.7, 9.3, 14.4, 15.9, 17.3, 17.6, 18.2, 18.8, 19.9, 20.6, 22.7, and 24.9 °2θ, each ±0.2 °2θ. In one embodiment, Compound I tosylate Form II is characterized by an X-ray powder diffractogram comprising at least six of the following peaks: 5.7, 9.3, 14.4, 15.9, 17.3, 17.6, 18.2, 18.8, 19.9, 20.6, 22.7, and 24.9 °2θ, each ±0.2 °2θ. In one embodiment, Compound I tosylate Form II is characterized by an X-ray powder diffractogram comprising at least eight of the following peaks: 5.7, 9.3, 14.4, 15.9, 17.3, 17.6, 18.2, 18.8, 19.9, 20.6, 22.7, and 24.9 °2θ, each ±0.2 °2θ. In one embodiment, Compound I tosylate Form II is characterized by an X-ray powder diffractogram comprising each of the following peaks: 5.7, 9.3, 14.4, 15.9, 17.3, 17.6, 18.2, 18.8, 19.9, 20.6, 22.7, and 24.9 °2θ, each ±0.2 °2θ. In one embodiment, Compound I tosylate Form II is characterized by the full X-ray powder diffractogram as substantially shown in FIG. 24.

In one embodiment, provided is a process for making Compound I tosylate Form II. In one embodiment, the process comprises contacting a solution of Compound I Form I in DMSO with p-tolyl sulfonic acid and a solvent such as IPA or acetonitrile, whereby Compound I tosylate Form II is formed. In one embodiment, the process for making Compound I tosylate Form II is as described in the Examples provided herein.

c. Compound I Tosylate Form III

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form III) characterized by the full X-ray powder diffractogram comprising the following peaks: 9.9, 16.2, and 19.5 °2θ, each ±0.2 °2θ, as determined on a diffractometer using Cu-Kα radiation. In one embodiment, the diffractogram of Compound I tosylate Form III further comprises one or more peaks at: 7.8, 22.2, and 24.3 °2θ, each ±0.2 °2θ.

Figure 25:
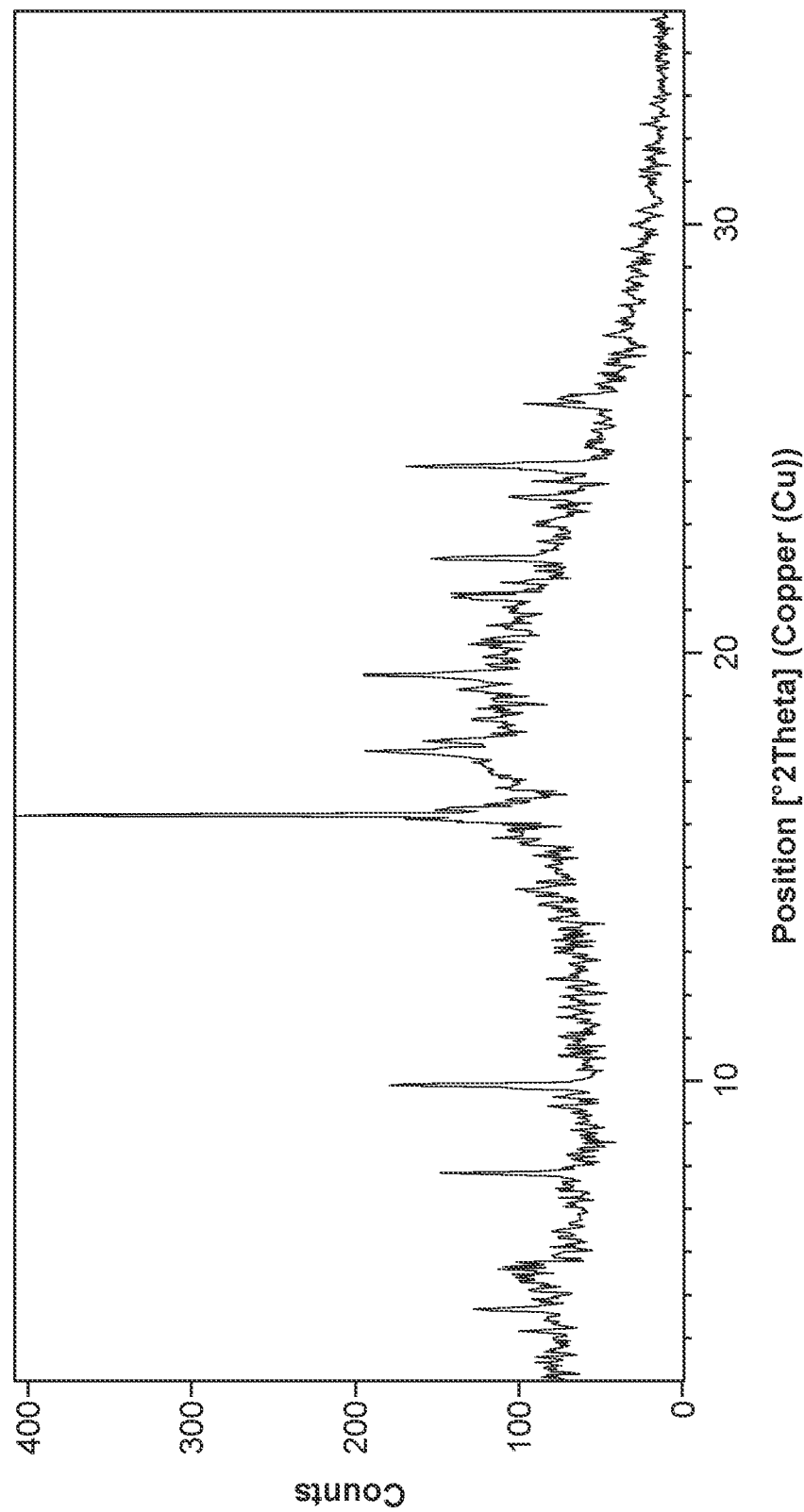
FIG. 25 is an X-ray powder diffractogram of Compound I tosylate Form III.

In one embodiment, Compound I tosylate Form III is characterized by an X-ray powder diffractogram comprising at least two of the following peaks: 7.8, 9.9, 16.2, 17.7, 19.5, 21.2, 22.2, 24.4, and 25.8 °2θ, each ±0.2 °2θ. In one embodiment, Compound I tosylate Form III is characterized by an X-ray powder diffractogram comprising at least four of the following peaks: 7.8, 9.9, 16.2, 17.7, 19.5, 21.2, 22.2, 24.4, and 25.8 °2θ, each ±0.2 °2θ. In one embodiment, Compound I tosylate Form III is characterized by an X-ray powder diffractogram comprising at least six of the following peaks: 7.8, 9.9, 16.2, 17.7, 19.5, 21.2, 22.2, 24.4, and 25.8 °2θ, each ±0.2 °2θ. In one embodiment, Compound I tosylate Form III is characterized by an X-ray powder diffractogram comprising at least eight of the following peaks: 7.8, 9.9, 16.2, 17.7, 19.5, 21.2, 22.2, 24.4, and 25.8 °2θ, each ±0.2 °2θ. In one embodiment, Compound I tosylate Form III is characterized by an X-ray powder diffractogram comprising each of the following peaks: 7.8, 9.9, 16.2, 17.7, 19.5, 21.2, 22.2, 24.4, and 25.8 °2θ, each ±0.2 °2θ. In one embodiment, Compound I tosylate Form III is characterized by the full X-ray powder diffractogram as substantially shown in FIG. 25.

In one embodiment, provided is a process for making Compound I tosylate Form III. In one embodiment, the process comprises contacting a solution of Compound I Form I in DMSO with p-tolyl sulfonic acid and a solvent such as toluene or THF, whereby Compound I tosylate Form III is formed. In one embodiment, the process for making Compound I tosylate Form III is as described in the Examples provided herein.

d. Compound I Tosylate Form IV

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form IV) characterized by the full X-ray powder diffractogram comprising the following peaks: 5.5, 17.3, and 20.0 °2θ, each ±0.2 °2θ, as determined on a diffractometer using Cu-Kα radiation. In one embodiment, the diffractogram of Compound I tosylate Form IV further comprises one or more peaks at: 4.7, 16.5, and 19.0 °2θ, each ±0.2 °2θ.

Figure 26:
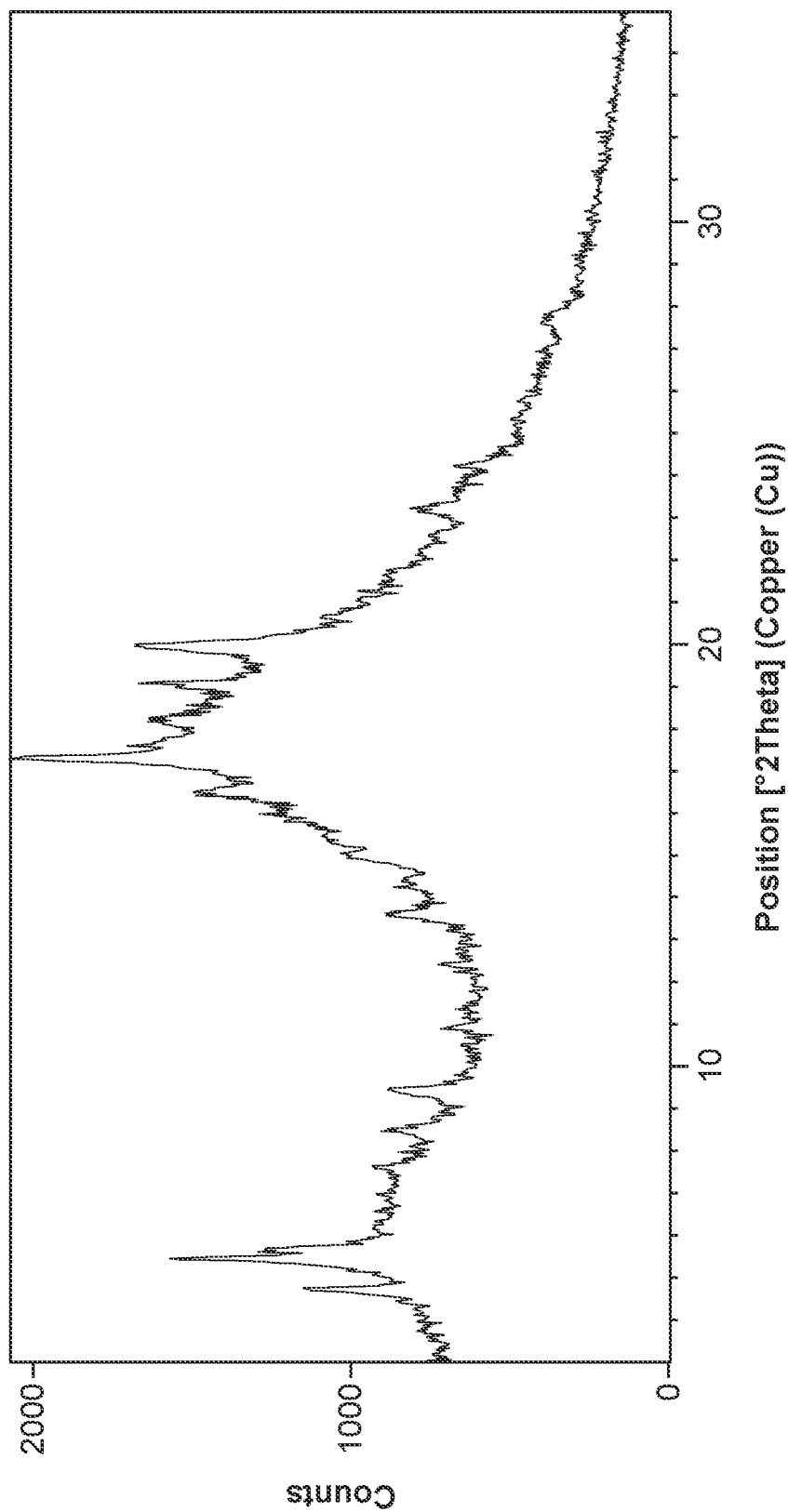
FIG. 26 is an X-ray powder diffractogram of Compound I tosylate Form IV.

In one embodiment, Compound I tosylate Form IV is characterized by an X-ray powder diffractogram comprising at least two of the following peaks: 4.7, 5.5, 8.5, 9.4, 13.6, 16.5, 17.3, 19.0, 20.0, and 23.2 °2θ, each ±0.2 °2θ. In one embodiment, Compound I tosylate Form IV is characterized by an X-ray powder diffractogram comprising at least four of the following peaks: 4.7, 5.5, 8.5, 9.4, 13.6, 16.5, 17.3, 19.0, 20.0, and 23.2 °2θ, each ±0.2 °2θ. In one embodiment, Compound I tosylate Form IV is characterized by an X-ray powder diffractogram comprising at least six of the following peaks: 4.7, 5.5, 8.5, 9.4, 13.6, 16.5, 17.3, 19.0, 20.0, and 23.2 °2θ, each ±0.2 °2θ. In one embodiment, Compound I tosylate Form IV is characterized by an X-ray powder diffractogram comprising at least eight of the following peaks: 4.7, 5.5, 8.5, 9.4, 13.6, 16.5, 17.3, 19.0, 20.0, and 23.2 °2θ, each ±0.2 °2θ. In one embodiment, Compound I tosylate Form IV is characterized by an X-ray powder diffractogram comprising each of the following peaks: 4.7, 5.5, 8.5, 9.4, 13.6, 16.5, 17.3, 19.0, 20.0, and 23.2 °2θ, each ±0.2 °2θ. In one embodiment, Compound I tosylate Form IV is characterized by the full X-ray powder diffractogram as substantially shown in FIG. 26.

In one embodiment, provided is a process for making Compound I tosylate Form IV. In one embodiment, the process comprises contacting a solution of Compound I Form I in DMSO with p-tolyl sulfonic acid and 3-Me-1-BuOH, whereby Compound I tosylate Form IV is formed. In one embodiment, the process for making Compound I tosylate Form IV is as described in the Examples provided herein.

e. Compound I Tosylate Form V

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form V) characterized by the full X-ray powder diffractogram comprising the following peaks: 4.7, 17.9, and 18.6 °2θ, each ±0.2 °2θ, as determined on a diffractometer using Cu-Kα radiation. In one embodiment, the diffractogram of Compound I tosylate Form V further comprises one or more peaks at: 6.7, 19.4, and 24.8 °2θ, each ±0.2 °2θ.

Figure 27:
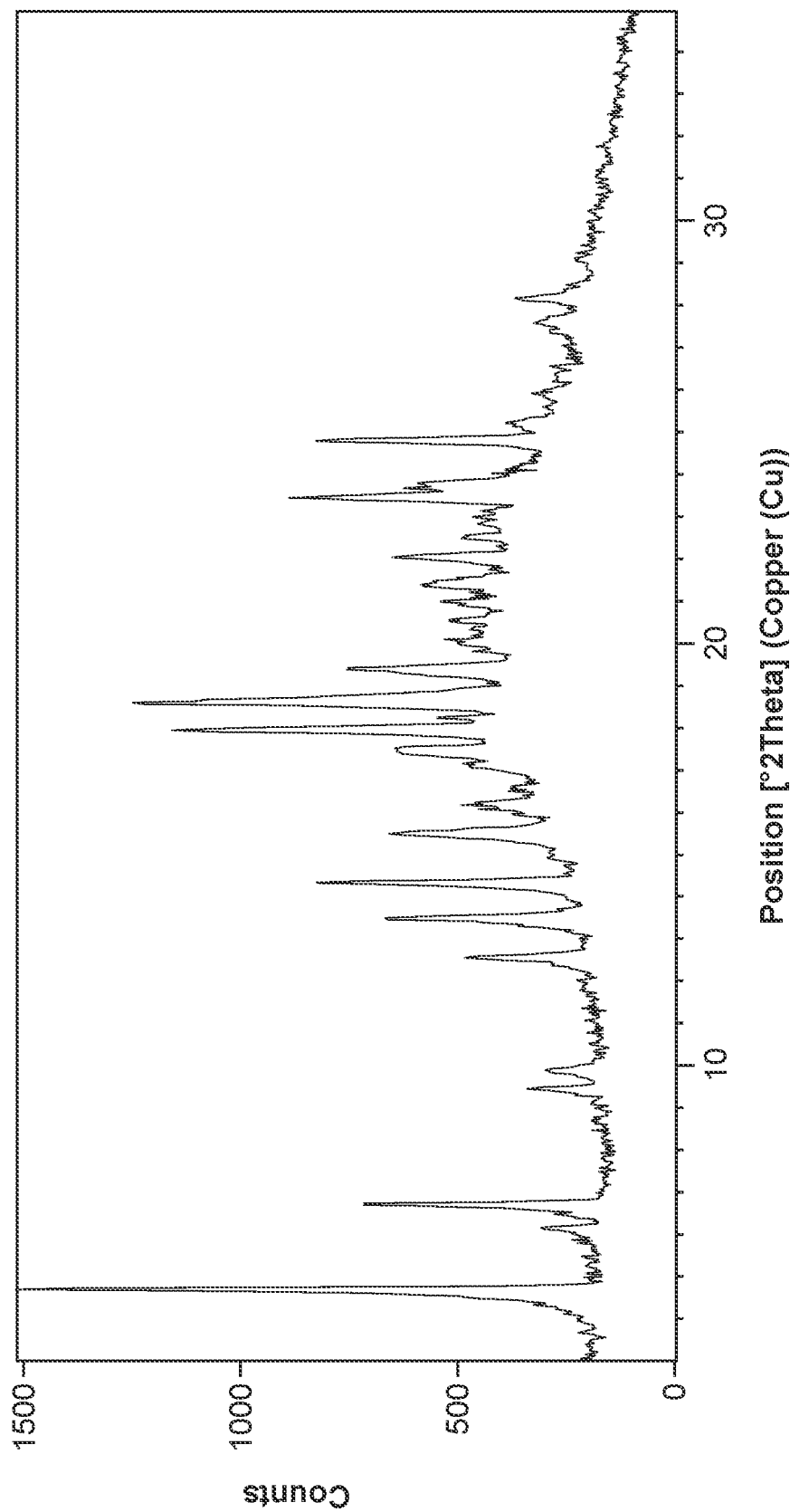
FIG. 27 is an X-ray powder diffractogram of Compound I tosylate Form V.

In one embodiment, Compound I tosylate Form V is characterized by an X-ray powder diffractogram comprising at least two of the following peaks: 4.7, 6.7, 12.6, 13.5, 14.3, 15.5, 17.9, 18.6, 19.4, 22.0, 23.4, and 24.8 °2θ, each ±0.2 °2θ. In one embodiment, Compound I tosylate Form V is characterized by an X-ray powder diffractogram comprising at least four of the following peaks: 4.7, 6.7, 12.6, 13.5, 14.3, 15.5, 17.9, 18.6, 19.4, 22.0, 23.4, and 24.8 °2θ, each ±0.2 °2θ. In one embodiment, Compound I tosylate Form V is characterized by an X-ray powder diffractogram comprising at least six of the following peaks: 4.7, 6.7, 12.6, 13.5, 14.3, 15.5, 17.9, 18.6, 19.4, 22.0, 23.4, and 24.8 °2θ, each ±0.2 °2θ. In one embodiment, Compound I tosylate Form V is characterized by an X-ray powder diffractogram comprising at least eight of the following peaks: 4.7, 6.7, 12.6, 13.5, 14.3, 15.5, 17.9, 18.6, 19.4, 22.0, 23.4, and 24.8 °2θ, each ±0.2 °2θ. In one embodiment, Compound I tosylate Form V is characterized by an X-ray powder diffractogram comprising each of the following peaks: 4.7, 6.7, 12.6, 13.5, 14.3, 15.5, 17.9, 18.6, 19.4, 22.0, 23.4, and 24.8 °2θ, each ±0.2 °2θ. In one embodiment, Compound I tosylate Form V is characterized by the full X-ray powder diffractogram as substantially shown in FIG. 27.

In one embodiment, provided is a process for making Compound I tosylate Form V. In one embodiment, the process comprises contacting a solution of Compound I Form I in DMSO with p-tolyl sulfonic acid and water, whereby Compound I tosylate Form V is formed. In one embodiment, the process for making Compound I tosylate Form V is as described in the Examples provided herein.

f. Compound I Tosylate Form VI

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form VI) characterized by the full X-ray powder diffractogram comprising the following peaks: 6.2, 16.2, and 20.3 °2θ, each ±0.2 °2θ, as determined on a diffractometer using Cu-Kα radiation. In one embodiment, the diffractogram of Compound I tosylate Form VI further comprises one or more peaks at: 4.2, 17.4, and 21.2 °2θ, each ±0.2 °2θ.

Figure 28:
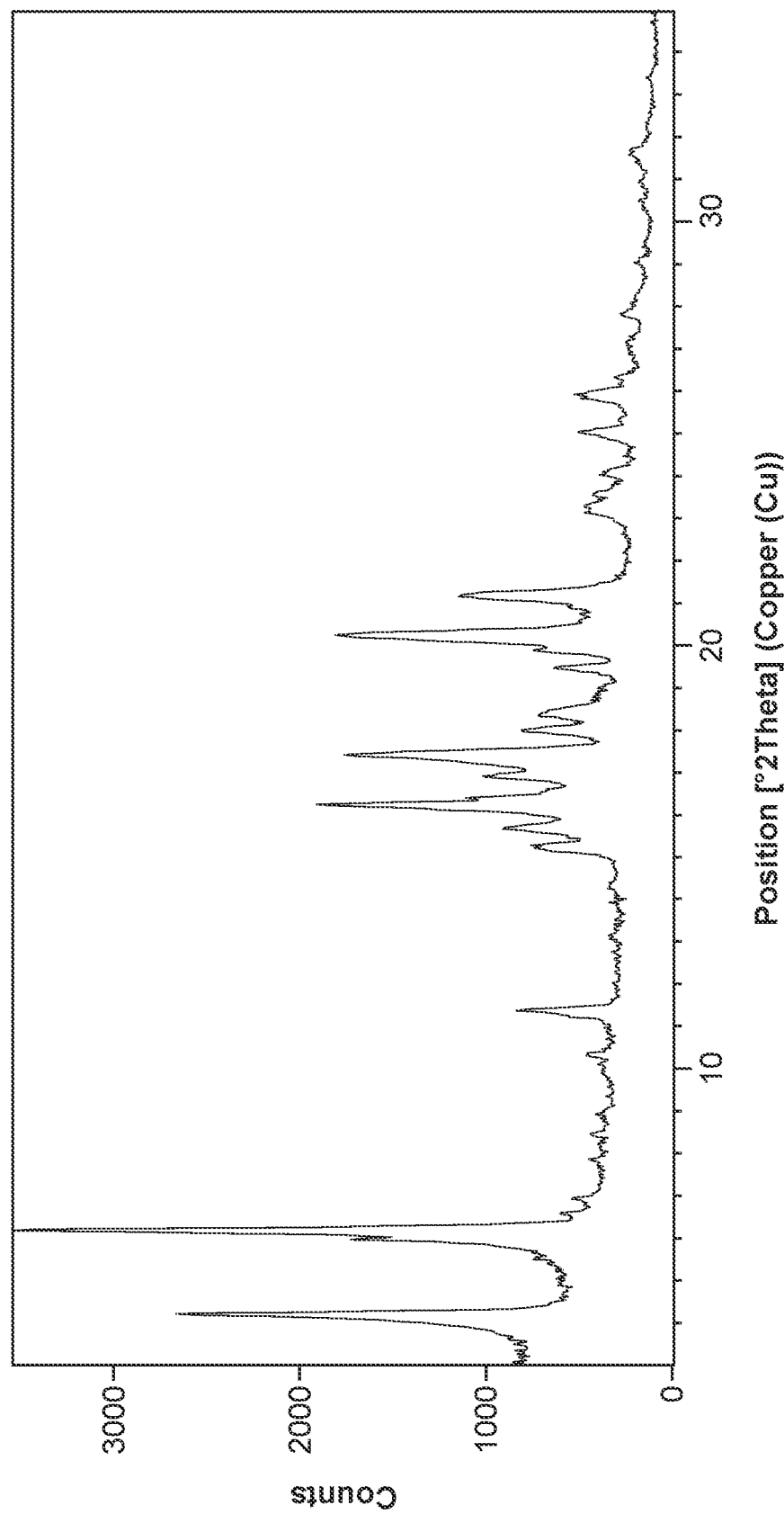
FIG. 28 is an X-ray powder diffractogram of Compound I tosylate Form VI.

In one embodiment, Compound I tosylate Form VI is characterized by an X-ray powder diffractogram comprising at least two of the following peaks: 4.2, 6.0, 6.2, 11.4, 15.7, 16.2, 16.9, 17.4, 18.0, 20.3, and 21.2 °2θ, each ±0.2 °2θ. In one embodiment, Compound I tosylate Form VI is characterized by an X-ray powder diffractogram comprising at least four of the following peaks: 4.2, 6.0, 6.2, 11.4, 15.7, 16.2, 16.9, 17.4, 18.0, 20.3, and 21.2 °2θ, each ±0.2 °2θ. In one embodiment, Compound I tosylate Form VI is characterized by an X-ray powder diffractogram comprising at least six of the following peaks: 4.2, 6.0, 6.2, 11.4, 15.7, 16.2, 16.9, 17.4, 18.0, 20.3, and 21.2 °2θ, each ±0.2 °2θ. In one embodiment, Compound I tosylate Form VI is characterized by an X-ray powder diffractogram comprising at least eight of the following peaks: 4.2, 6.0, 6.2, 11.4, 15.7, 16.2, 16.9, 17.4, 18.0, 20.3, and 21.2 °2θ, each ±0.2 °2θ. In one embodiment, Compound I tosylate Form VI is characterized by an X-ray powder diffractogram comprising each of the following peaks: 4.2, 6.0, 6.2, 11.4, 15.7, 16.2, 16.9, 17.4, 18.0, 20.3, and 21.2 °2θ, each ±0.2 °2θ. In one embodiment, Compound I tosylate Form VI is characterized by the full X-ray powder diffractogram as substantially shown in FIG. 28.

In one embodiment, provided is a process for making Compound I tosylate Form VI. In one embodiment, the process comprises contacting a solution of Compound I Form I in DMSO with p-tolyl sulfonic acid and THF, whereby Compound I tosylate Form VI is formed. In one embodiment, the process for making Compound I tosylate Form VI is as described in the Examples provided herein.

g. Compound I Tosylate Form VII

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Form VII) characterized by the full X-ray powder diffractogram comprising the following peaks: 14.5, 18.5, and 20.2 °2θ, each ±0.2 °2θ, as determined on a diffractometer using Cu-Kα radiation. In one embodiment, the diffractogram of Compound I tosylate Form VII further comprises one or more peaks at: 9.5, and 19.9 °2θ, each ±0.2 °2θ.

Figure 29:
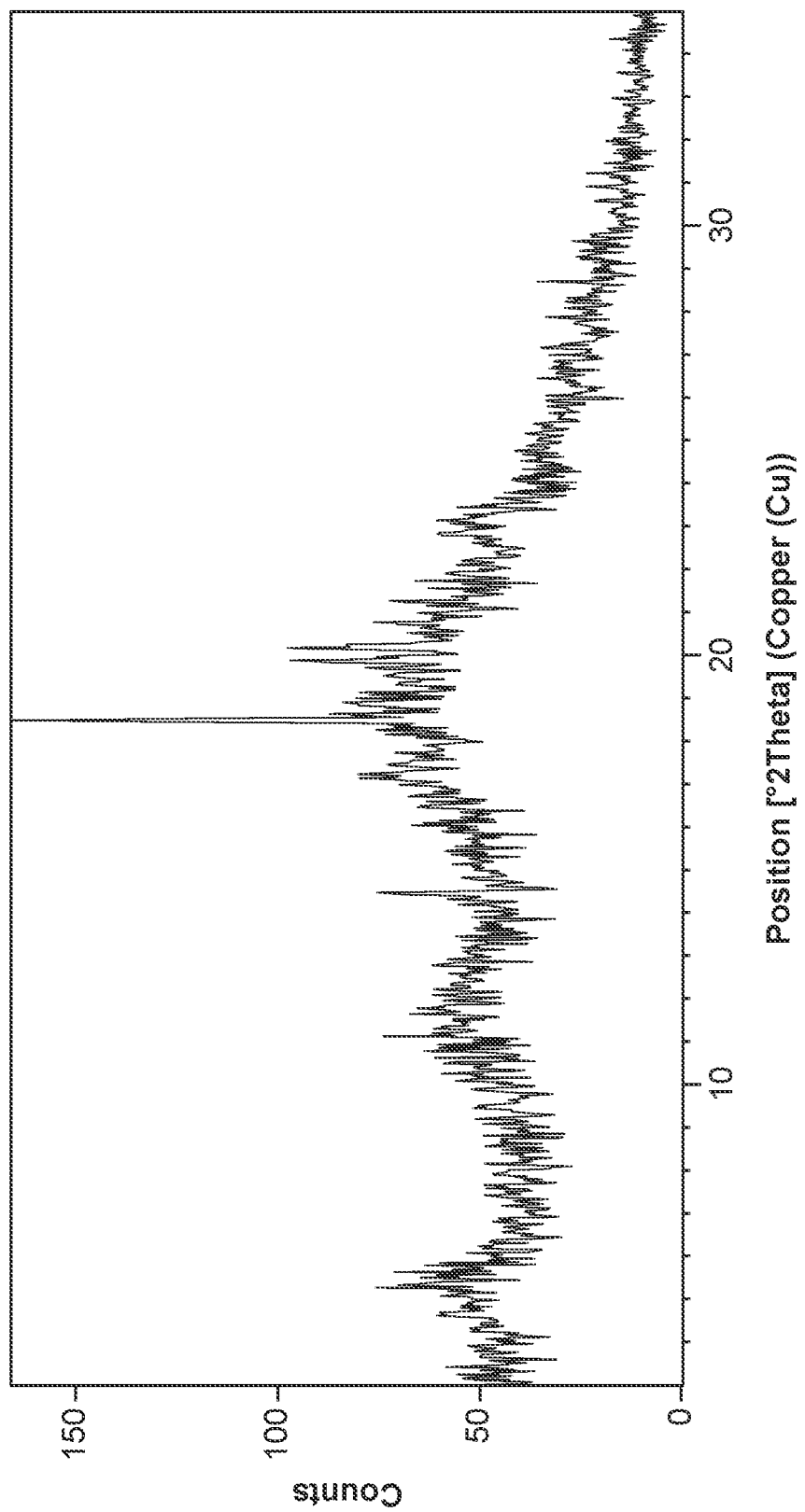
FIG. 29 is an X-ray powder diffractogram of Compound I tosylate Form VII.

In one embodiment, Compound I tosylate Form VII is characterized by an X-ray powder diffractogram comprising at least one of the following peaks: 9.5, 14.5, 18.5, 19.9, and 20.2 °2θ, each ±0.2 °2θ. In one embodiment, Compound I tosylate Form VII is characterized by an X-ray powder diffractogram comprising at least two of the following peaks: 9.5, 14.5, 18.5, 19.9, and 20.2 °2θ, each ±0.2 °2θ. In one embodiment, Compound I tosylate Form VII is characterized by an X-ray powder diffractogram comprising at least three of the following peaks: 9.5, 14.5, 18.5, 19.9, and 20.2 °2θ, each ±0.2 °2θ. In one embodiment, Compound I tosylate Form VII is characterized by an X-ray powder diffractogram comprising at least four of the following peaks: 9.5, 14.5, 18.5, 19.9, and 20.2 °2θ, each ±0.2 °2θ. In one embodiment, Compound I tosylate Form VII is characterized by an X-ray powder diffractogram comprising each of the following peaks: 9.5, 14.5, 18.5, 19.9, and 20.2 °2θ, each ±0.2 °2θ. In one embodiment, Compound I tosylate Form VII is characterized by the full X-ray powder diffractogram as substantially shown in FIG. 29.

In one embodiment, provided is a process for making Compound I tosylate Form VII. In one embodiment, the process comprises contacting a solution of Compound I Form I in DMSO with p-tolyl sulfonic acid and EtOH, whereby Compound I tosylate Form VII is formed. In one embodiment, the process for making Compound I tosylate Form VII is as described in the Examples provided herein.

h. Compound I Tosylate Type A

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Type A).

In one embodiment, provided is a process for making Compound I tosylate Type A. In one embodiment, the process for making Compound I tosylate Type A is as described in the Examples provided herein.

i. Compound I Tosylate Type B

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Type B).

In one embodiment, provided is a process for making Compound I tosylate Type B. In one embodiment, the process for making Compound I tosylate Type B is as described in the Examples provided herein.

j. Compound I Tosylate Type C

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Type C) characterized by the full X-ray powder diffractogram comprising the following peaks: 7.5, 15.0, and 8.9 °2θ, each ±0.2 °2θ, as determined on a diffractometer using Cu-Kα radiation. In one embodiment, the diffractogram of Compound I tosylate Type C further comprises one or more peaks at: 9.5, 17.2, and 11.4 °2θ, each ±0.2 °2θ.

In one embodiment, provided is a process for making Compound I tosylate Type C. In one embodiment, the process for making Compound I tosylate Type C is as described in the Examples provided herein.

k. Compound I Tosylate Type D

The present disclosure provides, in one embodiment, a crystalline form of a tosylate salt of 4-(cyclopropylamino)-2-(4-(4-(ethylsulfonyl)piperazin-1-yl)phenylamino)pyrimidine-5-carboxamide (Compound I tosylate Type D) characterized by the full X-ray powder diffractogram comprising the following peaks: 9.2, 19.2, and 6.3 °2θ, each ±0.2 °2θ, as determined on a diffractometer using Cu-Kα radiation. In one embodiment, the diffractogram of Compound I tosylate Type D further comprises one or more peaks at: 17.2, 13.5, and 12.6 °2θ, each ±0.2 °2θ.

In one embodiment, provided is a process for making Compound I tosylate Type D. In one embodiment, the process for making Compound I tosylate Type D is as described in the Examples provided herein.

Glycollate Salts a. Compound I Glycollate Type A

The present disclosure provides, in one embodiment, a crystalline form of a glycollate salt of 4-(cyclopropylamino)-2-(4-(4-(ethylsulfonyl)piperazin-1-yl)phenylamino)pyrimidine-5-carboxamide (Compound I glycollate Type A).

In one embodiment, provided is a process for making Compound I glycollate Type A. In one embodiment, the process for making Compound I glycollate Type A is as described in the Examples provided herein.

Adipate Salts a. Compound I Adipate Type A

The present disclosure provides, in one embodiment, a crystalline form of a adipate salt of 4-(cyclopropylamino)-2-(4-(4-(ethylsulfonyl)piperazin-1-yl)phenylamino)pyrimidine-5-carboxamide (Compound I adipate Type A).

In one embodiment, provided is a process for making Compound I adipate Type A. In one embodiment, the process for making Compound I adipate Type A is as described in the Examples provided herein.

b. Compound I Adipate Type B

The present disclosure provides, in one embodiment, a crystalline form of a adipate salt of 4-(cyclopropylamino)-2-(4-(4-(ethylsulfonyl)piperazin-1-yl)phenylamino)pyrimidine-5-carboxamide (Compound I adipate Type B).

In one embodiment, provided is a process for making Compound I adipate Type B. In one embodiment, the process for making Compound I adipate Type B is as described in the Examples provided herein.

Oxalate Salts a. Compound I Oxalate Type A

The present disclosure provides, in one embodiment, a crystalline form of a oxalate salt of 4-(cyclopropylamino)-2-(4-(4-(ethylsulfonyl)piperazin-1-yl)phenylamino)pyrimidine-5-carboxamide (Compound I oxalate Type A).

In one embodiment, provided is a process for making Compound I oxalate Type A. In one embodiment, the process for making Compound I oxalate Type A is as described in the Examples provided herein.

Phosphate Salts a. Compound I Phosphate Type A

The present disclosure provides, in one embodiment, a crystalline form of a phosphate salt of 4-(cyclopropylamino)-2-(4-(4-(ethylsulfonyl)piperazin-1-yl)phenylamino)pyrimidine-5-carboxamide (Compound I phosphate Type A).

In one embodiment, provided is a process for making Compound I phosphate Type A. In one embodiment, the process for making Compound I phosphate Type A is as described in the Examples provided herein.

Maleate Salts a. Compound I Maleate Type A

The present disclosure provides, in one embodiment, a crystalline form of a maleate salt of 4-(cyclopropylamino)-2-(4-(4-(ethylsulfonyl)piperazin-1-yl)phenylamino)pyrimidine-5-carboxamide (Compound I maleate Type A).

In one embodiment, provided is a process for making Compound I maleate Type A. In one embodiment, the process for making Compound I maleate Type A is as described in the Examples provided herein.

a. Compound I Maleate Type B

The present disclosure provides, in one embodiment, a crystalline form of a maleate salt of 4-(cyclopropylamino)-2-(4-(4-(ethylsulfonyl)piperazin-1-yl)phenylamino)pyrimidine-5-carboxamide (Compound I maleate Type B).

In one embodiment, provided is a process for making Compound I maleate Type B. In one embodiment, the process for making Compound I maleate Type B is as described in the Examples provided herein.

L-Tartrate Salts a. Compound I L-Tartrate Type A

The present disclosure provides, in one embodiment, a crystalline form of a L-tartrate salt of 4-(cyclopropylamino)-2-(4-(4-(ethylsulfonyl)piperazin-1-yl)phenylamino)pyrimidine-5-carboxamide (Compound I L-tartrate Type A).

In one embodiment, provided is a process for making Compound I L-tartrate Type A. In one embodiment, the process for making Compound I L-tartrate Type A is as described in the Examples provided herein.

Fumarate Salts a. Compound I Fumarate Type A

The present disclosure provides, in one embodiment, a crystalline form of a fumarate salt of 4-(cyclopropylamino)-2-(4-(4-(ethylsulfonyl)piperazin-1-yl)phenylamino)pyrimidine-5-carboxamide (Compound I fumarate Type A).

In one embodiment, provided is a process for making Compound I fumarate Type A. In one embodiment, the process for making Compound I fumarate Type A is as described in the Examples provided herein.

Citrate Salts a. Compound I Citrate Type A

The present disclosure provides, in one embodiment, a crystalline form of a citrate salt of 4-(cyclopropylamino)-2-(4-(4-(ethylsulfonyl)piperazin-1-yl)phenylamino)pyrimidine-5-carboxamide (Compound I citrate Type A).

In one embodiment, provided is a process for making Compound I citrate Type A. In one embodiment, the process for making Compound I citrate Type A is as described in the Examples provided herein.

b. Compound I Citrate Type B

The present disclosure provides, in one embodiment, a crystalline form of a citrate salt of 4-(cyclopropylamino)-2-

(4-(4-(ethylsulfonyl)piperazin-1-yl)phenylamino)pyrimidine-5-carboxamide (Compound I citrate Type B).

In one embodiment, provided is a process for making Compound I citrate Type B. In one embodiment, the process for making Compound I citrate Type B is as described in the Examples provided herein.

c. Compound I Citrate Type C

The present disclosure provides, in one embodiment, a crystalline form of a citrate salt of 4-(cyclopropylamino)-2-(4-(4-(ethylsulfonyl)piperazin-1-yl)phenylamino)pyrimidine-5-carboxamide (Compound I citrate Type C).

In one embodiment, provided is a process for making Compound I citrate Type C. In one embodiment, the process for making Compound I citrate Type C is as described in the Examples provided herein.

Malate Salts a. Compound I Malate Type A

The present disclosure provides, in one embodiment, a crystalline form of a malate salt of 4-(cyclopropylamino)-2-(4-(4-(ethylsulfonyl)piperazin-1-yl)phenylamino)pyrimidine-5-carboxamide (Compound I malate Type A).

In one embodiment, provided is a process for making Compound I malate Type A. In one embodiment, the process for making Compound I malate Type A is as described in the Examples provided herein.

b. Compound I Malate Type B

The present disclosure provides, in one embodiment, a crystalline form of a malate salt of 4-(cyclopropylamino)-2-(4-(4-(ethylsulfonyl)piperazin-1-yl)phenylamino)pyrimidine-5-carboxamide (Compound I malate Type B).

In one embodiment, provided is a process for making Compound I malate Type B. In one embodiment, the process for making Compound I malate Type B is as described in the Examples provided herein.

Gluconate Salts a. Compound I Gluconate Type A

The present disclosure provides, in one embodiment, a crystalline form of a gluconate salt of 4-(cyclopropylamino)-2-(4-(4-(ethylsulfonyl)piperazin-1-yl)phenylamino)pyrimidine-5-carboxamide (Compound I gluconate Type A).

In one embodiment, provided is a process for making Compound I gluconate Type A. In one embodiment, the process for making Compound I gluconate Type A is as described in the Examples provided herein.

Succinate Salts a. Compound I Succinate Type A

The present disclosure provides, in one embodiment, a crystalline form of a succinate salt of 4-(cyclopropylamino)-2-(4-(4-(ethylsulfonyl)piperazin-1-yl)phenylamino)pyrimidine-5-carboxamide (Compound I succinate Type A).

In one embodiment, provided is a process for making Compound I succinate Type A. In one embodiment, the process for making Compound I succinate Type A is as described in the Examples provided herein.

Malonate Salts a. Compound I Malonate Type A

The present disclosure provides, in one embodiment, a crystalline form of a malonate salt of 4-(cyclopropylamino)-2-(4-(4-(ethylsulfonyl)piperazin-1-yl)phenylamino)pyrimidine-5-carboxamide (Compound I malonate Type A).

In one embodiment, provided is a process for making Compound I malonate Type A. In one embodiment, the process for making Compound I malonate Type A is as described in the Examples provided herein.

Gentisate Salts a. Compound I Gentisate Type A

The present disclosure provides, in one embodiment, a crystalline form of a gentisate salt of 4-(cyclopropylamino)-2-(4-(4-(ethylsulfonyl)piperazin-1-yl)phenylamino)pyrimidine-5-carboxamide (Compound I gentisate Type A).

In one embodiment, provided is a process for making Compound I gentisate Type A. In one embodiment, the process for making Compound I gentisate Type A is as described in the Examples provided herein.

Besylate Salts a. Compound I Besylate Type A

The present disclosure provides, in one embodiment, a crystalline form of a besylate salt of 4-(cyclopropylamino)-2-(4-(4-(ethylsulfonyl)piperazin-1-yl)phenylamino)pyrimidine-5-carboxamide (Compound I besylate Type A) characterized by the full X-ray powder diffractogram comprising the following peaks: 7.4, 14.9, and 15.3 °2θ, each ±0.2 °2θ, as determined on a diffractometer using Cu-Kα radiation. In one embodiment, the diffractogram of Compound I besylate Type A further comprises one or more peaks at: 22.3, 23.7, and 17.6 °2θ, each ±0.2 °2θ.

In one embodiment, provided is a process for making Compound I besylate Type A. In one embodiment, the process for making Compound I besylate Type A is as described in the Examples provided herein.

b. Compound I Besylate Type B

The present disclosure provides, in one embodiment, a crystalline form of a besylate salt of 4-(cyclopropylamino)-2-(4-(4-(ethylsulfonyl)piperazin-1-yl)phenylamino)pyrimidine-5-carboxamide (Compound I besylate Type B) characterized by the full X-ray powder diffractogram comprising the following peaks: 6.0, 11.9, and 6.9 °2θ, each ±0.2 °2θ, as determined on a diffractometer using Cu-Kα radiation. In one embodiment, the diffractogram of Compound I besylate Type B further comprises one or more peaks at: 20.6, 25.3, and 14.9 °2θ, each ±0.2 °2θ.

In one embodiment, provided is a process for making Compound I besylate Type B. In one embodiment, the process for making Compound I besylate Type B is as described in the Examples provided herein.

Isethionate Salts a. Compound I Isethionate Type A

The present disclosure provides, in one embodiment, a crystalline form of a isethionate salt of 4-(cyclopropylamino)-2-(4-(4-(ethylsulfonyl)piperazin-1-yl)phenylamino)pyrimidine-5-carboxamide (Compound I isethionate Type A) characterized by the full X-ray powder diffractogram comprising the following peaks: 15.8, 17.9, and 20.1 °2θ, each ±0.2 °2θ, as determined on a diffractometer using Cu-Kα radiation. In one embodiment, the diffractogram of Compound I isethionate Type A further comprises one or more peaks at: 12.9, 24.5, and 9.9 °2θ, each ±0.2 °2θ.

In one embodiment, provided is a process for making Compound I isethionate Type A. In one embodiment, the process for making Compound I isethionate Type A is as described in the Examples provided herein.

Naphthlenesulfonate Salts a. Compound I Naphthlenesulfonate Type A

The present disclosure provides, in one embodiment, a crystalline form of a naphthlenesulfonate salt of 4-(cyclopropylamino)-2-(4-(4-(ethylsulfonyl)piperazin-1-yl)phenylamino)pyrimidine-5-carboxamide (Compound I naphthlenesulfonate Type A) characterized by the full X-ray powder diffractogram comprising the following peaks: 14.4, 20.2, and 7.5 °2θ, each ±0.2 °2θ, as determined on a diffractometer using Cu-Kα radiation. In one embodiment, the diffractogram of Compound I naphthlenesulfonate Type A further comprises one or more peaks at: 13.4, 8.1, and 11.1 °2θ, each ±0.2 °2θ.

In one embodiment, provided is a process for making Compound I naphthlenesulfonate Type A. In one embodiment, the process for making Compound I naphthlenesulfonate Type A is as described in the Examples provided herein.

b. Compound I Naphthlenesulfonate Type B

The present disclosure provides, in one embodiment, a crystalline form of a naphthlenesulfonate salt of 4-(cyclopropylamino)-2-(4-(4-(ethylsulfonyl)piperazin-1-yl)phenylamino)pyrimidine-5-carboxamide (Compound I naphthlenesulfonate Type B) characterized by the full X-ray powder diffractogram comprising the following peaks: 9.0, 15.6, and 19.7 °2θ, each ±0.2 °2θ, as determined on a diffractometer using Cu-Kα radiation. In one embodiment, the diffractogram of Compound I naphthlenesulfonate Type B further comprises one or more peaks at: 5.7, 13.4, and 25.1 °2θ, each ±0.2 °2θ.

In one embodiment, provided is a process for making Compound I naphthlenesulfonate Type B. In one embodiment, the process for making Compound I naphthlenesulfonate Type B is as described in the Examples provided herein.

c. Compound I Naphthlenesulfonate Type C

The present disclosure provides, in one embodiment, a crystalline form of a naphthlenesulfonate salt of 4-(cyclopropylamino)-2-(4-(4-(ethylsulfonyl)piperazin-1-yl)phenylamino)pyrimidine-5-carboxamide (Compound I naphthlenesulfonate Type C) characterized by the full X-ray powder diffractogram comprising the following peaks: 6.9, 13.6, and 13.3 °2θ, each ±0.2 °2θ, as determined on a diffractometer using Cu-Kα radiation. In one embodiment, the diffractogram of Compound I naphthlenesulfonate Type C further comprises one or more peaks at: 20.3, 18.0, and 16.7 °2θ, each ±0.2 °2θ.

In one embodiment, provided is a process for making Compound I naphthlenesulfonate Type C. In one embodiment, the process for making Compound I naphthlenesulfonate Type C is as described in the Examples provided herein.

Chlorobenzenesulfate Salts a. Compound I Chlorobenzenesulfate Type A

The present disclosure provides, in one embodiment, a crystalline form of a chlorobenzenesulfate salt of 4-(cyclopropylamino)-2-(4-(4-(ethylsulfonyl)piperazin-1-yl)phenylamino)pyrimidine-5-carboxamide (Compound I chlorobenzenesulfate Type A).

In one embodiment, provided is a process for making Compound I chlorobenzenesulfate Type A. In one embodiment, the process for making Compound I chlorobenzenesulfate Type A is as described in the Examples provided herein.

b. Compound I Chlorobenzenesulfate Type B

The present disclosure provides, in one embodiment, a crystalline form of a chlorobenzenesulfate salt of 4-(cyclopropylamino)-2-(4-(4-(ethylsulfonyl)piperazin-1-yl)phenylamino)pyrimidine-5-carboxamide (Compound I chlorobenzenesulfate Type B) characterized by the full X-ray powder diffractogram comprising the following peaks: 8.8, 18.5, and 9.5 °2θ, each ±0.2 °2θ, as determined on a diffractometer using Cu-Kα radiation. In one embodiment, the diffractogram of Compound I chlorobenzenesulfate Type B further comprises one or more peaks at: 17.7, 4.7, and 12.7 °2θ, each ±0.2 °2θ.

In one embodiment, provided is a process for making Compound I chlorobenzenesulfate Type B. In one embodiment, the process for making Compound I chlorobenzenesulfate Type B is as described in the Examples provided herein.

Camphorsulfonate Salts a. Compound I Camphorsulfonate Type A

The present disclosure provides, in one embodiment, a crystalline form of a camphorsulfonate salt of 4-(cyclopropylamino)-2-(4-(4-(ethylsulfonyl)piperazin-1-yl)phenylamino)pyrimidine-5-carboxamide (Compound I camphorsulfonate Type A) characterized by the full X-ray powder diffractogram comprising the following peaks: 5.9, 14.3, and 17.8 °2θ, each ±0.2 °2θ, as determined on a diffractometer using Cu-Kα radiation. In one embodiment, the diffractogram of Compound I camphorsulfonate Type A further comprises one or more peaks at: 11.4, 23.0, and 14.0 °2θ, each ±0.2 °2θ.

In one embodiment, provided is a process for making Compound I camphorsulfonate Type A. In one embodiment, the process for making Compound I camphorsulfonate Type A is as described in the Examples provided herein.

b. Compound I Camphorsulfonate Type B

The present disclosure provides, in one embodiment, a crystalline form of a camphorsulfonate salt of 4-(cyclopropylamino)-2-(4-(4-(ethylsulfonyl)piperazin-1-yl)phenylamino)pyrimidine-5-carboxamide (Compound I camphorsulfonate Type B) characterized by the full X-ray powder diffractogram comprising the following peaks: 4.7, 14.0, and 17.2 °2θ, each ±0.2 °2θ, as determined on a diffractometer using Cu-Kα radiation. In one embodiment, the diffractogram of Compound I camphorsulfonate Type B further comprises one or more peaks at: 18.3, 19.5, and 15.9 °2θ, each ±0.2 °2θ.

In one embodiment, provided is a process for making Compound I camphorsulfonate Type B. In one embodiment, the process for making Compound I camphorsulfonate Type B is as described in the Examples provided herein.

c. Compound I Camphorsulfonate Type C

The present disclosure provides, in one embodiment, a crystalline form of a camphorsulfonate salt of 4-(cyclopropylamino)-2-(4-(4-(ethylsulfonyl)piperazin-1-yl)phenylamino)pyrimidine-5-carboxamide (Compound I camphorsulfonate Type C) characterized by the full X-ray powder diffractogram comprising the following peaks: 13.5, 16.8, and 9.5 °2θ, each ±0.2 °2θ, as determined on a diffractometer using Cu-Kα radiation. In one embodiment, the diffractogram of Compound I camphorsulfonate Type C further comprises one or more peaks at: 19.3, 8.0, and 22.7 °2θ, each ±0.2 °2θ.

In one embodiment, provided is a process for making Compound I camphorsulfonate Type C. In one embodiment, the process for making Compound I camphorsulfonate Type C is as described in the Examples provided herein.

3. Pharmaceutical Compositions and Modes of Administration

The forms of Compound I as described herein may be administered in a pharmaceutical composition. Thus, the present disclosure provides pharmaceutical compositions comprising one or more of the forms of Compound I or of a salt/co-crystal thereof as described herein and one or more pharmaceutically acceptable vehicles such as carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). The pharmaceutical compositions may be administered alone or in combination with other therapeutic agents.

Some embodiments are directed to pharmaceutical compositions comprising a form of Compound I as described herein. In one embodiment a pharmaceutical composition comprises Compound I, wherein at least 75% of Compound I is in a form as described herein. In one embodiment, a pharmaceutical composition comprises Compound I, wherein at least 75% of Compound I is in Form I. In one embodiment, a pharmaceutical composition comprises Compound I, wherein at least 75% of Compound I is in Form II.

In one embodiment a pharmaceutical composition comprises Compound I, wherein at least 80% of Compound I is in a form as described herein. In one embodiment, a pharmaceutical composition comprises Compound I, wherein at least 80% of Compound I is in Form I. In one embodiment, a pharmaceutical composition comprises Compound I, wherein at least 80% of Compound I is in Form II.

In one embodiment a pharmaceutical composition comprises Compound I, wherein at least 85% of Compound I is in a form as described herein. In one embodiment, a pharmaceutical composition comprises Compound I, wherein at least 85% of Compound I is in Form I. In one embodiment, a pharmaceutical composition comprises Compound I, wherein at least 85% of Compound I is in Form II.

In one embodiment a pharmaceutical composition comprises Compound I, wherein at least 90% of Compound I is in a form as described herein. In one embodiment, a pharmaceutical composition comprises Compound I, wherein at least 90% of Compound I is in Form I. In one embodiment, a pharmaceutical composition comprises Compound I, wherein at least 90% of Compound I is in Form II.

In one embodiment a pharmaceutical composition comprises Compound I, wherein at least 95% of Compound I is in a form as described herein. In one embodiment, a pharmaceutical composition comprises Compound I, wherein at least 95% of Compound I is in Form I. In one embodiment, a pharmaceutical composition comprises Compound I, wherein at least 95% of Compound I is in Form II.

In one embodiment, a pharmaceutical composition comprises Compound I, wherein at least 97% of Compound I is in a form as described herein. In one embodiment, a pharmaceutical composition comprises Compound I, wherein at least 97% of Compound I is in Form I. In one embodiment, a pharmaceutical composition comprises Compound I, wherein at least 97% of Compound I is in Form II.

In one embodiment, a pharmaceutical composition comprises Compound I, wherein at least 99% of Compound I is in a form as described herein. In one embodiment, a pharmaceutical composition comprises Compound I, wherein at least 97% of Compound I is in Form I. In one embodiment, a pharmaceutical composition comprises Compound I, wherein at least 97% of Compound I is in Form II.

Some embodiments are directed to a pharmaceutical composition comprising a hydrochloride salt of Compound I in a form as described herein. In one embodiment, a pharmaceutical composition comprised Compound I HCl, wherein at least 75% of Compound I HCl is in Form I as described herein. In one embodiment, a pharmaceutical composition comprised Compound I HCl, wherein at least 80% of Compound I HCl is in Form I as described herein. In one embodiment, a pharmaceutical composition comprised Compound I HCl, wherein at least 85% of Compound I HCl is in Form I as described herein. In one embodiment, a pharmaceutical composition comprised Compound I HCl, wherein at least 90% of Compound I HCl is in Form I as described herein. In one embodiment, a pharmaceutical composition comprised Compound I HCl, wherein at least 95% of Compound I HCl is in Form I as described herein. In one embodiment, a pharmaceutical composition comprised Compound I HCl, wherein at least 97% of Compound I HCl is in Form I as described herein. In one embodiment, a pharmaceutical composition comprised Compound I HCl, wherein at least 99% of Compound I HCl is in Form I as described herein.

Some embodiments are directed to a pharmaceutical composition comprising a hydrochloride salt of Compound I in an amorphous form as described herein. In one embodiment, a pharmaceutical composition comprised Compound I HCl, wherein at least 95% of Compound I HCl is in an amorphous form as described herein. In one embodiment, a pharmaceutical composition comprised Compound I HCl, wherein at least 97% of Compound I HCl is in an amorphous form as described herein. In one embodiment, a pharmaceutical composition comprised Compound I HCl, wherein at least 99% of Compound I HCl is in an amorphous form as described herein.

Some embodiments are directed to pharmaceutical compositions comprising one or more pharmaceutically acceptable carriers and a therapeutically effective amount of a compound selected from: Compound I Form I, Compound I Form II, Compound I HCl Form I, Compound I HCl Form II, Compound I bis-HCl Form I, Compound I HCl amorphous, Compound I esylate Form I, Compound I edisylate Form I, Compound I edisylate Form II, Compound I edisylate Form III, Compound I edisylate Form IV, Compound I mesylate Form I, Compound I mesylate Form II, Compound I mesylate Form III, Compound I bis-mesylate Form I, Compound I naphthalene disulfonate Form I, Compound I naphthalene disulfonate Form II, Compound I naphthalene disulfonate Form III, Compound I naphthalene disulfonate Form IV, Compound I sulfate Form I, Compound I sulfate Form II, Compound I sulfate Form III, Compound I tosylate Form I, Compound I tosylate Form II, Compound I tosylate Form III, Compound I tosylate Form IV, Compound I tosylate Form V, Compound I tosylate Form VI, Compound I tosylate Form VII, Compound I HCl Type B, Compound I sulfate Type A, Compound I sulfate Type B, Compound I sulfate Type C, Compound I glycollate Type A, Compound I adipate Type A, Compound I adipate Type B, Compound I oxalate Type A, Compound I esylate Type A, Compound I phosphate Type A, Compound I maleate Type A, Compound I maleate Type B, Compound I L-tartrate Type A, Compound I fumarate Type A, Compound I citrate Type A, Compound I citrate Type B, Compound I citrate Type C, Compound I L-malate Type A, Compound I L-malate Type B, Compound I gluconate Type A, Compound I succinate Type A, Compound I tosylate Type A, Compound I tosylate Type B, Compound I tosylate Type C, Compound I tosylate Type D, Compound I mesylate Type A, Compound I mesylate Type B, Compound I malonate Type A, Compound I gentisate Type A, Compound I edisylate Type A, Compound I edisylate Type B, Compound I edisylate Type C, Compound I edisylate Type D, Compound I besylate Type A, Compound I besylate Type B, Compound I isethionate Type A, Compound I naphthalene disulfonate Type A, Compound I naphthalenesulfonate Type A, Compound I naphthalenesulfonate Type B, Compound I naphthalenesulfonate Type C, Compound I chlorobenzenesulfate Type A, Compound I chlorobenzenesulfate Type B, Compound I camphorsulfonate Type A, Compound I camphorsulfonate Type B, and Compound I camphorsulfonate Type C.

Some embodiments are directed to pharmaceutical compositions comprising one or more pharmaceutically acceptable carriers and a therapeutically effective amount of Compound I HCl Form I.

Pharmaceutical compositions described herein may be presented in single or multiple doses. Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, Pa., 2005 (hereby incorporated by reference herein).

The compounds as described herein (e.g., the solid forms of Compound I or salts/co-crystals thereof) can be administered by different routes including intravenous, intraperitoneal, subcutaneous, intramuscular, oral, transmucosal, rectal, transdermal, or inhalant. In some embodiments, the compounds as described herein can be administered by oral administration. For oral administration, for example, the compounds can be formulated into conventional oral dosage forms such as capsules, tablets, and liquid preparations such as syrups, elixirs, and concentrated drops.

For inhalants, compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the compounds described herein with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds described herein may be formulated in sterile liquid solutions, such as in physiologically compatible buffers or solutions, such as saline solution, Hank's solution, or Ringer's solution. In addition, the compounds described herein may be formulated in solid form and redissolved or suspended immediately prior to use. Lyophilized forms can also be produced.

Administration of the compound described herein can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The compounds described herein may also be used in combination with other therapies, drugs, medical procedures, etc. for treating the same disease. In some embodiments, such combination use includes administration of one or more other therapies, drugs, or medical procedures at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. In some embodiments, use in combination includes use with at least one other therapy, drug or medical procedure that is administered once or infrequently, such as surgery, along with a compound described herein administered within a short time or longer time before or after the other therapy, drug or procedure. In some embodiments, use in combination includes delivery of a compound described herein and one or more other drug therapeutics by the same route or different routes of administration. In some embodiments, a compound described herein and one or more other drug therapeutics may be delivered together in any formulation by the same route of administration, including formulations where the compounds and other drug therapeutic(s) are chemically linked in such a way that they maintain their therapeutic activity when administered. In some embodiments, the other drug therapeutic(s) may be co-administered with a compound described herein. In some embodiments, co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapeutics delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components. In some embodiments, the compounds as disclosed herein may be used in adjuvant or neoadjuvant therapy in combination with other therapies or therapeutic agents as described herein. In some embodiments involving combination use, dosage may be modified for one or more of the compounds of the present disclosure or other therapeutics used in combination, e.g., reduction in the amount dosed relative to a compound or therapy used alone, by methods well known to those of ordinary skill in the art. Exemplary combination therapies are discussed below.

4. Methods of Use

The present disclosure provides, in some embodiments, a method for treating a subject suffering from or at risk of a protein kinase mediated disease or condition. The method includes administering to the subject a therapeutically effective amount of a form described herein (e.g., any one or more solid forms of Compound I or salts/co-crystals thereof such as Compound I Form I, Compound I Form II, Compound I HCl Form I, Compound I HCl Form II, Compound I bis-HCl Form I, Compound I HCl amorphous, Compound I esylate Form I, Compound I edisylate Form I, Compound I edisylate Form II, Compound I edisylate Form III, Compound I edisylate Form IV, Compound I mesylate Form I, Compound I mesylate Form II, Compound I mesylate Form III, Compound I bis-mesylate Form I, Compound I naphthalene disulfonate Form I, Compound I naphthalene disulfonate Form II, Compound I naphthalene disulfonate Form III, Compound I naphthalene disulfonate Form IV, Compound I sulfate Form I, Compound I sulfate Form II, Compound I sulfate Form III, Compound I tosylate Form I, Compound I tosylate Form II, Compound I tosylate Form III, Compound I tosylate Form IV, Compound I tosylate Form V, Compound I tosylate Form VI, Compound I tosylate Form VII, Compound I HCl Type B, Compound I sulfate Type A, Compound I sulfate Type B, Compound I sulfate Type C, Compound I glycollate Type A, Compound I adipate Type A, Compound I adipate Type B, Compound I oxalate Type A, Compound I esylate Type A, Compound I phosphate Type A, Compound I maleate Type A, Compound I maleate Type B, Compound I L-tartrate Type A, Compound I fumarate Type A, Compound I citrate Type A, Compound I citrate Type B, Compound I citrate Type C, Compound I L-malate Type A, Compound I L-malate Type B, Compound I gluconate Type A, Compound I succinate Type A, Compound I tosylate Type A, Compound I tosylate Type B, Compound I tosylate Type C, Compound I tosylate Type D, Compound I mesylate Type A, Compound I mesylate Type B, Compound I malonate Type A, Compound I gentisate Type A, Compound I edisylate Type A, Compound I edisylate Type B, Compound I edisylate Type C, Compound I edisylate Type D, Compound I besylate Type A, Compound I besylate Type B, Compound I isethionate Type A, Compound I naphthalene disulfonate Type A, Compound I naphthalenesulfonate Type A, Compound I naphthalenesulfonate Type B, Compound I naphthalenesulfonate Type C, Compound I chlorobenzenesulfate Type A, Compound I chlorobenzenesulfate Type B, Compound I camphorsulfonate Type A, Compound I camphorsulfonate Type B, and Compound I camphorsulfonate Type C). In certain embodiments, the method involves administering to the subject an effective amount of any one or more solid forms of Compound I or a salt/co-crystal thereof as described herein in combination with one or more other therapies for the disease or condition.

In some embodiments, the present disclosure provides a method for treating a subject suffering from or at risk of a protein kinase mediated disease or condition, where the method involves administering to the subject a therapeutically effective amount of Compound I HCl Form I or a pharmaceutical composition comprising Compound I HCl Form I.

In some embodiments, the diseases or conditions treatable with the compounds as described herein include diseases or conditions mediated, at least in part, by JAK and/or SYK activity. Exemplary JAK and/or SYK mediated diseases or conditions include, but are not limited to, cardiovascular disease; allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoriasis, and Sjogren's syndrome; Type II inflammatory diseases such as vascular inflammation (including vasculitis, arteritis, atherosclerosis, and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome; diseases of the central nervous system such as stroke; pulmonary diseases such as bronchitis obliteraus and primary pulmonary hypertension; delayed or cell mediated Type IV hypersensitivity reactions; and solid and hematologic malignancies such as leukemia and lymphomas.

In some embodiments, the present disclosure provides a method for treating or preventing a condition in a subject characterized by undesired thrombosis comprising administering to the subject in need thereof a therapeutically effective amount of a compound disclosed herein (e.g., any one or more solid forms of Compound I or salts/co-crystals thereof). Such conditions (i.e., undesired thrombosis) include, but are not limited to, restenosis, acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In some embodiments, the present disclosure provides a method for treating an autoimmune or inflammatory disease or condition in a subject in need thereof by administering to the subject a therapeutically effective amount of a compound disclosed herein (e.g., any one or more solid forms of Compound I or salts/co-crystals thereof). Exemplary autoimmune or inflammatory diseases or conditions include, but are not limited to, multiple sclerosis (MS), psoriasis, Sjogren's syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, systemic lupus erythematosis, rheumatoid arthritis, Reiter's syndrome, polymyositis-dermatomyositis, systemic sclerosis, polyarteritis nodosa, bullous pemphigoid, beta-cell (humoral) based or T-cell based autoimmune diseases such as Cogan's syndrome, ankylosing spondylitis, Wegener's granulomatosis, autoimmune alopecia, Type I or juvenile onset diabetes, and thyroiditis.

In some embodiments, the present disclosure provides a method for treating a hematological cancer in a subject in need thereof by administering to the subject a therapeutically effective amount of a compound disclosed herein (e.g., any one or more solid forms of Compound I or salts/co-crystals thereof). Exemplary hematological cancers include, but are not limited to, chronic lymphocytic leukemia (CLL), small lymphocytic lymphoma (SLL), follicular lymphoma (FL), transformed follicular lymphoma (tFL), diffuse large B-cell lymphoma (DLBCL), mantle cell lymphoma (MCL), B-cell non-Hodgkin's lymphoma (NHL), aggressive NHL, T-cell lymphoma such as peripheral T-cell lymphoma (PTCL), peripheral T-cell lymphoma not otherwise specified (PTCL-NOS), angioimmunoblastic T-cell lymphoma (AITL), follicular T-cell lymphoma (FTCL), anaplastic large cell lymphoma (ALCL), enteropathy-associated T-cell lymphoma (EATL), adult T-cell leukemia/lymphoma (ATLL), nasal NK/T-cell lymphoma, hepatosplenic T-cell lymphoma, or cutaneous T-cell lymphoma (CTCL) (such as mycosis fungoides or Sézary syndrome), marginal zone lymphoma, mucosa-associated lymphoid Tissue (MALT), and Waldenstrom macrogloblunemia (WM).

In some embodiments, the present disclosure provides a method for treating a relapsed or refractory hematologic cancer in a patient in need thereof, comprising administering to the patient an effective amount of a compound disclosed herein (e.g., any one or more solid forms of Compound I or salts/co-crystals thereof).

In some embodiments, the disease or condition treatable by the compounds described herein (e.g., any one or more solid forms of Compound I or salts/co-crystals thereof) is selected from: thrombosis, hemolytic anemia, immune thrombocytic purura, heparin induced thrombocytopenia, dilated cardiomyopathy, sickle cell disease, atherosclerosis, myocardial infarction, vascular inflammation, unstable angina and acute coronary syndromes. In one embodiment, the disease or condition is thrombosis. In one embodiment, the disease or condition is anemia. In one embodiment, the disease or condition is immune thrombocytic purura. In one embodiment, the disease or condition is thrombosis. In one embodiment, the disease or condition is heparin induced thrombocytopenia. In one embodiment, the disease or condition is dilated cardiomyopathy. In one embodiment, the disease or condition is sickle cell disease. In one embodiment, the disease or condition is atherosclerosis. In one embodiment, the disease or condition is myocardial infarction. In one embodiment, the disease or condition is vascular inflammation. In one embodiment, the disease or condition is unstable angina or an acute coronary syndrome.

In some embodiments, the disease or condition treatable by the compounds described herein (e.g., any one or more solid forms of Compound I or salts/co-crystals thereof) is selected from: allergy, asthma, rheumatoid arthritis, anti-phospholipids syndrome, lupus, psoriasis, multiple sclerosis, and end stage renal disease. In one embodiment, the disease or condition is an allergy. In one embodiment, the disease or condition is asthma. In one embodiment, the disease or condition is rheumatoid arthritis. In one embodiment, the disease or condition is anti-phospholipids syndrome. In one embodiment, the disease or condition is lupus. In one embodiment, the disease or condition is psoriasis. In one embodiment, the disease or condition is multiple sclerosis. In one embodiment, the disease or condition is end stage renal disease.

In some embodiments, the disease or condition treatable by the compounds described herein (e.g., any one or more solid forms of Compound I or salts/co-crystals thereof) is selected from: B-cell non-Hodgkin's lymphoma (NHL), aggressive NHL, transformed NHL, chronic lymphocytic leukemia (CLL), small lymphocytic lymphoma (SLL), peripheral T-cell lymphoma (PTCL), cutaneous T-cell lymphoma (CTCL), follicular lymphoma (FL) (e.g., of grade 1, grade 2, grade 3A, or grade 3B (FL3b), transformed follicular lymphoma (tFL), diffuse large B-cell lymphoma (DLBCL), marginal zone lymphoma, mucosa-associated lymphoid tissue (MALT), and Waldenstrom macroglobluinemia (WM). In one embodiment, the disease or condition is B-cell non-Hodgkin's lymphoma (NHL). In one embodiment, the disease or condition is aggressive NHL. In one embodiment, the disease or condition is transformed NHL. In one embodiment, the disease or condition is chronic lymphocytic leukemia (CLL). In one embodiment, the disease or condition is small lymphocytic lymphoma (SLL). In one embodiment, the disease or condition is peripheral T-cell lymphoma (PTCL). In one embodiment, the disease or condition is cutaneous T-cell lymphoma (CTCL). In one embodiment, the disease or condition is follicular lymphoma (FL). In one embodiment, the disease or condition is FL grade 1. In one embodiment, the disease or condition is FL grade 2. In one embodiment, the disease or condition is FL grade 3A. In one embodiment, the disease or condition is FL3b. In one embodiment, the disease or condition is a transformed follicular lymphoma (FL). In one embodiment, the disease or condition is diffuse large B-cell lymphoma (DLBCL). In one embodiment, the disease or condition is marginal zone lymphoma. In one embodiment, the disease or condition is mucosa-associated lymphoid tissue (MALT). In one embodiment, the disease or condition is Waldenstrom macroglobluinemia (WM).

It is contemplated that the compounds disclosed herein (e.g., any one or more solid forms of Compound I or salts/co-crystals thereof) may be useful for heavily pre-treated subjects (patients) and/or relapse/refractory hematological cancers, including but not limited to CLL, FL, NHL, and DLBCL. In some embodiments, a compound as described herein may induce apoptosis in primary Diffuse Large B Cell Lymphoma (DLBCL) cells in vitro. In some embodiments, a compound as described herein may induce apoptosis in primary CLL, with preferential activity in cases of poor prognosis such as unmutated IGHV, high CD49d, ZAP-70, or surface IgM expression.

In some embodiments, the subject (patient) in need thereof is a patient having a B cell malignancy. In some embodiments, the subject has a myeloid malignancy, such as multiple myeloma and acute myeloid leukemia.

In some embodiments, the subject (patient) in need thereof is a patient exhibiting drug resistance to, and/or a relapse for, a hematological cancer for a number of reasons. For example, the patient may have a mutation linked to relapse and/or a resistance to a drug for treating a hematological cancer. Accordingly, some embodiments provide for a method for treating a hematological cancer in a patient in need thereof comprising administering to the patient an effective amount of a compound disclosed herein (e.g., any one or more solid forms of Compound I or salts/co-crystals thereof), wherein the patient has a mutation linked to relapse and/or a resistance to another drug for treating a hematological cancer.

In some embodiments, the patient may have a del17p mutation, del11q mutation, a TP53 mutation, an ATM mutation, a STAT mutation, a STAT 6 mutation, a C481S STAT6 mutation, a mutation associated with the NOTCH pathway, a mutation associated with the Caderin pathway, or a combination thereof. In some embodiments, the patient may have a S86A mutation in STAT. In some some embodiments, the patient does not have a mutation in each of P53, BTK, and EP300.

In some embodiments, the patient may comprise a del17p mutation, del11q mutation, a P 53 mutation, an ATM mutation, a STAT mutation, a STAT 6 mutation, a C481S STAT6 mutation, a mutation associated with the NOTCH pathway, a mutation associated with the Cadherin pathway, or a combination thereof. In some embodiments, the patient may comprise a del17p mutation, del11q mutation, a TP 53 mutation, an ATM mutation, a STAT mutation, a STAT 6 mutation, a C481S BTK mutation, a mutation associated with the NOTCH pathway, a mutation associated with the Cadherin pathway, or a combination thereof.

In some embodiments, the patient has a MYD88 mutation, a CARD11 mutation, or a A20 mutation. In some embodiments, the patient has high-risk genetic abnormalities including del11q, trisomy 12, and del17p. In some embodiments, the patient has a del17p mutation. In some embodiments, the patient has a del11q mutation.

In some embodiments, the patient has a CD79B mutation, a MYD88 mutation, a CARD11 mutation, or a A20 mutation. In some embodiments, the patient has a CD79B mutation. In some embodiments, the patient does not have a IKB deletion.

In some embodiments, the patient has a PLCγ2 mutation.

In some embodiments, the patient has a BTK mutation. In some embodiments, the patient does not have a IKB deletion. In some embodiments, the patient does not have a deletion of IkB-alpha, IkB-beta, IkB-episilon, or IkB-gamma.

In some embodiments, the patient may have a poor prognosis such as unmutated IGHV, high CD49d, ZAP-70, or surface IgM expression.

In some embodiments, the patient has resistance to a drug, which is not cerdulatinib. Non-limiting examples of these drugs are an anti-CD20 antibody, a BCL-2 inhibitor, a BTK inhibitor, a P13Kδ inhibitor, rituximab, a platinum-based drug, an antimetabolite, ibrutinib, idelalisib, fludararbine (fludarabine phosphate, FLUDARA®), anthracyclines, a BCR pathway inhibitor, ABT-199 (venetoclax), or another chemotherapeutic agent used for treating a hematologic cancer. Other non-limiting examples of chemotherapeutic agents include alkylating agents, cytoskeletal disruptors, epothiolones, histone deacetylase inhibitors, inhibitors of topoisomerase I, inhibitors of topoisomerase II, nucleotide analogs and precursor analogs, antibiotics, platinum-based agents, retinoids, vinca alkaloids, or a combination thereof. In some embodiments, the patient has a resistance to a chemotherapeutic agent.

In some embodiments, the patient has resistance to an anti-CD20 antibody, a BCL-2 inhibitor, a BTK inhibitor, a P13Kδ inhibitor, a platinum-based drug, an antimetabolite, an anthracycline, a BCR pathway inhibitor, or another chemotherapeutic agent used for treating a hematologic cancer. In some embodiments, the patient has resistance to a drug selected from the group consisting of ABT-199 (venetoclax), rituximab, ibrutinib, idelalisib, and fludararbine (fludarabine phosphate, FLUDARA®). In some embodiments, the patient has resistance to ibrutinib.

In some embodiments, the patient was previously administered a drug for treating a hematological cancer. Non-limiting examples the drug include an alkylating agent, an anti-CD20 antibody, a BCL-2 inhibitor, a BTK inhibitor, a P13Kδ inhibitor, rituximab, a platinum-based drug, an anti-metabolite, ibrutinib, idelalisib, fludararbine (fludarabine phosphate, FLUDARA®), anthracyclines, a BCR pathway inhibitor, ABT-199 (venetoclax), and other agents used for treating a hematologic cancer. Other non-limiting examples of chemotherapeutic agents include cytoskeletal disruptors, epothiolones, histone deacetylase inhibitors, inhibitors of topoisomerase I, inhibitors of topoisomerase II, nucleotide analogs and precursor analogs, antibiotics, platinum-based agents, retinoids, vinca alkaloids, or a combination thereof.

In some embodiments, the patient was previously administered a drug selected from the group consisting of an alkylating agent, an anti-CD20 antibody, a BCL-2 inhibitor, a BTK inhibitor, a P13Kδ inhibitor, a platinum-based drug, an antimetabolite, an anthracycline, a BCR pathway inhibitor, and another chemotherapeutic agent used for treating a hematologic cancer. In some embodiments, the patient was previously administered a drug selected from the group consisting of venetoclax, rituximab, ibrutinib, idelalisib, and fludararbine. In some embodiments, the drug is R-CHOP (Rituximab; Cyclophosphamide; Doxorubicin hydrochloride; Oncovin(vincristine); Prednisone). In some embodiments, the drug is R-CVP (Rituximab; Cyclophosphamide; Vincristine; Prednisone). In some embodiments, the drug is bevacizumab. In some embodiments, the drug is a combination of fludarabine and rituximab, a combination of bendamustine and rituximab, or a combination of bevacizumab and rituximab In some embodiments, the patient was previously administered a drug selected from venetoclax, rituximab, ibrutinib, idelalisib, and fludararbine.

In some embodiments, the patient is 60 years or older and relapsed after a first line cancer therapy. In some embodiments, the patient is 18 years or older and is relapsed or refractory after a second line cancer therapy. In some embodiments, the patient is 60 years or older and is primary refractory to a first line cancer therapy. In some embodiments, the patient is 70 years or older and is previously untreated. In some embodiments, the patient is 70 years or older and is ineligible and/or unlikely to benefit from cancer therapy.

5. Combination Therapy

In some embodiments, the solid forms described herein (e.g., solid forms of Compound I or salts/co-crystals thereof such as Compound I Form I, Compound I Form II, Compound I HCl Form I, Compound I HCl Form II, Compound I bis-HCl Form I, Compound I HCl amorphous, Compound I esylate Form I, Compound I edisylate Form I, Compound I edisylate Form II, Compound I edisylate Form III, Compound I edisylate Form IV, Compound I mesylate Form I, Compound I mesylate Form II, Compound I mesylate Form III, Compound I bis-mesylate Form I, Compound I naphthalene disulfonate Form I, Compound I naphthalene disulfonate Form II, Compound I naphthalene disulfonate Form III, Compound I naphthalene disulfonate Form IV, Compound I sulfate Form I, Compound I sulfate Form II, Compound I sulfate Form III, Compound I tosylate Form I, Compound I tosylate Form II, Compound I tosylate Form III, Compound I tosylate Form IV, Compound I tosylate Form V, Compound I tosylate Form VI, Compound I tosylate Form VII, Compound I HCl Type B, Compound I sulfate Type A, Compound I sulfate Type B, Compound I sulfate Type C, Compound I glycollate Type A, Compound I adipate Type A, Compound I adipate Type B, Compound I oxalate Type A, Compound I esylate Type A, Compound I phosphate Type A, Compound I maleate Type A, Compound I maleate Type B, Compound I L-tartrate Type A, Compound I fumarate Type A, Compound I citrate Type A, Compound I citrate Type B, Compound I citrate Type C, Compound I L-malate Type A, Compound I L-malate Type B, Compound I gluconate Type A, Compound I succinate Type A, Compound I tosylate Type A, Compound I tosylate Type B, Compound I tosylate Type C, Compound I tosylate Type D, Compound I mesylate Type A, Compound I mesylate Type B, Compound I malonate Type A, Compound I gentisate Type A, Compound I edisylate Type A, Compound I edisylate Type B, Compound I edisylate Type C, Compound I edisylate Type D, Compound I besylate Type A, Compound I besylate Type B, Compound I isethionate Type A, Compound I naphthalene disulfonate Type A, Compound I naphthalenesulfonate Type A, Compound I naphthalenesulfonate Type B, Compound I naphthalenesulfonate Type C, Compound I chlorobenzenesulfate Type A, Compound I chlorobenzenesulfate Type B, Compound I camphorsulfonate Type A, Compound I camphorsulfonate Type B, and Compound I camphorsulfonate Type C) may be combined with another therapeutic agent, or with two or more other therapeutic agents, particularly in the treatment of cancer or other diseases or conditions described herein. In one embodiment, Compound I HCl Form I may be combined with another therapeutic agent, or with two or more other therapeutic agents, particularly in the treatment of cancer or other diseases or conditions described herein.

In some embodiments, a composition includes any one or more compound(s) as described (e.g., any one or more solid forms of Compound I or salts/co-crystals thereof) along with one or more compounds that are therapeutically effective for the same disease indication, wherein the compounds have a synergistic effect on the disease indication. For instance, in one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides methods for treating a disease or condition mediated, in part by, SYK or JAK activity in a subject in need thereof by administering to the subject an effective amount of any one or more compound(s) as described herein (e.g., any one or more solid forms of Compound I or salts/co-crystals thereof), or a composition comprising a compound as described herein, in combination with one or more other therapeutic agents as described herein. In some embodiments, the one or more therapeutic agents include, but are not limited to common immunosuppressive therapies such as mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)); irradiation; and combinations thereof.

In some embodiments, the present disclosure provides methods for treating a hematological cancer in a subject in need thereof by administering to the subject an effective amount of any one or more compound(s) as described herein (e.g., any one or more solid forms of Compound I or salts/co-crystals thereof), or a composition comprising a compound as described herein, in combination with one or more other therapeutic agents that are effective in treating hematological cancer. Exemplary therapeutic agents effective in treating a hematological cancer include but are not limited to an anti-CD20 antibody, a BCL-2 inhibitor, a BTK inhibitor, a P13Kδ inhibitor, rituximab, a platinum-based drug, an antimetabolite, ibrutinib, idelalisib, fludararbine (fludarabine phosphate, FLUDARA®), R-CHOP (Rituximab; Cyclophosphamide; Doxorubicin hydrochloride; (vincristine); Prednisone), R-CVP (Rituximab; Cyclophosphamide; Vincristine; Prednisone), bevacizumab, bendamustine, anthracyclines, a BCR pathway inhibitor, ABT-199 (venetoclax), cytoskeletal disruptors, epothilones, histone deacetylase inhibitors, inhibitors of topoisomerase I, inhibitors of topoisomerase II, nucleotide analogs and precursor analogs, antibiotics, retinoids, vinca alkaloids, an alkylating agent, and combinations thereof.

In some embodiments, the present disclosure provides methods of for treating hemotalogic cancer in a patient in need thereof, where said method comprises administering to a patient an effective amount a compound as described herein (e.g., a solid form of Compound I or salts/co-crystals thereof) and an effective amount of venetoclax to treat a hematologic cancer. In some embodiments, a compound as described herein and venetoclax are administered concurrently or sequentially.

In some embodiments, the present disclosure provides methods for treating a hematologic cancer in a patient in need thereof, where said method comprises administering a therapeutically effective amount of a combination of a compound as described herein (e.g., a solid form of Compound I or salts/co-crystals thereof) and a chemotherapeutic agent used for treating the same hematologic cancer (such as venetoclax), the combination including a sub-therapeutically effective amount of the compound as disclosed herein and a sub-therapeutically effective amount of the chemotherapeutic agent.

Some embodiments provide for a method for treating B-cell lymphoma in a patient having a cancerous cell having down-regulation of the IκBα gene, comprising administering to the patient an effective amount of a compound as described herein (e.g., any one or more solid forms of Compound I or salts/co-crystals thereof) and an NF-κB inhibitor. In some embodiments, the cell has deregulated CD40 receptor signaling or deregulated toll like receptor signaling. In some embodiments, the deregulation of the CD40 receptor signaling pathway comprises activation of CD40.

In some embodiments, the present disclosure provides a method of treating a cancer in a subject in need thereof by administering to the subject an effective amount of any one or more compound(s) as described herein (e.g., any one or more solid forms of Compound I or salts/co-crystals thereof), or a composition comprising a compound as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, -ray, or electron, proton, neutron, or particle beam), hyperthermia heating (e.g. microwave, ultrasound, radiofrequency ablation), vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e g aminolevulinic acid, motexatin lutetium), surgery, or bone marrow and stem cell transplantation. Some embodiments provide for a composition comprising a compound as described herein (e.g., any one or more solid forms of Compound I or salts/co-crystals thereof), and a chemotherapeutic agent selected from a BCL-2 inhibitor, a BTK inhibitor, a PI3Kδ inhibitor, a platinum-based drug, an antimetabolite, and a combination thereof.

Some embodiments provide for a composition comprising a compound as described herein (e.g., any one or more solid forms of Compound I or salts/co-crystals thereof), and a chemotherapeutic agent selected from a BCL-2 inhibitor, a BTK inhibitor, a PI3Kδ inhibitor, an anti-CD20 antibody, ABT-199 (venetoclax), rituximab (Rituxan®, Mabthera®, Zytux®), a platinum-based drug, an antimetabolite, ibrutinib (Imbruvica®), idelalisib (Zydelig®), and a combination thereof. In some embodiments, the chemotherapeutic agent is selected from venetoclax, rituximab, ibrutinib, idelalisib, gemcitabine, oxaliplatin, and a combination thereof.

Some embodiments provide for a composition comprising a compound as described herein (e.g., any one or more solid forms of Compound I or salts/co-crystals thereof), and a chemotherapeutic agent selected from duvelisib (PI3K-δ and PI3K-γ inhibitor), ublituximab (an anti-CD20 antibody), obinutuzumab (an anti-CD20 antibody), ACP-196 (a BTK inhibitor), TGR-1202 (PI3K-δ inhibitor), nivolumab (an anti-PD-1 antibody), pembrolizumab (an anti-PD-1 antibody), pidilizumab (an anti-PD-1 antibody), CTL019 (a CAR-T inhibitor), KTE-C19 CAR (a CAR-T inhibitor), or EPZ-6438 (an EZH2 inhibitor), alisertib (aurora kinase inhibitor), and mogamulizumab (anti-CCR4 antibody).

In some embodiments, a compound as described herein (e.g., any one or more solid forms of Compound I or salts/co-crystals thereof) and the chemotherapeutic agent can provide a synergistic effect in apoptosis. In some embodiments, a compound as described herein and the chemotherapeutic agent can provide a synergistic effect in cell lines expressing a Bcl-2 protein. In some embodiments, a compound as described herein and the chemotherapeutic agent can provide a synergistic effect in cell lines expressing a Bim protein.

In some embodiments, a compound as described herein (e.g., any one or more solid forms of Compound I or salts/co-crystals thereof) is administered in a therapeutic dose and the amount of the other chemotherapeutic agent may be in an amount that is reduced by about 10% to about 65% of the agent's therapeutic dose, which dose is described herein.

Some embodiments provide for a composition comprising a compound as described herein (e.g., any one or more solid forms of Compound I or salts/co-crystals thereof), and a chemotherapeutic agent in a mole ratio of about 300:1 to about 3:1.

Some embodiments provide for a composition comprising a compound as described herein (e.g., any one or more solid forms of Compound I or salts/co-crystals thereof), and ABT-199 (venetoclax), and at least one pharmaceutically acceptable carrier or excipient. Venetoclax is a BCL2 inhibitor and is described, for example, in U.S. Pat. Nos. 8,722,657 and 8,580,794. Venetoclax has a chemical name of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}-sulfonyl)-2-(1H-pyrrolo[2,3-b]pyridin-5-yloxy)benzamide.

In embodiments described herein, venetoclax may also refer to a pharmaceutically acceptable salt thereof (as defined above).

In some embodiments, a compound as described herein (e.g., any one or more solid forms of Compound I or salts/co-crystals thereof) and venetoclax provide a synergistic effect in apoptosis.

Some embodiments provide for a composition comprising a compound as described herein (e.g., any one or more solid forms of Compound I or salts/co-crystals thereof), and venetoclax in a mole ratio of about 300:1 to about 3:1. In some embodiments, the composition comprises a compound as described herein and/or venetoclax in sub-therapeutic amounts. For example, it is contemplated that a compound as described herein is administered in a therapeutic dose and the amount of venetoclax may be in an amount that is reduced by about 10% to about 65% of the agent's therapeutic dose, which dose is described herein. In some embodiments, a compound as described herein is administered in a therapeutically effective amount as defined herein and the amount of venetoclax may be in an amount that is reduced by about 10% to about 50% of venetoclax's therapeutic dose.

Some embodiments provide for a composition comprising a compound as described herein (e.g., any one or more solid forms of Compound I or salts/co-crystals thereof), and venetoclax of about 9:1 to about 1:9. In some embodiments, the composition includes a compound as described herein and venetoclax in a mole ratio of about 2:1 to about 1:2. In some embodiments, the composition includes a compound as described herein and venetoclax in a mole ratio of about 2:1 to about 1:5. In some embodiments, the composition includes a compound as described herein and venetoclax in a mole ratio of about 1:1. In some embodiments, the composition includes a compound as described herein and venetoclax in a mole ratio about 1:1, about 1:2, about 1:9, about 2:1, or about 9:1.

In some embodiments, venetoclax, whether alone or in combination with a compound as described herein (e.g., any one or more solid forms of Compound I or salts/co-crystals thereof), is administered at from about 0.01 and 50 mg/kg, or 0.1 and 20 mg/kg of the subject being treated. In some embodiments, venetoclax, whether alone or in combination with a compound as described herein, is administered at from about 10 mg, 20 mg, 50 mg, 100 mg, 150 mg, 200 mg, 250 mg, 300 mg, 350 mg, 400 mg, or about 450 mg once daily. In some embodiments, venetoclax, whether alone or in combination with a compound as described herein, is administered at less than about 600 mg, about 550 mg, about 500 mg, about 450 mg, about 400 mg, about 350 mg, about 300 mg, about 250 mg, about 200 mg, about 150 mg, about 100 mg, or about 50 mg daily.

In some embodiments, venetoclax, whether alone or in combination with a compound as described herein (e.g., any one or more solid forms of Compound I or salts/co-crystals thereof), is administered at about 400 mg daily. In some embodiments, venetoclax, whether alone or in combination with a compound disclosed herein, is administered at 20 mg daily for the first 7 days the subject is taking venetoclax.

Some embodiments provide for a composition comprising a compound as described herein (e.g., any one or more solid forms of Compound I or salts/co-crystals thereof), and ibrutinib. Ibrutinib (Imbruvica®) is a BTK inhibitor and is described, for example, in U.S. Pat. No. 7,514,444. Ibrutinib has a chemical name of 1-[(3R)-3-[4-Amino-3-(4-phenoxyphenyl)-1H-pyrazolo[3,4-d]pyrimidin-1-yl]piperidin-1-yl] prop-2-en-1-one.

In some embodiments, a compound as described herein and ibrutinib are administered in a mole ratio of about 300:1 to about 3:1.

In some embodiments, a compound as described herein (e.g., any one or more solid forms of Compound I or salts/co-crystals thereof), and ibrutinib are administered in a mole ratio of about 1:5. In some embodiments, a compound as described herein and ibrutinib are administered in subtherapeutic amounts.

In some embodiments, a compound as described herein (e.g., any one or more solid forms of Compound I or salts/co-crystals thereof) and ibrutinib are administered in a mole ratio of about 9:1 to about 1:9. In some embodiments, a compound as described herein and ibrutinib are administered in a mole ratio about 2:1 to about 1:2. In some embodiments, a compound as described herein and ibrutinib are administered in a mole ratio of about 1:1. In some embodiments, a compound as described herein and ibrutinib are administered in a mole ratio of about 1:1, about 1:2, about 1:9, about 2:1, or about 9:1.

In some embodiments, ibrutinib is administered at about 420 mg to about 560 mg per day. In some embodiments, ibrutinib is administered at about 140 mg and is administered three or four times per day. In some embodiments, ibrutinib, when administered in combination with a compound as described herein (e.g., any one or more solid forms of Compound I or salts/co-crystals thereof), is administered at about 210 mg to about 280 mg per day. In some embodiments, ibrutinib, when administered in combination with a compound as described herein, is administered at about 140 mg and is administered once, once and a half, or twice daily. In some embodiments, ibrutinib is administered at 560 mg per day. In some embodiments, ibrutinib is administered at 420 mg per day. In some embodiments, ibrutinib is administered at 280 mg per day. In some embodiments, ibrutinib is administered at 140 mg per day.

In some embodiments, a compound as described herein (e.g., any one or more solid forms of Compound I or salts/co-crystals thereof) is administered in a therapeutically effective amount as defined herein and the amount of ibrutinib may be in an amount that is reduced by about 10% to about 50% of ibrutinib's therapeutic dose.

Additional examples of therapeutic agents, therapies or medical treatments useful for use in combinations with the compounds described herein (e.g., any one or more solid forms of Compound I or salts/co-crystals thereof) are described in U.S. Patent Application Publication No. 2013/0237493, and PCT Application Nos. PCT/US16/34861, PCT/US2016/64824, and PCT/US2016/046862, which are each incorporated herein by reference in entirety.

6. Dosages

The amounts of any one of the compounds described herein (e.g., any one of the solid forms of Compound I or salts/co-crystals thereof) to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

In some embodiments, the therapeutically effective amount of a compound as described herein is an amount that exhibits less than a 15% reduction in apoptosis in vitro in the presence of IL-4 and/or CD40L, wherein IL-4 and/or CD40L are present in any amounts that are expected to be present in lymph node tissue sites. In some embodiments, the chemotherapeutic agent is administered at an amount to result in a reduction in apoptosis in vitro by at least 15% in the presence of IL-4 and/or CD40L, wherein IL-4 and/or CD40L are present in any amount that is expected to be present in lymph node tissue sites.

In some embodiments, the therapeutically effective amount of a compound as described herein (e.g., a solid form Compound I or salts/co-crystals thereof) used in the methods, either alone or in one of the prescribed combinations, is at least about 10 mg per day. In one embodiment, the therapeutically effective amount of a compound as described herein is at least about 10, 20, 30, 40, or 50 mg per dosage. In one embodiment, the therapeutically effective amount of cerdulatinib is at least about 10, 20, 30, 40, 50, 60, 70, 80, 90 or 100 mg per day.

In one embodiment, the therapeutically effective amount of a compound as described herein (e.g., a solid form Compound I or salts/co-crystals thereof) is at least 30 mg, 35 mg, 40 mg, 45 mg, 50 mg, 55 mg, 60 mg, or 65 mg per day. In one embodiment, the therapeutically effective amount of a compound as described herein is at least about 15 mg, 20 mg, 25 mg, 30 mg, or 35 mg and is administered twice daily.

In some embodiments, the therapeutically effective amount of a compound as described herein (e.g., a solid form Compound I or salts/co-crystals thereof) is no more than about 500, 400, 300, 200, 150, 120, or 100 mg per day. In one embodiment, the therapeutically effective amount of a compound as described herein is no more than about 300, 200, 150, 120, 100, 90, 80, 70, 60, 55 or 50 mg per dosage.

In some embodiments, the therapeutically effective amount of a compound as described herein (e.g., a solid form Compound I or salts/co-crystals thereof) is no more than about 100 mg, 95 mg, 90 mg, 85 mg, 80 mg, or 75 mg per day. In certain embodiments, the therapeutically effective amount of a compound as described herein is no more than 45 mg, 40 mg, 35 mg, or 30 mg and is administered twice daily.

In one embodiment, a compound as described herein (e.g., a solid form Compound I or salts/co-crystals thereof), whether alone or in combination with another agent, is administered at from about 10 mg to 200 mg, from about 25 mg to 150 mg, from about 50 to 120 mg, or from about 80 to 100 mg a day.

In one embodiment, the therapeutically effective amount of a compound as described herein (e.g., a solid form Compound I or salts/co-crystals thereof), whether alone or in combination with another agent, is 25 mg to 120 mg daily. In some embodiments, the effective amount of a compound as described herein is 25 mg to 50 mg twice daily.

In one embodiment, a compound as described herein (e.g., a solid form Compound I or salts/co-crystals thereof), whether alone or in combination with another agent, is administered at from about 10 mg to 150 mg, from about 25 mg to 120 mg, from about 30 to 80 mg, from about 40 to 50 mg a dosage, once or twice a day. In certain embodiments, a compound as described herein, whether alone or in combination with another agent, is administered once, twice, three times or four times a day.

In one embodiment, a compound as described herein (e.g., a solid form Compound I or salts/co-crystals thereof), whether alone or in combination with another agent, is administered from about 30 mg to about 80 mg once a day. In one embodiment, a compound as described herein, whether alone or in combination with another agent, is administered from about 15 mg to about 40 mg twice a day.

In one embodiment, 45 mg of a compound as described herein (e.g., a solid form Compound I or salts/co-crystals thereof), whether alone or in combination with another agent, is administered twice daily. In one embodiment, 35 mg of a compound as described herein, whether alone or in combination with another agent, is administered twice daily.

In some embodiments, the effective amount of a compound as described herein (e.g., a solid form Compound I or salts/co-crystals thereof), or a pharmaceutically acceptable salt thereof, is about 40 mg to about 50 mg administered twice daily.

In some embodiments, the effective amount of a compound as described herein (e.g., a solid form Compound I or salts/co-crystals thereof), or a pharmaceutically acceptable salt thereof, is about 30 mg to about 40 mg administered twice daily.

In some embodiments, the effective amount of a compound as described herein (e.g., a solid form Compound I or salts/co-crystals thereof), or a pharmaceutically acceptable salt thereof, whether alone or in combination with another agent, is administered from about 30 mg to about 45 mg a day.

In some embodiments, 30 mg of a compound as described herein (e.g., a solid form Compound I or salts/co-crystals thereof), or a pharmaceutically acceptable salt thereof, whether alone or in combination with another agent, is administered twice daily.

7. Kits

In some embodiments, the present disclosure provides kits that include any one of the compounds or combinations as described herein, or a pharmaceutical composition thereof. In some embodiments, the compound(s) or composition is packaged, e.g., in a vial, bottle, flask, which may be further packaged, e.g., within a box, envelope, or bag; the compound(s) or composition is approved by the U.S. Food and Drug Administration or similar regulatory agency for administration to a mammal, e.g., a human; the compound(s) or composition is approved for administration to a mammal, e.g., a human, for a protein kinase mediated disease or condition; the kits described herein may include written instructions for use and/or other indication that the compound(s) or composition is suitable or approved for administration to a mammal, e.g., a human, for a protein kinase-mediated disease or condition; and the compound(s) or composition may be packaged in unit dose or single dose form, e.g., single dose pills, capsules, or the like.

EXAMPLES

1. Experimental Methods a. X-Ray Powder Diffraction (XRPD)

X-Ray Powder Diffraction patterns were collected on a PANalytical X'Pert PRO diffractometer using Cu K radiation (45 kV, 40 mA, 1.54 Å), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

Samples were run under ambient conditions and were analyzed by transmission foil XRPD, using the powder as received. Approximately 2-5 mg of the sample was mounted on a 96 position sample plate supported on a polyimide (Kapton, 12.7 μm thickness) film. Data was collected in the range 3-40 °2 with a continuous scan (speed of 0.146 °2/s).

b. Differential Scanning calorimetry (DSC)

DSC data was collected on a PerkinElmer Pyris 6 DSC. The instrument was verified for energy and temperature calibration using certified indium. A predefined amount in milligrams mg of the sample was placed in a pin holed aluminum pan and heated at 20° C.·min$^{-1}$ from 30° C. to 350° C. The instrument control and data analysis was Pyris Software v9.0.1.0174.

c. Thermo-Gravimetric Analysis (TGA)

TGA data were collected on a Pyris 1 TGA equipped with a 20 position autosampler. The instrument was calibrated using certified alumel and perkalloy. A predefined amount in milligrams of the sample was loaded onto a pre-weighed aluminum crucible and was heated at 40° C.·min$^{-1}$ from ambient temperature to 500° C. A nitrogen purge at 20 mL·min$^{-1}$ was maintained over the sample. The instrument control and data analysis was Pyris Software v9.0.1.0174.

d. Gravimetric Vapor Sorption (GVS)

Sorption isotherms were obtained using a Hiden Isochema moisture sorption analyser (model IGAsorp), controlled by IGAsorp Systems Software v6.50.48. The sample was maintained at a constant temperature (25° C.) by the instrument controls. The humidity was controlled by mixing streams of dry and wet nitrogen, with a total flow of 250 mL·min$^{-1}$. The instrument was verified for relative humidity content by measuring three calibrated Rotronic salt solutions (10-50-88%). The weight change of the sample was monitored as a function of humidity by a microbalance (accuracy+/−0.005 mg). A defined amount of sample was placed in a tared mesh stainless steel basket under ambient conditions. A full experimental cycle consisted of two scans (sorption and desorption) at a constant temperature (25° C.) and 10% RH intervals over a 10-90% range (90 minutes for each humidity level). This type of experiment should demonstrate the ability of samples studied to absorb moisture (or not) over a set of well determined humidity ranges.

e. Nuclear Magnetic Resonance (NMR) $^1$H

NMR spectra were collected on a Bruker 270 MHz instrument equipped with an auto-sampler and controlled by a DRX400 console. Automated experiments were acquired using Delta NMR Processing & Control Software version 4.3. Samples were prepared in d6-DMSO, unless otherwise stated. Analysis was carried out using (ACD/Specmanager 7.11).

f. Hot Stage Microscopy (HSM)

Hot Stage Microscopy was carried out using a Leica DME polarized light microscope combined with a Mettler-Toledo MTFP82HT hot-stage and a digital video camera for image capture. A small amount of each sample was placed onto a glass slide with individual particles separated as well as possible. The sample was viewed with appropriate magnification and partially polarized light, whilst being heated from ambient temperature typically at 20° C.·min-1.

g. Thermodynamic Aqueous Solubility by HPLC

Aqueous solubility was determined by suspending sufficient compound in HPLC grade water to give a maximum final concentration of ≥10 mg mL$^{-1}$ of the parent free-form of the compound. The suspension was equilibrated at 25° C. for 24 hours. The suspension was then passed through a filter into an HPLC vial. The filtrate was then diluted by an appropriate factor. Quantification was executed by HPLC with reference to a standard solution of approximately 1 mg·mL$^{-1}$ in acetonitrile:water (1:1). Different volumes of the standard, diluted and undiluted sample solutions were injected. The solubility was calculated using the peak areas determined by integration of the peak found at the same retention time as the principal peak in the standard injection. HPLC method parameters are described in Table 1 and Table 2.

Analysis was performed on an Agilent 1100 series liquid chromatography, equipped with a UV detector (DAD or VWD) @ 254 nm and using Chemstation Rev.B.01.03 software for data processing.

TABLE 1

Experimental Parameters for LC Measurements

| | |
|---|---|
| Type of Method | Reverse phase analysis on a gradient method |
| Column | Zorbax XDB-C18 5 µm 4.6 × 150 mm |
| Mobile Phase A | 10 mM ammonium bicarbonate buffer, pH 7.0 |
| Mobile Phase B | Acetonitrile |
| Flow Rate (mL · min$^{-1}$) | 1.0 mL · min$^{-1}$ |
| Injection volume (µl) | 15 µl/8 µl |
| Column temperature (° C.) | 25° C. |
| Detection wavelength (nm) | UV at 235 nm |
| Post run time (mm) | 7.5 minutes |

| | Time (min) | % A | % B |
|---|---|---|---|
| Gradient | 0 | 90 | 10 |
| | 2 | 90 | 10 |
| | 15 | 65 | 35 |
| | 22 | 65 | 35 |
| | 30 | 5 | 95 |
| | 37 | 5 | 95 |
| | 37.5 | 90 | 10 |

TABLE 2

Experimental Details for LC Analysis

| | |
|---|---|
| Diluent | Acetonitrile:Water (1:1) |
| Sample preparation | Check first that the supplied solution is filtered and if not filter through a 0.22 µm syringe filter. Determine the approximate level of sample solubility as estimated by the chemist and prepare sample as follows: Estimated Solubility LT 1 mg/mL-1 in 1 dilution Inject as is. Estimated Solubility LT 5 mg/mL-1 in 10 dilution Accurately pipette 200 µl of filtered solution into a 14 mL glass vial containing 1800 µl of diluent, mix well and use this solution for injection. Estimated Solubility 20 mg/mL-1 in 50 dilution Accurately pipette 200 µl of filtered solution into a 10 mL volumetric flask containing approximately 2 mL of diluent, dilute to volume with diluent, mix well and use this solution for injection. Estimated Solubility 50 mg/mL-1 in 100 dilution Accurately pipette 100 µl of filtered solution into a 10 mL volumetric flask containing approximately 2 mL of diluent, dilute to volume with diluent, mix well and use this solution for injection. Estimated Solubility 100 mg/mL-1 in 200 dilution Accurately pipette 100 µl of filtered solution into a 20 mL volumetric flask containing approximately 2 mL of diluent, dilute to volume with diluent, mix well and use this solution for injection |
| Typical reaction time | 19.7 mins |

2. Solid Forms of Compound I (Free Base)

a. Compound I and Compound I Hydrochloride Salt

Compound I and Compound I hydrochloride salt can be prepared according to Scheme 1. An exemplifying synthesis is described below.

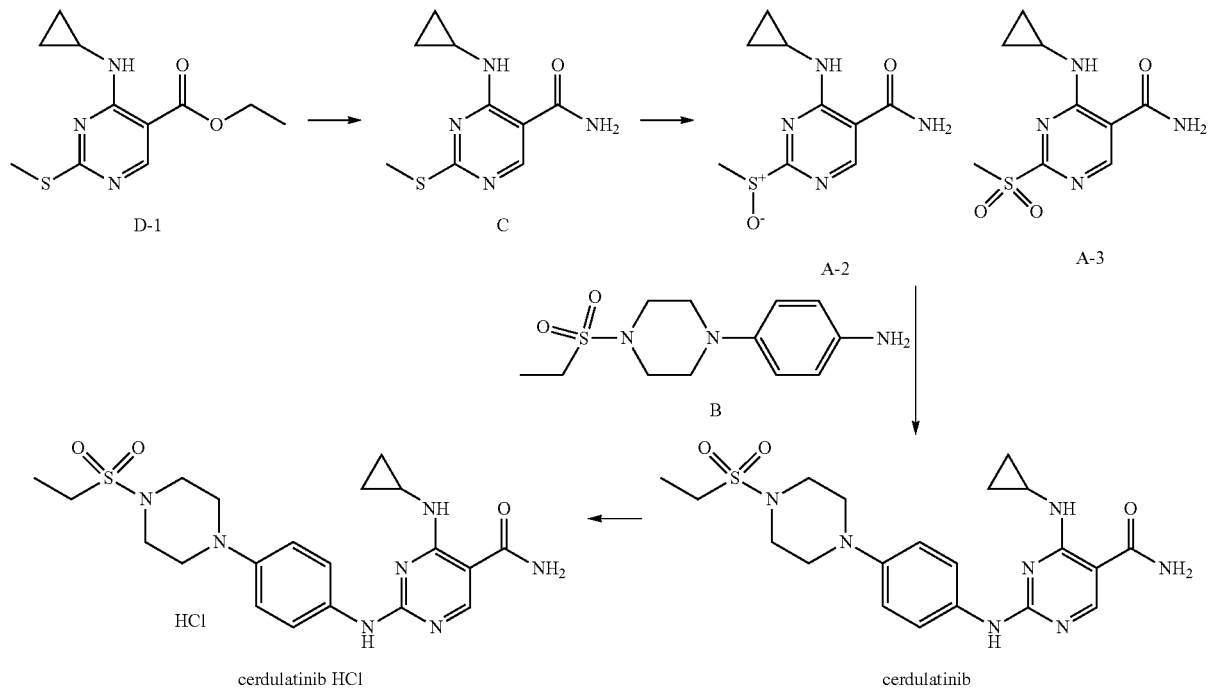

Scheme 1

Step 1: Conversion of Compound D-1 to Compound C 86.0 Kg of DMF, 76.5 kg of formamide, and 45.5 kg of Compound D-1, were charged in a reactor. To this mixture after having reached an internal temperature of 0-10° C., 84.0 kg of sodium ethoxide 21% were added keeping the internal temperature between 0-10° C. The mixture was warmed up to 50° C. and stirred for 60 minutes. In-process control showed that residual content of Compound D-1 was 3.14%. The mixture was cooled till 0° C. and 900 L of water were added, after having finished the water addition, the reaction was cooled down again till −5° C. and it was left stirring for 16 hours. The mixture was filtered and the filter cake was washed with 50 kg of cold methyl tert-butylether.

The filter cake (52.95 kg) containing Compound C was forwarded to a dryer. Drying of Compound C crude wet product (60° C. for 21 hours and 40 minutes) gave 37.30 kg (92.6% yield) of Compound C crude dry product. Purity 97.54%.

Step 2: Synthesis of Compound I

235 Kg of NMP, and 32.1 kg of Compound C crude dry product were charged to a reactor. The internal temperature was set at between 0-10° C. 72.95 Kg of MCPBA were charged while keeping the temperature under 5° C. The mixture was then warmed up till 25° C. and stirred for 1 hour. IPC showed that residual content of Compound C was 0.00% for oxidative reaction. The mixture was kept stirring at 25° C. for a further hour.

To the above mixture, 40.05 kg of Compound B was added. The internal temperature was set at 40° C. and the mixture was stirred overnight for 17 hours and 17 minutes, and then for additional 4 hours. In-process control showed that residual content of Compound A-2+Compound A-3 was 2.05%. The mixture was cooled down to 3° C., and a pre-cooled basic solution of water (642 L) and NaHCO$_3$ (48 kg) was added to the mixture. The mixture was stirred for 1 hour and then water (193 L) was added keeping the internal temperature between 0-10° C. The mixture was stirred for 40 minutes. Solid was isolated by filtration (filter-dryer equipped with 20 μm mesh) keeping squeezing the cake with both N$_2$/vacuum for 51 hours.

Compound I crude wet product (106.9 kg) was then re-charged in the reactor and slurried at 25° C. for 9 hours with water (1434 L).

Solid was isolated by filtration (filter-dryer equipped with 20 μm mesh cloth) keeping squeezing the cake with both N$_2$/vacuum for 60 hours.

Wet solid was respectively slurried and squeezing four times more in the filter-dryer using water (877 L).

Solid was then forwarded to the filter-dryer for isolation and drying (43° C. under vacuum for 20 hours). Compound I crude dry product overall yield was 88% (63.76 kg) with purity of 90.84%.

Step 3: Synthesis of Compound I Hydrochloride Salt

252 Kg of DMSO and 56.2 kg of Compound I were charged in the reactor. The mixture was warmed up to 75° C. and stirred till complete dissolution. 664 Kg of EtOH abs. was added and the reaction was stirred for 30 minutes. Keeping the internal temperature in between 70-80° C. (72.9° C.), an acidic solution made by mixing 347 kg of water and 43 kg of HCl 33% w/w was added. The reaction was stirred for further 30 minutes. The mixture was then cooled down to 20° C. and stirred for 19 hours. Solid was then forwarded to the filter-dryer (20 μm mesh cloth) for isolation. Wet solid was respectively slurried and squeezing twice directly in the filter-dryer using EtOH (1073 L), and then dried (at 35° C. under vacuum for 50 hours). Compound I hydrochloride salt yield was 58.4% (35.44 kg) with a purity of 99.41%.

b. Compound I Form I

Compound I Form I is crystalline as determined via XRPD analysis (FIG. 1). Compound I Form I can be characterized by an X-ray powder diffractogram comprising the following peaks: 16.6, 18.0, and 23.7 °2θ±0.2 °2θ.

In one embodiment, Compound I Form I is formed from a hydrochloride salt of Compound I, where said hydrochloride salt is prepared according to:

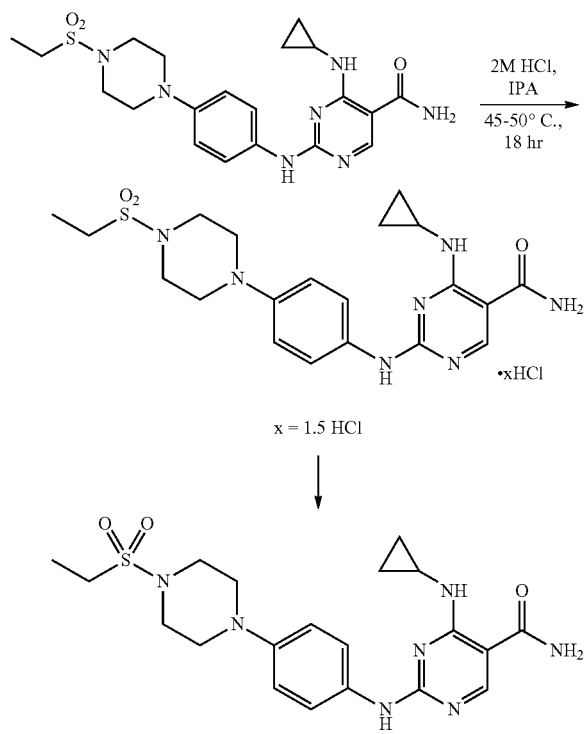

x = 1.5 HCl

A suspension of Compound I (10.0 g) in IPA (50 mL) and 2 M aq. HCl (50 mL) was heated to 45-50° C. and stirred at this temperature for 18 hours before cooling to 25° C. The solid was collected via vacuum filtration and washed with 1:1 IPA:2M aq. HCl (100 mL), IPA (100 mL) and methyl tert-butylether (100 mL). The dried solid gave a Compound I hydrochloride salt in a yield of 7.9 g (73.15%).

The Compound I hydrochloride (about 3.5 g, about 7 mmol) was suspended in EtOAc (about 35 mL) and stirred during the addition of saturated $K_2CO_3$ (about 35 mL). The suspension was mixed and heated at about 50° C. for about 4 hours, then cooled, filtered, and washed with EtOAc and water. The resulting solid was dried in vacuo at about 45° C. to produce Compound I Form I.

In one embodiment, Compound I Form I is also formed from the hydrochloride salt starting material using THF and 1N NaOH.

b. Compound I Form II

Figure 2:
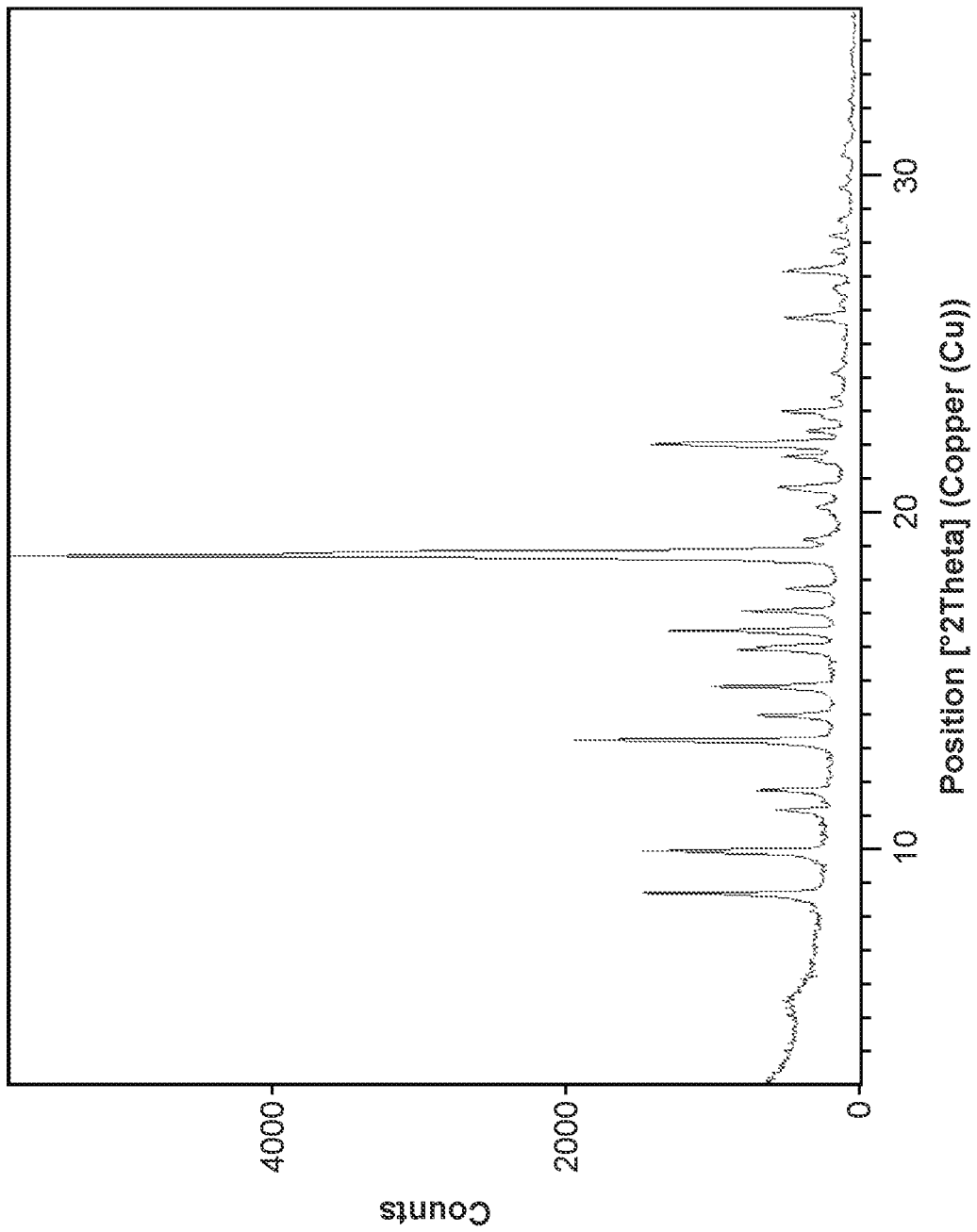
FIG. 2 is an X-ray powder diffractogram of Compound I Form II.

Compound I Form II is crystalline as determined via XRPD analysis (FIG. 2). Compound I Form II can be characterized by an X-ray powder diffractogram comprising the following peaks: 13.2, 18.7, and 22.0 °2θ±0.2 °2θ.

In one embodiment, Compound I Form II is formed from the aforementioned hydrochloride starting material using EtOAc/THF (9:1) and 1N NaOH at 50° C. Compound I Form II was isolated from a slurry in THF and EtOAc.

3. Salt/Co-Crystal Screen of Compound I

A salt/co-crystal screen was performed using Compound I Form I as the starting material.

The solubility of Compound I Form I in various solvents was first determined and summarized in Table 3.

TABLE 3

Solubility of Compound I Form I

| Mass/vol | Solvent | Observations |
|---|---|---|
| 25 mg/1 mL | DCM | about 10 mg |
| 25 mg/1 mL | EtOAc | <5 mg |
| 25 mg/1 mL | Heptane | <5 mg |
| 25 mg/1 mL | IPA | <5 mg |
| 25 mg/1 mL | THF | <5 mg |
| 25 mg/1 mL | Acetone | <5 mg |
| 25 mg/1 mL | MeOH | <5 mg |
| 25 mg/1 mL | TBME | <5 mg |
| 25 mg/1 mL | Toluene | about 10 mg |
| 25 mg/1 mL | Acetonitrile | <5 mg |

The combination of Compound I Form I in THF, toluene, or acetonitrile formed slurries. A solution of Compound I Form I in DMSO was selected for the salt/co-crystal screen.

Co-formers used in the salt/co-crystal screen included hydrochloric acid, naphthalene-1,5-disulfonic acid, sulfuric acid, ethane-1,2-disulfonic acid, ethane sulfonic acid, p-tolyl sulfonic acid, and methane sulfonic acid.

Salts/co-crystals of Compound I were obtained by combining about 20 mg of Compound I Form I in DMSO (about 5 M) and about 1 equivalent of a selected co-former (1M stock THF) in various solvents such as NMP, DMSO, DMF, 3-Me-1-BuOH, n-BuOAc, toluene, water, IPA, $CH_3CN$, MEK, EtOH and THF. Samples that resulted in solid material were dried at 40° C. in vacuo and analyzed by XRPD. Exemplary salts/co-crystals of Compound I and their respective solid forms are summarized in Table 4 below.

TABLE 4

XRPD Results for Salts/Co-Crystals of Compound I

| | Comp. I Esylate | Comp. I Edisylate | Comp. I HCl | Comp. I Mesylate | Comp. I Naphthalene Disulfonate | Comp. I Sulfate | Comp. I Tosylate |
|---|---|---|---|---|---|---|---|
| NMP | 0 | 0 | 0 | 0 | 0 | 0 | 0 |
| DMSO | 0 | 0 | 0 | 0 | 0 | 0 | 0 |
| DMF | 0 | 0 | I | II | I* | II | 0 |
| 3-Me-1-BuOH | I + E | I | PD (I) | II | III + E | II/I | IV |

TABLE 4-continued

XRPD Results for Salts/Co-Crystals of Compound I

|  | Comp. I Esylate | Comp. I Edisylate | Comp. I HCl | Comp. I Mesylate | Comp. I Naphthalene Disulfonate | Comp. I Sulfate | Comp. I Tosylate |
|---|---|---|---|---|---|---|---|
| n-BuOAc | I | II | I | II | I | III (PO) | I |
| Toluene | I | II | I | II | III | I | III |
| Water | PD (I) | III | I | II | IV | II* | V |
| IPA | PD (I) | I | I | I | III | I | II |
| CH₃CN | I | IV | II | II | II* | I | II |
| MEK | I | II | PD (I) | II | II | I | I |
| EtOH | I | II | I | PD (II) | I | III | VII |
| THF | I | II | I | II | II | I | III |

0: no solid
I, II, III, . . .: observed forms of a particular Compound I salt/co-crystal
PD: poor diffraction
PO: preferred orientation
*good diffraction profile
E: extra peaks

4. Scale Up Formation of Salts/Co-Crystals of Compound I

An initial scale up formation ("first scale up") of various crystalline salts/co-crystals of Compound I was performed. The solvents selected for the first scale up were those that yielded a good diffraction pattern in the salt screening experiments described in Table 4 above. The results for the first scale up are summarized below in Table 5.

TABLE 5

First Scale Up Formation of Salts/Co-Crystals of Compound I

|  | Solvent | XRPD | HSM | TGA | GVS |
|---|---|---|---|---|---|
| Comp. I Esylate | Toluene IPA | Form I Form I | Melt around 250° C. | Gradual weight loss of about 7% up to about 250° C. with major onset at about 316° C. | Not hygroscopic between 0 to about 60% RH; about 5 mg of weight uptake between about 60% to about 90% |
| Comp. I Edisylate | Water | Form 3 | Spike at about 110° C.; melt observed above about 260° C. | Probable solvent loss (about 2.9%) between RT and about 150° C., followed by about 1.5% of weight loss before decomposition above about 300° C. | — |
|  | Acetonitrile | Form I | Melt at about 210° C.; decomposition above about 260° C. | Continuous weight loss (about 3.6%) up to about 200° C.; Another weight loss of 3.2% between 200 Gradual weight loss of 3.65% up to 200° C. and 270° C. | — |
| Comp. I Mesylate | Water | Form II | Melt at about 235° C. | Weight loss of about 1.74% between about 150° C. and about 300° C. (onset at about 296° C.) | About 12 mg of water absorbed |

TABLE 5-continued

First Scale Up Formation of Salts/Co-Crystals of Compound I

| | Solvent | XRPD | HSM | TGA | GVS |
|---|---|---|---|---|---|
| | ethanol | Form III | Small portion recrystallizes at about 210° C.; melt above about 250° C. | About 0.1% weight loss over temperature range (RT to about 500° C.) | — |
| Comp. I Naphthalene Disulfonate | 3-Me-Butanol | Similar to Form II | Melt observed above about 210° C. | Gradual weight loss of about 2.42% up to about 200° C.; onset at about 209° C. | — |
| | Acetonitrile | Similar to Form IV | No melting observed; proceeds directly to decomposition | Weight loss below about 150° C.; onset at about 182° C. (weight loss of about 10%) | — |
| Comp. I Sulfate | Water | Similar to Form II | Crystallization occurring before a final melt at about 240° C. | Gradual weight loss of about 3.65% up to about 200° C.; degradation at about 275° C. | About 0.5 mg of water absorbed increasingly with RH |
| | IPA | Similar to Form I | Melt above about 250° C. | Gradual weight loss of about 5.15% up to about 271° C.; decomposition observed at about 271° C. Gradual weight loss of 3.65% up to 200° C. | — |
| Comp. I Tosylate | Water | XRPD results different from XRPD results for Comp. I tosylate presented in Table 4 | Melt about 220° C. | About 0.73% weight loss below about 100° C.; $1^{st}$ onset at about 141° C. with weight loss of about 4.6%; $2^{nd}$ onset at about 300° C. | — |
| | Toluene | XRPD results different from XRPD results for Comp. I tosylate presented in Table 4 | Melting values at about 210° C. and about 260° C. | About 0.4% weight loss below about 100° C.; $1^{st}$ onset at about 132.6° C. with weight loss of about 6%; $2^{nd}$ onset at about 298° C. | — |
| Comp. I HCl (dry, 1:1) | Water | Form I | Melt above about 250° C. | About 3.3% weight loss below about 100° C.; onset at about 267° C. | — |
| | Acetonitrile | Form I | — | | |
| Comp. I HCl (aq., 1:2) | ethanol | Form I | — | — | About 5.9% weight gain at about 70% RH |

—No data available

Comparison of the XRPD results provided in tables 4 and 5 reveals form variation between the initial salt screening experiments and the initial scale up formation for the edisylate, naphthalene disulfonate, and tosylate salts/co-crystals of Compound I. The esylate, mesylate sulfate and hydrochloride salts/co-crystals of Compound I did not appear to exhibit such form variation, and were thus selected for subsequent scale-up experiments ("second scale up") as described in sub-sections (a)-(d) and Table 6 below.

a. Compound I Esylate

About 200 mg of Compound I (free base) in DMSO (about 0.5M, about 0.9 mL) was charged to a hot (about 70° C.) tube comprising toluene or IPA (about 15 vols.). About 1 equivalent of an ethane sulfonic acid was added as a 1M solution in THF to the Compound I (free base) solution. The resulting solution/suspension was held isothermal for about 4 hours and cooled overnight prior to filtration, drying, and analysis.

X-ray powder diffractograms for Compound I esylate prepared from toluene and IPA in the second scale up process are shown in FIG. 30A and FIG. 30B, respectively. X-ray powder diffractograms for Compound I esylate Form I prepared from IPA and toluene during the first scale up process are provided in FIG. 30C and FIG. 30D, respectively.

Comparison of FIG. 30A and FIG. 30D indicates that the first and second scale up formation of Compound I esylate via toluene resulted in different crystalline forms. The second scale up formation of Compound I esylate via toluene resulted in a crystalline material (Compound I esylate Material A), which is likely a mixture of crystalline forms.

Comparison of FIG. 30B and FIG. 30C indicates that the first and second scale up formation of Compound I esylate via IPA also resulted in different crystalline forms. The second scale up formation of Compound I esylate via IPA resulted in a crystalline material (Compound I esylate Material B), which is likely a mixture of crystalline forms.

Figure 31:
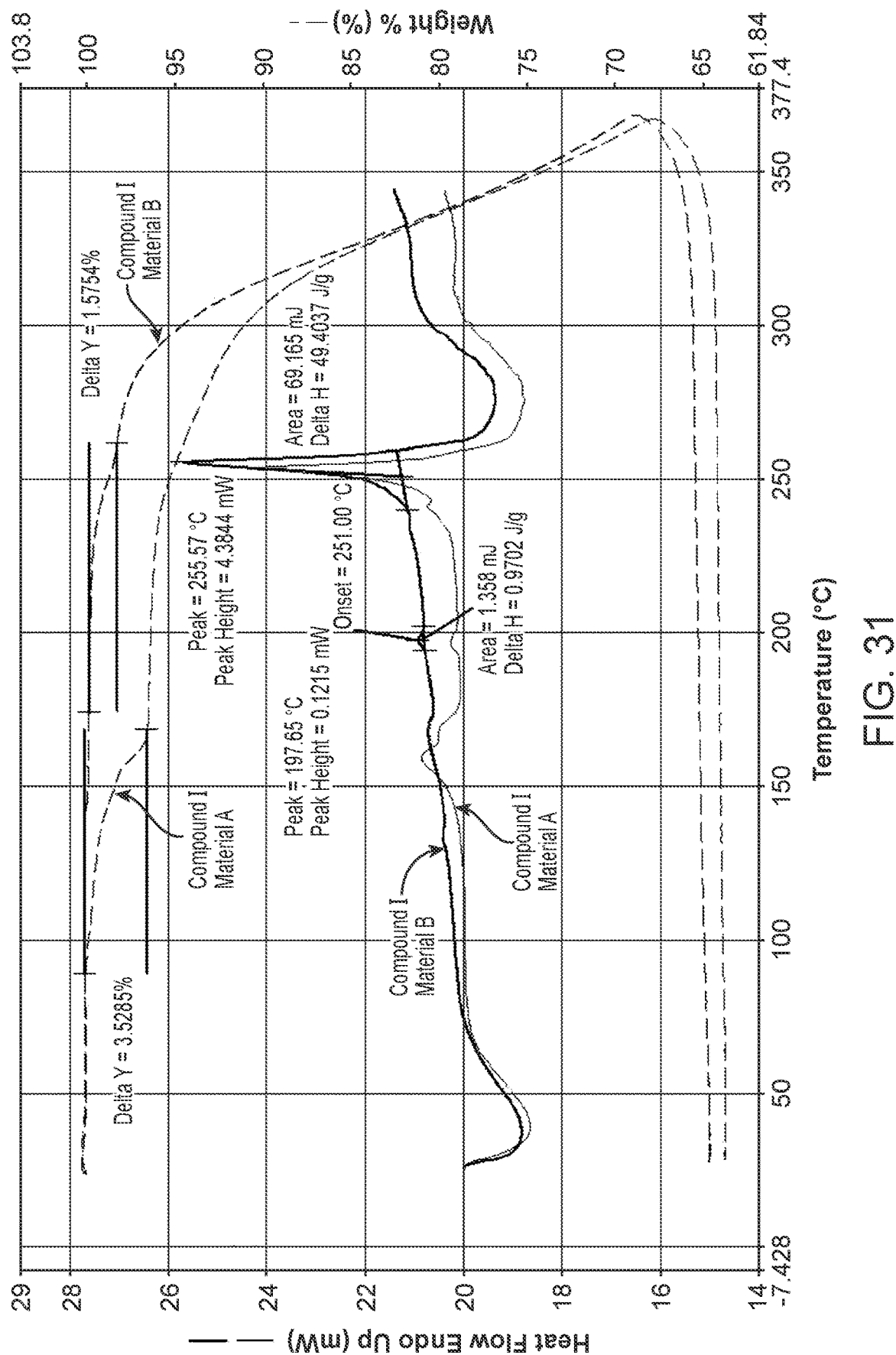
FIG. 31 shows differential scanning calorimetry (DSC) curves and thermogravimetric analysis (TGA) thermograms for Compound I esylate Material A and Compound I esylate Material B.

FIG. 31 shows an overlay of the differential scanning calorimetry (DSC) curves and thermogravimetric analysis (TGA) thermograms for Compound I esylate Material A and Material B. The DSC/TGA data for both samples produce a significant endotherm at about 250° C., followed by decomposition, indicating that both samples likely include at least one same form. Compound I Material A shows the presence of at least one other crystalline form by DSC, for example, at about 155° C. by DSC that corresponds to a mass loss by TGA from greater than about 100° C. The mass loss may correspond to about one mole of water, suggesting a hydrated sample. The mass loss of about 1.57% for Compound I Material B may equate to a hemi-hydrate. Both these materials (Compound I Material A and Material B) are hygroscopic.

b. Compound I Sulfate

About 200 mg of Compound I (free base) in DMSO (about 0.5M, about 0.9 mL) was charged to a hot (about 70° C.) tube comprising water or IPA (about 15 vols.). About 1 equivalent of a sulfuric acid was added as a 1M solution in THF to the Compound I (free base) solution. The resulting solution/suspension was held isothermal for about 4 hours and cooled overnight prior to filtration, drying, and analysis.

X-ray powder diffractograms for Compound I sulfate prepared from water and IPA in the second scale up process are shown in FIG. 32A and FIG. 32B, respectively. X-ray powder diffractograms for Compound I sulfate Form I prepared from water and Compound I sulfate Form I prepared from IPA during the first scale up process are provided in FIG. 32C and FIG. 32D, respectively.

Comparison of FIG. 32A and FIG. 32C indicates that the first and second scale up formation of Compound I sulfate via water resulted in substantially the same crystalline form (Compound I sulfate Form II).

Comparison of FIG. 32B and FIG. 32D indicates that the first and second scale up formation of Compound I sulfate via IPA resulted in substantially similar crystalline forms. For instance, the second scale up formation of Compound I sulfate via IPA resulted in crystalline form substantially similar to Compound I sulfate Form I, with the likely presence of at least one additional form.

Figure 33:
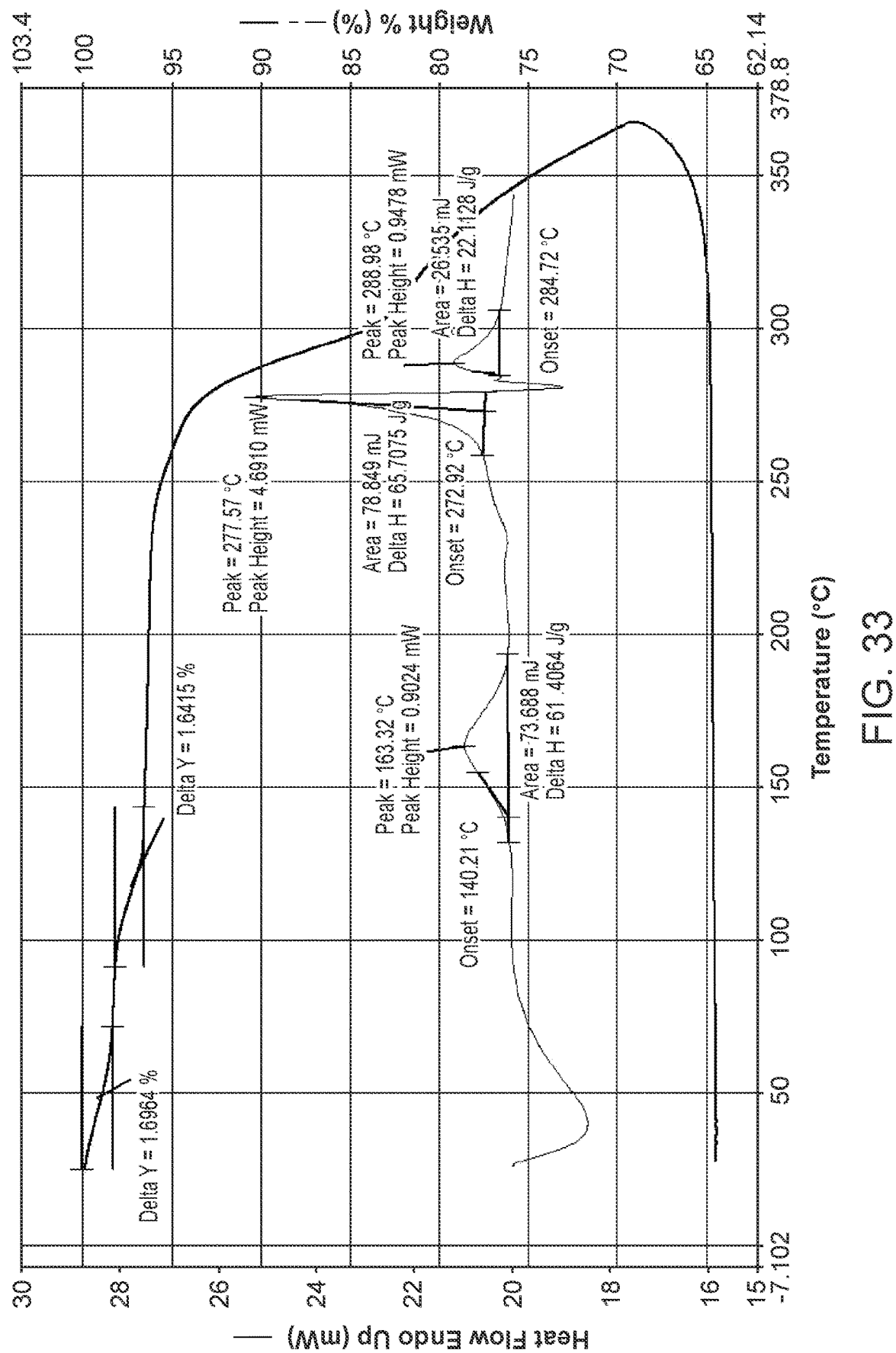
FIG. 33 shows a differential scanning calorimetry (DSC) curve and thermogravimetric analysis (TGA) thermogram for Compound I sulfate having a form similar to Form II thereof.
Figure 34:
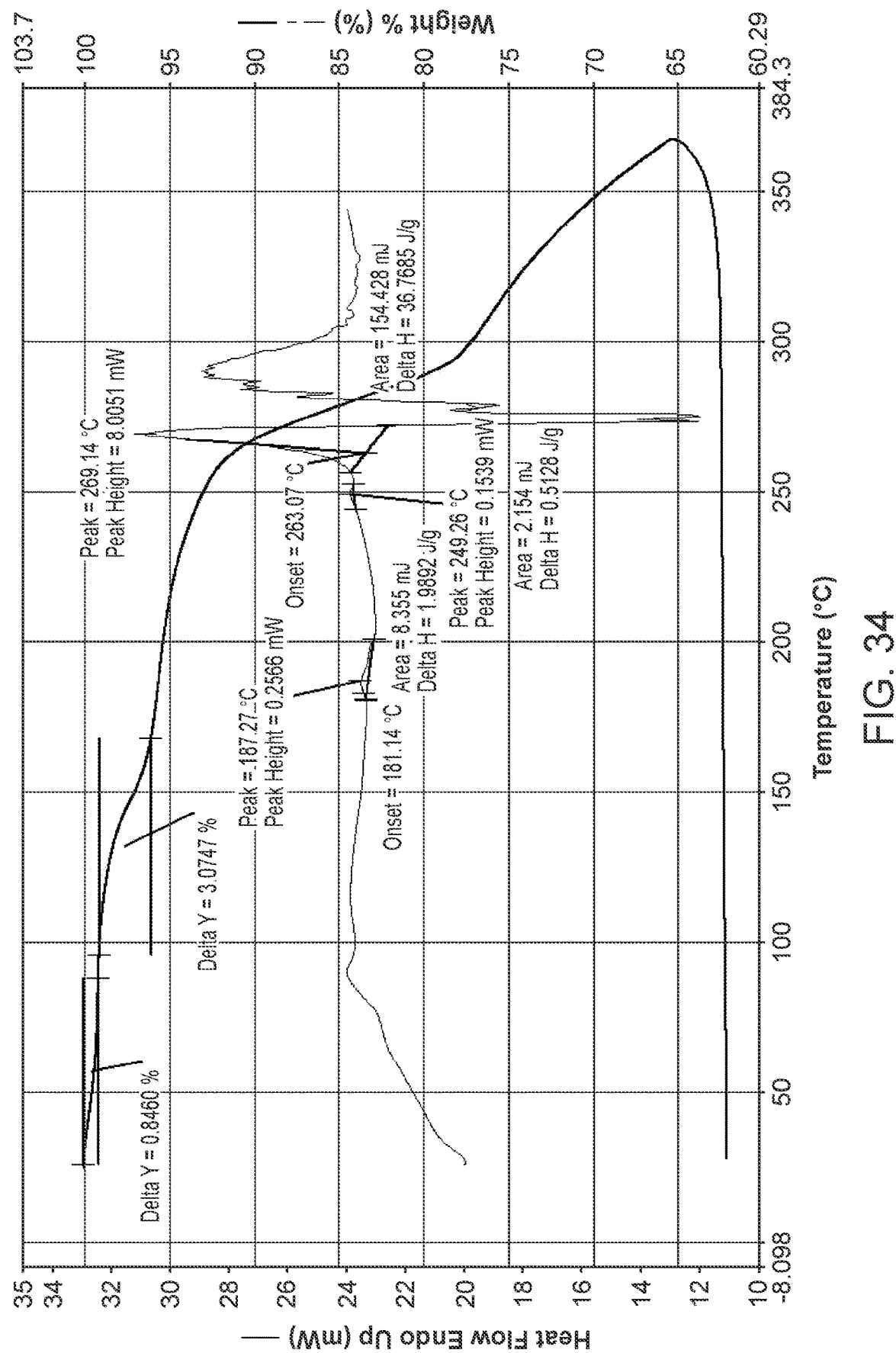
FIG. 34 shows a differential scanning calorimetry (DSC) curve and thermogravimetric analysis (TGA) thermogram for Compound I sulfate having a form similar to Form I thereof.

FIG. 33 shows an overlay of the DSC curve and TGA thermogram for the crystalline form of Compound I sulfate prepared from water during the second scale up process. FIG. 34 shows an overlay of the DSC curve and TGA thermogram for the crystalline form of Compound I sulfate prepared from IPA during the second scale up process. The thermal analysis indicates that the Compound I sulfate sample prepared from water dries in the TGA (surface water likely under $N_2$ stream below about 100° C.), followed by loss of water above about 100° C., which may equate to a hemi-hydrate monosulfate or mono-hydrate hemisulfate. The gravimetric vapor sorption (GVS) isotherm (not shown) also indicates a facile pick-up of surface moisture for this sample. A similar result is obtained for the Compound I sulfate sample prepared from IPA, with about one mole mass of water being lost after about 100° C., and no significant endotherms present in the DSC before the melting decomposition at about 269° C.

c. Compound I HCl

About 200 mg of Compound I (free base) in DMSO (about 0.5M, about 0.9 mL) was charged to a hot (about 70° C.) tube comprising ethanol or acetonitrile (about 15 vols.). About 2 equivalents of hydrochloric acid (aq.) was added as a 1M solution in THF to the Compound I (free base) solution comprising ethanol. About 1 equivalent of hydrochloric acid (dry) was added as a 1M solution in THF to the Compound I (free base) solution comprising acetonitrile. The resulting solutions/suspensions were held isothermal for about 4 hours and cooled overnight prior to filtration, drying, and analysis.

Figures 35A, 35B, 35C, 35D:
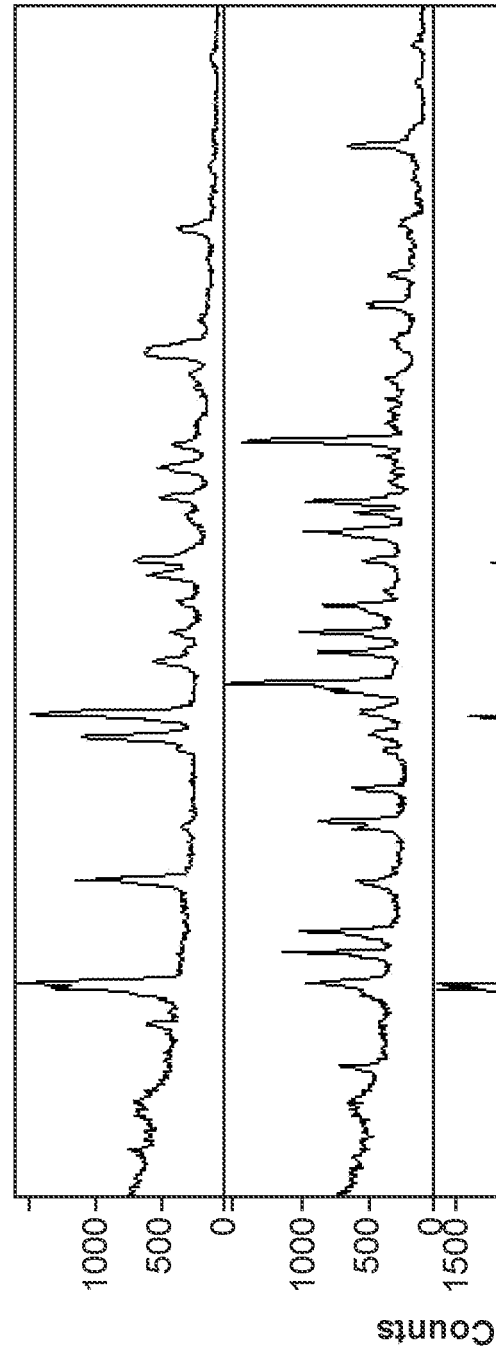
FIG. 35A, FIG. 35B, FIG. 35C, and FIG. 35D are X-ray powder diffractograms of hydrochloride salts/co-crystals of Compound I prepared from different solvents and/or during different scale up processes.

The X-ray powder diffractogram for Compound I HCl prepared from aqueous HCl (about 2 equiv.) and ethanol in the second scale up process is shown in FIG. 35A. The X-ray powder diffractogram for Compound I HCl prepared from dry HCl (about 1 equiv.) and acetonitrile in the second scale up process is shown in FIG. 35B. X-ray powder diffractograms for Compound I HCl Form I formed from dry HCl (about 1 equivalent) and water, and from dry HCl (about 1 equivalent) and acetonitrile during the first scale up process are provided in FIG. 35C and FIG. 35D, respectively.

Comparison of FIG. 35A, FIG. 35C, and FIG. 35D indicates that the second scale up formation of Compound I HCl using about 2 equivalents of HCl (aq.) and ethanol resulted in substantially the same crystalline form (Compound I HCl Form I) as the first scale up formation of Compound I HCl using about 2 equivalents of HCl (aq.) and ethanol or about 1 equivalent of HCl (dry) and acetonitrile.

However, as shown in FIG. 35B, the second scale up formation of Compound I HCl using about 1 equivalent of HCl (dry) and acetonitrile resulted in a new form (herein referred to as Form II) not observed in the previous slurry or solution based experiments described in the Examples.

Figure 36:
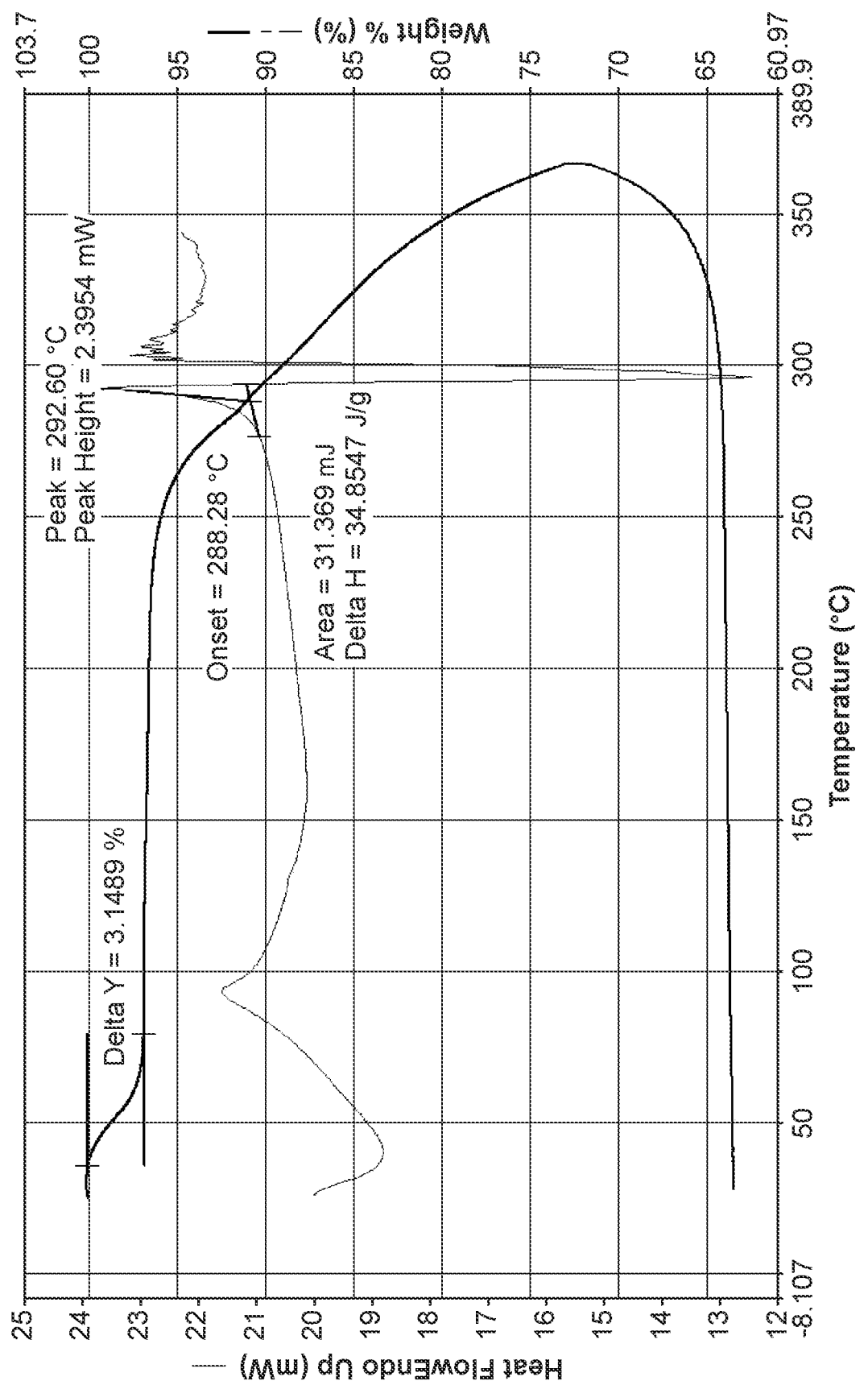
FIG. 36 shows a differential scanning calorimetry (DSC) curve and thermogravimetric analysis (TGA) thermogram for Compound I HCl Form I.

FIG. 36 shows an overlay of the DSC curve and TGA thermogram for the Compound I HCl Form I prepared using HCl (aq.) and ethanol during the second scale up process. The TGA thermogram of said sample ethanol shows a mass loss of approximately 3%; accordingly, said sample may be a hydrate. The DSC curve of said sample comprises an endotherm with an onset at about 288° C. and a peak at about 292° C.

Figure 37:
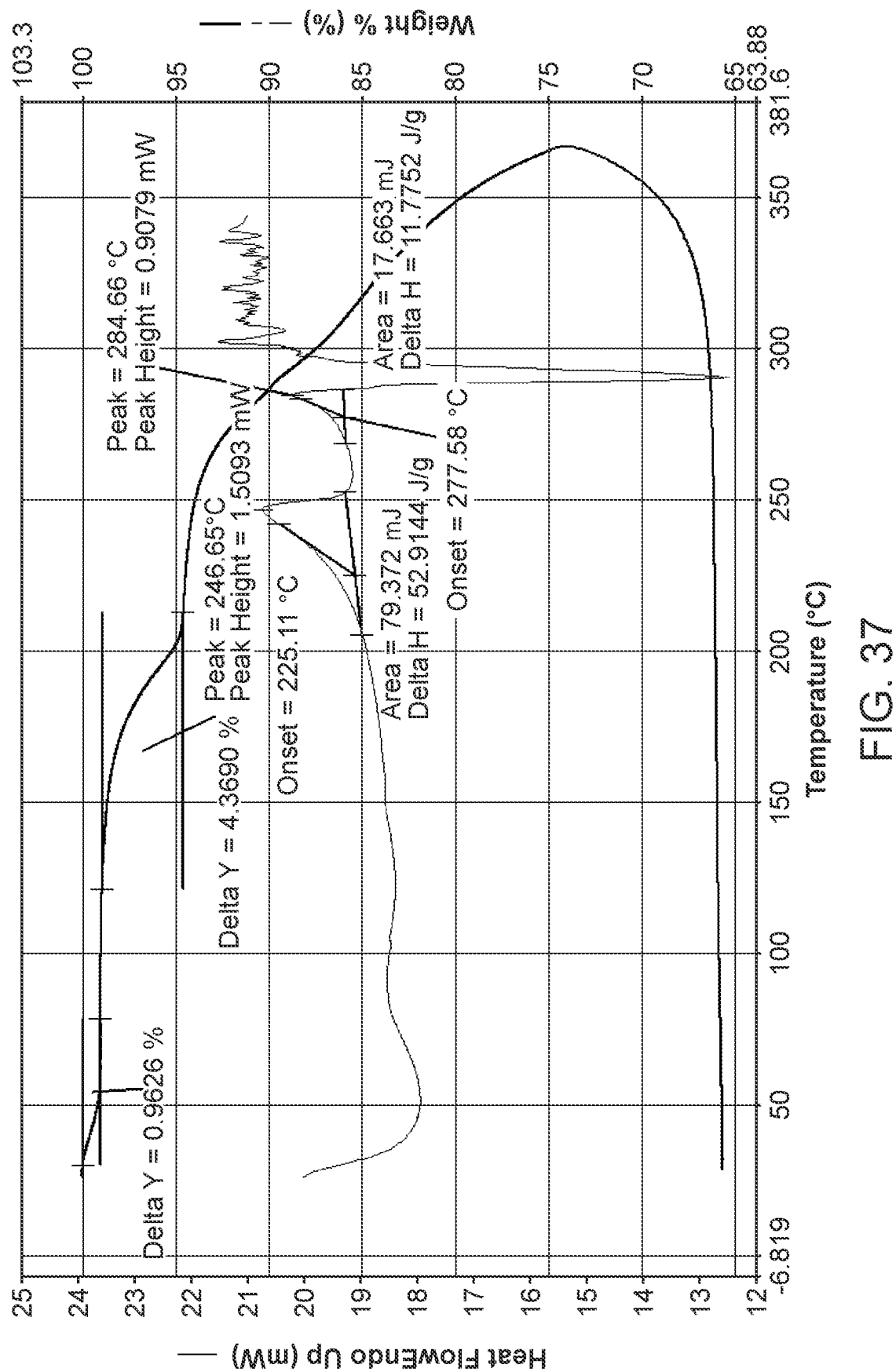
FIG. 37 shows a differential scanning calorimetry (DSC) curve and thermogravimetric analysis (TGA) thermogram for Compound I HCl Form II.

FIG. 37 shows an overlay of the DSC curve and TGA thermogram for Compound I HCl form II formed using about 1 equivalent of HCl (dry) and acetonitrile during the second scale up process. The TGA thermogram of said sample shows a small mass loss below about 50° C., a more significant weight loss of about 4.3% at about 150° C. The DSC curve of said sample comprises an endotherm with an onset at about 225° C. and a peak at about 246° C., and an additional endotherm at with onset at about 277° C. and a peak at 284° C.

Other methods for preparing Compound I HCl Form I include: To ethanol (825 mL) heated at reflux under nitrogen, a polish filtered solution of Compound I free base (55 g) in DMSO (248 mL) was added as a steady stream whilst maintaining the temperature above 74° C. The resulting solution was stirred at reflux for 5 minutes. 1M aqueous HCl (370.4 mL) was then added to the solution as a steady stream maintaining the temperature above 70° C. The resulting green suspension was stirred at 75° C. for 30 minutes before cooling to room temperature overnight. The solid was filtered, washed with ethanol (3×220 mL), water (2×220 mL) and pulled dry for 72 hours. KF analysis at this point indicated 23.7% water. The solid was therefore dried in a vacuum oven at 30° C. for 24 hours. KF analysis indicated 2.4% water. Re-hydration (carried out at 20° C.) increased the water content to 5.37%. Further drying for 30 minutes at 20° C. gave an average KF of 4.3%. The yield of Compound I HCl Form I produced was 55.7 g, 94%. $^1$H NMR and HPLC analysis confirmed the identity and purity (98.78%).

d. Compound I Mesylate

About 200 mg of Compound I (free base) in DMSO (about 0.5M, about 0.9 mL) was charged to a hot (about 70° C.) tube comprising ethanol or EtOAc (about 15 vols.). About 1 equivalent of a methane sulfonic acid was added as a 1M solution in THF to the Compound I (free base) solution. The resulting solution/suspension was held isothermal for about 4 hours and cooled overnight prior to filtration, drying, and analysis.

Figures 38A, 38B, 38C, 38D:
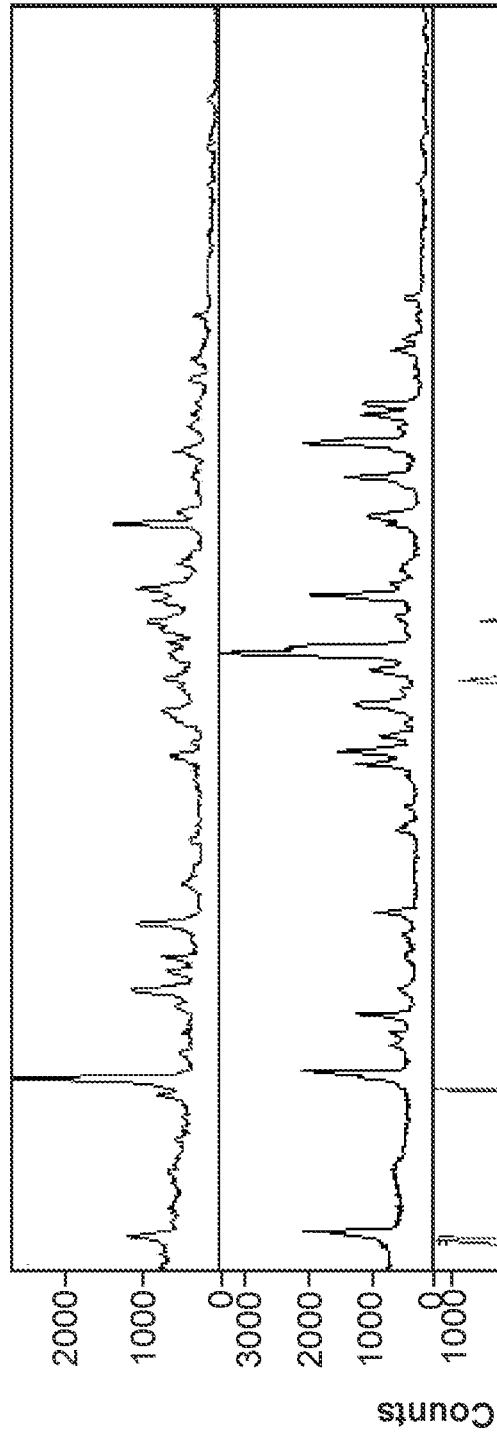
FIG. 38A, FIG. 38B, FIG. 38C, and FIG. 38D are X-ray powder diffractograms of mesylate salts/co-crystals of Compound I prepared from different solvents and/or during different scale up processes.

X-ray powder diffractograms for Compound I mesylate prepared from ethanol and EtOAc in the second scale up process are shown in FIG. 38A and FIG. 38B, respectively. X-ray powder diffractograms for Compound I mesylate Form II prepared from water, and Compound I mesylate Form III prepared from ethanol during the first scale up process are provided in FIG. 38C and FIG. 38D, respectively.

Comparison of FIG. 38A and FIG. 38D indicates that the first and second scale up formation of Compound I mesylate via ethanol resulted in different crystalline forms. In particular, the second scale up formation of Compound I mesylate via ethanol resulted in a new crystalline material (Compound I mesylate Material A), which is likely a mixture of crystalline forms.

Comparison of FIG. 38B and FIG. 38D indicates that the second scale up formation of Compound I mesylate via EtOAc and the first scale up formation of Compound I mesylate via ethanol resulted in substantially the same form (Form III), with a few minor differences.

Figure 39:
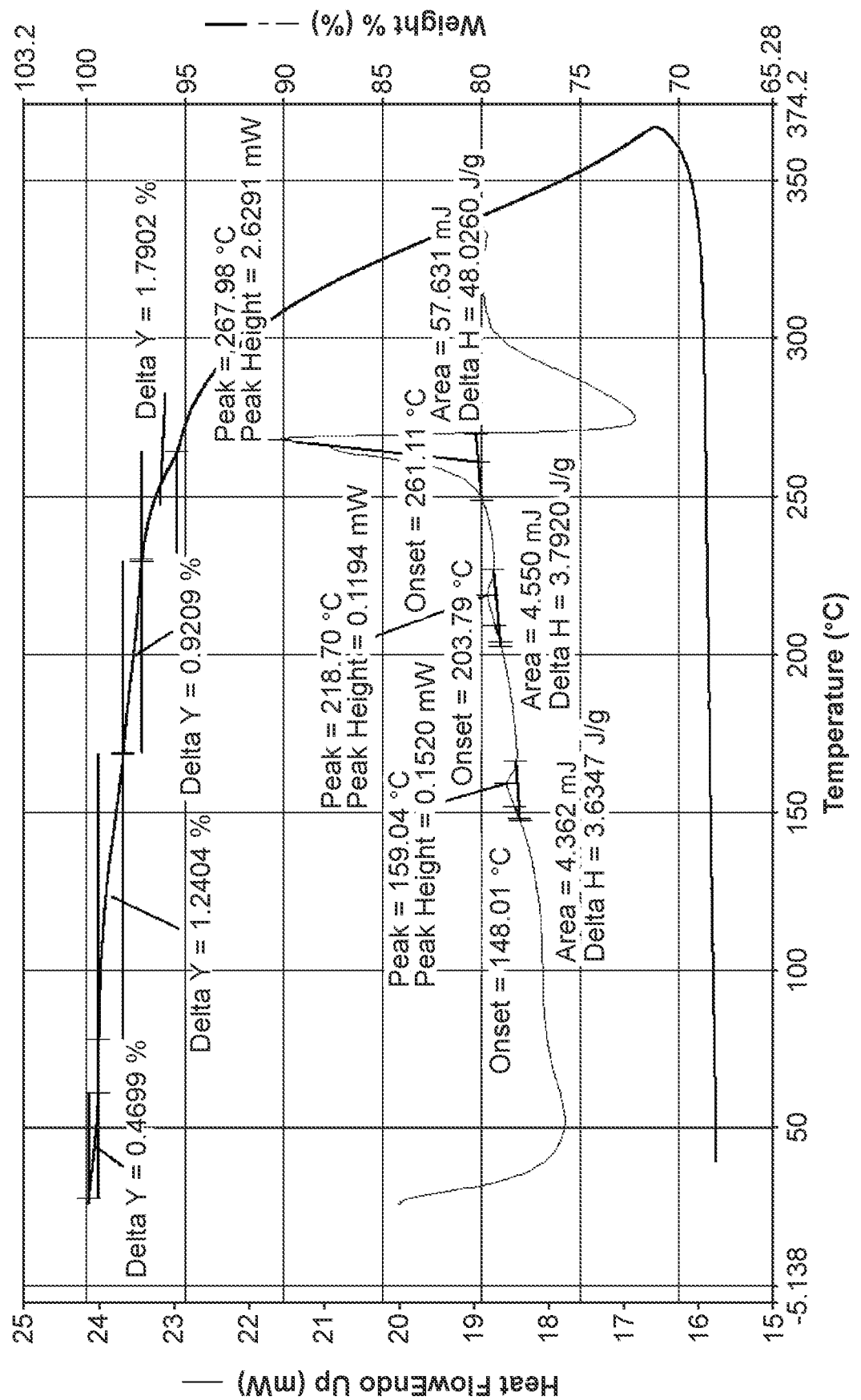
FIG. 39 shows a differential scanning calorimetry (DSC) curve and thermogravimetric analysis (TGA) thermogram for Compound I mesylate Material A.

FIG. 39 shows an overlay of the DSC curve and TGA thermogram for Compound I mesylate Material A prepared from ethanol during the second scale up process. The TGA thermogram for Compound I Material A indicates that said material comprises a mixture of forms, with a significant number of small mass losses. The DSC curve for Compound I Material A comprises an endotherm with onset at about 261° C., followed by decomposition.

Figure 40:
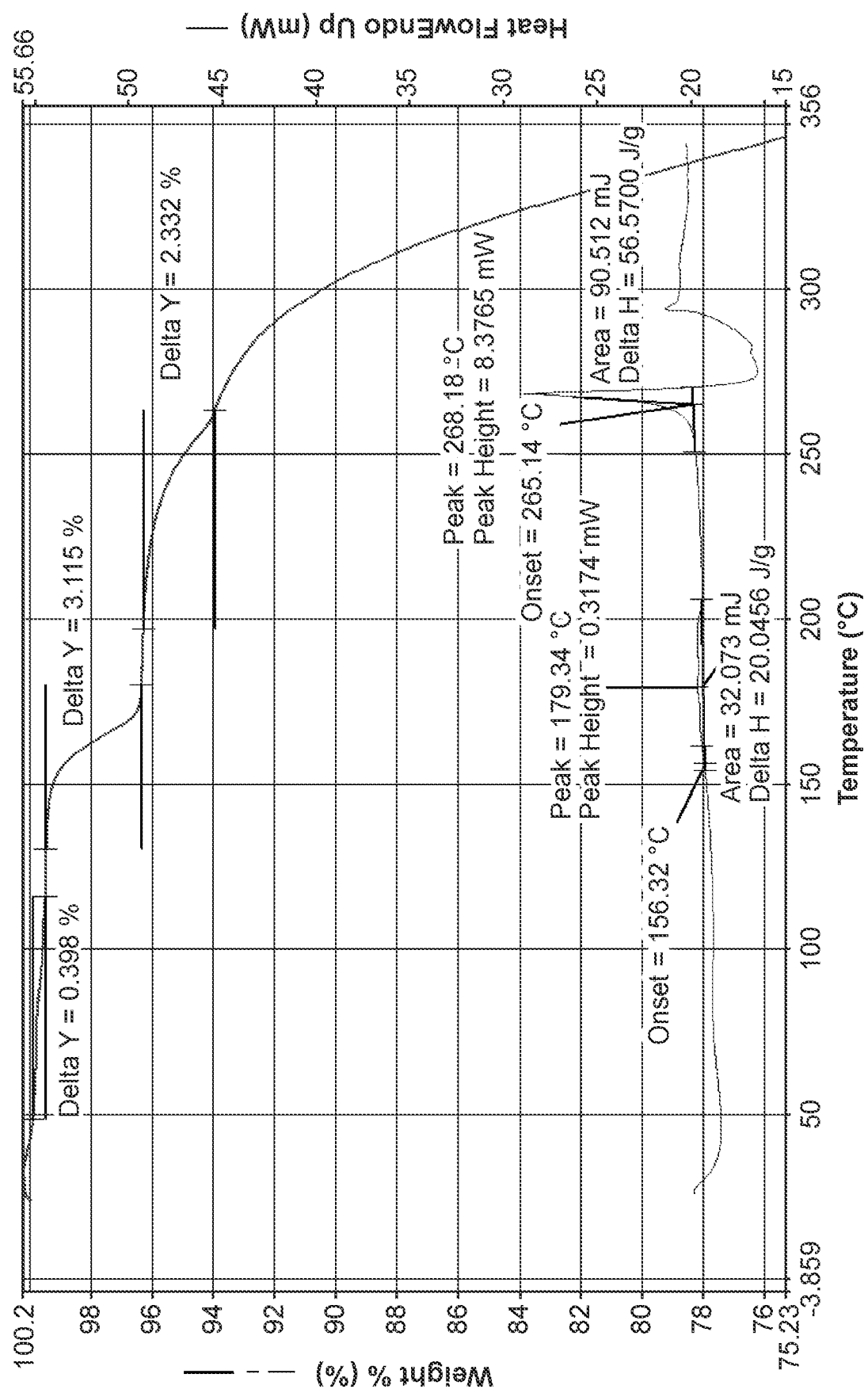
FIG. 40 shows a differential scanning calorimetry (DSC) curve and thermogravimetric analysis (TGA) thermogram for Compound I mesylate having a form similar to Form III thereof.

FIG. 40 shows an overlay of the DSC curve and TGA thermogram for Compound I mesylate Form III prepared from EtOAc during the second scale up process. The thermal analysis for said sample shows a broad endotherm with an onset at about 156° C. corresponding with a mass loss of about 3.1% (indicative of a monohydrate), followed by a subsequent loss of about 2.3%, decomposition, and an endotherm with an onset at about 266° C.

TABLE 6

Second Scale Up Formation of Salts/Co-Crystals of Compound I

| | Solvent | XRPD | DSC | TGA | Solubility (mg/mL) |
|---|---|---|---|---|---|
| Comp. I Esylate | Toluene | Crystalline material (Material A) comprising a mixture of forms, contains a same form as Material B | Endotherms with onsets at about 150° C., 190° C., and 250° C. | About 3.5% weight loss between RT and about 160° C. before an onset of decomposition at about 250° C. | 1.98 |
| | IPA | Poorly crystalline material (Material B) comprising a mixture of forms, contains a same form as Material A | A potential glass transition at about 160° C., small endotherm with peak at about 197° C., main endotherm with onset at about 251° C. | About 1.6% weight loss between about 200° C. and about 250° C. before an onset of decomposition at about 275° C. | 2.84 |
| Comp. I Mesylate | EtOAc | Similar to Form III (with minor differences) | Broad endotherm with onset at about 160° C., about 3.1% weight loss below about 200° C., main endotherm with onset at 265 ° C. | Gradual weight loss of about 0.4% between RT and about 100° C., followed by about 3.1% weight loss between about 130° C. and about 180° C., final weight | 2.32 |

TABLE 6-continued

Second Scale Up Formation of Salts/Co-Crystals of Compound I

| | Solvent | XRPD | DSC | TGA | Solubility (mg/mL) |
|---|---|---|---|---|---|
| | ethanol | Crystalline material (Material A) comprising mixture of forms | Broad endotherms with onsets at about 148° C. and 204° C., with a main endotherm composed of two specific entities with onset at about 261° C. (with presence of a shoulder on left-hand side of main endotherm) | loss of about 2.3% between about 200° C. and about 270° C., onset of decomposition above about 275° C. About 1.7% weight loss between RT and about 160° C., followed by about 0.93% weight loss between about 160° C. and about 230° C., and a final weight loss between about 230° C. and about 260° C., onset of decomposition at about 275° C. | 2.01 |
| Comp. I Sulfate | Water | Similar to Form II | Broad endotherm with onset at about 140° C. due to true desolvation, main endotherm with onset at about 273° C. | About 1.7% weight loss between RT and about 80° C., weight loss of about 1.6% between about 100° C. and about 130° C., onset of decomposition at about 260° C. | 0.007 |
| | IPA | Similar to Form I | Endotherms with onsets at about 90° C. and about 181° C., main endotherm with onset at about 263° C. | About 0.84% weight loss between RT and about 80° C., a second weight loss of about 3.07% between about 100° C. and about 160° C., onset of decomposition at about 240° C. | 0.01 |
| Comp. I HCl (formed using dry HCl) | ACN | New crystalline form (Form II) | Broad endotherm with onset at about 225° C., main endotherm with at about 277° C. | About 1% weight loss between RT and about 70° C., a weight loss of about 4.4% between about 130° C. and about 210° C., onset of decomposition at about 250° C. | 0.12 |
| Comp. I HCl (formed using aqueous HCl) | ethanol | Form I | Broad endotherm between about 50° C. and about 120° C., main endotherm with onset at about 288° C. | About 3.1% weight loss between RT and about 80° C., onset of decomposition at about 250° C. | 0.35 |

5. Solubility of Salts/Co-Crystals of Compound I

The solubility of the salts/co-crystals of Compound I prepared from the second scale up process was analyzed. The materials recovered after the solubility analysis were evaluated by XRPD to observe any form changes. The results are shown in subsections (a)-(d) below.

a. Compound I HCl

Compound I HCl Form I prepared from about 2 equivalents of aqueous HCl and ethanol was not affected by the solubility analysis (i.e., there was no form change), as shown in the X-ray powder diffractograms of FIG. 41A and FIG. 41B for said sample post and pre solubility analysis, respectively. However, solubility analysis of Compound I HCl Form II formed under anhydrous conditions resulted in phase changes and form change to Compound I HCl Form I, as shown in the X-ray powder diffractograms of FIG. 41C and FIG. 41D for said sample post and pre solubility analysis, respectively.

For the second scale up and solubility experiments, Compound I HCl Form I returned the best results in terms of form reproducibility/stability and actual solubility.

b. Compound I Mesylate

The Compound I mesylate input materials for the solubility analysis were of different crystalline forms (i.e., Compound I mesylate Material A prepared from ethanol (FIG. 42B), and the form of Compound I mesylate prepared from EtOAc (i.e., a form substantially similar to Form III, FIG.

42D). The recovered materials (post solubility analysis) from Compound I mesylate Material A (FIG. 42A) and Compound I mesylate Form III (FIG. 42C) are each characterized by the same form, which is different than the forms of either input material.

c. Compound I Sulfate

The form of Compound I sulfate prepared from water (i.e., a form similar to Compound I sulfate Form II) was not affected by the solubility analysis (i.e., there was no form change), as shown in the X-ray powder diffractograms of FIG. 43A and FIG. 43B for said sample post and pre solubility analysis, respectively. However, solubility analysis of the crystalline form of Compound I sulfate prepared from IPA (i.e., a form substantially similar to Compound I sulfate Form I) resulted in a form change to Compound I sulfate Form II, as shown in the X-ray powder diffractograms of FIG. 43C and FIG. 43D for said sample pre and post solubility analysis, respectively.

d. Compound I Esylate

The Compound I esylate input materials for the solubility analysis were of different crystalline forms (i.e., Compound I esylate Material A prepared from toluene, and Compound I esylate Material B prepared from IPA). The recovered materials (post solubility analysis) from Compound I mesylate Material A (FIG. 44A) and Compound I esylate Material B (FIG. 44B) are each characterized by the same form, which is different than the forms of either input material.

6. Hygroscopicity for Salts/Co-Crystals of Compound I

The hygroscopicity of the esylate, mesylate, HCl, and sulfate salts/co-crystals of Compound I formed via the first scale up process was analyzed. All hygroscopicity experiments covered a wide range of humidity (0 to about 90% relative humidity) and were performed at about 25° C. to assess behavior. The results are provided in subsections (a)-(d) below.

a. Compound I Esylate Form I

Figure 45:
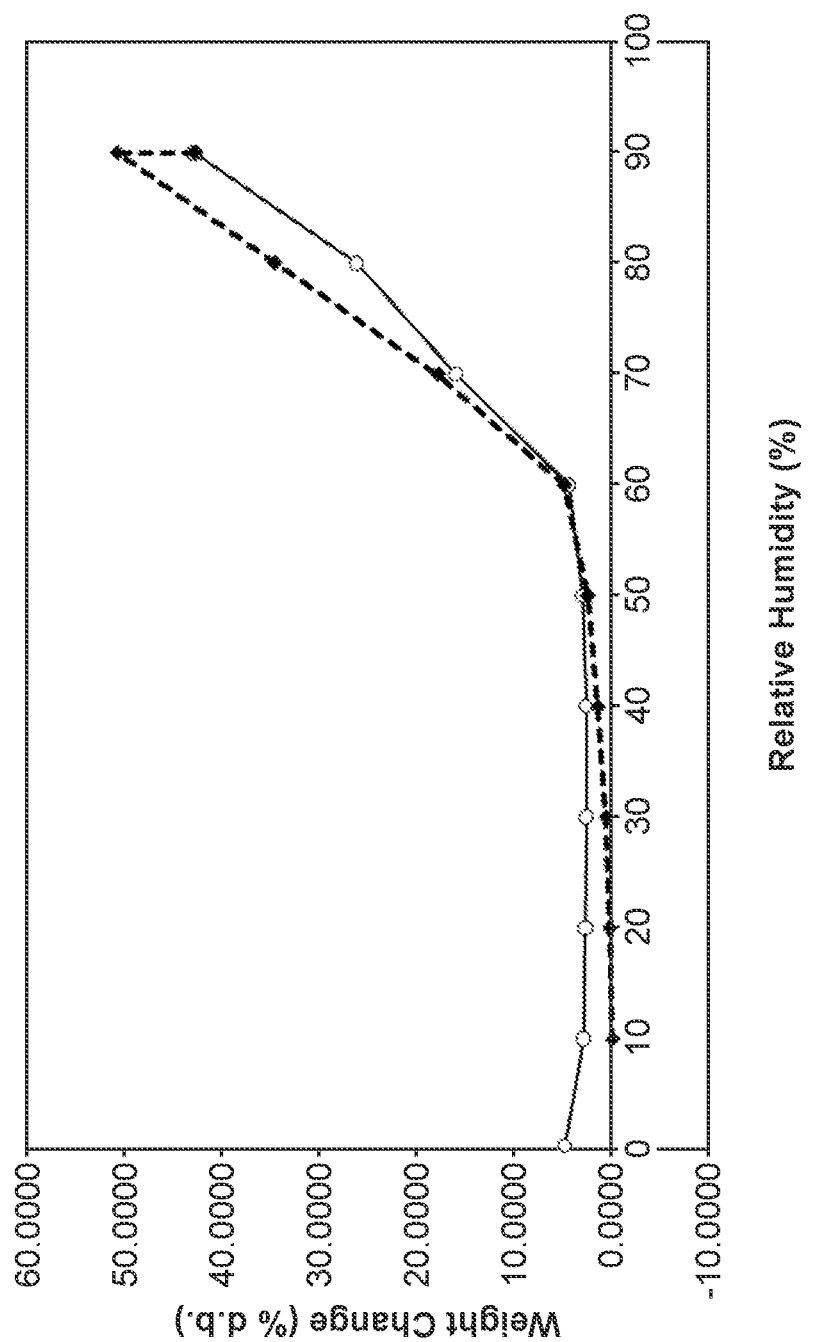
FIG. 45 is a gravimetric vapor sorption (GVS) isotherm of Compound I esylate Form I.

Compound I esylate Form I prepared from IPA in the first scale up process was assessed for hygroscopicity. The results of a GVS analysis are shown in FIG. 45 and indicate a strong influence of humidity on the sample, mainly above about 60% RH. The sample was not subject to moisture uptake in the sorption cycle between 0 and about 60% RH. The weight variation is effectively nonexistent despite the minimal weight loss observed between 0 and about 10% RH, mainly due to drying. Above about 60% RH, the sudden increase in weight (e.g., about a 35% weight change) demonstrates the marked influence of water into the sample. This trend is reversed in the desorption cycle, between about 90 and about 60% RH, where the sample loses all the water and returns to the same value measured in the sorption cycle at about 60% RH. While a large water uptake was noted, deliquescence did not result, indicating a high hydration level and surface moisture uptake. If dried to about 10% RH, the sample loses about 4.6% of mass relative to the input weight. These results indicate that the sample (Compound I esylate Form I) is hydrated.

Figures 46A, 46B:
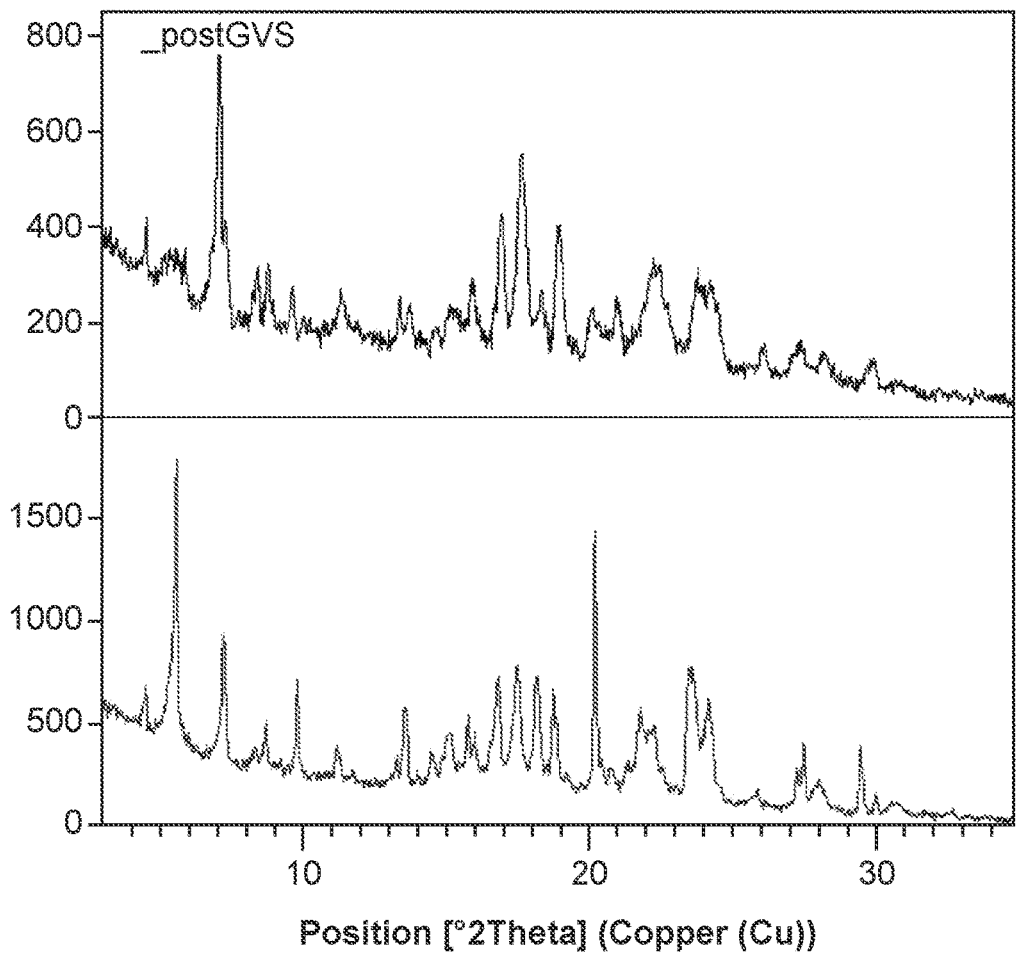
FIG. 46A and FIG. 46B are X-ray powder diffractograms of Compound I esylate Form I as measured after (FIG. 46A) and prior to (FIG. 46B) gravimetric vapor sorption (GVS) analysis thereof, respectively.

FIG. 46A and FIG. 46B show the X-ray powder diffractograms for Compound I esylate Form I sample post and pre GVS analysis, respectively. Exposure to humidity has a strong impact on the crystalline form of the sample. Post GVS analysis, the sample shows loss of crystallinity, and the disappearance of some peaks in the X-ray powder diffractogram (FIG. 46A). Such results illustrate the structural change due to the drying effect (potentially due to the water loss) and changes that may have occurred as a result of the reversible water uptake between about 60 and about 90% RH.

b. Compound I Mesylate Form II

Figure 47:
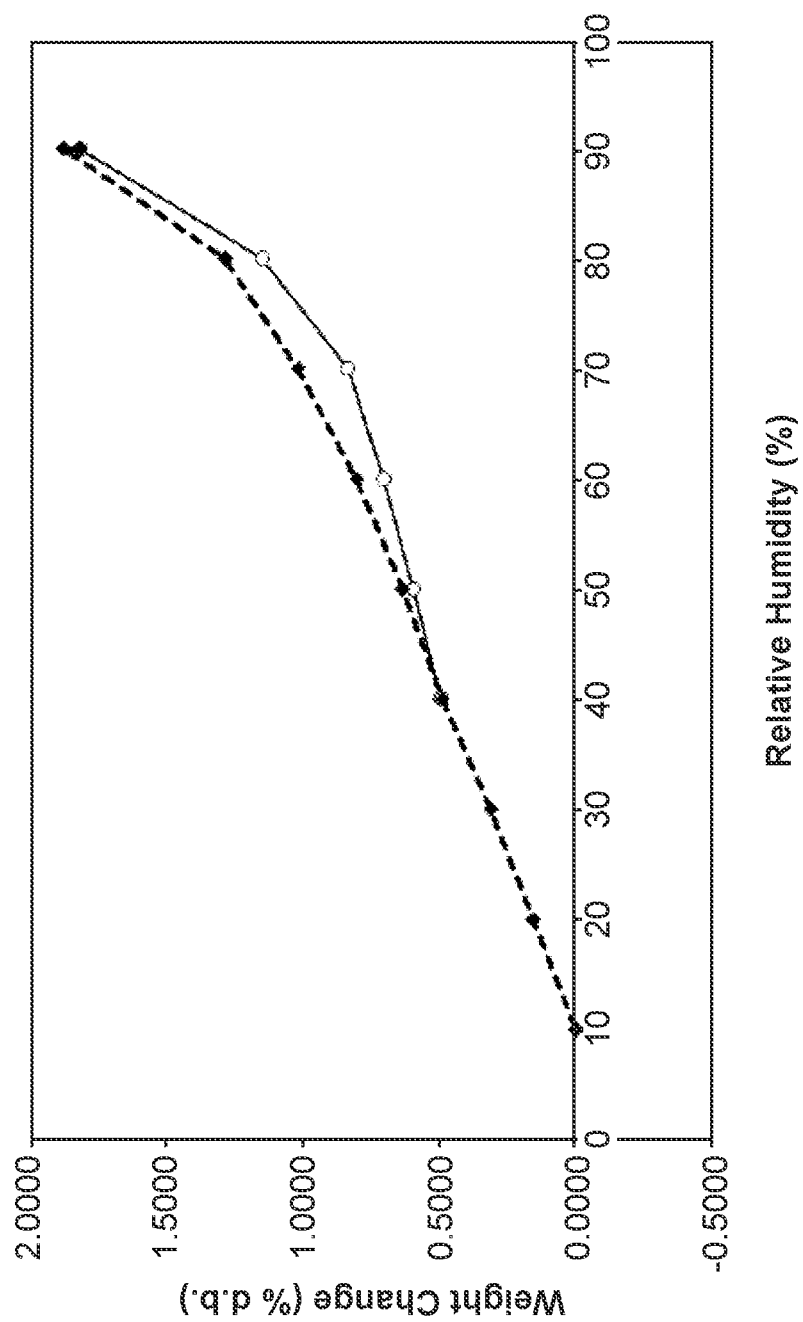
FIG. 47 is a gravimetric vapor sorption (GVS) isotherm of Compound I mesylate Form II.

Compound I mesylate Form II prepared from water in the first scale up process was assessed for hygroscopicity. The results of a GVS analysis are shown in FIG. 47 and indicate the relative influence of humidity on the sample. In particular, as the relative humidity increases, the weight uptake varies accordingly. The total weight uptake from the starting point does not exceed about 1.4%. The desorption indicates that only a total of about 2% mass is lost. If this sample was fully hydrated (a mono-hydrate), the total weight loss upon drying should equate to about 3.2%.

Figure 48:
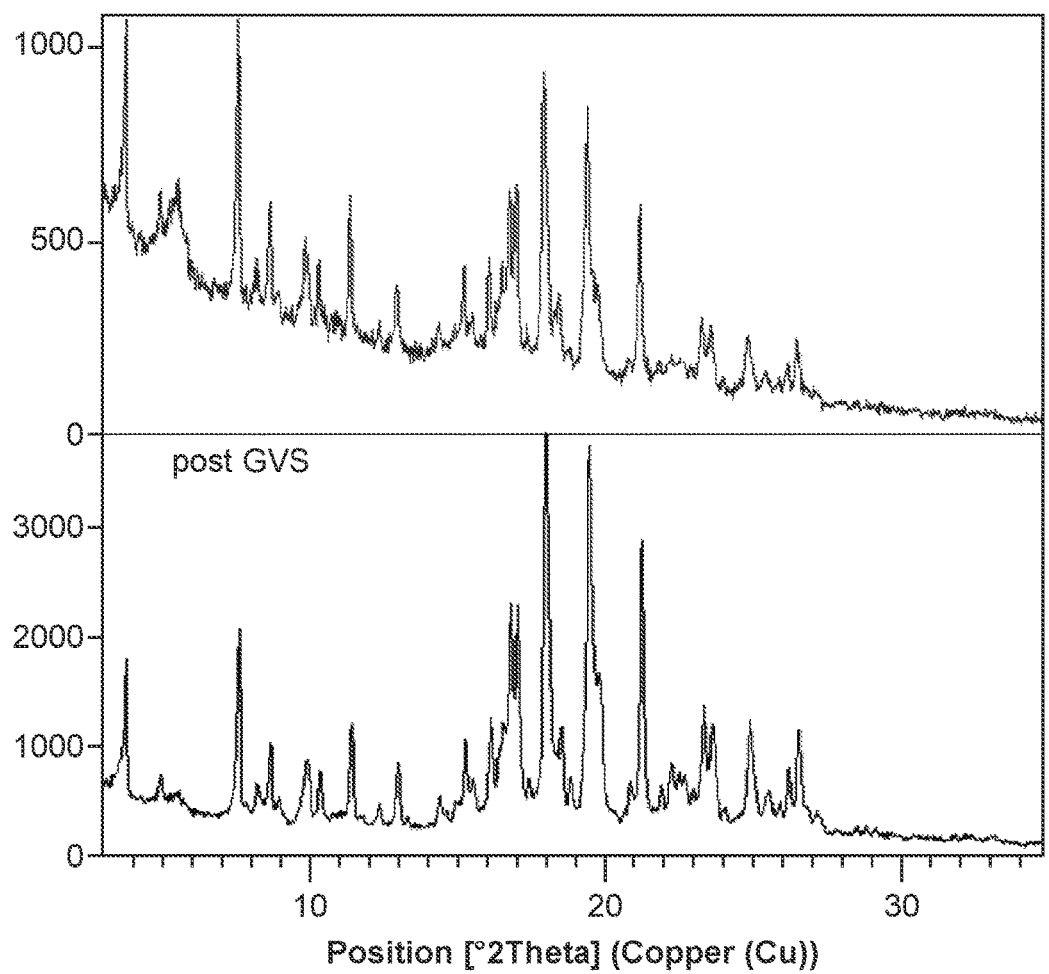
FIG. 48A and FIG. 48B are X-ray powder diffractograms of Compound I mesylate Form II as measured prior to (FIG. 48A) and after (FIG. 48B) gravimetric vapor sorption (GVS) analysis thereof, respectively.

FIG. 48A and FIG. 48B show the X-ray powder diffractograms for the Compound I mesylate Form II sample pre and post GVS analysis, respectively. Exposure to humidity does not result in a form change for this sample.

c. Compound I HCl Form I

Figure 49:
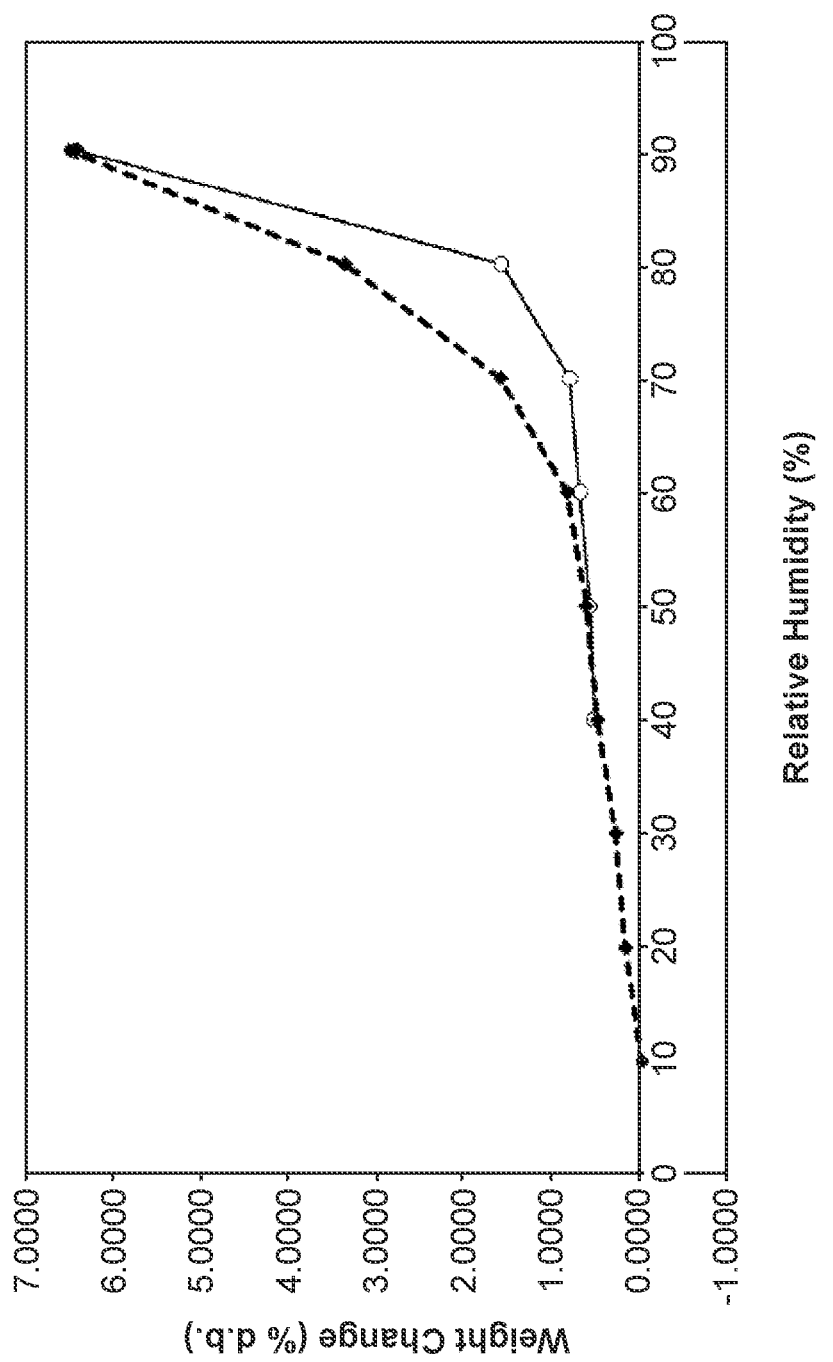
FIG. 49 is a gravimetric vapor sorption (GVS) isotherm of Compound I HCl Form I.

Compound I HCl Form I prepared from water in the first scale up process was assessed for hygroscopicity. The results of a GVS analysis are shown in FIG. 49 and indicate the relative influence of humidity on the sample. In particular, the weight of the sample does not vary significantly up to about 70% RH, after which a total weight uptake of about 5.9% is observed. The desorption cycle for the sample indicates that the weight thereof reverts, at about 50% RH, to its same weight value as at the beginning of GVS analysis. Additionally, about 0.5% of mass is lost when the sample is kept under about 100% dry atmosphere.

FIG. 50A and FIG. 50B show the X-ray powder diffractograms for the Compound I HCl Form I sample post and pre GVS analysis, respectively. Exposure to humidity does not result in a form change for this sample.

d. Compound I Sulfate Form II

Figure 51:
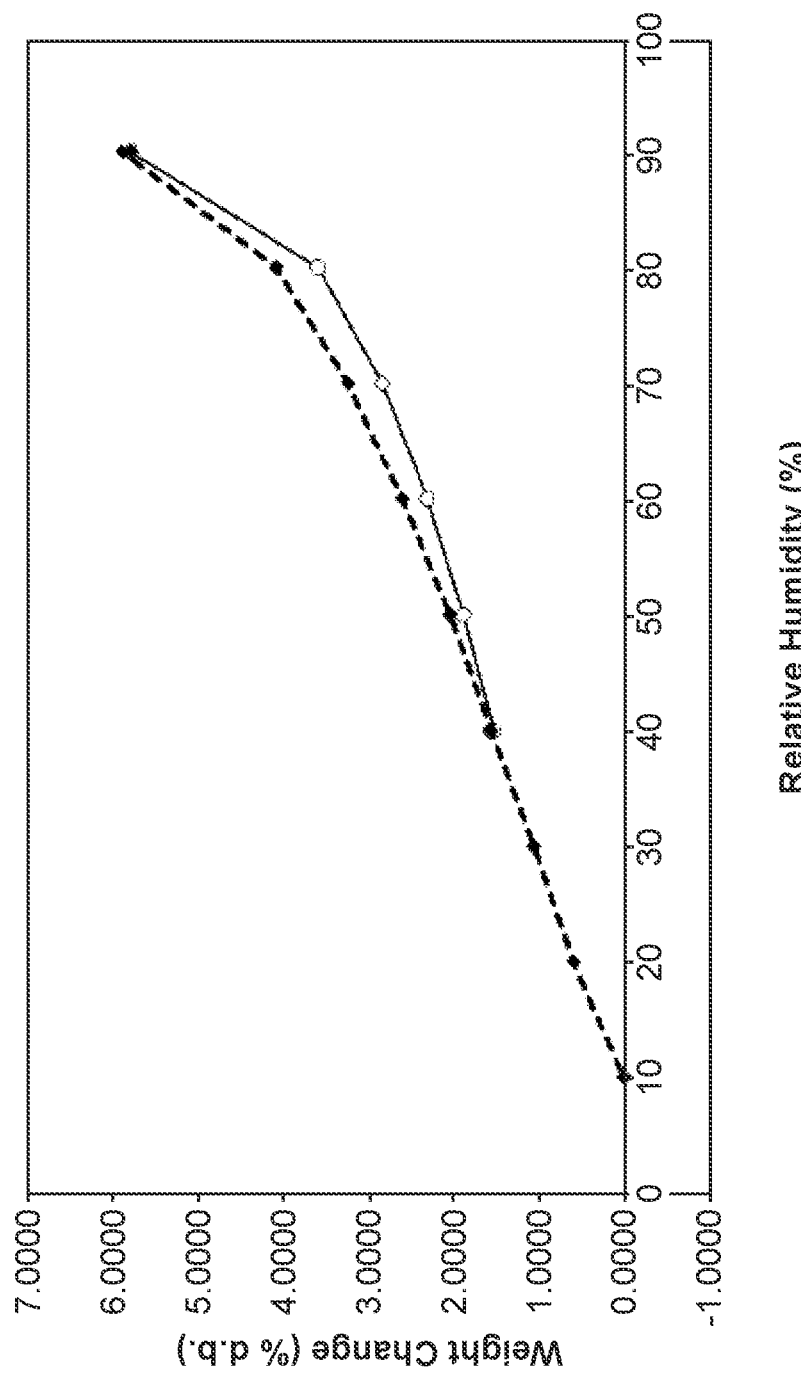
FIG. 51 is a gravimetric vapor sorption (GVS) isotherm of Compound I sulfate Form II.

The form of Compound I sulfate prepared from water in the first scale up process (i.e., a form substantially similar to Form II) was assessed for hygroscopicity. The results of a GVS analysis are shown in FIG. 51 and indicate the relative influence of humidity on the sample. The GVS isotherm indicates a gradual weight gain of about 4.2% up to about 80% RH before a steep increase in weight when exposed to about 90% RH. This weight gain is lost in the same fashion in the desorption isotherm. The total weight loss when dried to 0% RH is about 5.9%.

Figures 52A, 52B:
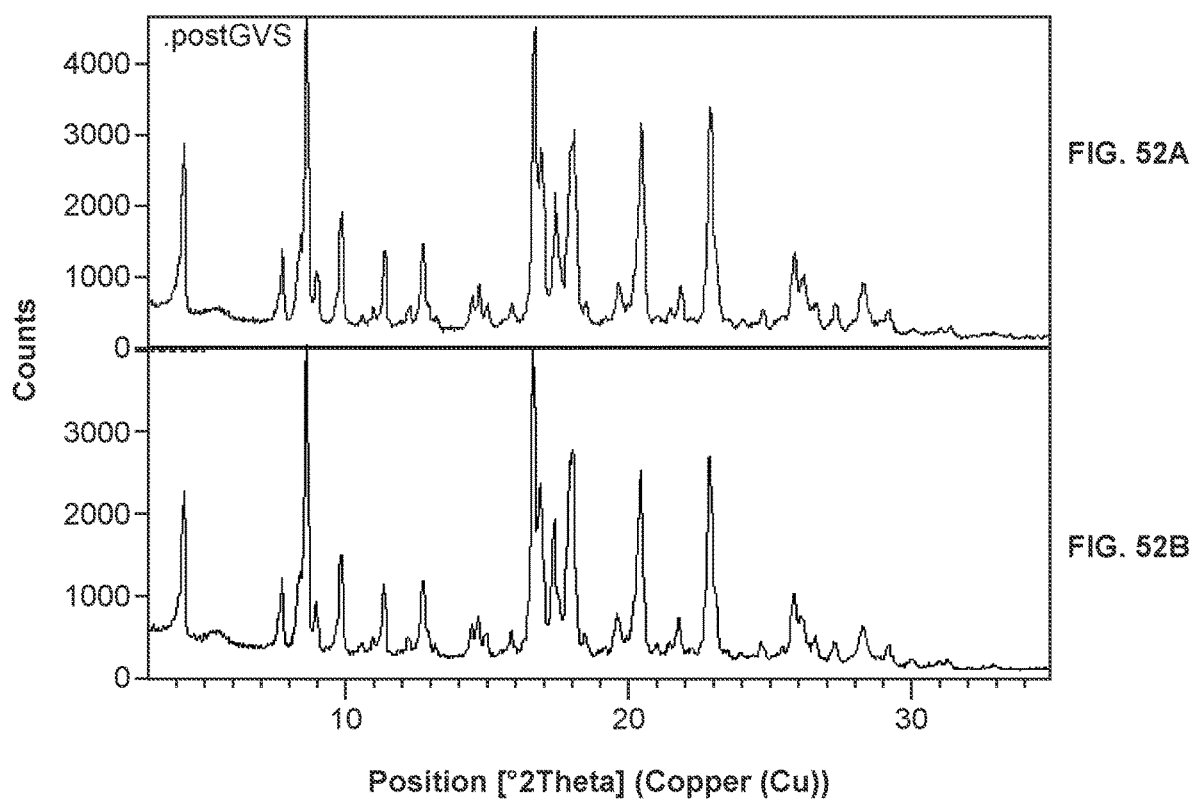
FIG. 52A and FIG. 52B are X-ray powder diffractograms of Compound I sulfate Form II as measured after (FIG. 52A) and prior to (FIG. 52B) gravimetric vapor sorption (GVS) analysis thereof, respectively.

FIG. 52A and FIG. 51B show the X-ray powder diffractograms for the crystalline Compound I sulfate sample post and pre GVS analysis, respectively. Exposure to humidity slightly increased the crystallinity of the sample without affecting the peak distribution.

7. Slurry Formation for Salts/Co-Crystals of Compound I

A series of slurry maturations in various solvents was performed to further analyze the form reproducibility/stability of the esylate, mesylate, HCl, and sulfate salts/co-crystals of Compound I. The solvents chosen were acetonitrile, EtOAc, ethanol, and IPA. The input materials were the salts/co-crystals of Compound I formed via the second scale up process. About 20 mg of each sample was charged to reflux tubes and heated with temperature cycling between about 25 and about 50° C. for about 4 days. The resulting materials were isolated by filtration and dried in vacuo at about 40° C. The results of the slurry maturations for the resulting HCl and mesylate salts/co-crystals are presented in subsections (a)-(d) below. The data for the resulting esylate and sulfate salts/co-crystals of Compound have been omitted due to notable form variation.

a. Compound I HCl Form I

The starting material used in these slurry maturations was Compound I HCl (mono-HCl) Form I prepared from about 2 equivalents of aqueous HCl and ethanol during the second scale up process. FIG. 53A shows the X-ray powder diffractograms for the Compound I HCl Form I starting material, and FIG. 53B, FIG. 53C, FIG. 53D, and FIG. 53E show the X-ray powder diffractograms for the crystalline materials isolated from the slurries comprising acetonitrile (53B), EtOAc (53C), ethanol (53D), and IPA (53E). As evident from FIG. 53A, FIG. 53B, FIG. 53C, FIG. 53D, and FIG. 53E, Compound I HCl Form I does not experience any form change upon slurrying, and experienced a minor improvement in crystallinity in all cases except EtOAc.

b. Compound I HCl Form II

The starting material used in these slurry maturations was Compound I HCl (mono-HCl) Form II prepared from about 1 equivalent of dry HCl and acetonitrile during the second scale up process. FIG. 54A shows the X-ray powder diffractograms for the Compound I HCl Form II starting material, and FIG. 54B, FIG. 54C, FIG. 54D, and FIG. 54E show the X-ray powder diffractograms for the crystalline materials isolated from the slurries comprising acetonitrile (MB), EtOAc (MC), ethanol (MD), and IPA (ME). The XRPD profiles for these materials are markedly different. Samples isolated from acetonitrile and EtOAc show a material comprised of a mixture of Compound I Form I, Compound I Form II, and possibly other forms. The sample isolated from IMA shows conversion to Compound I Form I. The sample isolated from IPA also shows conversion to Compound I Form I, yet retains some mixed features.

c. Compound I Mesylate Material A

Figure 55A:
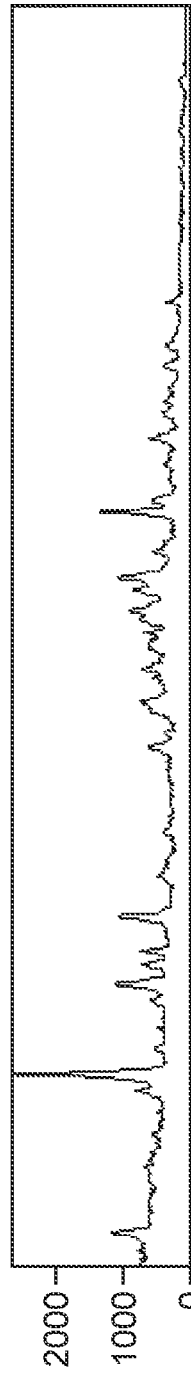
FIG. 55A is an X-ray powder diffractogram of Compound I mesylate Material A starting material used in various slurry maturations.
Figure 55B:
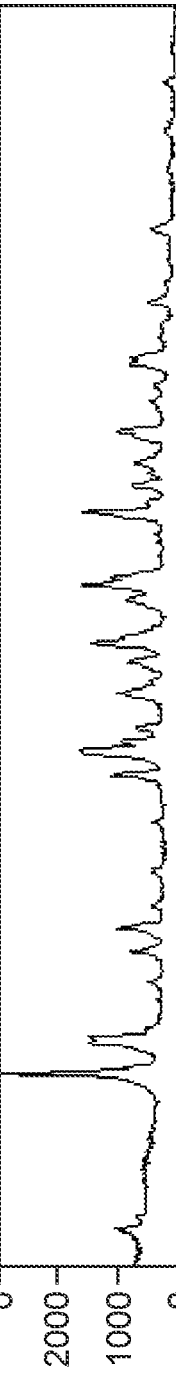
FIG. 55B, FIG. 55C, FIG. 55D, and FIG. 55E are X-ray powder diffractograms of the resulting crystalline materials isolated from the slurries comprising acetonitrile (FIG. 55B), EtOAc (FIG. 55C), ethanol (FIG. 55D), and IPA (FIG. 55E).
Figure 55C:
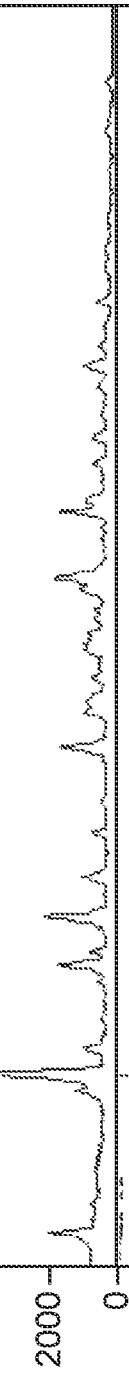
Figure 55D:
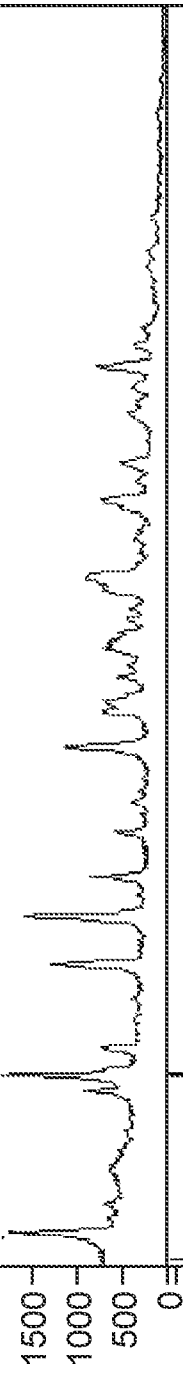
Figure 55E:
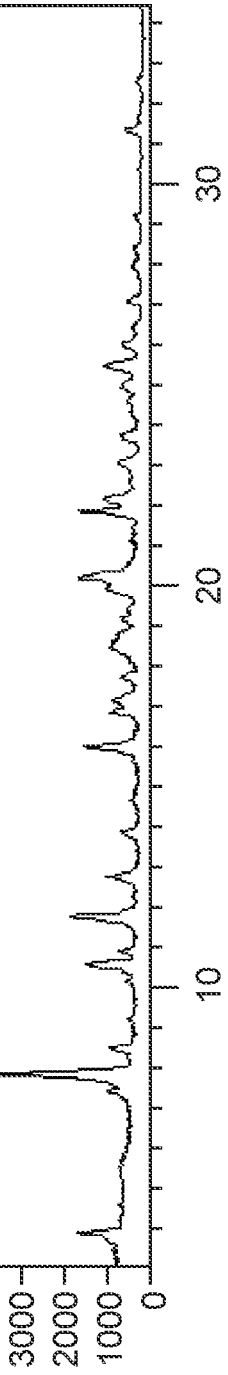

The starting material used in these slurry maturations was Compound I mesylate (mono-mesylate) Material A prepared from ethanol during the second scale up process. FIG. 55A shows the X-ray powder diffractograms for the Compound I mesylate Material A starting material, and FIG. 55B, FIG. 55C, FIG. 55D, and FIG. 55E show the X-ray powder diffractograms for the crystalline materials isolated from the slurries comprising acetonitrile (55B), EtOAc (55C), ethanol (55D), and IPA (55E). Samples isolated from each of the solvents, while different from the input material, are nearly identical to one another in terms of their crystalline structure, which results from a mixture of forms.

d. Compound I Mesylate Form III

The starting material used in these slurry maturations was Compound I mesylate (mono-mesylate) Form III prepared from EtOAc during the second scale up process. FIG. 56A shows the X-ray powder diffractograms for the Compound I mesylate Form III starting material, and FIG. 56B, FIG. 56C, FIG. 56D, and FIG. 56E show the X-ray powder diffractograms for the crystalline materials isolated from the slurries comprising acetonitrile (56B), EtOAc (56C), ethanol (56D), and IPA (56E). Each sample isolated post slurry shows a complicated pattern likely indicative of a mixture of forms comprising Compound I mesylate Form III and other forms.

8. Polymorph Screen for the Mono-HCl Salt/Co-Crystal of Compound I

About 7 mL of 0.5M DMSO solution of Compound I free base was added slowly to about 40 mL of stirred hot ethanol (about 70° C.). About 10.5 mL of 1M aq HCl was added slowly to the stirring solution at the same temperature (about 70° C.). The solution was left to cool overnight to room temperature. The material was filtered and dried in an oven for about 72 hours.

For the polymorph screening, about 20 mg of the resulting mono-HCl salt/co-crystal of Compound I and about 1 mL of a selected solvent was added to a tube and heated to about 50° C. for about three hours to improve dissolution. Samples were filtered hot through PTFE fits to avoid crash precipitation and remove any seed. Solvents of very high boiling point that would not evaporate were placed in a genevac to speed evaporation and allow materials to crash out. XRPD was the primary tool of analysis, followed by DSC/TGA if a new form was revealed. The diffractograms used for comparisons were those of Compound I mono-HCl Form I and Compound I bis-HCl Form I. The results are presented in Table 7 below.

TABLE 7

Summary of Results for the Mono-HCl Salt/Co-Crystal Polymorph Study

| Solvent | XRPD |
| --- | --- |
| Tetralin | Gum |
| NMP | Gum |
| Ethylene glycol | Poor diffraction |
| DMSO | Compound I di-HCl Form I |
| Anisole | Compound I mono-HCl Form I |
| DMF | Compound I di-HCl Form I |
| Cumene | Compound I mono-HCl Form I |
| 3-Me-1-BuOH | Compound I mono-HCl Form I |
| n-BuOAc | Compound I mono-HCl Form I |
| Toluene | Compound I mono-HCl Form I |
| Dioxane | Compound I mono-HCl Form I |
| Water | Compound I mono-HCl Form I |
| Heptane | Compound I mono-HCl Form I |
| n-PrOH | Compound I mono-HCl Form I |
| IPA | Compound I mono-HCl Form I |
| $CH_3CN$ | Compound I mono-HCl Form I |
| MEK | Compound I mono-HCl Form I |
| EtOH | Compound I mono-HCl Form I |
| EtOAc | Compound I mono-HCl Form I |
| THF | Poorly diffracting |
| MeOH | Compound I mono-HCl Form I |
| Acetone | Compound I mono-HCl Form I |
| TBME | Compound I mono-HCl Form I |
| DCM | Compound I mono-HCl Form I |

As consistently found by the various studies discussed in the Examples, Compound I mono-HCl Form I exhibits superior thermodynamically stability relative to the other salts/co-crystals of Compound I described herein.

9. Compound I HCl Amorphous

Compound I HCl amorphous was obtained via lyophilization of a THF/water solution comprising Compound I HCl Form I over about 4-5 days at high vacuum. The material was then subject to slurry maturations in 12 solvents, using heat/cool cycles between room temperature and about 45° C. (for about 4 days). The resulting solids were filtered and dried in vacuo at about 40° C. overnight prior to analysis by XRPD. FIG. 57A, FIG. 57B, FIG. 57C, FIG. 57D, FIG. 57E, FIG. 57F, and FIG. 57G show the X-ray powder diffractograms of the Compound I HCl amorphous starting material (57A), and the resulting Compound I HCl amorphous samples formed from slurries with cumene (57B), n-BuOAc (57C), dioxane (57D), water (57E), IPA (57F), and acetonitrile (57G). Similarly, FIG. 58A, FIG. 58B, FIG. 58C, FIG. 58D, FIG. 58E, and FIG. 58F show the X-ray powder diffractograms of the Compound I HCl amorphous starting material (58A), and the resulting Compound I HCl amorphous samples formed from slurries with MEK (58B), EtOH (58C), EtOAc (58D), TBME (58E), and DCM (58F). As evident in the diffractograms, Compound I HCl amorphous comprises an amount of Compound I HCl Form I.

Figure 59:
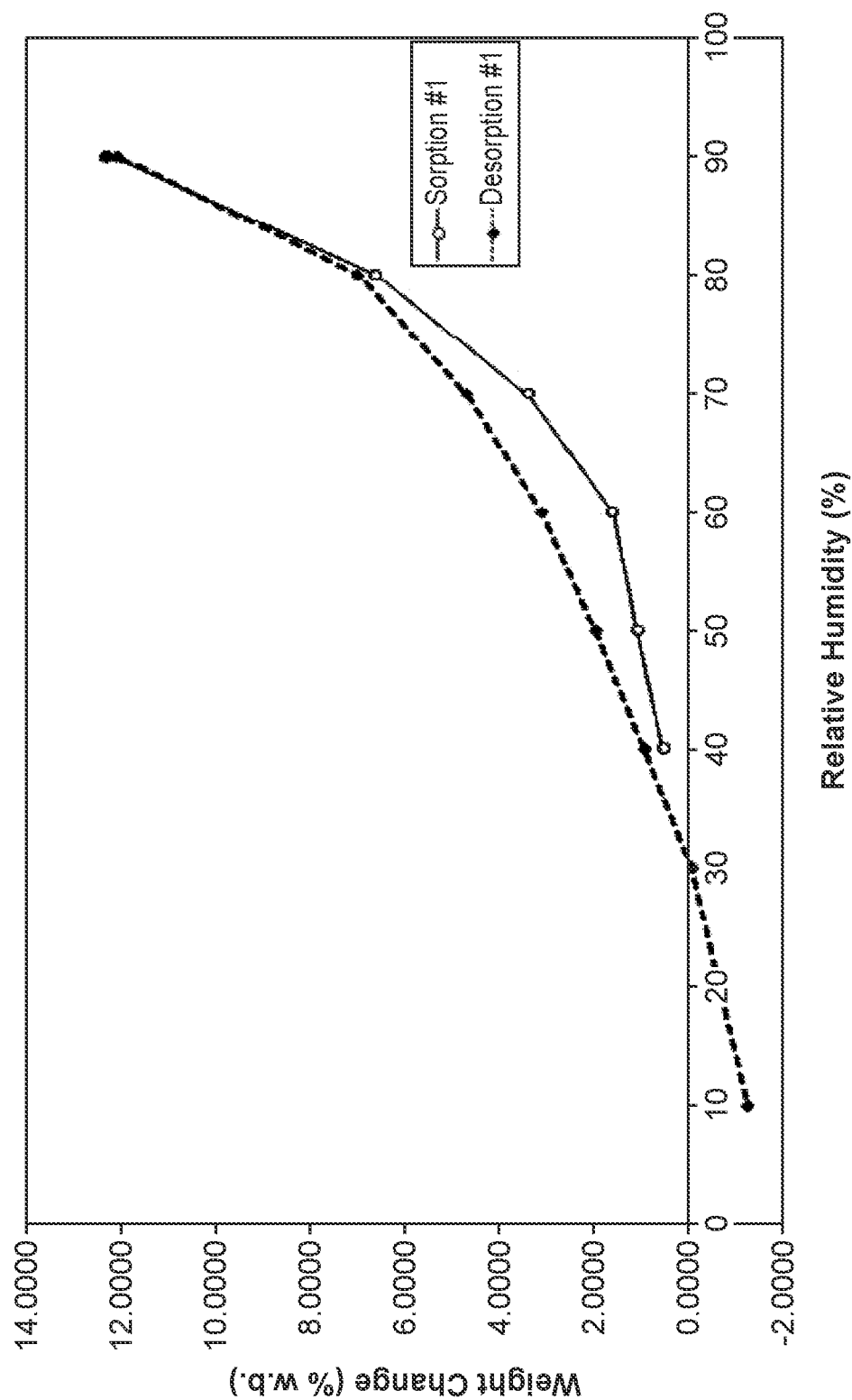
FIG. 59 is a gravimetric vapor sorption isotherm for Compound I HCl amorphous.

FIG. 59 shows a GVS isotherm for Compound I HCl amorphous. As shown in the GVS isotherm, a large increase in mass above about 40% RH, most markedly above about 80% RH, is observed, which can be removed by exposure to drying.

A study of moisture uptake for Compound I HCl amorphous was also performed and demonstrated a gradual increase in crystallinity was observed simply by exposure to ambient conditions.

10. Compound I HCl Form I

As indicated in Table 4, Compound I HCl Form I is obtained from combining Compound I Form I and about 1 equivalent of hydrochloric acid in various solvents including DMF, 3-Me-1-BuOH, n-BuOAc, toluene, water, IPA, MEK, EtOH, DMSO or THF. Processes utilizing about 2, about 3, or about 4 equivalents of hydrochloric acid were also found to yield Compound I HCl Form I.

Figure 3:
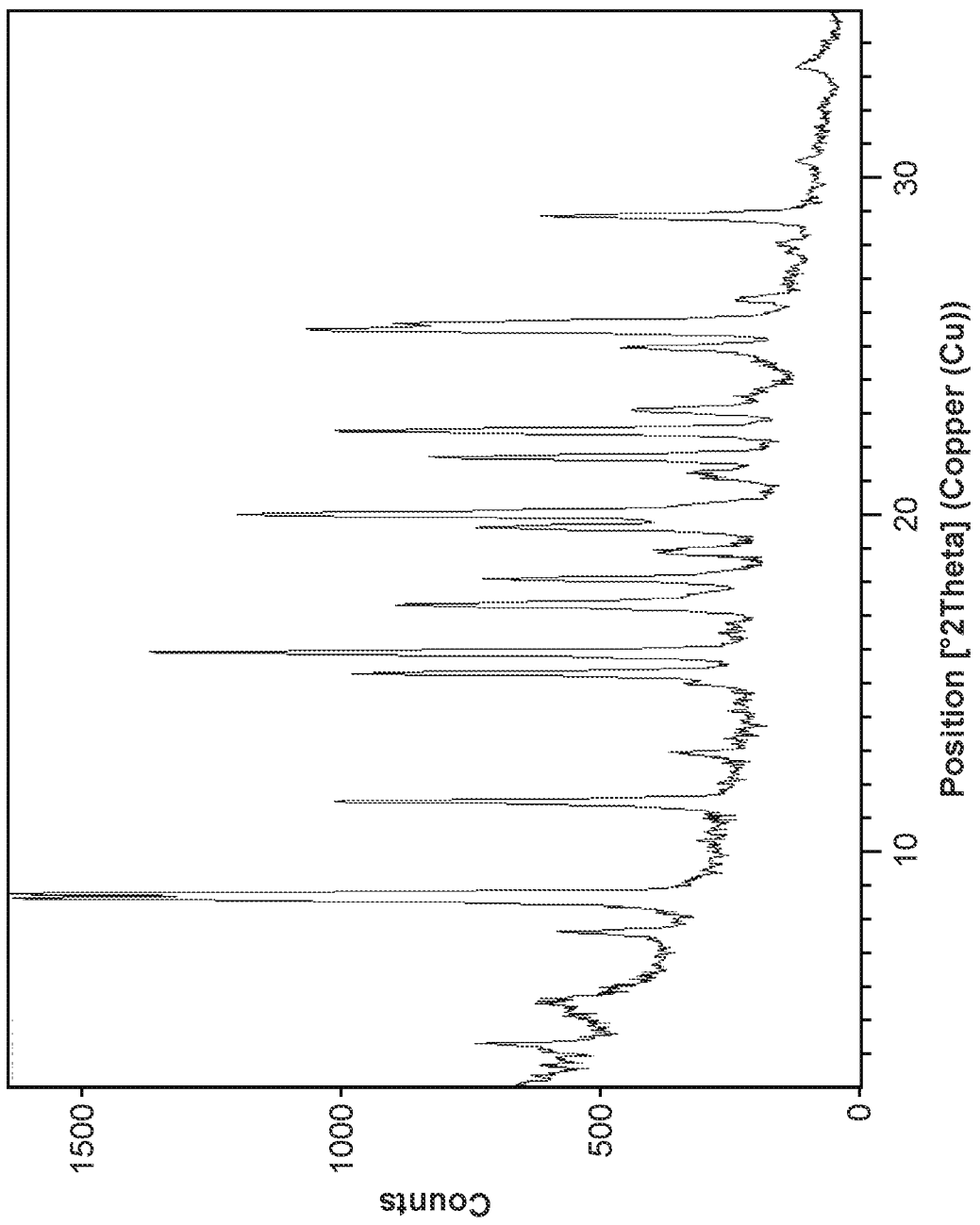
FIG. 3 is an X-ray powder diffractogram of Compound I HCl Form I.

Compound I HCl Form I is crystalline as determined via XRPD analysis (FIG. 3). Compound I HCl Form I can be characterized by an X-ray powder diffractogram comprising the following peaks: 8.7, 15.9, and 20.0 °2θ±0.2 °2θ.

Single crystal analysis of Compound I HCl Form I yields the following unit cell dimensions:

Crystal System: Triclinic

Space Group: P-1

Unit cell dimensions: a=5.2441(3) Å, α=89.428(6)° b=11.3283(9) Å, β=85.493(5)° c=20.1798(13) Å, γ=84.008(6)°

Compound I HCl Form I can be characterized by a differential scanning calorimetry (DSC) curve comprising an endotherm with onset at about 288° C. and a peak maximum at about 293° C. (FIG. 36).

Compound I HCl Form I is characterized by a thermogravimetric analysis (TGA) thermogram showing a weight loss of about 3.5% below about 100° C., and a weight loss of about 4.5% at about 270° C. (FIG. 36).

Figure 60:
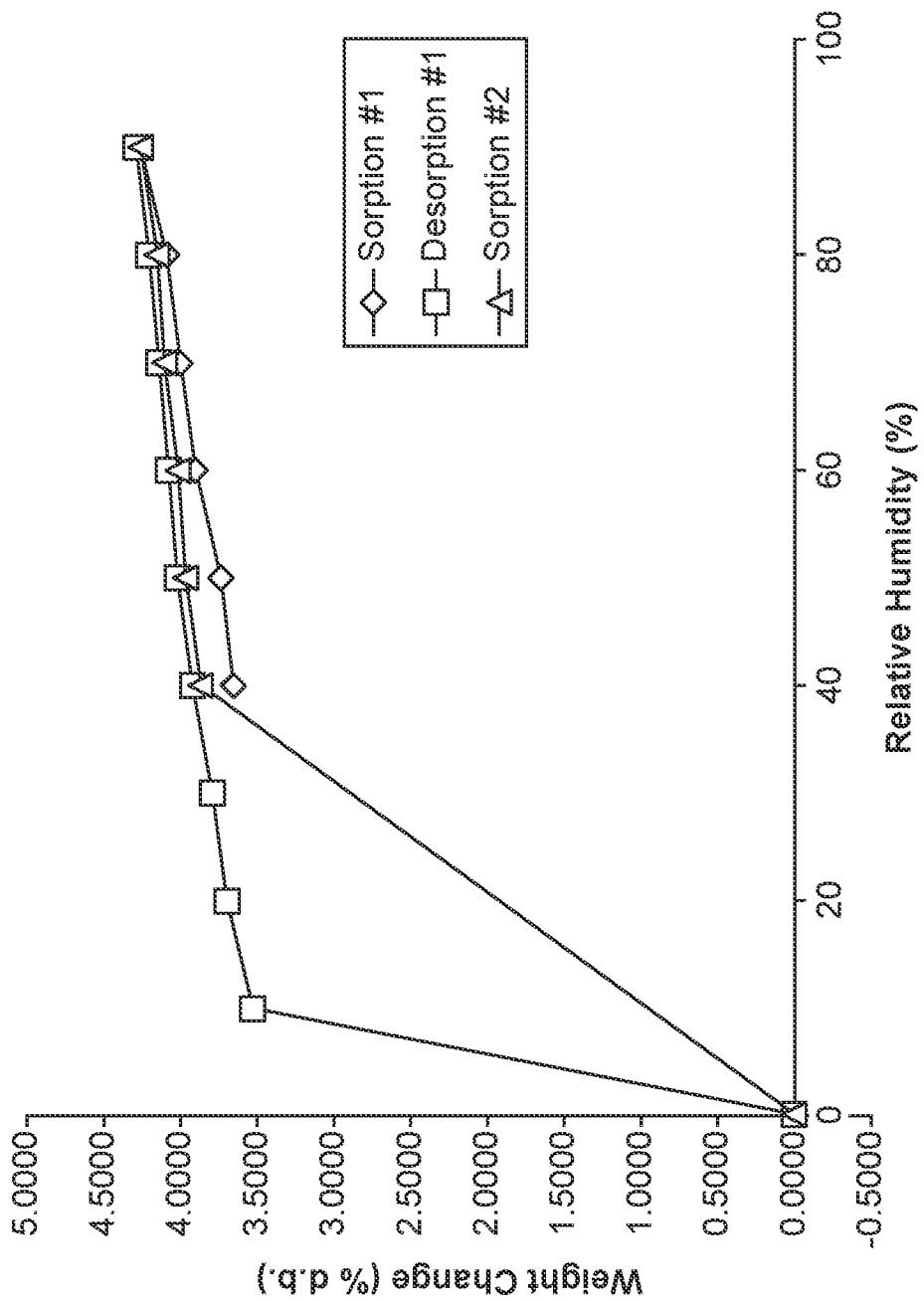
FIG. 60 is a dynamic vapor sorption (DVS) curve of Compound I HCl Form I.

Compound I HCl Form I is characterized by dynamic vapor sorption (DVS) analysis showing minimal moisture uptake with no hysteresis between about 40% and about 90% RH. While the DVS analysis additionally shows a weight of up to about 3.5% below about 10% RH, complete moisture re-uptake is observed about 20% RH. Accordingly, de-hydration and re-hydration of Compound I HCl Form I was found to be reversible and does not disturb the crystalline structure thereof. An exemplary DVS curve of Compound I HCl Form I is provided in FIG. 60. In view of the DVS analysis, compound I HCl Form I may be characterized as a monohydrate.

Compound I HCl Form I exhibits solubility in a variety of solvents and solvent systems. A summary of the approximate kinetic solubility of Compound I HCl Form I in organic solvents, simulated biological fluids, and common pharmaceutical co-solvents is provided in Tables 8-10, respectively.

TABLE 8

Approximate Kinetic Solubility of Compound I HCl Form I in Organic Solvents

| Solvent | Approximate kinetic solubility (mg/mL) |
|---|---|
| DMSO | 10-33.3 |
| DMF, PEG300 | 1-10 |
| Methanol, Ethanol, PG, Safflower Seed Oil, Tween 80 | 0.1-1 |
| Acetone, MeCN, IPA, EtOAc, THF, Dioxane, DCM | <0.1 |

TABLE 9

Approximate Kinetic Solubility of Compound I HCl Form I in Simulated Biological Fluids at about 37° C.

| Simulated biological fluid | Approximate kinetic solubility (μg/mL) | |
|---|---|---|
| | Equilibrated for 2 hrs | Equilibrated for 1 day |
| SGF (pH 1.2) | 67 | 78 |
| FeSSIF (pH 5.0) | 35 | 39 |
| FaSSIF (pH 6.1) | 3 | 3 |

TABLE 10

Approximate Kinetic Solubility of Compound I HCl Form I in Pharmaceutical Co-solvents (no-pH adjustment)

| Co-solvents (in aqueous solution) | Approximate kinetic solubility (mg/mL) | | |
|---|---|---|---|
| | 2 hrs. | 24 hrs. | 7 days |
| 10% Labrasol *** | 1.15 | 0.82 | 0.70 |
| 20% Labrasol *** | 1.84 | 1.85 | 1.71 |
| 35% Labrasol *** | 1.90 | 2.01 | 1.80 |
| 50% Labrasol *** | 2.05 | 2.65 | 2.20 |
| 20% PEG | 0.27 | 0.37 | — |
| 30% PEG | 0.42 | 0.45 | 0.41 |
| 50% PEG | 2.17 | 0.87 | 0.69 |
| 3% HP-β-CD | 0.99 | 1.12 | 1.02 |
| 5% HP-β-CD | 1.45 | 1.39 | 1.59 |
| 10% HP-β-CD | 1.88 | 2.03 | 1.93 |
| 20% HP-β-CD | 2.63 | 2.81 | 2.65 |
| 30% HP-β-CD | 2.98 | 2.94 | — |
| 40% HP-β-CD | 3.86 | 3.84 | 4.12 |
| 2% Captisol * | 2.04 | 2.51 | 2.54 |
| 5% Captisol * | 3.01 | 3.61 | 3.75 |
| 10% Captisol * | 3.04 | 3.41 | 3.67 |
| 40% Captisol * | 4.25 | 4.40 | 4.33 |
| 5% Poloxamer F68 | 0.23 | 0.18 | — |
| 10% Poloxamer F68 | 0.26 | 0.21 | — |
| 5% Pharmasolve ** | 0.43 | 0.69 | — |
| 10% Pharmasolve ** | 0.70 | 0.57 | — |
| 3% TPGS **** | 1.06 | 0.64 | 0.54 |
| 5% TPGS **** | 1.61 | 1.53 | 1.32 |
| 10% TPGS **** | 1.80 | 1.93 | 1.72 |
| 20% TPGS **** | 2.45 | 2.42 | 2.62 |

* Captisol: SulfoButyl Ether β-cyclodextrins (SBE-β-CD)
** Pharmasolve: N-Methyl-2-Pyrrolidone (NMP)
*** Labrasol: Caprylocaproyl polyoxyl-8 glycerides
**** TPGS: alpha-tocopheryl succinate esterified to polyethylene glycol 1000

Figure 61:
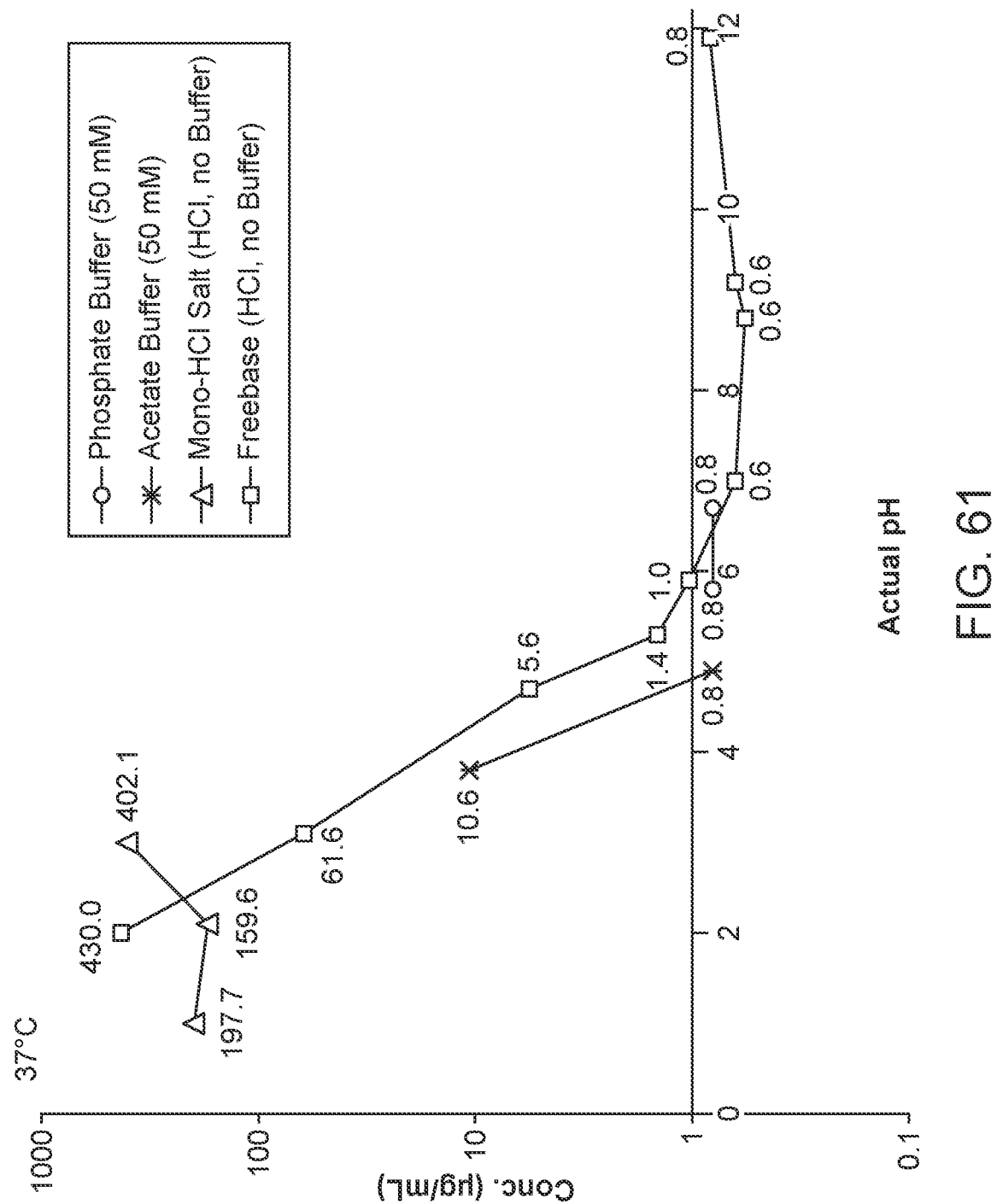
FIG. 61 is a thermodynamic pH-solubility profile of Compound I HCl Form I in various buffer or non-buffer solutions.

A thermodynamic pH-solubility profile of Compound I HCl Form I in various buffer or non-buffer solutions is further provided in FIG. 61. FIG. 61 additionally includes the thermodynamic pH-solubility profile of Compound I free base. It is of note that no data is shown in the profile of Compound I free base below a pH of about 2.0, as Compound I free base converted to Compound I HCl Form I below a pH of about 2.0. Similarly, no data is shown in the profile of Compound I HCl Form I above a pH of about 3.0, as Compound I HCl Form I converted to Compound I free base above a pH of about 3.0. The thermodynamic solubility of the Compound I free base and Compound I HCl Form I systems was determined after 7 days of shaking the respective system at about 37° C. water bath.

Compound I HCl Form I additionally exhibits desirable stability. For instance, Compound I HCl Form I in powder form did not exhibit any form change after about 6 months at about 40° C./75% RH under open dish conditions as determined by XRPD, TGA and DSC.

Figure 62:
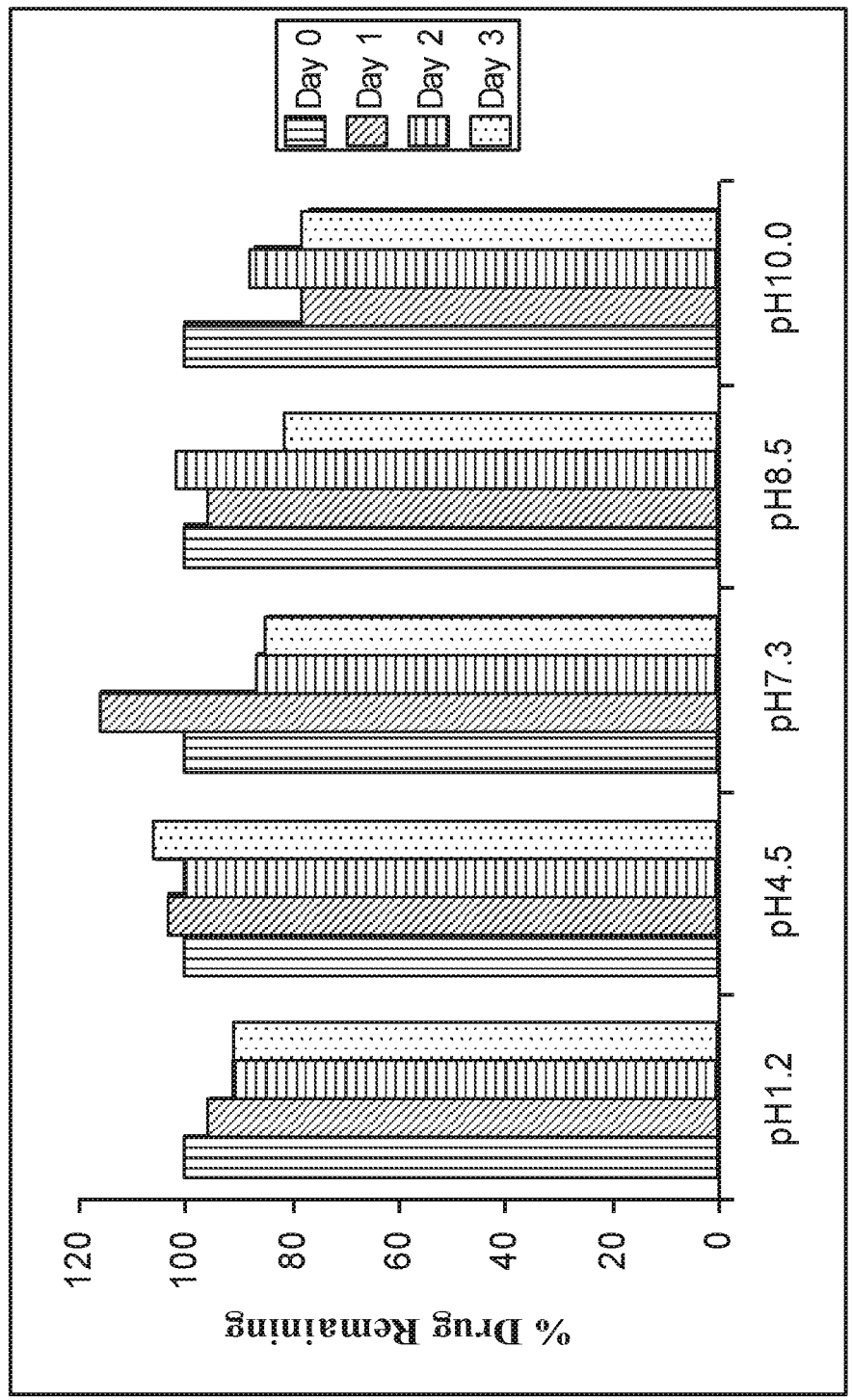
FIG. 62 is a plot showing the solution stability of Compound I HCl Form I in various buffer solutions over a pH range of about 1.2 to about 10.0.

The stability of Compound I HCl Form I in buffer solutions over a pH range of about 1.2 to about 10.0 was also evaluated. These solutions were stored at about 60° C., and assayed for pH and % remaining at 2 days. Data indicated that Compound I HCl Form I was most stable at a pH of about 4.5 (FIG. 62).

Compound I HCl Form I also exhibited polymorphic stability at elevated temperatures. Dry-heating Compound I HCl Form I at about 50° C. for about 72 hours did not change the crystalline form of Compound I HCl Form I as determined by XRPD, DSC and proton NMR. Heating Compound I HCl Form I up to about 120° C. inside TGA until approximately 3% weight loss showed a slight loss of crystallinity, but without a new form appearing. After re-hydrating this post-TGA material (3 days at about 60% RH), DSC showed no gross effect upon the polymorphism, but amorphous content did appear (Tg at about 250° C.).

11. Salt Screening

Additional salt screening for solid forms was conducted by combining Compound I with various acids. The procedure used was as follows: About 20 mg of Compound I free base Form I was weighed into a 2-mL glass vial. A corresponding amount of acid, with the molar ratio of 1:1 acid:Compound I, was added. 0.5 mL of the corresponding solvent was added into the glass vial. The mixture was stirred at RT (25±3° C.) for 3 days. The solid was isolated via centrifugation, and the solid was dried at RT overnight. XRPD analysis was conducted on dried solids. Where provided, the molar ratio of acid:free base was determined by integration of NMR peaks. A summary of the screening experiments is presented in Table 11. Summary of characterization of the salt forms is presented in Table 12.

TABLE 11

| Acid | Mw | pKa | Safety Class | Acetone A | THF/H2O (19:1, v/v) B | EtOAc C |
|---|---|---|---|---|---|---|
| blank | | | | Freebase Form II | Freebase Form II | Freebase Form II |
| $H_2SO_4$ | 98.08 | −3.00 | 1 | Sulfate Type A | Sulfate Type B | Sulfate Type C |
| $H_3PO_4$ | 98.00 | 1.96 | 1 | Phosphate Type A | Phosphate Type A | Phosphate Type A |
| Maleic acid | 116.08 | 1.92 | 1 | Maleate Type A | Maleate Type B | Maleate Type A |
| L-tartaric acid | 150.09 | 3.02 | 1 | L-tartrate Type A | L-tartrate Type A | L-tartrate Type A |
| Fumaric acid | 116.08 | 3.03 | 1 | Fumarate Type A | Fumarate Type A | Fumarate Type A |
| Citric acid | 192.13 | 3.13 | 1 | Citrate Type A | Citrate Type B | Citrate Type C |
| Glycolic acid | 76.05 | 3.28 | 1 | Glycollate Type A | Glycollate Type A | Glycollate Type A |
| L-malic acid | 134.09 | 3.46 | 1 | Malate Type A | Malate Type B | Malate Type A |
| Hippuric acid | 179.17 | 3.55 | 1 | Freebase Form II | Freebase Form II | Freebase Form II |
| Gluconic acid | 196.16 | 3.76 | 1 | Freebase Form II | Freebase Form II | Gluconate Type A |
| Succinic acid | 118.09 | 4.21 | 1 | Succinate Type A | Freebase Form II | Succinate Type A |
| Adipic acid | 146.14 | 4.44 | 1 | Adipate Type A | Freebase Form II | Adipate Type B |
| 1,2-Ethanedisulfonic acid | 190.20 | −2.10 | 2 | Edisylate Type A | Edisylate Type B | Edisylate Type C |
| p-Toluenesulfonic acid | 190.22 | −1.34 | 2 | Tosylate Type A | Tosylate Type B | Tosylate Type B |
| Methanesulfonic acid | 96.10 | −1.20 | 2 | Mesylate Type A | Mesylate Type B | Mesylate Type B |
| Oxalic acid | 126.04 | 1.27 | 2 | Oxalate Type A | Oxalate Type A | Oxalate Type A |
| Ethanesulfonic acid | 110.13 | 2.05 | 2 | Esylate Type A | Esylate Type A | Esylate Type A |
| Malonic acid | 104.06 | 2.83 | 2 | Malonate Type A | Malonate Type A | Malonate Type A + freebase Form II |
| Gentisic acid | 154.12 | 2.93 | 2 | Gentisate Type A | Freebase Form II | Gentisate Type A |
| Benzoic acid | 122.12 | 4.19 | 2 | Freebase Form II | Freebase Form II | Freebase Form II + extra peaks |

TABLE 12

| Crystal Form | Acid Safety Class | Weight Loss (%) | Endotherm (onset, °C) | Molar Ratio (acid:free base) | Residual Solvent |
|---|---|---|---|---|---|
| Sulfate Type A | I | 2.8 | 244.8 | 1.0 | 0.9% acetone |
| Glycollate Type A | I | 2.0 | 245.6 | 1.0 | 0.9% acetone |
| Adipate Type B | I | 1.2 | 212.8 | 1.0 | 0.3% EtOAc |
| Oxalate Type A | II | 2.0 | 269.4 | ND | ND |
| Esylate Type A | II | 1.1 | 262.9 | 1.0 | 0.2% acetone |
| Phosphate Type A | I | 0.1 | 233.4, 287.9 | 1.0 | ND |
| Maleate Type B | I | 4.2 | 84.4*, 100.8*, 172.7, 213.8, 249.9* | 1.0 | ND |
| L-tartrate Type A | I | 6.9 | 203.0*, 249.6 | 0.6 | 0.7% THF |
| Fumarate Type A | I | 0.7 | 132.1, 196.7, 263.9 | 0.9 | 0.5% THF |
| Citrate Type B | I | 6.9 | 78.8*, 159.3, 191.4, 242.2 | 0.7 | 4.5% THF |
| L-malate Type B | I | 8.5 | 94.7*, 170.6*, 174.9*, 226.3, 247.3* | 0.7 | 0.7% THF |
| Gluconate Type A | I | 8.8 | 69.7, 99.5, 136.9 | 1.0 | 0.2% EtOAc |
| Succinate Type A | I | 4.0 | 184.3, 236.7 | 0.6 | 0.3% EtOAc |
| Tosylate Type A | II | 2.6 | 220.4, 256.6 | 0.8 | ND |
| Mesylate Type A# | II | 0.4 | 243.1, 259.4* | 1.0 | 0.1% acetone |
| Malonate Type A | II | 4.1 | 193.6, 255.1 | 1.0 | 0.5% acetone |
| Gentisate Type A | II | 1.7 | 228.7, 241.7 | 1.0 | 0.6% acetone |

*Peak temperature

12. Follow-Up Salt Screening

Additional Compound I solid forms were investigated by combining Compound I with various acids as indicated below.

Edisylate: Compound I free base Form II was slurried with ethane-1,2-disulfonic acid with molar ratio of 1:1 in THF at RT.

Besylate Type A: Compound I free base Form II was slurried with benzenesulfonic acid with molar ratio of 1:1 in EtOH/water (19:1, v/v) at RT. Besylate Type B: Compound I free base Form II was slurried with benzenesulfonic acid with molar ratio of 1:1 in THF at RT.

Tosylate Type C: Compound I free base Form II was slurried with p-toluenesulfonic acid with molar ratio of 1:1 in EtOH/water (19:1, v/v) at RT. Tosylate Type D: Compound I free base Form II was slurried with p-toluenesulfonic acid with molar ratio of 1:1 in ACN at RT.

Isethionate Type A: Compound I free base Form II was slurried with 2-hydroxyethanesulphonic acid with molar ratio of 1:1 in EtOH/water (19:1, v/v) at RT.

Naphthalene disulfonate Type A: Compound I free base Form II was slurried with naphthalene-1,5-disulfonic acid with molar ratio of 1:1 in EtOH/water (19:1, v/v) at RT.

Naphthalenesulfonate Type A: Compound I free base Form II was slurried with naphthalene-2-sulfonic acid with molar ratio of 1:1 in EtOH/water (19:1, v/v) at RT. Naphthalenesulfonate Type B: Compound I free base Form II was slurried with naphthalene-2-sulfonic acid with molar ratio of 1:1 in IPAc at RT. Naphthalenesulfonate Type C: Compound I free base Form II was slurried with naphthalene-2-sulfonic acid with molar ratio of 1:1 in ACN at RT.

Chlorobenzenesulfate Type A: Compound I free base Form II was slurried with 4-chlorobenzenesulfonic acid with molar ratio of 1:1 in IPAc at RT. Chlorobenzenesulfate Type B: Compound I free base Form II was slurried with 4-chlorobenzenesulfonic acid with molar ratio of 1:1 in THF at RT.

Camphorsulfonate Type A: Compound I free base Form II was slurried with camphorsulfonic acid with molar ratio of 1:1 in EtOH/water (19:1, v/v) at RT. Camphorsulfonate Type B: Compound I free base Form II was slurried with camphorsulfonic acid with molar ratio of 1:1 in IPAc at RT. Camphorsulfonate Type C: Compound I free base Form II was slurried with camphorsulfonic acid with molar ratio of 1:1 in ACN at RT.

HCl Type B: 2559.0 mg of Compound I HCl salt Form I was suspended in 50 mL MeOH and slurried at 50° C. for 2 days. The solid was isolated via filtration and washed with MeOH (2×10 mL). The solid was dried at RT under vacuum overnight to provide 2253.3 mg of material.

A summary of results of the salt form screening is presented in Table 13.

TABLE 13

| Crystal Form | Weight Loss (%) | Endotherm (onset, °C.) | Molar Ratio (acid:freebase) |
|---|---|---|---|
| Edisylate Type C | 7.3 | 119.5*, 134.9* | 0.6 |
| Edisylate Type D | 5.2 | 107.3*, 246.9* | 0.6 |
| Besylate Type A | 3.3 | 94.0, 167.3, 221.5, 246.9 | 0.8 |

TABLE 13-continued

| Crystal Form | Weight Loss (%) | Endotherm (onset, ° C.) | Molar Ratio (acid:freebase) |
|---|---|---|---|
| Besylate Type B | 3.2 | 158.8, 257.9 | 0.8 |
| Tosylate Type B | 6.9 | 218.2*, 254.2, 182.1# | 1.0 |
| Tosylate Type C | 4.6 | 181.5*, 259.0, 187.5# | 1.0 |
| Tosylate Type D | 3.9 | 210.7, 225.8*, 251.2*, 229.1# | 0.7 |
| Esylate Type A | 1.0 | 251.3*, 257.5 | 1.0 |
| Isethionate Type A | 1.0 | 250.1 | 1.0 |
| Naphthalene disulfonate Type A | 3.6 | 197.6* | 0.9 |
| Naphthalenesulfonate Type A | 3.5 | 91.1*, 188.9*, 250.8* 195.1# | 1.0 |
| Naphthalenesulfonate Type B | 6.8 | 207.6, 242.1 | 1.0 |
| Naphthalenesulfonate Type C | 1.6 | 108.4*, 212.6, 243.7* | 0.9 |
| Chlorobenzenesulfate Type A | 4.4 | 83.4*, 139.9, 185.2# | 1.1 |
| Chlorobenzenesulfate Type B | 6.3 | 82.9*, 213.8*, 262.1, 219.7# | 1.0 |
| Camphorsulfonate Type A | 2.3 | 68.3*, 199.3, 256.7*, 263.1* | 0.9 |
| Camphorsulfonate Type B | 7.0 | 160.0, 256.3, 172.2# | 1.0 |
| Camphorsulfonate Type C | 2.4 | 60.5*, 256.1, 194.4# | 1.0 |
| HCl Type B | 0.5 | 285.9 | ND |

*Peak temperature
Exotherm

13. Free Base Solid Form Screening

Based on DSC results, VT-XRPD was conducted to further characterize Compound I free base Form I. Form change was observed after heating free base Form I to 150° C. The new form was assigned as free base Type C and converted to free base Form I after cooling to 30° C., which was consistent with the reversible endothermic signal at 135° C. observed in DSC cycle result.

Based on DSC results, VT-XRPD was conducted to further characterize Compound I free base Form II. A new form assigned as free base Type D was observed after heating free base Form II to 250° C., and it converted to another new form (assigned as Type E) during cooling to 30° C. with color change from white to yellow.

A summary of results of the free base form screening is presented in Table 14.

TABLE 14

| Crystal Form | Weight Loss (%) | Endotherm (onset, ° C.) | Speculated Form |
|---|---|---|---|
| Form I | 1.2 | 136.3, 232.0, 257.5 | anhydrate |
| Form II | 2.2 | 240.1, 255.1 | anhydrate |
| Type C | NA | NA | anhydrate |
| Type D | NA | NA | anhydrate |
| Type E | 0.8 | 126.4, 257.3 | anhydrate |
| Type F | 9.2 | 91.5*, 231.3* | unidentified |

Slurry competition was performed to evaluate the stability of Compound I free base Form II and Type E. A mixture of Compound I free base Form II and Type E were added into 1.0 mL of saturated EtOH or MEK solution (slurry of Form I at 5° C./RT/50° C. overnight). The suspensions were stirred at target temperatures. Only Compound I free base Form II was observed after the suspensions were stirred at 5° C., RT, and 50° C., indicating free base Form II is more thermodynamically stable than Type E from 5° C. to 50° C. The results are presented in Table 15.

TABLE 15

| Starting Form | Solvent | Temperature (° C.) | Solid Form |
|---|---|---|---|
| Free base Form II and Type E | EtOH | 5 | Free base Form II |
| | | RT | |
| | | 50 | |
| Free base Form II and Type E | MEK | 5 | Free base Form II |
| | | RT | |
| | | 50 | |

Slurry competition was performed to evaluate the stability of free base Form I and Form II. A mixture of free base Form I and Form II were added into 1.0 mL of saturated EtOH or MEK solution (slurry of Form I at 5° C./RT/50° C. overnight). The suspensions were stirred at target temperatures for 3 days. Only free base Form II was observed after the suspensions were stirred at 5° C., RT, and 50° C., indicating free base Form II is more thermodynamically stable from 5° C. to 50° C. The results are presented in Table 16.

TABLE 16

| Starting Form | Solvent | Temperature (° C.) | Solid Form |
|---|---|---|---|
| Free base Form I and Form II | EtOH | 5 | Free base Form II |
| | | RT | |
| | | 50 | |
| Free base Form I and Form II | MEK | 5 | Free base Form II |
| | | RT | |
| | | 50 | |

Compound I free base Type E was prepared at 100-mg scale by heating Compound I free base Form II to 250° C. for 15 min. Compound I free base Type E TGA showed a weight loss of 0.8% up to 150° C.; while the DSC analysis showed two endothermic peaks at 126.4 and 257.3° C. (onset temperatures).

Compound I free base Form I was subjected to additional screening as indicated below in Table 17.

TABLE 17

| Method | Solid Form (FB = free base) |
|---|---|
| Anti-solvent addition | FB Form I, Form II, amorphous, limited solid |
| Slow evaporation | FB Form I, Form II |
| Slow cooling | FB Form II |
| Slurry at RT | FB Form II |
| Slurry at 50° C. | FB Form I, Form II |
| Solid vapor diffusion | FB Form I, Form II |
| Liquid vapor diffusion | FB Form II, limited solid |
| Humidity induced crystallization | FB Form I |
| Temperature cycling | FB Form I, Form II, amorphous |
| Total | FB Form I, Form II, amorphous, limited solid |

Compound I free base Form I anti-solvent addition experiments were conducted as indicated below in Table 18.

TABLE 18

| Solvent | Anti-solvent | Solid Form |
| --- | --- | --- |
| NMP | $H_2O$ | FB Form I + Form II |
|  | EtOAc | Limited solid |
|  | EtOH | FB Form II |
|  | 2-MeTHF | FB Form II |
| DMF | MeOH | FB Form II |
|  | Toluene | FB Form II |
|  | $H_2O$ | FB Form I |
|  | Acetone | FB Form II |
| DMAc | MEK | Limited solid |
|  | EtOH | FB Form I |
|  | IPAc | FB Form I |
|  | $H_2O$ | FB Form II |
| DMSO | $H_2O$ | Amorphous |
|  | MIBK | Amorphous |
|  | EtOH | FB Form II |
|  | EtOAc | FB Form II |
| THF/$H_2O$, 9:1 | EtOH | FB Form II |
|  | EtOAc | FB Form II |
|  | Acetone | FB Form II |

Compound I free base Form I slow evaporation experiments were conducted as indicated below in Table 19.

TABLE 19

| Solvent, v/v | Solid Form |
| --- | --- |
| THF/$H_2O$, 9:1 | FB Form I |
| MeOH/DCM, 1:1 | FB Form II |
| 1,4-Dioxane/$H_2O$, 9:1 | FB Form II |

Compound I free base Form I slow cooling experiments (50° C. to 5° C.) were conducted as indicated below in Table 20.

TABLE 20

| Solvent, v/v | Solid Form |
| --- | --- |
| THF/$H_2O$, 4:1 | FB Form II |
| 1,4-dioxane/$H_2O$, | FB Form II |
| acetone/$H_2O$, 4:1 | FB Form II |
| MeOH/DCM, 1:1 | FB Form II |
| EtOH/DMSO, 1:2 | FB Form II |
| NMP/$H_2O$, 3:1 | FB Form II |
| EtOAc/DMAc, 1:2 | FB Form II |

Compound I free base Form I slurry experiments at room temperature were conducted as indicated below in Table 21.

TABLE 21

| Solvent | Solid Form |
| --- | --- |
| MeOH | FB Form II |
| EtOH | FB Form II |
| ACN | FB Form II |
| acetone | FB Form II |
| MIBK | FB Form II |
| EtOAc | FB Form II |
| anisole | FB Form II |
| CPME | FB Form II |
| 1,4-dioxane | FB Form II |
| 2-MeTHF | FB Form II |
| DCM | FB Form II |
| $H_2O$ | FB Form II |
| toluene | FB Form II |
| THF | FB Form II |

TABLE 21-continued

| Solvent | Solid Form |
| --- | --- |
| THF/$H_2O$, aw 0.2, 98:2 | FB Form II |
| THF/$H_2O$, aw 0.4, 96:4 | FB Form II |
| THF/$H_2O$, aw 0.6, 93:7 | FB Form II |
| THF/$H_2O$, aw 0.8, 87:13 | FB Form II |
| MeOH/DCM, 1:1 | FB Form II |
| MEK/DMSO, 3:1 | FB Form II |

Compound I free base Form I slurry experiments at 50° C. were conducted as indicated below in Table 22.

TABLE 22

| Solvent, v/v | Solid Form |
| --- | --- |
| MeOH | FB Form II |
| IPA | FB Form II |
| ACN | FB Form II |
| MEK | FB Form II |
| IPAc | FB Form II |
| 2-MeTHF | FB Form II |
| 1,4-dioxane | FB Form II |
| $CHCl_3$ | FB Form II |
| Toluene | FB Form II |
| $H_2O$ | FB Form I + Form II |
| DMSO/EtOH, 1:2 | FB Form II |
| DMAc/IPAc, 1:2 | FB Form II |
| DMF/MEK, 1:2 | FB Form II |
| NMP/$H_2O$, 1:1 | FB Form II |
| Acetone | FB Form II |
| acetone/$H_2O$, aw 0.2 | FB Form II |
| acetone/$H_2O$, aw 0.4 | FB Form II |
| acetone/$H_2O$, aw 0.6 | FB Form II |
| acetone/$H_2O$, aw 0.8 | FB Form II |

Compound I free base Form I solid vapor diffusion experiments were conducted as indicated below in Table 23.

TABLE 23

| Solvent | Solid Form |
| --- | --- |
| DCM | FB Form I + Form II |
| MEK | FB Form I |
| MeOH | FB Form II |
| EtOH | FB Form I + Form II |
| ACN | FB Form I + Form II |
| THF | FB Form I + Form II |
| Acetone | FB Form II |
| EtOAc | FB Form I + Form II |
| IPA | FB Form I |

Compound I free base Form I solution vapor diffusion experiments were conducted as indicated below in Table 24.

TABLE 24

| Solvent | Anti-solvent | Solid Form |
| --- | --- | --- |
| NMP | acetone | On-going |
|  | $H_2O$ | FB Form II |
| DMSO | EtOH | Limited solid |
|  | IPAc | Limited solid |
| DMAc | ACN | Limited solid |
| THF/$H_2O$, 4:1 | MeOH | FB Form II |
|  | MEK | FB Form II |
| MeOH/DCM, 1:1 | $H_2O$ | FB Form II |
|  | EtOH | FB Form II |

Compound I free base Form I humidity induced crystallization experiments were conducted as indicated below in Table 25.

TABLE 25

| RH % at RT | Solid Form |
|---|---|
| ~43 (K$_2$CO$_3$) | FB Form I |
| ~58 (NaBr) | FB Form I |
| ~84 (KCl) | FB Form I |
| 100 (H$_2$O) | FB Form I |

Compound I free base Form I temperature cycling (50° C. to 5° C.) experiments were conducted as indicated below in Table 26.

TABLE 26

| Solvent, v/v | Solid Form |
|---|---|
| DCM/MeOH, 1:1 | FB Form II |
| Acetone/H$_2$O, 9:1 | FB Form II |
| EtOAc/THF, 9:1 | FB Form II |
| NMP/IPA, 1:2 | FB Form II |
| DMSO/MeOH, 1:2 | FB Form II |
| DMAc/EtOAc, 1:2 | FB Form II |
| NMP/MEK, 1:2 | FB Form II |
| DMF/toluene, 1:2 | FB Form II |
| DMSO/IPAc, 1:2 | Amorphous |
| DMAc/acetone, 1:2 | FB Form I + Form II |

14. Stability Testing

Storage under vacuum at 40° C. and at 60° C.: Compound I HCl Form I was stored under vacuum at 40° C. and at 60° C. Initial HPLC purity was 99.3%. No form change or decrease in purity by HPLC was observed after 4 days in either experiment.

Storage at 25° C./60% RH and at 40° C./75% RH: Compound I HCl Form I was stored at 25° C./60% RH and at 40° C./75% RH. Initial HPLC purity was 99.3%. No form change or decrease in purity by HPLC was observed after 2 weeks in either experiment.

Low Humidity testing: Compound I HCl salt Form I was placed under N$_2$ and checked by in situ XRPD at 20 min and 60 minutes. A new form was observed under N$_2$ bleeding for 20 min (relative humidity was measured as 10.2% RH). The new form converted back to HCl salt Form I quickly after being exposed to ambient conditions. HCl salt Form I was placed under N$_2$ bleeding for ~60 min and TGA and DSC were measured. The TGA result showed a weight loss of 1.6% up to 150° C.; the DSC result showed two endothermic peaks at 244.4 (onset temperature) and 265.5° C. (peak temperature).

Further solubility testing of Compound I HCl Form I gave results as indicated in Table 27.

TABLE 27

| Solvent | Solubility (mg/mL) | Solvent (v/v) | Solubility (mg/mL) |
|---|---|---|---|
| DMSO | S > 36.0 | CPME | S < 2.0 |
| NMP | 4.0 < S < 6.7 | ACN | S < 2.2 |
| MeOH | 1.9 < S < 6.3 | n-heptane | S < 1.9 |
| EtOH | S < 2.2 | Toluene | S < 2.1 |
| IPA | S < 1.9 | DCM | S < 2.1 |
| Acetone | S < 2.2 | 1,4-dioxane | S < 2.1 |
| CHCl$_3$ | S < 2.3 | MTBE | S < 2.0 |
| MIBK | S < 2.3 | MeOH/H$_2$O, 4:1 | S < 2.0 |
| EtOAc | S < 2.0 | EtOH/H$_2$O, 4:1 | S < 2.0 |
| IPAc | S < 2.3 | Acetone/H$_2$O, 4:1 | S < 1.9 |
| Anisole | S < 2.3 | THF/H$_2$O, 4:1 | 2.0 < S < 2.5 |
| THF | S < 1.9 | ACN/H$_2$O, 4:1 | 2.9 < S < 3.8 |
| 2-MeTHF | S < 2.1 | MeOH/DCM, 1:1 | 6.8 < S < 12.5 |

15. Additional Salt Screening

Certain salt forms were prepared and analyzed as indicated below. A summary of the results is presented in Table 28.

TABLE 28

| Crystal Form (Sample ID) | Weight Loss (%) | Endotherm (onset, ° C.) | Molar Ratio (acid: freebase) | Residual Solvent |
|---|---|---|---|---|
| Esylate Form I | 1.4 | 209.3, 255.4 | 1.0 | Not detected |
| Isethionate Type A | 1.8 | 249.6 | 1.0 | Not detected |
| Naphthalene disulfonate Type A | 3.8 | 191.8* | 1.0 | 0.9% wt EtOH |
| Mesylate Type A | 2.4 | 273.4 | 0.9 | 0.1% wt acetone |
| HCl salt Form I | 4.0 | 66.9, 281.3 | 1.0 | NA |

*Peak temperature

Compound I esylate Type A was prepared from ethanol/water (19:1 v/v) at 300 mg scale by the following procedure: 299.5 mg of Compound I free base Form II and 84.3 mg of ethanesulfonic acid were weighed into 20-mL glass vial. 7 mL of EtOH/water (19:1, v/v) was added to form a suspension. The mixture was stirred at RT for 3 days, the solid was isolated via centrifugation and dried at RT under vacuum overnight. The XRPD pattern of dried solid showed that a small amount of free base remained. The solid was suspended in 5 mL EtOH and about 10 mg acid was added. The mixture was stirred at RT for 1.5 hrs. No peaks from free base were observed in the XRPD pattern of wet material. The solid was isolated via centrifugation and dried at RT under vacuum for 3 hrs. 323.7 mg of white powder was collected.

Compound I isethionate Type A was prepared from ethanol/water (19:1 v/v) at 300 mg scale by the following procedure: 301.5 mg of Compound I free base Form II and 84.9 mg of 2-hydroxyethanesulfonic acid (80%) were weighed into 20-mL glass vial. 5 mL of EtOH/water (19:1, v/v) was added to form a suspension. The mixture was stirred at RT for 3 days, the solid was isolated via centrifugation and dried at RT under vacuum overnight. The XRPD pattern of dried solid showed that a small amount of free base remained. The solid was suspended in 5 mL EtOH and about 10 mg acid was added. The mixture was stirred at RT for 1.5 hrs. No peaks from free base were observed in the XRPD pattern of wet material. The solid was isolated via centrifugation and dried at RT under vacuum for 3 hrs. 337.1 mg of white powder was collected.

Compound I naphthalene disulfonate Type A was prepared from ethanol/water (19:1 v/v) at 300 mg scale by the following procedure: 299.7 mg of Compound I free base Form II and 226.8 mg of naphthalene-1,5-disulfonic acid were weighed into 20-mL glass vial. 5 mL of EtOH/water (19:1, v/v) was added to form a suspension. The mixture was stirred at RT for 3 days, the solid was isolated via centrifugation and dried at RT under vacuum overnight. The XRPD pattern of dried solid showed that a small amount of free base remained About 20 mg acid was added, and the mixture was stirred at RT for 1 hr. No peaks from free base were observed in the XRPD pattern of wet material. The solid was isolated via centrifugation and dried at RT under vacuum for 3 hrs. 475.9 mg of pink powder was collected.

Compound I mesylate Type A was prepared from acetone at 500 mg scale by the following procedure: 500.4 mg of Compound I free base Form II and 114.3 mg of methanesulfonic acid were weighed into 20-mL glass vial. 9 mL of acetone was added to form a suspension. The mixture was stirred at RT for 3 days, and the XRPD pattern of wet material confirmed conversion. The solid was isolated via centrifugation and dried at RT under vacuum overnight. 563.9 mg of white powder was collected.

16. Kinetic Solubility Testing

Kinetic solubility testing was conducted as follows: About 40-55 mg material was weighed into a 5-mL EP pipe. 4 mL of water/bio-relevant media (SGF, FaSSIF, or FeSSIF) was added into the corresponding sample pipe (drug loading: ~10 mg/mL calculated as freebase). The pipes were capped tightly and the material was verified to be in contact with the media. The sample vials were placed on a roller and start rolling at 37° C. (rate: 25 r/min). Samples were taken at 1, 2, 4, 24 h. For each time point, 1.0 mL of suspension was transferred into a 2-mL centrifuge tube and the samples were centrifuged. The supernatant was filtered via 0.45 μm PTFE membrane and solubility and pH were measured. An XRPD test on residual solids was conducted.

A summary of kinetic solubility results in water is presented in Table 29.

TABLE 29

| Crystal Form | Solubility (mg/mL) | | | | pH* | | | | Final Form | | | |
|---|---|---|---|---|---|---|---|---|---|---|---|---|
| (Sample ID) | 1 h | 2 h | 4 h | 24 h | 1 h | 2 h | 4 h | 24 h | 1 h | 2 h | 4 h | 24 h |
| Esylate Type A | 1.7 | 1.5 | 1.4 | 1.3 | 2.3 | 2.0 | 2.2 | 2.1 | Freebase Form II | | | |
| Isethionate Type A | 1.5 | 1.3 | 1.3 | 1.2 | 2.1 | 2.0 | 2.1 | 2.1 | Freebase Form II | | | |
| Naphthalene disulfonate Type A | 0.0014 | 0.0025 | 0.0015 | 0.0016 | 2.8 | 2.6 | 2.5 | 2.4 | Naphthalene disulfonate Type A and one extra peak | | | |
| Mesylate Type A | 1.4 | 1.3 | 1.3 | 1.3 | 1.9 | 1.9 | 2.2 | 2.0 | Freebase Form II | | | |
| HCl salt Form I | 0.22 | 0.25 | 0.18 | 0.18 | 3.1 | 2.9 | 3.0 | 2.9 | HCl salt Form I and Freebase Form II | | | |

*native pH of water was 7.6

A summary of kinetic solubility results in SGF is presented in Table 30.

TABLE 30

| Crystal Form | Solubility (mg/mL) | | | | pH* | | | | Final Form | | | |
|---|---|---|---|---|---|---|---|---|---|---|---|---|
| (Sample ID) | 1 h | 2 h | 4 h | 24 h | 1 h | 2 h | 4 h | 24 h | 1 h | 2 h | 4 h | 24 h |
| Esylate Type A | 0.092 | 0.10 | 0.087 | 0.083 | 2.1 | 1.9 | 2.1 | 1.9 | HCl salt Form I | | | |
| Isethionate Type A | 0.077 | 0.081 | 0.073 | 0.069 | 1.9 | 1.9 | 2.1 | 2.0 | HCl salt Form I and one extra peak | | | |
| Naphthalene disulfonate Type A | 0.019 | 0.016 | 0.018 | 0.016 | 2.0 | 1.9 | 2.0 | 1.8 | Naphthalene disulfonate Type A | | | |
| Mesylate Type A | 0.081 | 0.096 | 0.080 | 0.076 | 1.9 | 2.0 | 2.0 | 1.9 | HCl salt Form I and one extra peak | | | |
| HCl salt Form I | 0.041 | 0.039 | 0.036 | 0.035 | 1.9 | 1.9 | 2.0 | 2.0 | HCl salt Form I | | | |

*native pH of SGF was 1.8

A summary of kinetic solubility results in FaSSIF is presented in Table 31.

TABLE 31

| Crystal Form | Solubility (mg/mL) | | | | pH* | | | | Final Form | | | |
|---|---|---|---|---|---|---|---|---|---|---|---|---|
| (Sample ID) | 1 h | 2 h | 4 h | 24 h | 1 h | 2 h | 4 h | 24 h | 1 h | 2 h | 4 h | 24 h |
| Esylate Type A | 0.015 | 0.012 | 0.024 | 0.0040 | 5.2 | 5.0 | 4.3 | 3.8 | Freebase Form II | | | |
| Isethionate Type A | 0.020 | 0.026 | 0.018 | 0.015 | 3.9 | 3.9 | 3.9 | 3.9 | Freebase Form II and isethionate Type A | | | |
| Naphthalene disulfonate Type A | 0.0035 | 0.0037 | 0.0030 | 0.0027 | 2.8 | 2.7 | 2.6 | 2.5 | New form X | | | |
| Mesylate Type A | 0.062 | 0.055 | 0.039 | 0.020 | 4.1 | 3.7 | 3.6 | 4.0 | Freebase Form II and one extra peak | | | |

TABLE 31-continued

| Crystal Form | Solubility (mg/mL) | | | | pH* | | | | Final Form | | | |
|---|---|---|---|---|---|---|---|---|---|---|---|---|
| (Sample ID) | 1 h | 2 h | 4 h | 24 h | 1 h | 2 h | 4 h | 24 h | 1 h | 2 h | 4 h | 24 h |
| HCl salt Form I | 0.012 | 0.013 | 0.013 | 0.011 | 5.4 | 5.1 | 5.2 | 4.6 | HCl salt Form I and Freebase Form II | | | |

*native pH of FaSSIF was 6.5

A summary of kinetic solubility results in FeSSIF is presented in Table 32.

TABLE 32

| Crystal Form | Solubility (mg/mL) | | | | pH* | | | | Final Form | | | |
|---|---|---|---|---|---|---|---|---|---|---|---|---|
| (Sample ID) | 1 h | 2 h | 4 h | 24 h | 1 h | 2 h | 4 h | 24 h | 1 h | 2 h | 4 h | 24 h |
| Esylate Type A | 0.060 | 0.027 | 0.014 | 0.011 | 4.8 | 4.7 | 4.7 | 4.4 | New form | Freebase Form II | | |
| Isethionate Type A | 0.0058 | 0.0053 | 0.0052 | 0.0054 | 4.6 | 4.7 | 4.7 | 4.6 | Freebase Form II | | | |
| Naphthalene disulfonate Type A | 0.0088 | 0.0079 | 0.0069 | 0.0059 | 4.6 | 4.6 | 4.6 | 4.6 | New form X | | | |
| Mesylate Type A | 0.023 | 0.020 | 0.0084 | 0.0083 | 4.7 | 4.5 | 4.6 | 4.6 | Freebase Form II | | | |
| HCl salt Form I | 0.049 | 0.031 | 0.010 | 0.0072 | 4.9 | 4.7 | 4.7 | 4.5 | HCl salt Form I | Freebase Form II | | |

The results presented in Table 32 indicate that Compound I HCl Form I has favorable kinetic solubility in FeSSIF.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

What is claimed is:

1. A crystalline salt of Compound I:

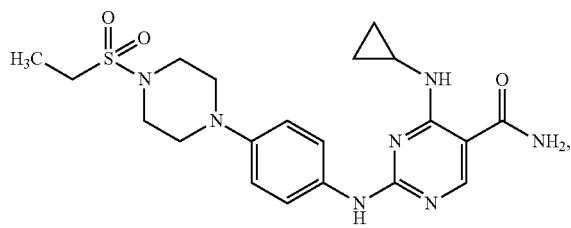

I (a) wherein the salt is esylate, characterized by an X-ray powder diffractogram comprising peaks at 7.5, 18.1, and 14.9 °2θ, each ±0.2 °2θ, as determined on a diffractometer using Cu-Kα radiation (Compound I esylate Type A);

(b) wherein the salt is mesylate, characterized by an X-ray powder diffractogram comprising peaks at 16.0, 16.4, and 16.7 °2θ, each ±0.2 °2θ, as determined on a diffractometer using Cu-Kα radiation (Compound I mesylate Type A);

(c) wherein the salt is isethionate, characterized by an X-ray powder diffractogram comprising peaks at 15.8, 17.9, and 20.1 °2θ, each ±0.2 °2θ, as determined on a diffractometer using Cu-Kα radiation (Compound I isethionate Type A);

(d) wherein the salt is naphthalenesulfonate, characterized by an X-ray powder diffractogram comprising peaks at 14.4, 20.2, and 7.5 °2θ, each ±0.2 °2θ, as determined on a diffractometer using Cu-Kα radiation (Compound I naphthalenesulfonate Type A);

(e) wherein the salt is naphthalenesulfonate, characterized by an X-ray powder diffractogram comprising peaks at 9.0, 15.6, and 19.7 °2θ, each ±0.2 °2θ, as determined on a diffractometer using Cu-Kα radiation (Compound I naphthalenesulfonate Type B);

(f) wherein the salt is naphthalenesulfonate, characterized by an X-ray powder diffractogram comprising peaks at 6.9, 13.6, and 13.3 °2θ, each ±0.2 °2θ, as determined on a diffractometer using Cu-Kα radiation (Compound I naphthalenesulfonate Type C)

(g) wherein the salt is besylate, characterized by an X-ray powder diffractogram comprising peaks at 7.4, 14.9, and 15.3 °2θ, each ±0.2 °2θ, as determined on a diffractometer using Cu-Kα radiation (Compound I besylate Type A);

(h) wherein the salt is besylate, characterized by an X-ray powder diffractogram comprising peaks at 6.0, 11.9, and 6.9 °2θ, each ±0.2 °2θ, as determined on a diffractometer using Cu-Kα radiation (Compound I besylate Type B)

(i) wherein the salt is edisylate, characterized by an X-ray powder diffractogram comprising peaks at 14.7, 24.5, and 19.1 °2θ, each ±0.2 °2θ, as determined on a diffractometer using Cu-Kα radiation (Compound I edisylate Type D);
(j) wherein the salt is camphorsulfonate, characterized by an X-ray powder diffractogram comprising peaks at 5.9, 14.3, and 17.8 °2θ, each ±0.2 °2θ, as determined on a diffractometer using Cu-Kα radiation (Compound I camphorsulfonate Type A);
(k) wherein the salt is camphorsulfonate, characterized by an X-ray powder diffractogram comprising peaks at 4.7, 14.0, and 17.2 °2θ, each ±0.2 °2θ, as determined on a diffractometer using Cu-Kα radiation (Compound I camphorsulfonate Type B);
(l) wherein the salt is camphorsulfonate, characterized by an X-ray powder diffractogram comprising peaks at 13.5, 16.8, and 9.5 °2θ, each ±0.2 °2θ, as determined on a diffractometer using Cu-Kα radiation (Compound I camphorsulfonate Type C);
(m) wherein the salt is chlorobenzenesulfate, characterized by an X-ray powder diffractogram comprising peaks at 8.8, 18.5, and 9.5 °2θ, each ±0.2 °2θ, as determined on a diffractometer using Cu-Kα radiation (Compound I chlorobenzenesulfate Type B);
(n) wherein the salt is tosylate, characterized by an X-ray powder diffractogram comprising peaks at 7.5, 15.0, and 8.9 °2θ, each ±0.2 °2θ, as determined on a diffractometer using Cu-Kα radiation (Compound I tosylate Type C); or
(o) wherein the salt is tosylate, characterized by an X-ray powder diffractogram comprising peaks at 9.2, 19.2, and 6.3 °2θ, each ±0.2 °2θ, as determined on a diffractometer using Cu-Kα radiation (Compound I tosylate Type D).

2. The salt of claim 1, wherein the Compound I esylate type A is further characterized by one or more peaks at 15.9, 16.2, and 24.6 °2θ, each ±0.2 °2θ.

3. The salt of claim 1, wherein the Compound I mesylate type A is further characterized by one or more peaks at 24.2, 8.1, and 18.3 °2θ, each ±0.2 °2θ.

4. The salt of claim 1, wherein the Compound I isethionate Type A is further characterized by one or more peaks at 12.9, 24.5, and 9.9 °2θ, each ±0.2 °2θ.

5. The salt of claim 1, wherein the Compound I naphthalenesulfonate Type A is further characterized by one or more peaks at 13.4, 8.1, and 11.1 °2θ, each ±0.2 °2θ.

6. The salt of claim 1, wherein the Compound I naphthalenesulfonate Type B is further characterized by one or more peaks at 5.7, 13.4, and 25.1 °2θ, each ±0.2 °2θ.

7. The salt of claim 1, wherein the Compound I naphthalenesulfonate Type C is further characterized by one or more peaks at 20.3, 18.0, and 16.7 °2θ, each ±0.2 °2θ.

8. The salt of claim 1, wherein the Compound I besylate Type A is further characterized by one or more peaks at 22.3, 23.7, and 17.6 °2θ, each ±0.2 °2θ.

9. The salt of claim 1, wherein the Compound I besylate Type B is further characterized by one or more peaks at 20.6, 25.3, and 14.9 °2θ, each ±0.2 °2θ.

10. The salt of claim 1, wherein the Compound I edisylate Type D is further characterized by one or more peaks at 10.7, 22.8, and 20.7 °2θ, each ±0.2 °2θ.

11. The salt of claim 1, wherein the Compound I camphorsulfonate Type A is further characterized by one or more peaks at 11.4, 23.0, and 14.0 °2θ, each ±0.2 °2θ.

12. The salt of claim 1, wherein the Compound I camphorsulfonate Type B is further characterized by one or more peaks at 18.3, 19.5, and 15.9 °2θ, each ±0.2 °2θ.

13. The salt of claim 1, wherein the Compound I camphorsulfonate Type C is further characterized by one or more peaks at 19.3, 8.0, and 22.7 °2θ, each ±0.2 °2θ.

14. The salt of claim 1, wherein the Compound I chlorobenzenesulfate Type B is further characterized by one or more peaks at 17.7, 4.7, and 12.7 °2θ, each ±0.2 °2θ.

15. The salt of claim 1, wherein the Compound I tosylate Type C is further characterized by one or more peaks at 9.5, 17.2, and 11.4 °2θ, each ±0.2 °2θ.

16. The salt of claim 1, wherein the Compound I tosylate Type D is further characterized by one or more peaks at 17.2, 13.5, and 12.6 °2θ, each ±0.2 °2θ.

17. A pharmaceutical composition comprising one or more pharmaceutically acceptable carriers, and a therapeutically effective amount of the salt of claim 1.

18. A pharmaceutical composition comprising the salt of claim 1, and another therapeutic agent.

19. A method for treating a disease or condition mediated by a protein kinase in a patient in need thereof, comprising administering to the patient a therapeutically effective amount of the salt of claim 1.

20. The method of claim 19, wherein the protein kinase is JAK or any mutation thereof.

21. The method of claim 19, wherein the protein kinase is SYK or any mutation thereof.

22. The method of claim 19, wherein the disease or condition is chronic lymphocytic leukemia (CLL), small lymphocytic lymphoma (SLL), follicular lymphoma (FL), transformed follicular lymphoma (tFL), diffuse large B-cell lymphoma (DLBCL), mantle cell lymphoma (MCL), B-cell non-Hodgkin's lymphoma (NHL), peripheral T-cell lymphoma (PTCL), cutaneous T-cell lymphoma (CTCL), marginal zone lymphoma, mucosa-associated lymphoid tissue (MALT), or Waldenstrom macroglobulinemia (WM).

23. The method of claim 19, wherein the disease or condition is chronic lymphocytic leukemia (CLL).

24. The method of claim 19, wherein the disease or condition is small lymphocytic lymphoma (SLL).

25. The method of claim 19, wherein the disease or condition is follicular lymphoma (FL) or transformed follicular lymphoma (tFL).

26. The method of claim 19, wherein the disease or condition is diffuse large B-cell lymphoma (DLBCL).

27. The method of claim 19, wherein the disease or condition is mantle cell lymphoma (MCL).

28. The method of claim 19, wherein the disease or condition is B-cell non-Hodgkin's lymphoma (NHL).

29. The method of claim 19, wherein the disease or condition is peripheral T-cell lymphoma (PTCL) or cutaneous T-cell lymphoma (CTCL).

30. The method of claim 19, wherein the disease or condition is marginal zone lymphoma.

31. The method of claim 19, wherein the disease or condition is mucosa-associated lymphoid tissue (MALT).

32. The method of claim 19, wherein the disease or condition is Waldenstrom macroglobulinemia (WM).

* * * * *